US011814623B2

(12) United States Patent
Messina

(10) Patent No.: US 11,814,623 B2
(45) Date of Patent: Nov. 14, 2023

(54) METHODS OF TREATING A WOUND USING EPIGENETIC REGULATION

(71) Applicant: University of Massachusetts, Boston, MA (US)

(72) Inventor: Louis M. Messina, Westborough, MA (US)

(73) Assignee: University of Massachusetts, Boston, MA (US)

( * ) Notice: Subject to any disclaimer, the term of this patent is extended or adjusted under 35 U.S.C. 154(b) by 1310 days.

(21) Appl. No.: 16/231,129

(22) Filed: Dec. 21, 2018

(65) Prior Publication Data

US 2019/0233828 A1  Aug. 1, 2019

Related U.S. Application Data

(63) Continuation-in-part of application No. PCT/US2018/040642, filed on Jul. 2, 2018.

(60) Provisional application No. 62/623,880, filed on Jan. 30, 2018.

(51) Int. Cl.
| | |
|---|---|
| C12N 15/113 | (2010.01) |
| A61K 35/28 | (2015.01) |
| A61K 31/19 | (2006.01) |
| A61P 17/02 | (2006.01) |
| A61K 31/7052 | (2006.01) |

(52) U.S. Cl.
CPC .......... *C12N 15/1137* (2013.01); *A61K 31/19* (2013.01); *A61K 31/7052* (2013.01); *A61K 35/28* (2013.01); *A61P 17/02* (2018.01); *C12Y 106/03001* (2013.01); *C12Y 201/01037* (2013.01); *C12N 2310/11* (2013.01); *C12N 2310/122* (2013.01); *C12N 2310/14* (2013.01); *C12N 2310/141* (2013.01); *C12N 2320/31* (2013.01)

(58) Field of Classification Search
CPC ............ C12N 15/1137; C12N 2310/11; C12N 2310/122; C12N 2310/14; C12N 2310/141; C12N 2320/31; A61K 31/19; A61K 31/7052; A61K 35/28; A61P 17/02
See application file for complete search history.

(56) References Cited

U.S. PATENT DOCUMENTS

| | | | |
|---|---|---|---|
| 7,741,345 | B2 | 6/2010 | Cannizzaro et al. |
| 8,790,655 | B2 | 7/2014 | Carson et al. |
| 8,795,678 | B2 | 8/2014 | Liang et al. |
| 10,034,901 | B2 | 7/2018 | Messina et al. |
| 2011/0236362 | A1 | 9/2011 | Watarai et al. |
| 2011/0236894 | A1 | 9/2011 | Rao et al. |
| 2012/0190731 | A1 | 7/2012 | Messina et al. |
| 2012/0272346 | A1 | 10/2012 | Stillman et al. |
| 2013/0323220 | A1 | 12/2013 | Joung et al. |
| 2015/0153349 | A1 | 6/2015 | Galon et al. |
| 2016/0213715 | A1 | 7/2016 | Messina et al. |
| 2020/0316123 | A1 | 10/2020 | Messina et al. |
| 2021/0277402 | A1 | 9/2021 | Messina et al. |

FOREIGN PATENT DOCUMENTS

| | | |
|---|---|---|
| WO | WO 2007/135195 | 11/2007 |
| WO | WO 2009/114547 | 9/2009 |
| WO | WO2009/145399 | 12/2009 |
| WO | WO 2009/146399 | 12/2009 |
| WO | WO 2011/022316 | 2/2011 |
| WO | WO 2013/173223 | 11/2013 |
| WO | WO 2015/113922 | 8/2015 |
| WO | WO 2016/014544 | 1/2016 |
| WO | WO 2016/109668 | 7/2016 |

OTHER PUBLICATIONS

CA Office Action in Canadian Appln. No. 2,973,878. dated Jan. 28, 2022, 5 pages.
EP Extended Search Report in European Appln. No. 18903173.5, dated Jan. 24, 2022, 19 pages.
Alder et al., "Kruppel-like factor 4 is essential for inflammatory monocyte differentiation in vivo," J. Immunol., Apr. 2008, 180:5645-5652.
Alexandrescu et al., "Immunotherapy for Melanoma: Current Status and Perspectives," J. Immunother., Jul.-Aug. 2010, 33(6):570-590.
American Diabetes Association, "2. Classification and Diagnosis of Diabetes," Diabetes Care, 2015, 38(Supplement 1):S8-S16.
American Diabetes, "11. Older Adults: Standards of Medical Care in Diabetes—2018," Diabetes Care, 2018, 41(Suppl 1):S119-S125.
Bannon et al., "Diabetes induces stable intrinsic changes to myeloid cells that contribute to chronic inflammation during wound healing in mice," Dis. Model Mech., Nov. 2013, 6(6):1434-1447.
Bedard and Krause, "The NOX family of ROS-generating NADPH oxidases: physiology and pathophysiology," Physiol. Rev., Jan. 2007, 87(1):245-313.
Bendelac et al., "The biology of NKT cells," Annu. Rev. Immunol., 2007, 25:297-336.
Bennouna et al., "Phase I study of bromohydrin pyrophosphate (BrHPP, IPH 1101), a Vγ9Vδ2 T lymphocyte agonist in patients with solid tumors," Cancer Immunol. Immunother., 2010, 59:1521-1530.
Berezhnoy et al., "A clinically useful approach to enhance immunological memory and antitumor immunity," Oncoimmunology, May 2014, 14(3):e28811-3.
Boesch et al., "Heterogeneity of cancer stem cells: rationale for targeting the stem cell niche," Biochimica Biophysica Acta, Dec. 2016, 1866(2):276-289.
Bollino and Webb, "Chimeric antigen receptor—engineered natural killer and natural killer T cells for cancer immunotherapy," Transl. Res., Sep. 2017, 187:32-43.
Bonomini et al., "Metabolic syndrome, aging and involvement of oxidative stress," Aging Dis., Mar. 2015, 6(2):109-120.
Boulton et al., "The global burden of diabetic foot disease," Lancet, Nov. 2005, 366(9498):1719-1724.

(Continued)

*Primary Examiner* — J. E. Angell
(74) *Attorney, Agent, or Firm* — Fish & Richardson P.C.

(57) ABSTRACT

Methods of treating wounds in a subject using one or both of a DNA methyltransferase 1 (DNMT1) inhibitor or a nicotinamide adenine dinucleotide phosphate oxidase 2 (NOX2) inhibitor, and compositions for use in these methods.

18 Claims, 47 Drawing Sheets

Specification includes a Sequence Listing.

(56) References Cited

OTHER PUBLICATIONS

Brem and Tomic-Canic, "Cellular and molecular basis of wound healing in diabetes," J. Clin. Invest., May 2007, 117(5):1219-1222.
Brem et al., "Evidence-based protocol for diabetic foot ulcers," Plast. Reconstr. Surg., Jun. 2006, 117(7 Suppl):193S-209S.
Brem et al., "The synergism of age and db/db genotype impairs wound healing," Exp. Gerontol., Jun. 2007, 42(6):523-531.
Breslin et al., "Mouse blood monocytes: Standardizing their identification and analysis using CD11," J. Immunol. Methods., Apr. 2013, 390(1-2):1-8.
Bryder et al., "Interleukin-3 supports expansion of long-term multilineage repopulating activity after multiple stem cell divisions in vitro," Blood, Sep. 2000, 96(5):1748-1755.
Buttigieg et al., "NOX2 (gp91phox) is a predominant O2 sensor in a human airway chemoreceptor cell line: biochemical, molecular, and electrophysiological evidence," Am. J. Physiol. Lung Cell. Mol. Physiol., Oct. 2012, 303(7):L598-L607.
Caravaggi et al., "Management of ischemic diabetic foot," J. Cardiovasc., Surg., Dec. 2013, 54(6):737-754.
Castellano et al., "Constrained analogues of procaine as novel small molecule inhibitors of DNA methyltransferase-1," J. Med. Chem., Apr. 2008, 51(7): 2321-2325.
Castillo-Aguilera et al., "DNA methylation targeting: the DNMT/HMT crosstalk challenge," Biomolecules, Mar. 2017, 7(1): 3.
Chambers et al., "Aging hematopoietic stem cells decline in function and exhibit epigenetic dysregulation," PLoS Biol., Aug. 2007, 5(8):e201:1750-1762.
Chapman et al., "TET-catalyzed 5-hydroxymethylcytosine regulates gene expression in differentiating colonocytes and colon cancer," Sci Rep., Dec. 2015, 5:17568.
Chen et al., "Absence of CD4 or CD8 lymphocytes changes infiltration of inflammatory cells and profiles of cytokine expression in skin wounds, but does not impair healing," Exp. Dermatol., Mar. 2014, 23(3):189-194.
Chen et al., "TET2 promotes histone O-GlcNAcylation during gene transcription," Nature, Jan. 2013, 493(7433):561-564.
Chien et al., "γδ T cells: first line of defense and beyond," Annu. Rev. Immunol., 2014, 32:121-155.
Choo et al., "MicroRNA-5p and -3p co-expression and cross-targeting in colon cancer cells," J. Biomed. Sci., Oct. 2014, 21:95, 14 pages.
Cieslewicz et al., "Targeted delivery of proapoptotic peptides to tumor-associated macrophages improves survival," PNAS, Oct. 2013, 110(40):15919-15924.
Cimmino et al., "TET1 is a tumor suppressor of hematopoietic malignancy," Nat. Immunol., Aug. 2015, 16:6(8)53-62.
Coffman et al., "Endothelin receptor-A is required for the recruitment of antitumor T cells and modulates chemotherapy induction of cancer stem cells," Cancer Biol. Ther., Feb. 2013, 14(2):184-192.
Corpuz et al., "Differential responsiveness of Innate-like IL-17- and IFN-γ-producing γδ T cells to homeostatic cytokines," J. Immunol., Jan. 2016, 196(2):645-654.
Crowe et al., "A critical role for natural killer T cells in immunosurveillance of methylcholanthrene-induced sarcomas," J. Exp. Med., Jul. 2002, 196(1):119-127.
Cubbon et al., "Effects of insulin resistance on endothelial progenitor cells and vascular repair," Clin. Sci., Aug. 2009, 117(5):173-190.
Cui et al., "Upregulated lncRNA SNHG1 contributes to progression of non-small cell lung cancer through inhibition of m1R-101-3p and activation of Wnt/P-catenin signaling pathway," Oncotarget, Mar. 2017, 8(11): 17785-17794.
Cullen et al., "Hematopoietic stem cell development: an epigenetic journey," Curr. Top. Dev. Biol., 2014, 107:39-75.
Daigneault et al., "The identification of markers of macrophage differentiation in PMA-stimulated THP-1 cells and monocyte-derived macrophages," PLoS One, Jan. 2010, 5(1):e8668, 31 pages.
Dakic et al., "PU.1 regulates the commitment of adult hematopoietic progenitors and restricts granulopoiesis," J. Exp. Med., May 2005, 201(9):1487-1502.

Deplus et al., "TET2 and TET3 regulate GlcNAcylation and H3K4 methylation through OCT and SET1/COMPASS," Mar. 2013, Embo J., 32(5):645-655.
Dhodapkar et al., "A reversible defect in natural killer T cell function characterizes the progression of premalignant to malignant multiple myeloma," J Exp. Med., Jun. 2003, 197(12):1667-1676.
Diebold et al., "NOX2 as a target for drug development: indications, possible complications, and progress," Antioxid. Redox. Signal., Aug. 2015, 23(5):375-405.
Dieterlen-Lievre, "Hematopoiesis: progenitors and their genetic program," Curr. Biol., Oct. 1998, 8(20):R727-R730.
Donovan et al., "Drugs for gestational diabetes," Australian Prescriber, Oct. 2010, 33(5):141-144.
Drechsler et al., "Hyperlipidemia-triggered neutrophilia promotes early atherosclerosis," Circulation, Nov. 2010, 122(18):1837-1845.
Dunn et al., "Cancer immunoediting: from immunosurveillance to tumor escape," Nat. Immunol., Nov. 2002, 3(11):991-998.
Dunn et al., "Interferons, immunity and cancer immunoediting," Nat. Rev. Immunol., Nov. 2006, 6(11): 836-848.
Dunn et al., "The immunobiology of cancer immunosurveillance and immunoediting," Immunity, Aug. 2004, 21(2):137-148.
Eggermont et al., "Anti-CTLA-4 antibody adjuvant therapy in melanoma," Semin. Oncol., Oct. 2010, 37(5):455-459.
Ensembl. Gene: DNMT1 ENSMUSG00000004099. Jul. 2018; downloaded from the internet <https://uswest.ensembl.org/Mus_musculus/Gene/Sequence?g=ENSMUSG00000004099;r=9:20907209-20959888> on Sep. 21, 2018, pp. 1-16.
Escamilla-Tilch et al., "The interplay between pathogen-associated and danger-associated molecular patterns: an inflammatory code in cancer?," Immunol. Cell Biol., Nov.-Dec. 2013, 91(10):601-610.
Esteve et al., "Direct interaction between DNMT1 and G9a coordinates DNA and histone methylation during replication," Genes Dev., Nov. 2006, 20(22):3089-3103.
European Search Report and Written Opinion in International Application No. 16740821.0, dated Jul. 25, 2018, 8 pages.
Fadini et al., "An unbalanced monocyte polarisation in peripheral blood and bone marrow of patients with type 2 diabetes has an impact on microangiopathy," Diabetologia, Aug. 2013, 56:(8):1856-1866.
Fagan et al., "Laccaic acid A is a direct DNA-competitive inhibitor of DNA methyltransferase 1," J. Biol. Chemistry, Aug. 2013, 288(33):23858-23867.
Falanga, "Wound healing and its impairment in the diabetic foot," Lancet, Nov. 2005, 366(9498):1736-1743.
Fan et al., "DNA methyltransferase 1 knockdown induces silenced CDH1 gene reexpression by demethylation of methylated CpG in hepatocellular carcinoma cell line SMMC-7721," Eur. J. Gastroenterol. Hepatol., Nov. 2007, 19(11):952-961.
Feinberg et al., "The Kruppel-like factor KLF4 is a critical regulator of monocyte differentiation," EMBO J., Sep. 2007, 26(18):4138-4148.
Fisher et al., "γδ cells for cancer immunotherapy: a systematic review of clinical trials," Oncoimmunology, Jan. 2014, 3(1): e27572.
Folli et al., "Altered insulin receptor signalling and β-cell cycle dynamics in type 2 diabetes mellitus," PLoS One, 2011, 6(11):e28050, 11 pages.
Font-Burgada et al., "Obesity and cancer: the oil that feeds the flame," Cell Metab., Jan. 2016, 23(1):48-62.
Foulks et al., "Epigenetic drug discovery: targeting DNA methyltransferases," J. Biol. Screen., Jan. 2012, 17(1):2-17.
Francke et al., "Generation of mature murine monocytes from heterogeneous bone marrow and description of their properties," J. Histochem. Cytochem., Sep. 2011, 59(9):813-825.
Frank et al., "Autophagic digestion of *Leishmania major* by host macrophages is associated with differential expression of BNIP3, CTSE, and the miRNAs miR-101c, miR-129, and miR-210," Parasit. Vectors, Jul. 2015, 8:404.
Gallagher et al., "Epigenetic changes in bone marrow progenitor cells influence the inflammatory phenotype and alter wound healing in type 2 diabetes," Diabetes, Apr. 2015, 64(4):1420-1430.
Galluzi et al., "Trial watch: experimental Toll-like receptor agonists for cancer therapy," Oncoimmunol., Aug. 2012, 1(5): 699-716.

(56) References Cited

OTHER PUBLICATIONS

Galon et al., "Cancer classification using the immunoscore: a worldwide task force," J. Transl. Med., Oct. 2012, 10:205-214.
Ganesan and Bakhshi, "Systemic therapy for melanoma," Natl. Med. J. India., 2010, 23(1):21-7.
Gangaraju and Lin, "MicroRNAs: key regulators of stem cells," Nat. Rev. Mol. Cell. Biol., Feb. 2009, 10(2):116-125.
Garbe et al., "TCR and Notch synergize in alphabeta versus gammadelta lineage choice," Trends Immunol., Mar. 2007, 28(3):124-131.
Geiger et al., "Hematopoietic stem cell aging," Curr. Opin. Immunol., Aug. 2014, 29:86-92.
Geissmann et al., "Development of monocytes, macrophages, and dendritic cells," Science, Feb. 2010, 327(5966):656-661.
Georgantas et al., "Microarray and serial analysis of gene expression analyses identify known and novel transcripts overexpressed in hematopoietic stem cells," Cancer Res., Jul. 2004, 64(13):4434-4441.
Gerstein et al., "Wound healing and aging," Dermatol.Clin., Oct. 1993, 11(4):749-757.
Gilbert et al., "DNA methylation affects nuclear organization, histone modifications, and linker histone binding but not chromatin compaction," J. Cell Biol., May 2007, 177(3):401-411.
Godfrey et al., "NKT cells: what's in a name?," Mar. 2004, Nat. Rev. Immunol, 4(3):231-237.
Golovina and Vonderheide, "Regulatory T cells: overcoming suppression of T-cell immunity," Cancer J., Jul.-Aug. 2010, 16(4):342-347.
Gomes et al., "Targeting γδ T lymphocytes for cancer immunotherapy: from novel mechanistic insight to clinical application," Cancer Res., Dec. 2010, 70(24):10024-10027.
Gore et al., "DNA methylation in hematopoietic development and disease," Exp. Hematol, Sep. 2016, 44(9):783-790.
Gosain et al., "Aging and wound healing," World J. Surg., Mar. 2004, 28(3):321-326.
Gould & Fulton, "Wound healing in older adults," R.I. Med. J., Feb. 2016, 99(2): 34-36.
Gould et al., "Chronic wound repair and healing in older adults: current status and future research," J. Am. Geriatr. Soc., Mar. 2015, 63(3):427-438.
Greten et al., "IKKbeta links inflammation and tumorigenesis in a mouse model of colitis-associated cancer," Cell, Aug. 2004, 118(3):285-296.
Guo and Dipietro, "Factors affecting wound healing," J. Dent. Res., Mar. 2010, 89(3): 219-229.
Guo et al., "Cancer stem cells," Pediatric Res., Apr. 2006, 59(4 Pt 2):59R-64R.
Guo et al., "Mapping cellular hierarchy by single-cell analysis of the cell surface repertoire," Cell Stem Cell, Oct. 2013, 13(4):492-505.
Haetscher et al., "STAT5-regulated microRNA-193b controls haematopoietic stem and progenitor cell expansion by modulating cytokine receptor signalling," Nat. Commun., Nov. 2015, 6:8928, 11 pages.
Hennekens and Andreotti, "Leading avoidable cause of premature deaths worldwide: case for obesity," Am. J. Med., Feb. 2013, 126(2):97-98.
Hirano et al., "Discovery of GSK2795039, a novel small molecule NADPH oxidase 2 inhibitor," Antioxid. Redox. Signal., Aug. 2015, 23(5):358-374.
Holmes and Zuniga-Pflucker, "The OP9-DL1 system: generation of T-lymphocytes from embryonic or hematopoietic stem cells in vitro," Cold Spring Harb. Protoc., Feb. 2009, 2009(2):pdb. prot5156.
Holtmeier et al., "γδ T cells link innate and adaptive immune responses," Chem. Immunol. Allergy, 2015, 86:151-183.
Huang et al., "Rates of complications and mortality in older patients with diabetes mellitus," JAMA Intern. Med., Feb. 2014, 174(2):251-258.
Huber et al., "Regulation of monocyte differentiation by specific signaling modules and associated transcription factor networks," Cell. Mol. Life Sci., Jan. 2014, 71(1):63-92.
International Search Report and Written Opinion in International Application No. PCT/US17/59367, dated Feb. 2, 2019.
International Search Report and Written Opinion in International Application No. PCT/US18/40642 dated Nov. 5, 2018, 16 pages.
International Search Report and Written Opinion in International Application No. PCT/US16/14477, dated Apr. 22, 2016, 15 pages.
Ito et al., "Role of Tet proteins in 5mC to 5hmC conversion, ES-cell self-renewal, and inner cell mass specification," Nature, Aug. 2010, 466(7310):1129-1133.
Ito et al., "Tet proteins can convert 5-methylcytosine to 5-formylcytosine and 5-carboxylcytosine," Science, Sep. 2011, 333(6047):1300-1303.
Jablonski et al., "Novel markers to delineate murine M1 and M2 macrophages," PLoS One, Dec. 2015, 10(12):e0145342, 25 pages.
Jackson et al., "Severe global DNA hypomethylation blocks differentiation and induces histone hyperacetylation in embiyonic stem cells," Mol. Cell. Biol., Oct. 2004, 24(20):8862-8871.
Jin et al., "DNA methyltransferase 3B (DNMT3B) mutations in ICF syndrome lead to altered epigenetic modifications and aberrant expression of genes regulating development, neurogenesis and immune function," Hum. Mol. Genet., Mar. 2008, 17(5):690-709.
Jin et al., "Long non-coding RNA SPRY4-IT1 promotes proliferation and invasion by acting as a ceRNA of miR-101-3p in colorectal cancer cells," Tumour Biol., Jul. 2017, 39(7): 1-6.
Katsarou et al., "Type 1 diabetes mellitus," Nat. Rev. Dis. Primers, Mar. 2017, 3:17016, 17 pages.
Kawasaki and Taira, "Induction of DNA methylation and gene silencing by short interfering RNAs in human cells," Nature, Sep. 2004, 431(7005):211-217.
Kerkar et al., "Cellular constituents of immune escape within the tumor microenvironment," Cancer Res., Jul. 2012, 72(13): 3125-3130.
Khanna et al., "Macrophage dysfunction impairs resolution of inflammation in the wounds of diabetic mice," PLoS One, Mar. 2010, 5(3):e9539, 12 pages.
Kim et al., "Discrete Notch signaling requirements in the specification of hematopoietic stem cells," EMBO J., Oct. 2014, 33(20):2363-2373.
Klein et al., "Mutations in DNMT1 cause hereditary sensory neuropathy with dementia and hearing loss," Nat. Genet., Jun. 2011, 43(6):595-600.
Klingenberg et al., "Depletion of FOXP3+ regulatory T cells promotes hypercholesterolemia and atherosclerosis," J. Clin. Invest., Mar. 2013, 12(3)3:1323-1334.
Klinke, "A multiscale systems perspective on cancer, immunotherapy, and Interleukin-12," Mol. Cancer., Sep. 2010, 9:242, 18 pages.
Ko et al., "Impaired hydroxylation of 5-methylcytosine in myeloid cancers with mutant TET2," Nature, Dec. 2010, 468(7325):839-843.
Ko et al., "Ten-Eleven-Translocation 2 (TET2) negatively regulates homeostasis and differentiation of hematopoietic stem cells in mice," Proc. Natl. Acad. Sci. USA, Aug. 2011, 108(35):14566-14571.
Kobayashi et al., "A new indicator of favorable prognosis in locally advanced renal cell carcinomas: gamma delta T-cells in peripheral blood," Anticancer Res., Mar. 2011, 31(3):1027-1032.
Kobayashi et al., "Safety profile and anti-tumor effects of adoptive immunotherapy using gamma-delta T cells against advanced renal cell carcinoma: a pilot study," Cancer Immunol. Immunother., Apr. 2007, 56(4):469-476.
Koene et al., "Shared risk factors in cardiovascular disease and cancer," Circulation, Mar. 2016, 133(11):1104-1114.
Kondo et al., "Zoledronate facilitates large-scale ex vivo expansion of functional γδ T cells from cancer patients for use in adoptive immunotherapy," Cytotherapy, 2008, 10(8):842-856.
Krüger et al., "Immune based therapies in cancer," Histol Histopathol., Jun. 2007, 22(6):687-696.
Krzyszczyk et al., "The role of macrophages in acute and chronic wound healing and interventions to promote pro-wound healing phenotypes," Front. Physiol., May 2018, 9:419, 22 pages.

(56) References Cited

OTHER PUBLICATIONS

Kurita et al., "DNMT1 and DNMT3b silencing sensitizes human hepatoma cells to TRAIL-mediated apoptosis via up-regulation of TRAIL-R2/DR5 and caspase-8," Cancer Sci., Jun. 2010, 101(6):1431-1439.

Lantz et al., "An invariant T cell receptor α chain is used by a unique subset of major histocompatibility complex class I-specific CD4+ and CD4-8− T cells in mice and humans," J. Exp. Med., Sep. 1994, 180(3):1097-1106.

Laslo et al., "Multilineage transcriptional priming and determination of alternate hematopoietic cell fates," Cell, Aug. 2006, 126(4):755-766.

Lee and Margolin, "Cytokines in Cancer Immunotherapy," Cancers, Oct. 2011, 3(4):3856-3893.

Li et al., "Epigenetic inactivation of the CpG demethylase TET1 as a DNA methylation feedback loop in human cancers," Sci. Rep., May 2016, 6:26591, 13 pages.

Li et al., "Targeted mutation of the DNA methyltransferase gene results in embryonic lethality," Cell, Jun. 1992, 69(6):915-926.

Li et al., "Tumor microenvironment: the role of tumor stroma in cancer," J. Cell. Biochem., Jul. 2007, 101(4):805-815.

Liao et al., "Krüppel-like factor 4 regulates macrophage polarization," J. Clin. Invest., Jul. 2011, 121(7):2736-2749.

Liao et al., "Targeted disruption of DNMT1, DNMT3A and DNMT3B in human embryonic stem cells," Nat. Genet., May 2015, 47(5):469-478.

Liguori et al., "Oxidative stress, aging, and diseases," Clin. Interv. Aging, Apr. 2018, 13:757-772.

Liu et al., "Age-dependent impairment of HIF-1a expression in diabetic mice: correction with electroporation-facilitated gene therapy increases wound healing, angiogenesis, and circulating angiogenic cells," J. Cell. Physiol., Nov. 2008, 217(2):319-327.

Liu et al., "MicroRNA-101-3p suppresses cell proliferation, invasion and enhances chemotherapeutic sensitivity in salivary gland adenoid cystic carcinoma by targeting Pim-1," Am. J. Cancer Res., Oct. 2015, 5(10): 3015-3029.

Lu et al., "Polysaccharide krestin is a novel TLR2 agonist that mediates inhibition of tumor growth via stimulation of CD8 T Cells and NK Cells," Clin. Cancer. Res., Jan. 2011, 17(1):67-76.

Luo et al., "Long non-coding RNAs control hematopoietic stem cell function," Cell Stem, Apr. 2015, 16(4):426-438.

Luo, et al., "Targeting tumor-associated macrophages as a novel strategy against breast cancer," J. Clin. Invest., Aug. 2006, 116(8):2132-2141.

MacLeod et al., "Skin-resident T cells sense ultraviolet radiation-induced injury and contribute to DNA repair," J. Immunol., Jun. 2014, 192(12):5695-5702.

Makrantonaki et al., "Pathogenesis of wound healing disorders in the elderly," J. Dtsch Dermatol. Ges., Mar. 2017, 15(3):255-275.

Mantovani et al., "Macrophage polarization comes of age," Immunity, Oct. 2005, 23(4):344-346.

Martinez et al., "Alternative activation of macrophages: an immunologic functional perspective," Annu. Rev. Immunol., 2009, 27:451-483.

Maruyama et al., "Decreased macrophage number and activation lead to reduced lymphatic vessel formation and contribute to impaired diabetic wound healing," Am. J. Pathol., Apr. 2007, 170(4):1178-1191.

Matsuda et al., "Developmental program of mouse Valpha14i NKT cells," Curr. Opin. Immunol., Apr. 2005, 17(2):122-130.

McKercher et al., "Targeted disruption of the PU.1 gene results in multiple hematopoietic abnormalities," EMBO J., Oct. 1996, 15(20):5647-5658.

Melero et al., "IL-12 gene therapy for cancer: in synergy with other immunotherapies," Trends. Immunol., Mar. 2001, 22(3):113-115.

Mercer et al., "Multilineage priming of enhancer repertoires precedes commitment to the B and myeloid cell lineages in hematopoietic progenitors," Immunity, Sep. 2011, 35(3):413-425.

Mineharu et al., "Blockade of mTOR signaling via rapamycin combined with immunotherapy augments antiglioma cytotoxic and memory T-Cell Functions," Mol. Cancer Ther., Dec. 2014, 13(12): 3024-3036.

Moschella et al., "Combination strategies for enhancing the efficacy of immunotherapy in cancer patients," Ann. NY Acad. Sci., Apr. 2010, 1194:169-178.

Motohashi et al., "A phase I study of in vitro expanded natural killer T cells in patients with advanced and recurrent non-small cell lung cancer," Clin Cancer Res., Oct. 2006, 12(20 Pt 1):6079-6086.

Munn, "Blocking IDO activity to enhance anti-tumor immunity," Front Biosci (Elite Ed), Jan. 2012, 4: 734-745.

NCEP, "Third Report of the National Cholesterol Education Program (NCEP) Expert Panel on Detection, Evaluation, and Treatment of High Blood Cholesterol in Adults (Adult Treatment Panel III) final report," Circulation, 2002, 106(25): 3143-421.

Neri et al., "TET1 is a tumour suppressor that inhibits colon cancer growth by derepressing inhibitors of the WNT pathway," Oncogene, Aug. 2015, 34(32): 4168-4176.

Notarnicola et al., "Serum lipid profile in colorectal cancer patients with and without synchronous distant metastases," Oncology, 2005, 68(4-6):371-374.

Nunez-Cruz et al., "Differential requirement for the SAP-Fyn interaction during NK T cell development and function," J. Immunol., Aug. 2008, 181(4):2311-2320.

Oh et al., "Stem cell aging: mechanisms, regulators and therapeutic opportunities," Nat. Med., Aug. 2014, 20(8):870-880.

Okano et al., "Cloning and characterization of a family of novel mammalian DNA (cytosine-5) methyltransferases," Nat. Genet., Jul. 1998, 19(3): 219-220.

Okano et al., "DNA methyltransferases Dnmt3a and Dnmt3b are essential for de novo methylation and mammalian development," Cell, Oct. 1999, 99(3):247-257.

Omar et al., "Enhanced beta cell function and anti-inflammatory effect after chronic treatment with the dipeptidyl peptidase-4 inhibitor vildagliptin in an advanced-aged diet-induced obesity mouse model," Diabetologia, Aug. 2013, 56(8):1752-1760.

Orkin, "Priming the hematopoietic pump," Immunity, Nov. 2003, 19(5):633-634.

Outtz et al., "Notch1 deficiency results in decreased inflammation during wound healing and regulates vascular endothelial growth factor receptor-1 and inflammatory cytokine expression in macrophages," J. Immunol., Oct. 2010, 185(7):4363-4373.

Papakonstantinou et al., "Differential microRNA profiles and their functional implications in different immunogenetic subsets of chronic lymphocytic leukemia," Mol. Med., May 2013, 19: 115-123.

Pattabiraman and Weinberg, "Tackling the cancer stem cells—what challenges do they pose?," Nat. Rev. Drug Discov., Jul. 2014, 13(7):497-512.

PCT International Preliminary Report On Patentability in International Application No. PCT/US17/59367, dated May 16, 2019, 11 pages.

PCT International Preliminary Report on Patentability in International Application No. PCT/US2016/014477, dated Jul. 25, 2017.

Pearce et al., "Enhancing CD8 T-cell memory by modulating fatty acid metabolism," Nature, Jul. 2009, 460(7251):103-107.

Pervaiz et al., "Oxidative stress regulation of stem and progenitor cells," Antioxid. Redox. Signal., Nov. 2009, 11(11):2777-2789.

Piccoli et al., "Bone-marrow derived hematopoietic stem/progenitor cells express multiple isoforms of NADPH oxidase and produce constitutively reactive oxygen species," Biochem. Biophys. Res. Commun., Feb. 2007, 353(4):965-972.

Plowden et al., "Innate immunity in aging: impact on macrophage function," Aging Cell, Aug. 2004, 3(4):161-167.

Porcelli et al., "Analysis of T cell antigen receptor (TCR) expression by human peripheral blood CD4-8- α/b T cells demonstrates preferential use of several Vb genes and an invariant TCR α chain," J. Exp. Med., Jul. 1993, 178(1):1-16.

Portielje et al., "IL-12: a promising adjuvant for cancer vaccination," Cancer Immunol. Immunother., Mar. 2003, 52(3):133-144.

Pradeu and Cooper, "The danger theory: 20 years later," Front Immunol., 2012, 3:287, 10 pages.

(56) References Cited

OTHER PUBLICATIONS

Prattichizzo et al., ""Inflammaging" as a druggable target: a senescence-associated secretory phenotype-centered view of type 2 diabetes," Oxid Med Cell. Longev., vol. 2016, Article ID 1810327, 10 pages.
Quail and Joyce, "Microenvironmental regulation of tumor progression and metastasis," Nat. Med., Nov. 2013, 19(11):1423-1437.
Rector et al., "Comprehensive hematopoietic stem cell isolation methods," Methods Mol. Biol., 2013, 976:1-15.
Reiber et al., "Causal pathways for incident lower-extremity ulcers in patients with diabetes from two settings," Diabetes Care, Jan. 1999, 22(1):157-162.
Robson et al., "Oxidative stress biomarkers in type 2 diabetes mellitus for assessment of cardiovascular disease risk," Diabetes Metab. Syndr., May 2018, 12(3):455-462.
Rogers et al., "A role for DNA hypomethylation and histone acetylation in maintaining allele-specific expression of mouse NKG2A in developing and mature NK cells," J. Immunol., Jul. 2006, 177(1):414-421.
Sag et al., "ATP-binding cassette transporter G1 intrinsically regulates invariant NKT cell development," J. Immunol., Dec. 2012, 189(11):5129-5138.
Sag et al., "The cholesterol transporter ABCG1 links cholesterol homeostasis and tumour immunity," Nat. Commun., Feb. 2015, 6:6354, 14 pages.
Satoh et al., "Unbalanced M1/M2 phenotype of peripheral blood monocytes in obese diabetic patients: effect of pioglitazone," Diabetes Care, Jan. 2010, 33(1):e7.
Schmitt et al., "Induction of T cell development and establishment of T cell competence from embiyonic stem cells differentiated in vitro," Nat. Immunol., Apr. 2004, 5(4):410-417.
Schroeder et al., "Notch signaling induces multilineage myeloid differentiation and up-regulates PU.1 expression," J. Immunol., Jun. 2003, 170(11):5538-5548.
Scott et al., "Antibody therapy of cancer," Nat. Rev. Cancer, Mar. 2012, 12(4):278-287.
Sesti et al., "Insulin receptor variant forms and Type 2 diabetes mellitus," Pharmacogenomics, Feb. 2000, 1(1):49-61.
Sesti et al., "Molecular mechanism of insulin resistance in type 2 diabetes mellitus: role of the insulin receptor variant forms," Diabetes Metab. Res. Rev., Sep.-Oct. 2001, 17(5):363-373.
Sgonc et al., "Age-related aspects of cutaneous wound healing: a mini-review," Gerontology, 2013, 59(2):159-164.
Shah et al., "DNMT3A mutations in acute myeloid leukemia," Nat. Genet., Mar. 2011, 43(4):289-290.
Shi et al., "Ten-Eleven Translocation 1 (TET1) is regulated by O-linked N-acetylglucosamine transferase (Ogt) for target gene repression in mouse embryonic stem cells," J. Biol. Chem., Jul. 2013, 288(29):20776-20784.
Shiao et al., "Immune microenvironments in solid tumors: new targets for therapy," Genes & Dev., Dec. 2011, 25(24):2559-2572.
Shibata et al., "Adiponectin regulates psoriasiform skin inflammation by suppressing IL-17 production from γ δ-T cells," Nat. Commun., Jul. 2015, 6:7687, 14 pages.
Shultz et al., "Human lymphoid and myeloid cell development in NOD/LtSz-scid IL2R null mice engrafted with mobilized human hemopoietic stem cells," J. Immunol., May 2005, 174(10):6477-6489.
Silva-Santos et al., "γδ T cells in cancer," Nat. Rev. Immunol., Nov. 2015, 15(11):883-889.
Smyth et al., "Tumor necrosis factor-related apoptosis-inducing ligand (TRAIL) contributes to interferon gamma-dependent natural killer cell protection from tumor metastasis," J. Exp. Med., Mar. 2001, 193(6):661-670.
Sosenko et al., "The prediction of type 1 diabetes by multiple autoantibody levels and their incorporation into an autoantibody risk score in relatives of type 1 diabetic patients," Diabetes Care, Sep. 2013, 36(9):2615-2620.

Spanholtz et al., "High log-scale expansion of functional human natural killer cells from umbilical cord blood CD34-positive cells for adoptive cancer immunotherapy," PLOS One, Feb. 2010, 5(2): e9221.
Strid et al., "Acute upregulation of an NKG2D ligand promotes rapid reorganization of a local immune compartment with pleiotropic effects on carcinogenesis," Nat. Immunol., Feb. 2008, 9(2):146-154.
Taniguchi et al., "The NKT cell system: bridging innate and acquired immunity," Nat. Immunol., Dec. 2003, 4(12):1164-1165.
Tarhini and Iqbal, "CTLA-4 blockade: therapeutic potential in cancer treatments," Onco. Targets Ther., Jun. 2010, 3:15-25.
Tavares et al., "Normal lymphocyte immunophenotype in an elderly population," Rev. Bras. Hematol. Hemoter., May-Jun. 2014, 36(3):180-183.
Tepper et al., "Decreased circulating progenitor cell number and failed mechanisms of stromal cell-derived factor-1 mediated bone marrow mobilization impair diabetic tissue repair," Diabetes, Aug. 2010, 59(8):1974-1983.
Themeli et al., "Generation of tumor-targeted human T lymphocytes from induced pluripotent stem cells for cancer therapy," Nat Biotechnol., Oct. 2013, 31(10):928-933.
Thermofisher Scientific, "hsa-miR-132-3p Product Details," Jan. 2, 2018; downloaded from the internet <https://https://www.thermofisher.com/order/genome-database/details/mirna/MC10166>, pp. 1-3.
Tie et al., "Hypercholesterolemia induces oxidant stress that accelerates the ageing of hematopoietic stem cells," J Am Heart Assoc., Jan. 2014, 3(1):e000241.
Todaro et al., "Efficient killing of human colon cancer stem cells by γδ T lymphocytes," J. Immunol., Jun. 2009, 182(11):7287-7296.
Topalian et al., "Safety, activity, and immune correlates of anti-PD-1 antibody in cancer," NEJM, Jul. 2012, 366(26):2443-2454.
Toura et al., "Cutting edge: inhibition of experimental tumor metastasis by dendritic cells pulsed with α-galactosylceramide," J. Immunol., Sep. 1999, 163(5):2387-2391.
TPA: Mus msuculus mRNA mmu-let-7d-3p; GenBank Accession LM379002.1. Mar. 3, 2015; downloaded from the internet <https://www.ncbi.nlm.nih.gov/nuccore/LM379002> on Sep. 25, 2018, p. 2.
Trowbridge et al., "DNA methyltransferase 1 is essential for and uniquely regulates hematopoietic stem and progenitor cells," Cell Stem Cell, Oct. 2009, 5(4):442-449.
Turley et al., "Immunological hallmarks of stromal cells in the tumor microenvironment," Nat. Rev. Immunol., Nov. 2015, 15(11):669-682.
Van Galen et al., "Reduced lymphoid lineage priming promotes human hematopoietic stem cell expansion," Cell Stem Cell, Jan. 2014, 14(1):94-106.
Vantourout and Hayday, "Six-of-the-best: unique contributions of γδ T cells to immunology," Nat. Rev. Immunol., Feb. 2013, 13(2):88-100.
Vella et al., "Tet proteins connect the O-linked N-acetylglucosamine transferase Ogt to chromatin in embryonic stem cells," Mol. Cell., Feb. 2013, 49(4):645-656.
Walsh et al., "Humanized mouse models of clinical disease," Annu. Rev. Pathol., Jan. 2017, 12:187-215.
Wang et al., "Total body irradiation causes residual bone marrow injury by induction of persistent oxidative stress in murine hematopoietic stem cells," Free Radic. Biol. Med., Jan. 2010, 48(2):348-356.
Wang et al.. "The effects of DNA methyltransferase inhibitors and histone deacetylase inhibitors on digit regeneration in mice," Regen. Med., Mar. 2010, 5(2):201-220.
Watarai et al., "Murine induced pluripotent stem cells can be derived from and differentiate into natural killer T cells," J. Clin. Invest., Jul. 2010, 120(7):2610-2618.
Willenborg and Eming, "Macrophages—sensors and effectors coordinating skin damage and repair," J. Dtsch Dermatol. Ges., Mar. 2014, 12(3): 214-221.
Wilson et al., "STAT3 is a critical cell-intrinsic regulator of human unconventional T cell numbers and function," J Exp. Med., Jun. 2015, 212(6):855-864.
Winkelmann et al., "Mutations in DNMT1 cause autosomal dominant cerebellar ataxia, deafness and narcolepsy," Hum. Mol. Genet., May 2012, 21(10):2205-2210.

(56) References Cited

OTHER PUBLICATIONS

Wojtowicz-Praga, "Reversal of tumor-induced immunosuppression by TGF-beta inhibitors," Invest. New Drugs, Feb. 2003, 21(1):21-32.

Wong et al., "Abstract 54: MicroRNA Let-7d-3p in Heart Failure," Circulation Research, Jul. 2016, 119:A54.

Wood et al., "Pro-inflammatory chemokine CCL2 (MCP-1) promotes healing in diabetic wounds by restoring the macrophage response," PLoS One, Mar. 2014, 9(3):e91574, 8 pages.

Wu et al., "Mechanisms and functions of Tet protein-mediated 5-methylcytosine oxidation," Genes Dev., Dec. 2011, 25(23):2436-2452.

Wu et al., "Suppression of TET1-dependent DNA demethylation is essential for KRAS-mediated transformation," Cell Reports, Dec. 2014, 9(5): 1827-1840.

Yan et al., "Diabetes impairs wound healing by Dnmt1-dependent dysregulation of hematopoietic stem cells differentiation towards macrophages," Nat. Commun., Jan. 2018, 9(1): 33, 13 pages.

Yan et al., "Type 2 diabetes restricts multipotency of mesenchymal stem cells and impairs their capacity to augment postischemic neovascularization in db/db Mice," J. Am. Heart Assoc., Dec. 2012, 1(6):e002238, 16 pages.

Yokota et al., "Complementary regulation of early B-lymphoid differentiation by genetic and epigenetic mechanisms," Int. J. Hematol., Oct. 2013, 98(4):382-389.

Yu et al., "Metabolic regulation by the mitochondrial phosphatase PTPMT1 is required for hematopoietic stem cell differentiation," Cell Stem Cell, Jan. 2013, 12(1):62-74.

Zarin et al., "Gamma delta T-cell differentiation and effector function programming, TCR signal strength, when and how much?," Cell Immunol., Jul. 2015, 296(1):70-75.

Zeisberger et al., "Clodronate-liposome-mediated depletion of tumour-associated macrophages: a new and highly effective antiangiogenic therapy approach," Br. J. Cancer., Aug. 2006, 95(3):272-281.

Zhao et al., "Inflammation in chronic wounds," Int J Mol Sci, Dec. 2016, 17(12). pii:E2085.

Zhu et al., "Developing new chemical tools for DNA methyltransferase 1 (DNMT 1): a small-molecule activity-based probe and novel tetrazole-containing inhibitors," Bioorganic & Med Chemistry, Jun. 2015, 23(12):2917-2927.

Ziegler et al., "Seroconversion to multiple islet autoantibodies and risk of progression to diabetes in children," JAMA, Jul. 2013, 309(23):2473-2479.

Zitvogel et al., "Mechanism of action of conventional and targeted anticancer therapies: reinstating immunosurveillance," Immunity, Jul. 2013, 39(1):74-88.

Zykova et al., "Altered cytokine and nitric oxide secretion in vitro by macrophages from diabetic type II—like db/db mice," Diabetes, Sep. 2000, 49(9):1451-1458.

PCT International Preliminary Report on Patentability in International Appln. No. PCT/US2018/040642, dated Aug. 4, 2020, 11 pages.

U.S. Appl. No. 15/004,132, filed Jan. 22, 2016, Louis M. Messina.
U.S. Appl. No. 15/538,690, filed Jun. 22, 2017, Louis M. Messina.
U.S. Appl. No. 16/332,588, filed Mar. 12, 2019, Louis M. Messina.

Liu et al., "mir-101-3p is a key regulator of tumor metabolism in triple negative breast cancer targeting AMPK," Oncotarget, Jun. 2016, 76(23):35188-35198.

Ma et al., "Abstract 5095: 1,25D3 inhibits migration and invasion through miR-101-3p in human bladder cancer cells," Cancer Research, Aug. 2015, 75(15), 6 pages.

Sheng et al., "Downregulation of miR-101-3p by hepatitis B virus promotes proliferation and migration of hepatocellular carcinoma cells by targeting Rab5A," Archives of Virology, Sep. 2014, 159(9):2397-2410.

EP Office Action in European Appln. No. 16740821.0, dated Jan. 27, 2020, 4 pages.

EP Supplementary European Search Report in European Appln. No. 17865070.1, dated Jun. 25, 2020.

Fan et al., "MicroRNA-101-3p reverses gemcitabine resistance by inhibition of ribonucleotide reductase M1 in pancreatic cancer," Cancer Letters, Apr. 1, 2016, 373(1):130-7.

AlMatar et al., "Therapeutic potential of N-acetylcysteine for wound healing, acute bronchiolitis, and congenital heart defects," Current Drug Metabolism, Feb. 1, 2016, 17(2):156-67.

EP European Search Report in European Appln. No. 18903173.5, dated Oct. 18, 2021, 22 pages.

Park et al., "Effects of genistein on early-stage cutaneous wound healing," Biochemical and Biophysical Research Communications, Jul. 8, 2011, 410(3):514-9.

Xie et al., "Genistein inhibits DNA methylation and increases expression of tumor suppressor genes in human breast cancer cells," Genes, Chromosomes and Cancer, May 2014, 53(5):422-31.

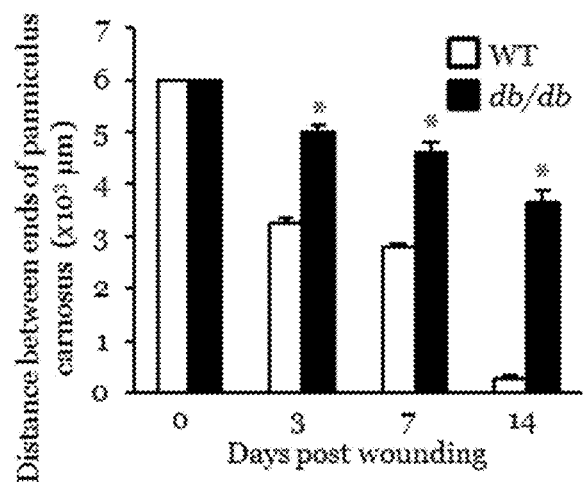
*FIG. 1E*
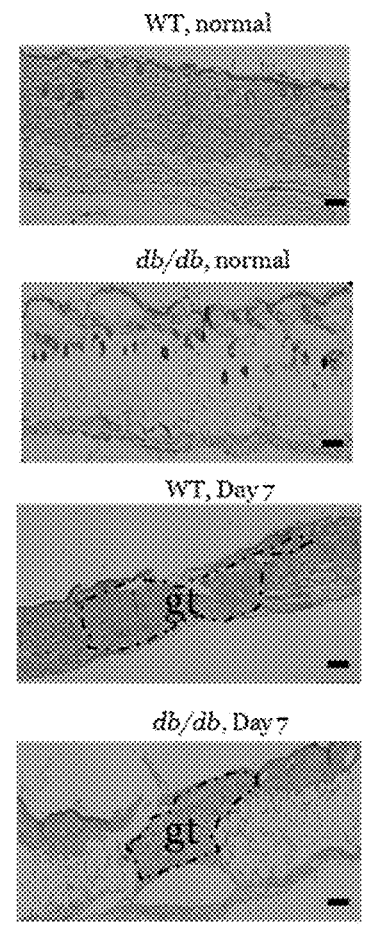
*FIG. 1F*
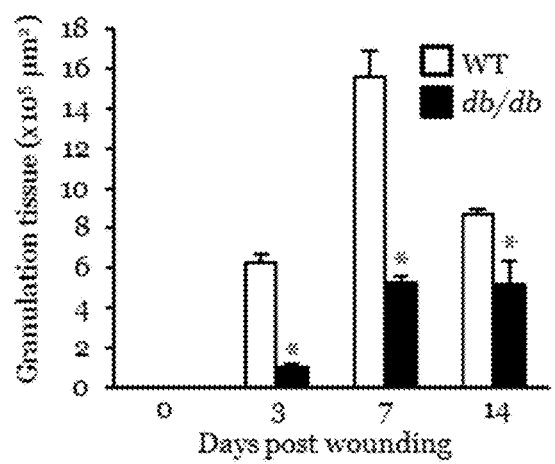
*FIG. 1G*
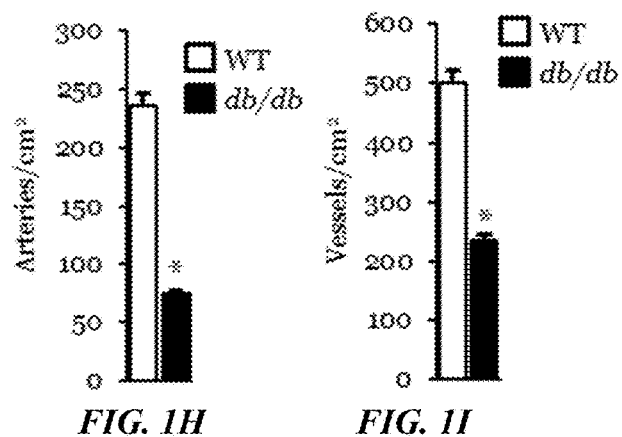
*FIG. 1H*   *FIG. 1I*

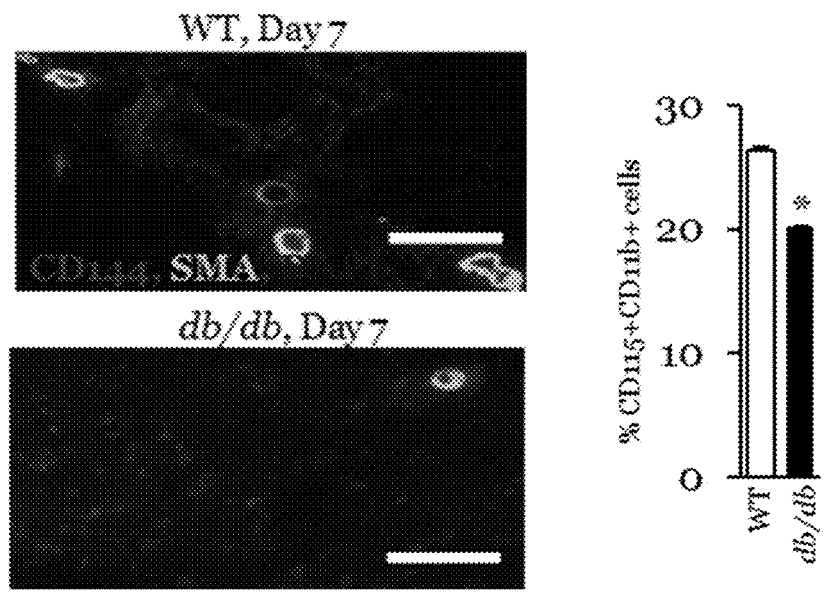
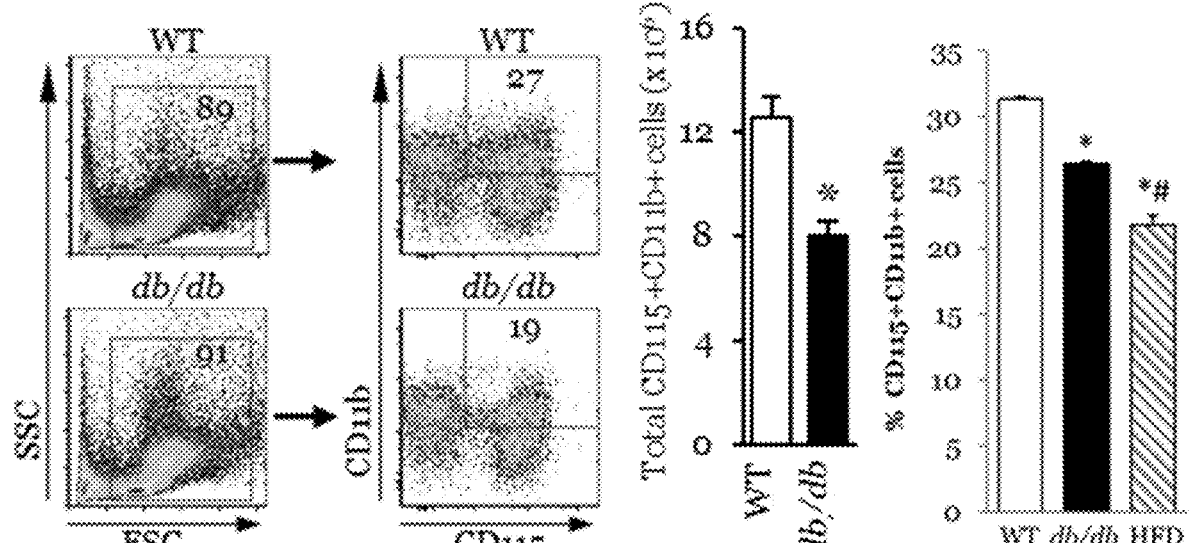
FIG. 1J   FIG. 2A
FIG. 2B   FIG. 2C   FIG. 2D

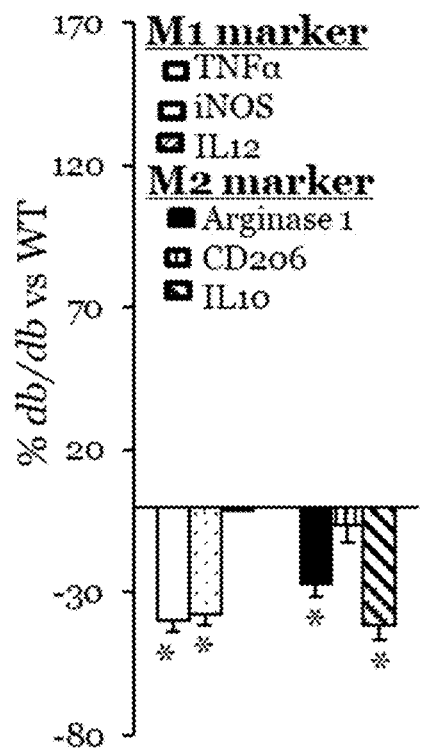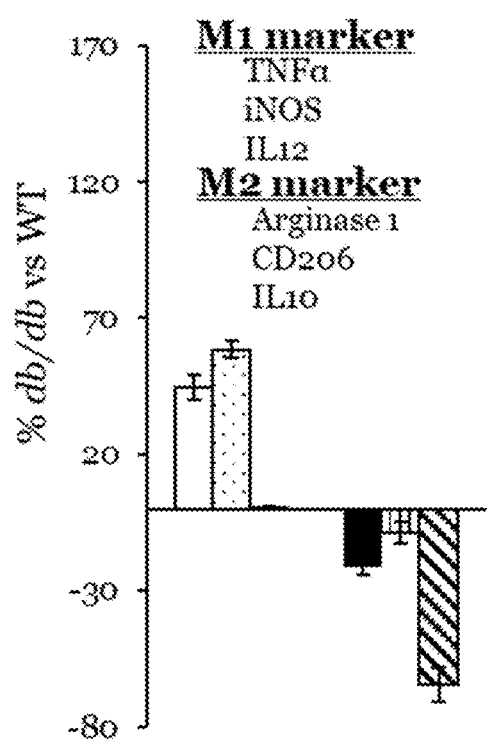
FIG. 2I  FIG. 2J
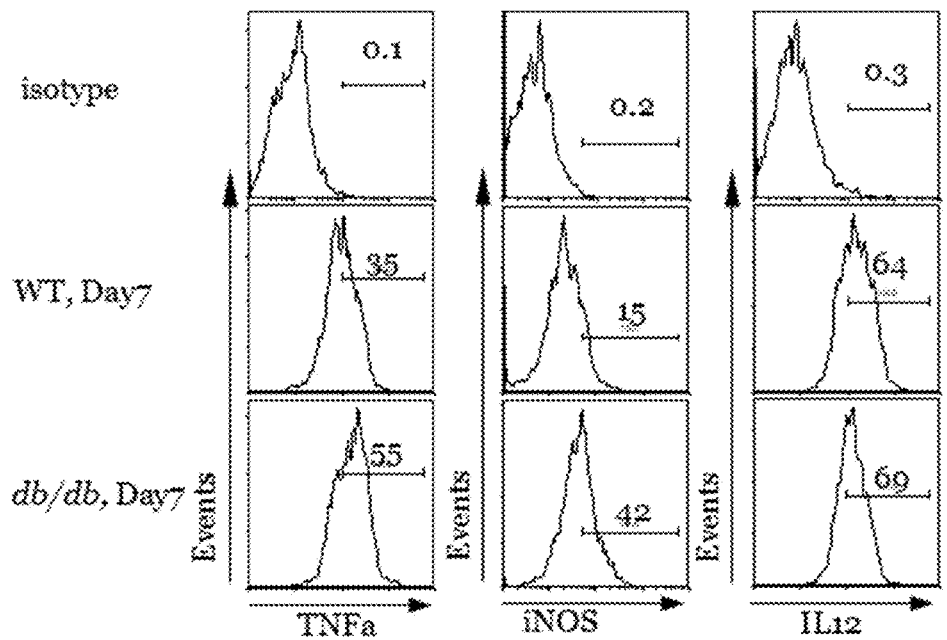
FIG. 3A

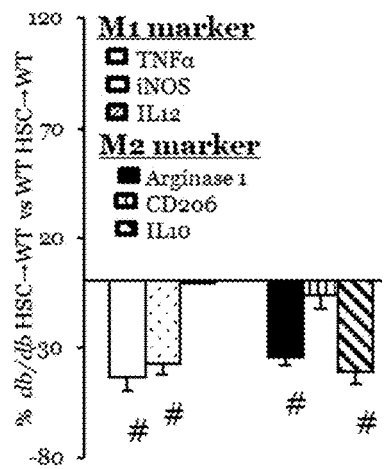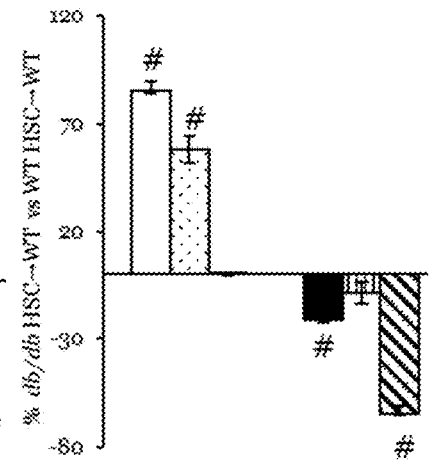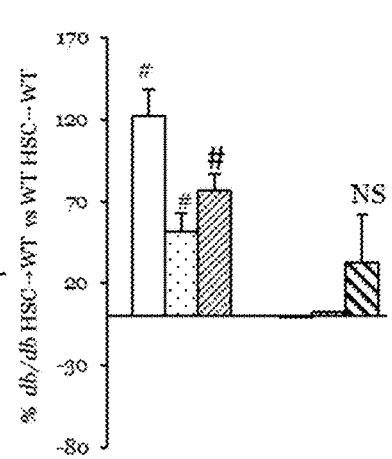
FIG. 5E  FIG. 5F  FIG. 5G
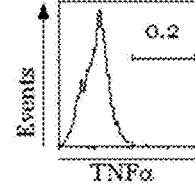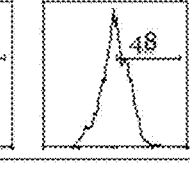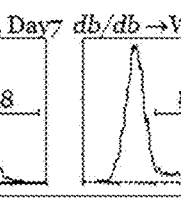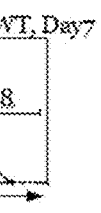
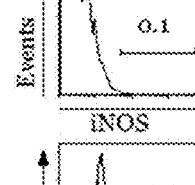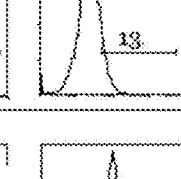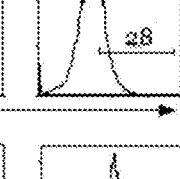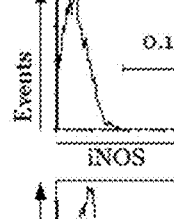
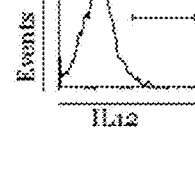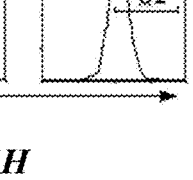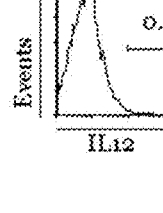
FIG. 5H  FIG. 5I

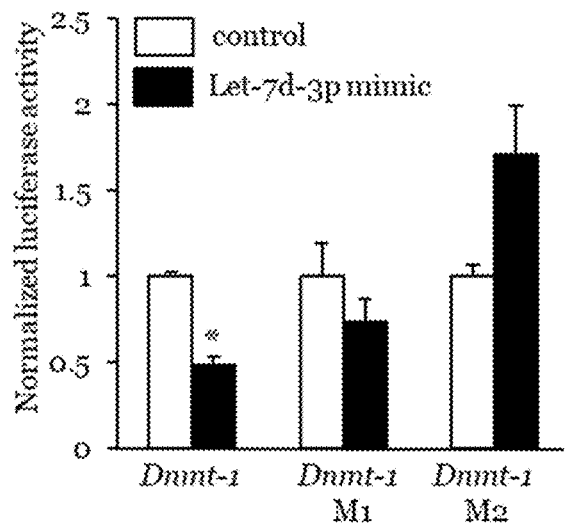
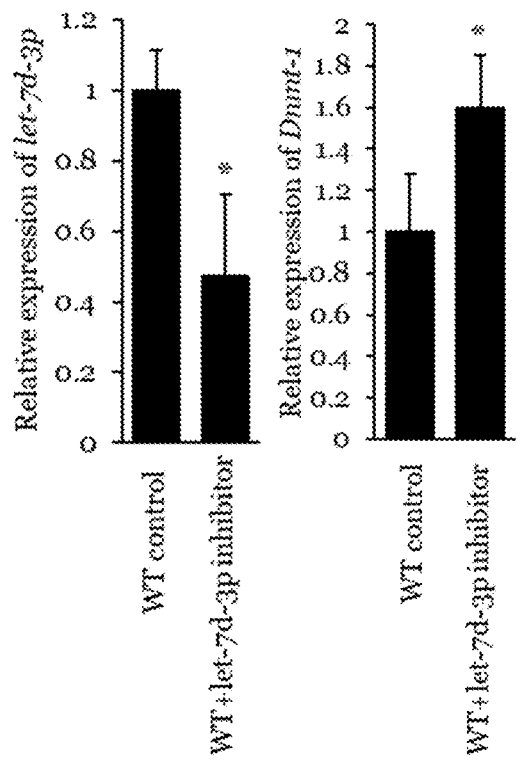
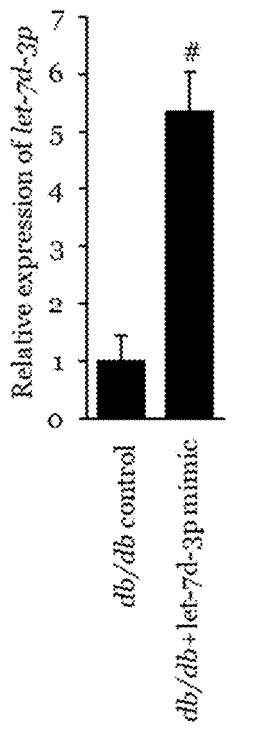
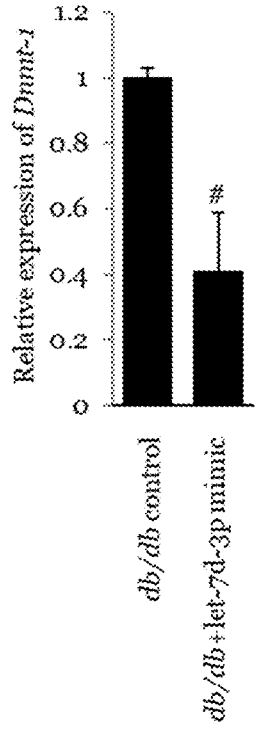
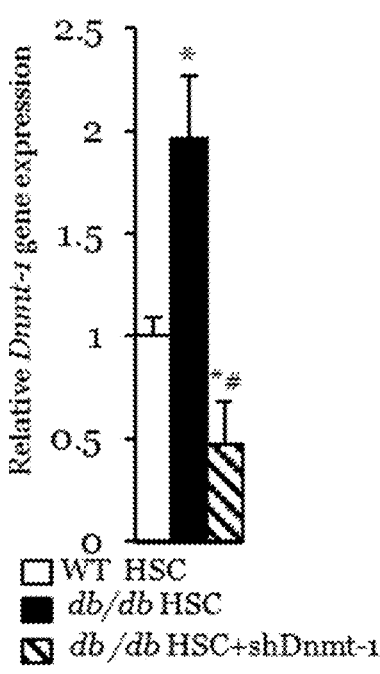
FIG. 8C  FIG. 8D  FIG. 8E
FIG. 8F  FIG. 8G  FIG. 9A

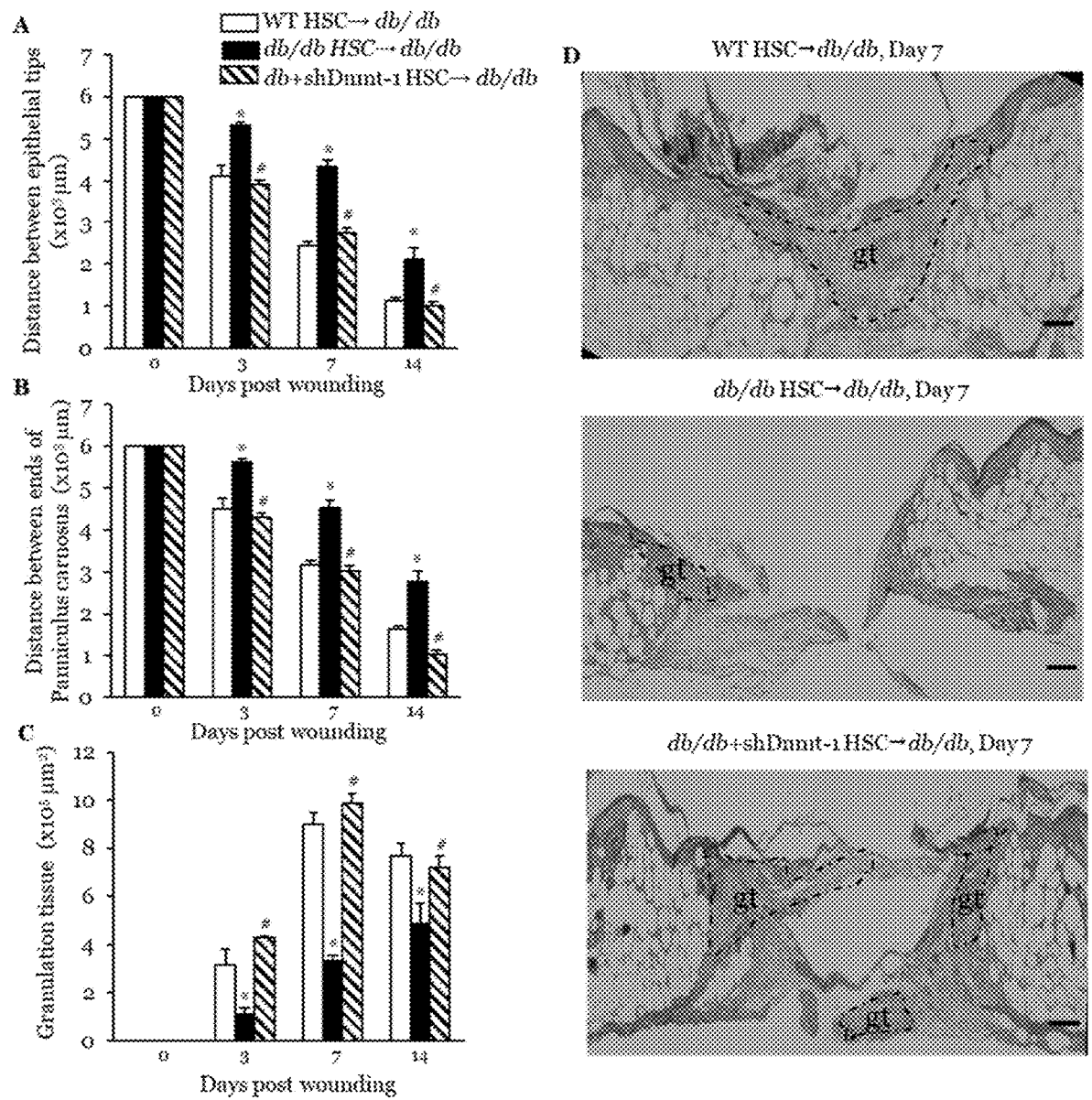
FIGs. 11A-D

A

B

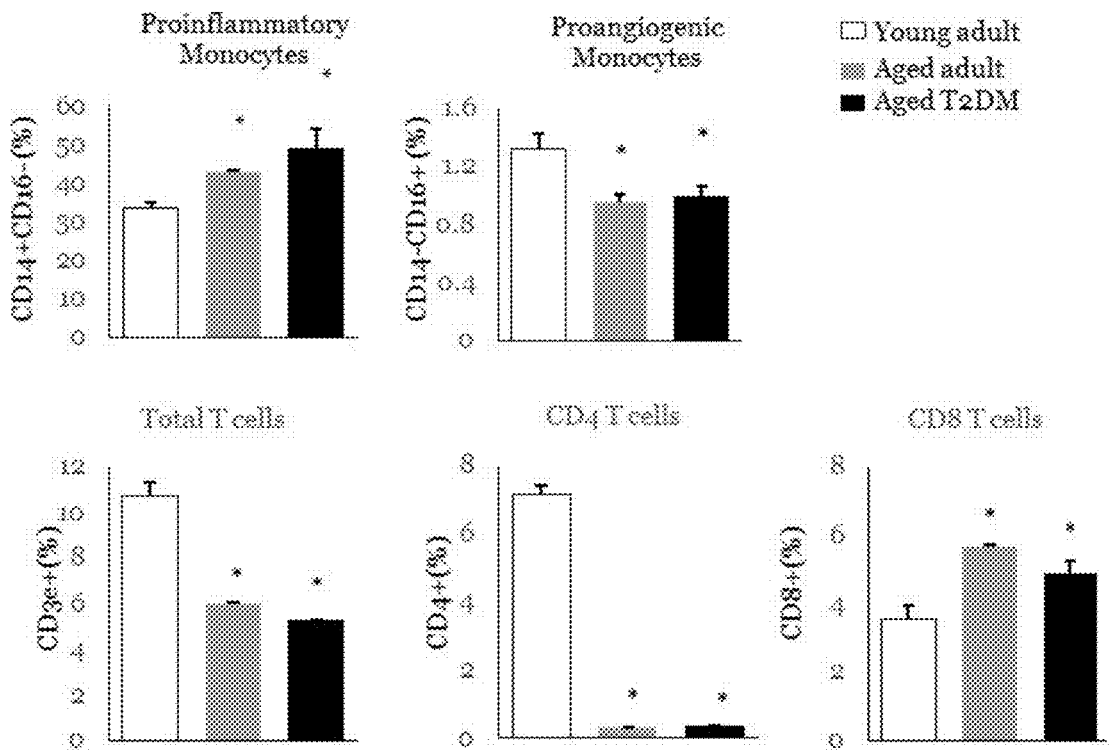
FIG. 28
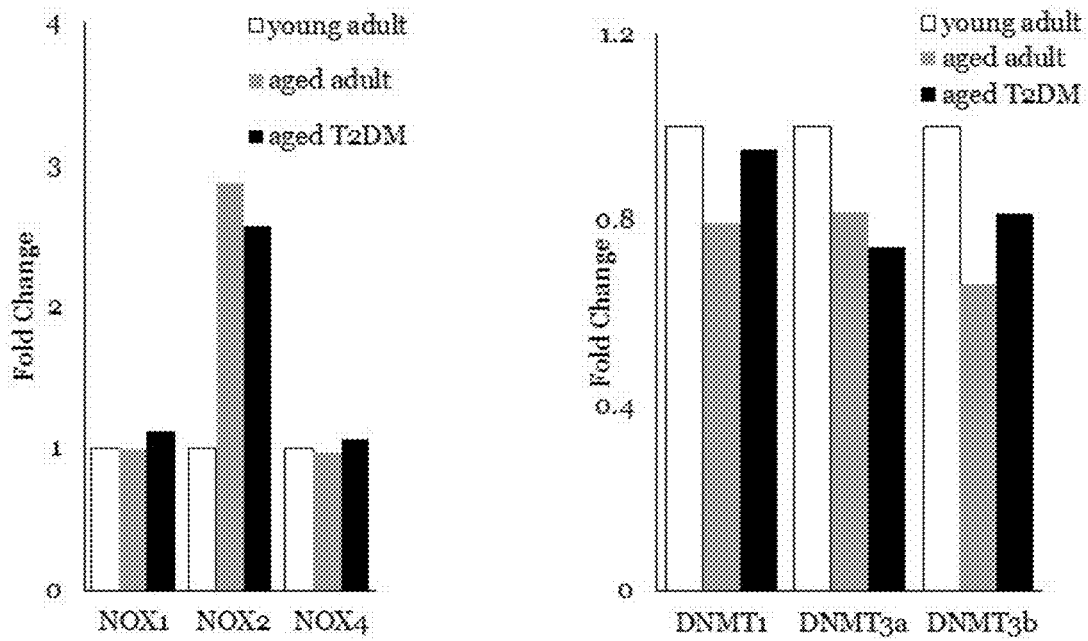
FIG. 29
FIG. 30A

SEQUENCE LISTING

<160> NUMBER OF SEQ ID NOS: 59

<210> SEQ ID NO 1
<211> LENGTH: 4899
<212> TYPE: DNA
<213> ORGANISM: Homo sapiens

<400> SEQUENCE: 1

| | | | | | |
|---|---|---|---|---|---|
| atgccggcgc | gtaccgcccc | agcccgggtg | cccacactgg | ccgtcccggc | catctcgctg | 60 |
| cccgacgatg | tccgcaggcg | gctcaaagat | ttggaaagag | acagcttaac | agaaaaggaa | 120 |
| tgtgtgaagg | agaaattgaa | tctcttgcac | gaatttctgc | aaacagaaat | aaagaatcag | 180 |
| ttatgtgact | tggaaaccaa | attacgtaaa | gaagaattat | ccgaggaggg | ctacctggct | 240 |
| aaagtcaaat | ccctttaaa | taagatttg | tccttggaga | acggtgctca | tgcttacaac | 300 |
| cgggaagtga | atggacgtct | agaaaacggg | aaccaagcaa | gaagtgaagc | ccgtagagtg | 360 |
| ggaatggcag | atgccaacag | ccccccaaa | cccctttcca | aacctcgcac | gcccaggagg | 420 |
| agcaagtccg | atggagaggc | taagcgttca | agagaccctc | ctgcctcagc | ctcccaagta | 480 |
| actgggatta | gagctgaacc | ttcacctagc | cccaggatta | caaggaaaag | caccaggcaa | 540 |
| accaccatca | catctcattt | tgcaaagggc | cctgccaaac | ggaaacctca | ggaagagtct | 600 |
| gaaagagcca | aatcggatga | gtccatcaag | gaagaagaca | aagaccagga | tgagaagaga | 660 |
| cgtagagtta | catccagaga | acgagttgct | agaccgcttc | ctgcagaaga | acctgaaaga | 720 |
| gcaaaatcag | gaacgcgcac | tgaaaaggaa | gaagaaagag | atgaaaaaga | agaaaagaga | 780 |
| ctccgaagtc | aaaccaaaga | accaacaccc | aaacagaaac | tgaaggagga | gccggacaga | 840 |
| gaagccaggg | caggcgtgca | ggctgacgag | gacgaagatg | gagacgagaa | agatgagaag | 900 |
| aagcacagaa | gtcaacccaa | agatctagct | gccaaacgga | ggcccgaaga | aaaagaacct | 960 |
| gaaaagtaa | atccacagat | ttctgatgaa | aaagacgagg | atgaaaagga | ggagaagaga | 1020 |
| cgcaaaacga | cccccaaaga | accaacggag | aaaaaaatgg | ctcgcgccaa | aacagtcatg | 1080 |
| aactccaaga | cccaccctcc | caagtgcatt | cagtgcgggc | agtacctgga | cgaccctgac | 1140 |
| ctcaaatatg | ggcagcaccc | accagacgcg | gtggatgagc | cacagatgct | gacaaatgag | 1200 |
| aagctgtcca | tctttgatgc | caacgagtct | ggctttgaga | gttatgaggc | gcttccccag | 1260 |
| cacaaactga | cctgcttcag | tgtgtactgt | aagcacggtc | acctgtgtcc | catcgacacc | 1320 |
| ggcctcatcg | agaagaatat | cgaactcttc | ttttctggtt | cagcaaaacc | aatctatgat | 1380 |
| gatgacccat | ctcttgaagg | tggtgttaat | ggcaaaaatc | ttggccccat | aaatgaatgg | 1440 |
| tggatcactg | gctttgatgg | aggtgaaaag | gccctcatcg | gcttcagcac | ctcatttgcc | 1500 |
| gaatacattc | tgatggatcc | cagtcccgag | tatgcgccca | tatttgggct | gatgcaggag | 1560 |
| aagatctaca | tcagcaagat | tgtggtggag | ttcctgcaga | gcaattccga | ctcgacctat | 1620 |
| gaggacctga | tcaacaagat | cgagaccacg | gttcctcctt | ctggcctcaa | cttgaaccgc | 1680 |
| ttcacagagg | actccctcct | gcgacacgcg | cagtttgtgg | tggagcaggt | ggagagttat | 1740 |
| gacgaggccg | gggacagtga | tgagcagccc | atcttcctga | cacctgcat | gcgggacctg | 1800 |
| atcaagctgg | ctggggtcac | gctgggacag | aggcgagccc | aggcgaggcg | gcagaccatc | 1860 |

```
aggcattcta ccagggagaa ggacagggga cccacgaaag ccaccaccac caagctggtc    1920
taccagatct tcgatacttt cttcgcagag caaattgaaa aggatgacag agaagacaag    1980
gagaacgcct ttaagcgccg gcgatgtggc gtctgtgagg tgtgtcagca gcctgagtgt    2040
gggaaatgta aagcctgcaa ggacatggtt aaatttggtg gcagtggacg gagcaagcag    2100
gcttgccaag agcggaggtg tcccaatatg gccatgaagg aggcagatga cgatgaggaa    2160
gtcgatgata acatcccaga gatgccgtca cccaaaaaaa tgcaccaggg gaagaagaag    2220
aaacagaaca agaatcgcat ctcttgggtc ggagaagccg tcaagactga tgggaagaag    2280
agttactata agaaggtgtg cattgatgcg gaaaccctgg aagtggggga ctgtgtctct    2340
gttattccag atgattcctc aaaaccgctg tatctagcaa gggtcacggc gctgtgggag    2400
gacagcagca acgggcagat gtttcacgcc cactggttct gcgctgggac agacacagtc    2460
ctcggggcca cgtcggaccc tctggagctg ttcttggtgg atgaatgtga ggacatgcag    2520
ctttcatata tccacagcaa agtgaaagtc atctacaaag ccccctccga aaactgggcc    2580
atggagggag gcatggatcc cgagtccctg ctggaggggg acgacgggaa gacctacttc    2640
taccagctgt ggtatgatca agactacgcg agattcgagt cccctccaaa aacccagcca    2700
acagaggaca acaagttcaa attctgtgtg agctgtgccc gtctggctga gatgaggcaa    2760
aaagaaatcc ccagggtcct ggagcagctc gaggacctgg atagccgggt cctctactac    2820
tcagccacca gaacggcat cctgtaccga gttggtgatg tgtgtacct gcccctgag    2880 gccttcacgt tcaacatcaa gctgtccagt cccgtgaaac gcccacggaa ggagcccgtg    2940
gatgaggacc tgtacccaga gcactaccgg aaatactccg actacatcaa aggcagcaac    3000
ctggatgccc ctgagcccta ccgaattggc cggatcaaag agatcttctg tcccaagaag    3060
agcaacggca ggcccaatga gactgacatc aaaatccggg tcaacaagtt ctacaggcct    3120
gagaacaccc acaagtccac tccagcgagc taccacgcag acatcaacct gctctactgg    3180
agcgacgagg aggccgtggt ggacttcaag gctgtgcagg gccgctgcac cgtggagtat    3240
ggggaggacc tgcccgagtg cgtccaggtg tactccatgg gcggccccaa ccgcttctac    3300
ttcctcgagg cctataatgc aaagagcaaa agctttgaag atcctcccaa ccatgcccgt    3360
agccctggaa acaaagggaa gggcaaggga aaagggaagg gcaagcccaa gtcccaagcc    3420
tgtgagccga gcgagccaga gatagagatc aagctgccca gctgcggac cctgatgtg    3480 ttttctggct gcgggggtt gtcggaggga ttccaccaag caggcatctc tgacacgctg    3540
tgggccatcg agatgtggga ccctgcggcc caggcgttcc ggctgaacaa ccccggctcc    3600
acagtgttca cagaggactg caacatcctg ctgaagctgg tcatggctgg ggagaccacc    3660
aactcccgcg ccagcggct gccccagaag ggagacgtgg agatgctgtg cggcgggccg    3720
ccctgccagg gcttcagcgg catgaaccgc ttcaattcgc gcacctactc caagttcaaa    3780
aactctctgg tggttccctt cctcagctac tgcgactact accggccccg gttcttcctc    3840
ctggagaatg tcaggaactt tgtctccttc aagcgctcca tggtcctgaa gctcaccctc    3900
cgctgcctgg tccgcatggg ctatcagtgc accttcggcg tgctgcaggc cggtcagtac    3960
ggcgtggccc agactaggag gcgggccatc atcctggccg cggcccctgg agagaagctc    4020
cctctgttcc cggagccact gcacgtgttt gctccccggg cctgccagct gagcgtggtg    4080
gtggatgaca agaagtttgt gagcaacata accaggttga gctcgggtcc tttccggacc    4140
atcacggtgc gagacacgat gtccgacctg ccggaggtgc ggaatggagc ctcggcactg    4200
gagatctcct acaacgggga gcctcagtcc tggttccaga ggcagctccg gggcgcacag    4260
```

```
taccagccca tcctcaggga ccacatctgt aaggacatga gtgcattggt ggctgcccgc    4320
atgcggcaca tccccttggc cccagggtca gactggcgcg atctgcccaa catcgaggtg    4380
cggctctcag acggcaccat ggccaggaag ctgcggtata cccaccatga caggaagaac    4440
ggccgcagca gctctgggc cctccgtggg gtctgctcct gcgtggaagc cggcaaagcc    4500
tgcgaccccg cagccaggca gttcaacacc ctcatcccct ggtgcctgcc ccacaccggg    4560
aaccggcaca accactgggc tggcctctat ggaaggctcg agtgggacgg cttcttcagc    4620
acaaccgtca ccaaccccga gcccatgggc aagcagggcc gcgtgctcca cccagagcag    4680
caccgtgtgg tgagcgtgcg ggagtgtgcc cgctcccagg gcttccctga cacctaccgg    4740
ctcttcggca acatcctgga caagcaccgg caggtgggca atgccgtgcc accgcccctg    4800
gccaaagcca ttggcttgga gatcaagctt tgtatgttgg ccaaagcccg agagagtgcc    4860
tcagctaaaa taaggagga ggaagctgct aaggactag                            4899
```

<210> SEQ ID NO 2
<211> LENGTH: 22
<212> TYPE: DNA
<213> ORGANISM: Artificial Sequence
<220> FEATURE:
<223> OTHER INFORMATION: Small interfering RNA sequence targeting DNMT1

<400> SEQUENCE: 2
aagcaugagc accguucucc tt                                              22

<210> SEQ ID NO 3
<211> LENGTH: 22
<212> TYPE: DNA
<213> ORGANISM: Artificial Sequence
<220> FEATURE:
<223> OTHER INFORMATION: Small interfering RNA sequence targeting DNMT1

<400> SEQUENCE: 3
ggagaacggu gcucaugcuu tt                                              22

<210> SEQ ID NO 4
<211> LENGTH: 21
<212> TYPE: RNA
<213> ORGANISM: Artificial Sequence
<220> FEATURE:
<223> OTHER INFORMATION: Small interfering RNA sequence targeting DNMT1

<400> SEQUENCE: 4
agaugacgga ugccuagagu u                                               21

<210> SEQ ID NO 5
<211> LENGTH: 21
<212> TYPE: RNA
<213> ORGANISM: Artificial Sequence
<220> FEATURE:
<223> OTHER INFORMATION: Small interfering RNA sequence targeting DNMT1

<400> SEQUENCE: 5
cucuaggcau ccgucaucuu u                                               21

<210> SEQ ID NO 6
<211> LENGTH: 22
<212> TYPE: RNA
<213> ORGANISM: Homo sapiens

<400> SEQUENCE: 6
cuauacgacc ugcugccuuu cu                                              22

<210> SEQ ID NO 7
<211> LENGTH: 1713
<212> TYPE: DNA
<213> ORGANISM: Homo sapiens

<400> SEQUENCE: 7
atggggaact gggctgtgaa tgagggctc tccattttg tcattctggt ttggctgggg       60
ttgaacgtct tcctctttgt ctggtattac cgggtttatg atattccacc taagttcttt   120
tacacaagaa aacttcttgg gtcagcactg gcactggcca gggcccctgc agcctgcctg   180
aatttcaact gcatgctgat tctcttgcca gtctgtcgaa atctgctgtc cttcctcagg   240
ggttccagtg cgtgctgctc aacaagagtt cgaagacaac tggacaggaa tctcaccttt   300
cataaaatgg tggcatggat gattgcactt cactctgcga ttcacaccat gcacatcta    360
tttaatgtgg aatggtgtgt gaatgcccga gtcaataatt ctgatcctta ttcagtagca   420
ctctctgaac ttggagacag gcaaaatgaa agttatctca attttgctcg aaagagaata   480
aagaaccctg aaggaggcct gtacctggct gtgaccctgt tggcaggcat cactggagtt   540
gtcatcacgc tgtgcctcat attaattatc acttcctcca ccaaaaccat ccggaggtct   600
tactttgaag tcttttggta cacacatcat ctctttgtga tcttcttcat tggccttgcc   660
atccatggag ctgaacgaat tgtacgtggg cagaccgcag agagtttggc tgtgcataat   720
ataacagttt gtgaacaaaa aatctcagaa tggggaaaaa taaggaatg cccaatccct   780
cagtttgctg gaaaccctcc tatgacttgg aaatggatag tgggtcccat gtttctgtat   840
ctctgtgaga ggttggtgcg gttttggcga tctcaacaga aggtggtcat caccaaggtg   900
gtcactcacc ctttcaaaac catcgagcta cagatgaaga agaaggggtt caaaatggaa   960
gtgggacaat acattttgt caagtgccca aaggtgtcca agctggagtg cacccttt    1020
acactgacat ccgcccctga ggaagacttc tttagtatcc atatccgcat cgttgggac   1080
tggacagagg ggctgttcaa tgcttgtggc tgtgataagc aggagtttca agatgcgtgg   1140
aaactaccta agatagcggt tgatgggccc tttggcactg ccagtgaaga tgtgttcagc   1200
tatgaggtgg tgatgttagt gggagcaggg attggggtca cccttcgc atccattctc   1260
aagtcagtct ggtacaaata ttgcaataac gccaccaatc tgaagctcaa aaagatctac   1320
ttctactggc tgtgccggga cacacatgcc tttgagtggt ttgcagatct gctgcaactg   1380
ctggagagcc agatgcagga aaggaacaat gccggcttcc tcagctacaa catctacctc   1440
actggctggg atgagtctca ggccaatcac tttgctgtgc accatgatga ggagaaagat   1500
gtgatcacag gcctgaaaca aaagactttg tatggacggc caactgggaa taatgaattc   1560
aagacaattg caagtcaaca ccctaatacc agaataggag ttttcctctg tggacctgaa   1620
gccttggctg aaaccctgag taaacaaagc atctccaact ctgagtctgg ccctcgggga   1680
gtgcatttca ttttcaacaa ggaaaacttc taa                                1713

<210> SEQ ID NO 8
<211> LENGTH: 21
<212> TYPE: DNA
<213> ORGANISM: Artificial Sequence
<220> FEATURE:
<223> OTHER INFORMATION: Small interfering RNA targeting NOX2

<400> SEQUENCE: 8
ggauacuaac caauaggaut t                                              21

<210> SEQ ID NO 9
<211> LENGTH: 21
<212> TYPE: DNA
<213> ORGANISM: Artificial Sequence
<220> FEATURE:
<223> OTHER INFORMATION: Small interfering RNA targeting NOX2

<400> SEQUENCE: 9
auccuauugg uuaguaucct t                                              21

<210> SEQ ID NO 10
<211> LENGTH: 97
<212> TYPE: DNA
<213> ORGANISM: Artificial Sequence
<220> FEATURE:
<223> OTHER INFORMATION: Short hairpin RNA sequence targeting human NOX2

<400> SEQUENCE: 10
tgctgttgac agtgagcgac agtgaagatg tgttcagcta tagtgaagcc acagatgtat    60
agctgaacac atcttcactg gtgcctactg cctcgga                             97

<210> SEQ ID NO 11
<211> LENGTH: 97
<212> TYPE: DNA
<213> ORGANISM: Artificial Sequence
<220> FEATURE:
<223> OTHER INFORMATION: Short hairpin RNA sequence targeting human NOX2

<400> SEQUENCE: 11
tgctgttgac agtgagcgcg ctcaaataat gctaattgat tagtgaagcc acagatgtaa    60
tcaattagca tatttgagc atgcctactg cctcgga                              97

<210> SEQ ID NO 12
<211> LENGTH: 97
<212> TYPE: DNA
<213> ORGANISM: Artificial Sequence
<220> FEATURE:
<223> OTHER INFORMATION: Short hairpin RNA sequence targeting human NOX2

<400> SEQUENCE: 12
tgctgttgac agtgagcgag ccaccaatct gaagctcaaa tagtgaagcc acagatgtat    60
ttgagcttca gattggtggc gtgcctactg cctcgga                             97

<210> SEQ ID NO 13
<211> LENGTH: 97
<212> TYPE: DNA
<213> ORGANISM: Artificial Sequence
<220> FEATURE:
<223> OTHER INFORMATION: Short hairpin RNA sequence targeting human NOX2

<400> SEQUENCE: 13
tgctgttgac agtgagcgac acctaagttc ttttacacaa tagtgaagcc acagatgtat    60
tgtgtaaaag aacttaggtg gtgcctactg cctcgga                             97

<210> SEQ ID NO 14
<211> LENGTH: 97
<212> TYPE: DNA
<213> ORGANISM: Artificial Sequence
<220> FEATURE:
<223> OTHER INFORMATION: Short hairpin RNA sequence targeting human NOX2

<400> SEQUENCE: 14

```
tgctgttgac agtgagcgcc cagtgcgtgc tgctcaacaa tagtgaagcc acagatgtat    60
tgttgagcag cacgcactgg atgcctactg cctcgga                             97
```

<210> SEQ ID NO 15
<211> LENGTH: 97
<212> TYPE: DNA
<213> ORGANISM: Artificial Sequence
<220> FEATURE:
<223> OTHER INFORMATION: Short hairpin RNA sequence targeting human NOX2

<400> SEQUENCE: 15

```
tgctgttgac agtgagcgat caacaagagt tcgaagacaa tagtgaagcc acagatgtat    60
tgtcttcgaa ctcttgttga gtgcctactg cctcgga                             97
```

<210> SEQ ID NO 16
<211> LENGTH: 97
<212> TYPE: DNA
<213> ORGANISM: Artificial Sequence
<220> FEATURE:
<223> OTHER INFORMATION: Short hairpin RNA sequence targeting human NOX2

<400> SEQUENCE: 16

```
tgctgttgac agtgagcgat aagttctttt acacaagaaa tagtgaagcc acagatgtat    60
ttcttgtgta aaagaactta gtgcctactg cctcgga                             97
```

<210> SEQ ID NO 17
<211> LENGTH: 21
<212> TYPE: DNA
<213> ORGANISM: Artificial Sequence
<220> FEATURE:
<223> OTHER INFORMATION: Forward primer for mouse DNMT1

<400> SEQUENCE: 17

```
cacctagacg accctaacct g                                              21
```

<210> SEQ ID NO 18
<211> LENGTH: 21
<212> TYPE: DNA
<213> ORGANISM: Artificial Sequence
<220> FEATURE:
<223> OTHER INFORMATION: Reverse primer for mouse DNMT1

<400> SEQUENCE: 18

```
aggtggagtc gtagatggac a                                              21
```

<210> SEQ ID NO 19
<211> LENGTH: 27
<212> TYPE: DNA
<213> ORGANISM: Artificial Sequence
<220> FEATURE:
<223> OTHER INFORMATION: Forward primer for mouse DNMT3A

<400> SEQUENCE: 19

```
agcgtcacac agaagcatat ccaggag                                        27
```

<210> SEQ ID NO 20
<211> LENGTH: 27
<212> TYPE: DNA
<213> ORGANISM: Artificial Sequence
<220> FEATURE:
<223> OTHER INFORMATION: Reverse primer for mouse DNTM3A

<400> SEQUENCE: 20

```
ggccagtacc ctcataaagt cccttgc                                        27
```

<210> SEQ ID NO 21
<211> LENGTH: 27
<212> TYPE: DNA
<213> ORGANISM: Artificial Sequence
<220> FEATURE:
<223> OTHER INFORMATION: Forward primer for mouse DNMT3B

<400> SEQUENCE: 21
atggaattgc aacggggtac ttggtgc                                    27

<210> SEQ ID NO 22
<211> LENGTH: 27
<212> TYPE: DNA
<213> ORGANISM: Artificial Sequence
<220> FEATURE:
<223> OTHER INFORMATION: Reverse primer for mouse DNMT3B

<400> SEQUENCE: 22
ctggccttca tgcttaacag ttcccac                                    27

<210> SEQ ID NO 23
<211> LENGTH: 19
<212> TYPE: DNA
<213> ORGANISM: Artificial Sequence
<220> FEATURE:
<223> OTHER INFORMATION: Forward primer for mouse NOTCH1

<400> SEQUENCE: 23
atgctgctgt tgtgctcct                                             19

<210> SEQ ID NO 24
<211> LENGTH: 21
<212> TYPE: DNA
<213> ORGANISM: Artificial Sequence
<220> FEATURE:
<223> OTHER INFORMATION: Reverse primer for mouse NOTCH1

<400> SEQUENCE: 24
cagtctcata gctgccctca c                                          21

<210> SEQ ID NO 25
<211> LENGTH: 23
<212> TYPE: DNA
<213> ORGANISM: Artificial Sequence
<220> FEATURE:
<223> OTHER INFORMATION: Forward primer for mouse PU.1

<400> SEQUENCE: 25
cctcagtcac caggtttcct aca                                        23

<210> SEQ ID NO 26
<211> LENGTH: 19
<212> TYPE: DNA
<213> ORGANISM: Artificial Sequence
<220> FEATURE:
<223> OTHER INFORMATION: Reverse primer for mouse PU.1

<400> SEQUENCE: 26
ctctcaccct cctcatctg                                             19

<210> SEQ ID NO 27
<211> LENGTH: 26
<212> TYPE: DNA
<213> ORGANISM: Artificial Sequence
<220> FEATURE:

<223> OTHER INFORMATION: Forward primer for mouse KLF4

<400> SEQUENCE: 27
cggatccgat gaggcagcca cctggc                                    26

<210> SEQ ID NO 28
<211> LENGTH: 32
<212> TYPE: DNA
<213> ORGANISM: Artificial Sequence
<220> FEATURE:
<223> OTHER INFORMATION: Reverse primer for mouse KLF4

<400> SEQUENCE: 28
cgacgcgtgc aaagtgcctc ttcatgtgta ag                             32

<210> SEQ ID NO 29
<211> LENGTH: 21
<212> TYPE: DNA
<213> ORGANISM: Artificial Sequence
<220> FEATURE:
<223> OTHER INFORMATION: Forward primer for human DNMT1

<400> SEQUENCE: 29
tacctggacg accctgacct c                                         21

<210> SEQ ID NO 30
<211> LENGTH: 21
<212> TYPE: DNA
<213> ORGANISM: Artificial Sequence
<220> FEATURE:
<223> OTHER INFORMATION: Reverse primer for human DNMT1

<400> SEQUENCE: 30
cgttggcatc aaagatggac a                                         21

<210> SEQ ID NO 31
<211> LENGTH: 22
<212> TYPE: DNA
<213> ORGANISM: Artificial Sequence
<220> FEATURE:
<223> OTHER INFORMATION: Forward primer for human NOTCH1

<400> SEQUENCE: 31
cacccatgac cactacccag tt                                        22

<210> SEQ ID NO 32
<211> LENGTH: 22
<212> TYPE: DNA
<213> ORGANISM: Artificial Sequence
<220> FEATURE:
<223> OTHER INFORMATION: Reverse primer for human NOTCH1

<400> SEQUENCE: 32
cctcggacca atcagagatg tt                                        22

<210> SEQ ID NO 33
<211> LENGTH: 25
<212> TYPE: DNA
<213> ORGANISM: Artificial Sequence
<220> FEATURE:
<223> OTHER INFORMATION: Forward primer for human PU.1

<400> SEQUENCE: 33
gagaaataac tttaggggac catgt                                     25

```
<210> SEQ ID NO 34
<211> LENGTH: 25
<212> TYPE: DNA
<213> ORGANISM: Artificial Sequence
<220> FEATURE:
<223> OTHER INFORMATION: Reverse primer for human PU.1

<400> SEQUENCE: 34
attgattcat tcattcagga aatgt                                          25

<210> SEQ ID NO 35
<211> LENGTH: 20
<212> TYPE: DNA
<213> ORGANISM: Artificial Sequence
<220> FEATURE:
<223> OTHER INFORMATION: Forward primer for human KLF4

<400> SEQUENCE: 35
ggcgggctga tgggcaagtt                                                20

<210> SEQ ID NO 36
<211> LENGTH: 20
<212> TYPE: DNA
<213> ORGANISM: Artificial Sequence
<220> FEATURE:
<223> OTHER INFORMATION: Reverse primer for human KL44

<400> SEQUENCE: 36
tgccgtcagg gctgcctttg                                                20

<210> SEQ ID NO 37
<211> LENGTH: 20
<212> TYPE: DNA
<213> ORGANISM: Artificial Sequence
<220> FEATURE:
<223> OTHER INFORMATION: Forward primer for human 18S

<400> SEQUENCE: 37
gtaacccgtt gaaccccatt                                                20

<210> SEQ ID NO 38
<211> LENGTH: 20
<212> TYPE: DNA
<213> ORGANISM: Artificial Sequence
<220> FEATURE:
<223> OTHER INFORMATION: Reverse primer for human 18S

<400> SEQUENCE: 38
ccatccaatc ggtagtagcg                                                20

<210> SEQ ID NO 39
<211> LENGTH: 24
<212> TYPE: DNA
<213> ORGANISM: Artificial Sequence
<220> FEATURE:
<223> OTHER INFORMATION: Forward primer for NOTCH1

<400> SEQUENCE: 39
gaaggtaggg gttttgtttt gata                                           24

<210> SEQ ID NO 40
<211> LENGTH: 23
<212> TYPE: DNA
<213> ORGANISM: Artificial Sequence
<220> FEATURE:
<223> OTHER INFORMATION: Reverse primer for NOTCH1
```

-continued

```
<400> SEQUENCE: 40
ccttccccca aacttaaaat act                                       23

<210> SEQ ID NO 41
<211> LENGTH: 19
<212> TYPE: DNA
<213> ORGANISM: Artificial Sequence
<220> FEATURE:
<223> OTHER INFORMATION: Sequencing primer for NOTCH1

<400> SEQUENCE: 41
aggggttttg ttttgataa                                            19

<210> SEQ ID NO 42

<400> SEQUENCE: 42

000

<210> SEQ ID NO 43
<211> LENGTH: 30
<212> TYPE: DNA
<213> ORGANISM: Artificial Sequence
<220> FEATURE:
<223> OTHER INFORMATION: Forward primer for PU.1

<400> SEQUENCE: 43
ttggtttttt tatagattat tattgggatt                                30

<210> SEQ ID NO 44
<211> LENGTH: 22
<212> TYPE: DNA
<213> ORGANISM: Artificial Sequence
<220> FEATURE:
<223> OTHER INFORMATION: Reverse primer for PU.1

<400> SEQUENCE: 44
aaccaacaac acacacctaa ta                                        22

<210> SEQ ID NO 45
<211> LENGTH: 25
<212> TYPE: DNA
<213> ORGANISM: Artificial Sequence
<220> FEATURE:
<223> OTHER INFORMATION: Sequencing primer for PU.1

<400> SEQUENCE: 45
ttttatagat tattattggg atttt                                     25

<210> SEQ ID NO 46
<211> LENGTH: 21
<212> TYPE: DNA
<213> ORGANISM: Artificial Sequence
<220> FEATURE:
<223> OTHER INFORMATION: Forward primer for KLF4

<400> SEQUENCE: 46
ggggatttgt gattgtattg g                                         21

<210> SEQ ID NO 47
<211> LENGTH: 22
<212> TYPE: DNA
<213> ORGANISM: Artificial Sequence
<220> FEATURE:
<223> OTHER INFORMATION: Reverse primer for KLF4
```

```
<400> SEQUENCE: 47
atccctaaaa acccatttaa ac                                              22

<210> SEQ ID NO 48
<211> LENGTH: 16
<212> TYPE: DNA
<213> ORGANISM: Artificial Sequence
<220> FEATURE:
<223> OTHER INFORMATION: Sequencing primer for KLF4

<400> SEQUENCE: 48
gtaggaaagg agggta                                                     16

<210> SEQ ID NO 49
<211> LENGTH: 20
<212> TYPE: DNA
<213> ORGANISM: Artificial Sequence
<220> FEATURE:
<223> OTHER INFORMATION: Forward primer for NOTCH1

<400> SEQUENCE: 49
gctgagtcac tgcaaaagcc                                                 20

<210> SEQ ID NO 50
<211> LENGTH: 21
<212> TYPE: DNA
<213> ORGANISM: Artificial Sequence
<220> FEATURE:
<223> OTHER INFORMATION: Reverse primer for NOTCH1

<400> SEQUENCE: 50
aagaaaagga tgcagggcct c                                               21

<210> SEQ ID NO 51
<211> LENGTH: 20
<212> TYPE: DNA
<213> ORGANISM: Artificial Sequence
<220> FEATURE:
<223> OTHER INFORMATION: Forward primer for PU.1

<400> SEQUENCE: 51
gatgggctgg agagatgagc                                                 20

<210> SEQ ID NO 52
<211> LENGTH: 20
<212> TYPE: DNA
<213> ORGANISM: Artificial Sequence
<220> FEATURE:
<223> OTHER INFORMATION: Reverse primer for PU.1

<400> SEQUENCE: 52 tccoctccca gctaagtacc                                                 20

<210> SEQ ID NO 53
<211> LENGTH: 20
<212> TYPE: DNA
<213> ORGANISM: Artificial Sequence
<220> FEATURE:
<223> OTHER INFORMATION: Forward primer for KLF4

<400> SEQUENCE: 53
actcgagagc gcgattatcc                                                 20

<210> SEQ ID NO 54
<211> LENGTH: 20
```

```
<212> TYPE: DNA
<213> ORGANISM: Artificial Sequence
<220> FEATURE:
<223> OTHER INFORMATION: Reverse primer for KLF4

<400> SEQUENCE: 54
ggccgctctc tttcatagca                                                  20

<210> SEQ ID NO 55
<211> LENGTH: 315
<212> TYPE: DNA
<213> ORGANISM: Mus musculus

<400> SEQUENCE: 55
tgctctcacc cagagcccca cgtgcactga tgttttaac cctttgagcc ccatcatttg        60
aagtcttgtg ctcagtgtct gtggccatgg ctgacactaa gctgtttgta tgaggtttgt      120
tttgtgacca agctgtgtag tactttgtgc attctgaatt ttaaggtttt ttttttttgtt    180 tggtttggtt tggtttggtt tttttcttat cctgtattct atcagatctg ccactgtgca     240
ggtggcaagt gagacttgat gtagttttat atgttgtaat atttcttcaa aataaagcgc     300
ttctgtcaag caccc                                                     315

<210> SEQ ID NO 56
<211> LENGTH: 199
<212> TYPE: DNA
<213> ORGANISM: Mus musculus

<400> SEQUENCE: 56
gcaggggctc tgctctgaca aaagcaacag gtcccctcag gggcggtact cacacacagg      60
cttcagtgcc gttggccact tcgcacctcc ctccattcag gtggacggag attaaagcca     120
tggtgcctat gcactagagt tattggcagt cctgaggggg tgcgggacgc ggtgggggg     180 gcggcttacg aatcaatgt                                                 199

<210> SEQ ID NO 57
<211> LENGTH: 72
<212> TYPE: DNA
<213> ORGANISM: Mus musculus

<400> SEQUENCE: 57
tcgccacatg gagctggaac agatgcacgt cctcgatact cccatggtgc caccccacac      60
cggcctcagt ca                                                         72

<210> SEQ ID NO 58
<211> LENGTH: 233
<212> TYPE: DNA
<213> ORGANISM: Mus musculus

<400> SEQUENCE: 58
cacctgacaa attcaccctc aaaattaggg atccacgctc tcgctattct gaccccgaa       60 gaggggactc ttggccacca gaggggactg agaagaaatc ggtattatta ggctaaaaga    120
acagtggact acttcagcaa tcttcccagg gctgcccttt gagaaccacc tgccccagcc    180
ggccagagac ttcctgtagc gcaagagatt tatgcaaacg gctggggcg gtg            233

<210> SEQ ID NO 59
<211> LENGTH: 353
<212> TYPE: DNA
<213> ORGANISM: Mus musculus
```

```
<400> SEQUENCE: 59
tggagagagg ggacttgtga ctgcatctgg tctggcagga aaggagggta gttgggcccc        60
ggatggggat ggaatcctgg gggaagaggc aggccagggt gacagtccct gctgttcagc       120
agttcctcgg gactcagtgt aggggtagtc ctggtgggga gctgccgccc caggggaag        180 tcgtgtgtgt tgggccggtg gccgttgctg agctggggtc cagcgctcaa atgggcctct       240
agggacgacc ggctgaccgt gcaggacggg accgcctctt gcttaatctt ggggcacatg       300
cgcggcgggc caccgctgta gggcgccact accacggggt ggctgccgtc tgg              353
```

METHODS OF TREATING A WOUND USING EPIGENETIC REGULATION

CLAIM OF PRIORITY

This application is a continuation-in-part of PCT/US2018/040642, filed on Jul. 2, 2018, which claims the benefit of U.S. Provisional Patent Application Ser. No. 62/623,880, filed Jan. 30, 2018. The entire contents of the foregoing are hereby incorporated by reference.

TECHNICAL FIELD

Methods of treating wounds in a subject using one or both of a DNA methyltransferase 1 (DNMT1) inhibitor or a nicotinamide adenine dinucleotide phosphate oxidase 2 (NOX2) inhibitor, and compositions for use in these methods.

SEQUENCE LISTING

The instant application contains a Sequence Listing which has been submitted electronically in ASCII format and is hereby incorporated by reference in its entirety. Said ASCII copy, created on Jun. 28, 2018, is named Sequence Listing.txt and is 21,638 bytes in size.

BACKGROUND

About 350 million people worldwide have type 2 diabetes mellitus (T2DM) and this is expected to grow to 440 million by 2030. One of the great scourges of diabetes is the threat of limb loss (Falanga et al. (2005) Lancet 366: 1736-1743). People with Type 2 Diabetes Mellitus (T2DM) have a 25-fold higher risk of limb loss than non-diabetics due in large part to impaired wound healing. Of the one million people who undergo leg amputation annually worldwide, 75% are performed on people who have T2DM (Carvaggi et al. (2013) J. Cardiovasc. Surg. 54: 737-754). Impaired wound healing is a hallmark of the pathophysiology of diabetic foot ulcers and limb amputations. Despite the magnitude of the clinical consequences, the mechanism by which T2DM impairs wound healing remains unknown.

SUMMARY

Without wishing to be bound by theory, the present results provide evidence that the impaired wound healing phenotype found in T2D mice was recapitulated in lethally irradiated wild type recipients whose hematopoiesis was reconstituted with hematopoietic stem cells (HSCs) from T2D mice, indicating an HSC-autonomous mechanism. This impaired wound healing phenotype of T2D mice is due to a Nox-2-dependent increase in HSC oxidant stress that decreased microRNA let-7d-3p, which, in turn, directly upregulated Dnmt1, leading to the hypermethylation of Notch1, PU.1 and KLF4. This HSC-autonomous mechanism reduces the number of wound macrophages and skews their polarization towards M1 macrophages throughout the three phases of wound healing. These findings reveal a novel mechanism by which a metabolic disorder induces an epigenetic mechanism in HSCs, which predetermines the gene expression of terminally differentiated inflammatory cells that controls their number and function.

Provided herein are methods of treating a wound or accelerating wound healing in a subject that include: administering to the subject a therapeutically effective amount of one or both of a DNA methyltransferase 1 (DNMT1) inhibitor or a nicotinamide adenine dinucleotide phosphate oxidase 2 (NOX2) inhibitor.

Also provided herein are methods of treating a wound or accelerating wound healing in a subject that include: providing a population of hematopoietic stem cells (HSCs); contacting the HSCs with one or both of a DNA methyltransferase 1 (DNMT1) inhibitor or a nicotinamide adenine dinucleotide phosphate oxidase 2 (NOX2) inhibitor; and administering a therapeutically effective amount of the HSCs to the subject.

In some embodiments of any of the methods described herein, the DNMT1 inhibitor or NOX2 inhibitor is an inhibitory nucleic acid.

In some embodiments, the DNMT1 inhibitory nucleic acid upregulates levels of Notch 1, PU.1, and/or KLF4.

In some embodiments, the DNMT1 inhibitory nucleic acid is an antisense molecule, a small interfering RNA, or a small hairpin RNA that is specific for a nucleic acid encoding SEQ ID NO: 1.

In some embodiments, the DNMT1 inhibitory nucleic acid is a nucleic acid comprising a sequence that is complementary to a contiguous sequence of at least 10 nucleotides present in DNMT1.

In some embodiments, the DNMT1 inhibitory nucleic acid is a let-7d-3p analogue. In some embodiments, the let-7d-3p analogue is a nucleic acid comprising a sequence that is at least 80% identical to SEQ ID NO: 6.

In some embodiments, the NOX2 inhibitory nucleic acid is an antisense molecule, a small interfering RNA, or a small hairpin RNA that is specific for a nucleic acid encoding SEQ ID NO: 7.

In some embodiments, the NOX2 inhibitory nucleic acid is a nucleic acid comprising a sequence that is complementary to a contiguous sequence of at least 10 nucleotides present in NOX2.

In some embodiments of any of the methods described herein, the DNMT1 inhibitor or the NOX2 inhibitor is a small molecule.

In some embodiments of any of the methods described herein, the subject is human.

In some embodiments of any of the methods described herein, the subject has diabetes.

In some embodiments of any of the methods described herein, the subject is between 1 and 60 years old.

In some embodiments of any of the methods described herein, the subject is over 45, 50, 55, 60, 65, 70, or 75 years old. In some embodiments, the subject who is over 45, 50, 55, 60, 65, 70, or 75 years old does not have a wound, and/or does not have diabetes.

In some embodiments, the HSCs are autologous HSCs.

In some embodiments of any of the methods described herein, the method further includes: administering a therapeutically effective amount of N-acetylcysteine (NAC) to the subject.

In some embodiments, the method further includes contacting the HSCs with NAC.

In some embodiments, the HSCs are autologous HSCs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1E: Histological quantification of distance between ends of panniculus carnosus (n=4, *, p<0.05 vs WT). Results are expressed as means±SEM. Two-tailed unpaired student's t-test was used.

FIG. 1F: Representative H&E staining wound images in T2D mice, magnification ×40. Scale bar, 100 μm. gt, granulation tissue.

FIG. 1G: Histological quantification of distance between granulation tissue (n=4, *, p<0.05 vs WT). Results are expressed as means±SEM. Two-tailed unpaired student's t-test was used.

FIG. 1H: Immunohistochemical (IHC) quantification of arteries by CD144 and α-SMA staining.

FIG. 1I: Immunohistochemical (IHC) quantification of vessels by CD144 and α-SMA staining.

FIG. 1J: Representative IHC staining images of vascularization in T2D mice, magnification ×200. Scale bar, 100 μm.

FIG. 2A: Quantification of CD115$^+$CD11b$^+$ monocytes concentration in bone marrow of WT and db/db mice by flow cytometry (n=6, *, p<0.05 vs WT). Results are expressed as means±SEM. Two-tailed unpaired student's t-test was used.

FIG. 2B: Schematic of flow cytometry gating of CD115 and CD11b in WT and db/db mice.

FIG. 2C: Quantification of absolute number of CD115$^+$CD11b$^+$ monocytes in bone marrow of WT and db/db mice (n=6, *, p<0.05 vs WT). Results are expressed as means±SEM. Two-tailed unpaired student's t-test was used.

FIG. 2D: Quantification of CD115+CD11b$^+$ monocytes concentration in the bone marrow of WT, db/db and high-fed diet (HFD) type 2 diabetic mice by flow cytometry (n=6. *, p<0.05 vs. WT; #, p<0.05 vs. db/db). Results are expressed as means±SEM. One way ANOVA was used.

FIG. 2I: Quantification of M1/M2 polarization in the cutaneous wounds on day 3 by flow cytometry (n=6, *, p<0.05 vs WT). Results are expressed as means±SEM. Two-tailed unpaired student's t-test was used.

FIG. 2J: Quantification of M1/M2 polarization in the cutaneous wounds on day 7 by flow cytometry (n=6, *, p<0.05 vs WT). Results are expressed as means±SEM. Two-tailed unpaired student's t-test was used.

FIG. 3A: Schematic of flow cytometry gating of M1 macrophages (TNFα, iNOS, IL-12).

FIG. 5E Quantification of M1/M2 polarization in cutaneous wounds on day 3 in by flow cytometry (n=6, *, p<0.05 vs WT HSC→WT). Results are expressed as means±SEM. Two-tailed unpaired student's t-test was used.

FIG. 5F: Quantification of M1/M2 polarization in cutaneous wounds on day 7 by flow cytometry (n=6, *, p<0.05 vs WT HSC→WT). Results are expressed as means±SEM. Two-tailed unpaired student's t-test was used.

FIG. 5G: Quantification of M1/M2 polarization in cutaneous wounds on day 14 by flow cytometry (n=6, *, p<0.05 vs WT HSC→WT). Results are expressed as means±SEM. Two-tailed unpaired student's t-test was used.

FIG. 5H: Flow cytometry gating of the M1 macrophage concentration in wounds (TNFα, iNOS, IL-12).

FIG. 5I: Flow cytometry gating of the M2 macrophage concentration in wounds.

FIG. 7C: Western blot analysis of Dnmt-1 protein levels in bone marrow monocytes and wound macrophages (n=6).

FIG. 7D: Quantification of Dnmt-1 protein levels in bone marrow monocytes and to wound macrophages as shown in FIG. 7C (n=6, *, p<0.05 vs wt, #, p<0.05 vs db/db). Results are expressed as means±SEM. Two-tailed unpaired student's t-test was used.

FIG. 8C: Quantification of luciferase activity assay (n=4, *, p<0.05 vs control). Dnmt1 M1 represents mutant #1 and Dnmt1 M2 represents mutant #2. Results are expressed as means±SEM. Two-tailed unpaired student's t-test was used.

FIG. 8D: Relative expression of let-7d-3p in WT HSCs following transfection with a let-7d-3p inhibitor (n=6, *, p<0.05 vs WT control). Results are expressed as means±SEM. Two-tailed unpaired student's t-test was used.

FIG. 8E: Relative expression of Dnmt1 in WT HSCs following transfection of let-7d-3p inhibitor (n=6, *, p<0.05 vs WT control). Results are expressed as means±SEM. Two-tailed unpaired student's t-test was used.

FIG. 8F: Relative expression of let-7d-3p in db/db HSCs following transfection with let-7d-3p mimic. Results are expressed as means±SEM. Two-tailed unpaired student's t-test was used.

FIG. 8G: Relative expression of Dnmt 1 in db/db HSCs following transfection of let-7d-3p mimic (n=6, #, p<0.05 vs db/db control). Results are expressed as means±SEM. Two-tailed unpaired student's t-test was used.

FIG. 9A: Relative expression of Dnmt 1 expression in WT HSC, db/db HSC and db/db HSC expressing shDnmt1 (n=6, *p<0.05 vs WT HSC, #, p<0.05 vs db/db HSC). Results are expressed as means±SEM. One way ANOVA was used.

FIGS. 11A-D. FIG. 11A: Morphometric quantification of distance between epithelial tips in wounds of db/db recipient mice (n=4, *, p<0.05 vs wt HSC→db/db; #, p<0.05 vs db/db HSC→db/db). Results are expressed as means±SEM. One way ANOVA was used.

FIG. 11B: Morphometric quantification of distance between ends of panniculus carnosus tissue in wounds of db/db recipient mice (n=4, *, p<0.05 vs wt HSC→db/db; #, p<0.05 vs db/db HSC→db/db). Results are expressed as means±SEM. One way ANOVA was used.

FIG. 11C: Morphometric quantification of distance between granulation tissue in wounds of db/db recipient mice (n=4, *, p<0.05 vs wt HSC→db/db; #, p<0.05 vs db/db HSC→db/db). Results are expressed as means±SEM. One way ANOVA was used.

FIG. 11D: Representative H&E staining of wounds on day 7, magnification ×40. Scale bar 100 mm. gt: granulation tissue.

Figure 25A:
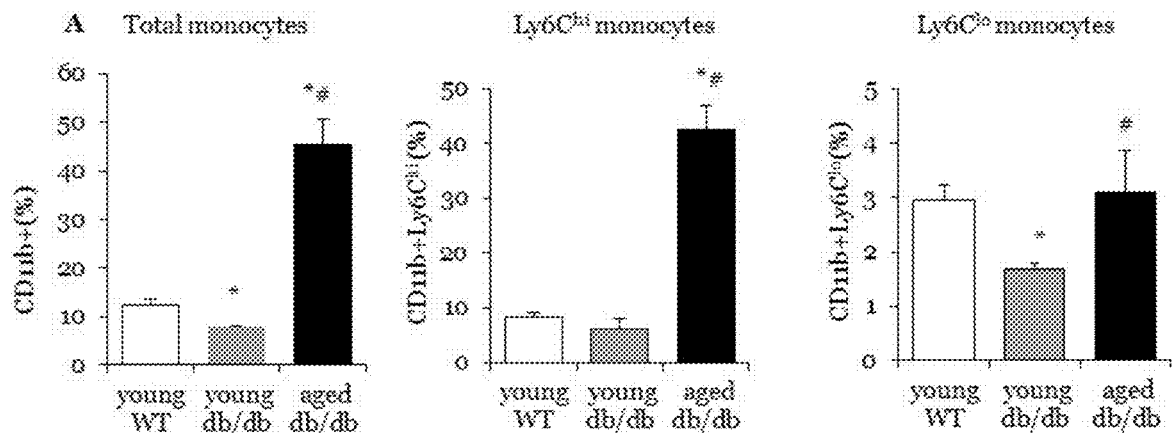
FIG. 25A: Quantification of peripheral blood monocytes in young WT mice, young db/db mice and aged db/db mice (*, p<0.05 vs young WT; #, p<0.05 vs young db/db). Results are expressed as means±SEM.
Figure 25B:
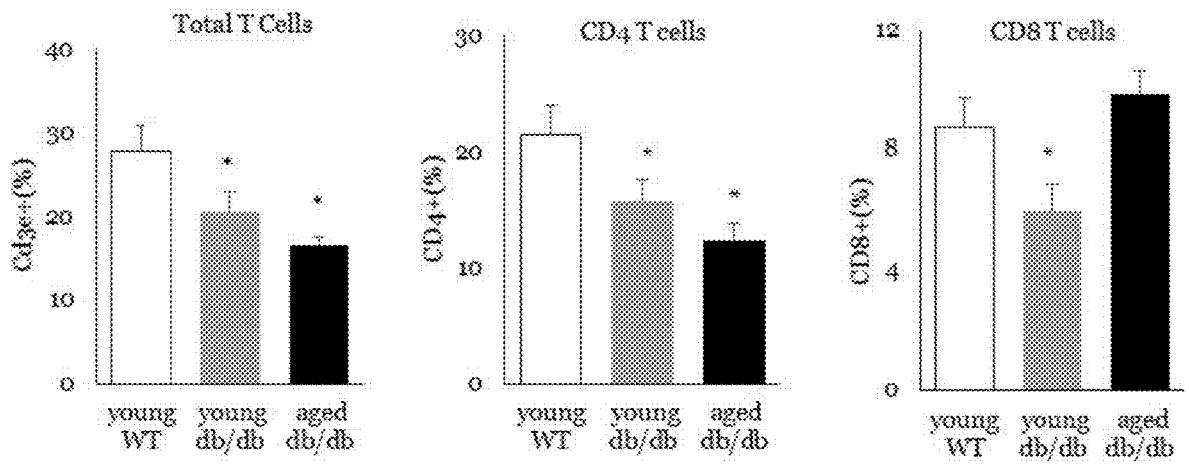

FIG. 25B: Quantification of T-lymphocytes (total T cells, CD4 T cells, and CD8 T cells) in young WT mice, young db/db mice and aged db/db mice (*, p<0.05 vs young WT; #, p<0.05 vs young db/db). Results are expressed as means±SEM.

Figure 25C:
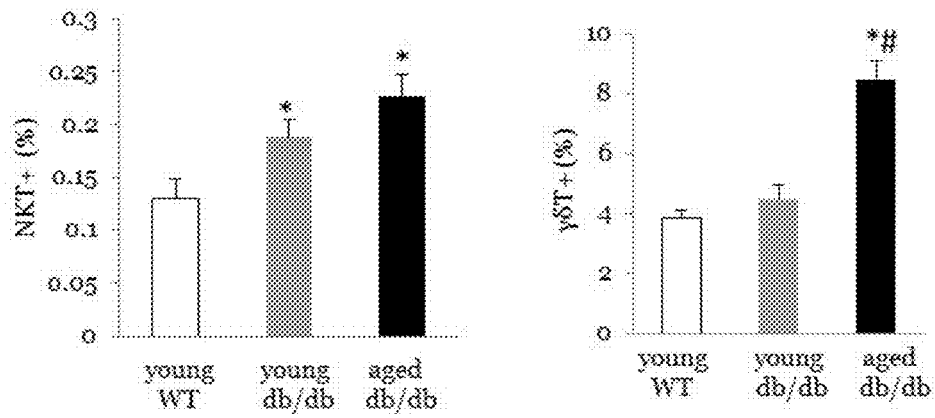

FIG. 25C: Quantification of NKT cells and γδT cells in young WT mice, young db/db mice and aged db/db mice (*, p<0.05 vs young WT; #, p<0.05 vs young db/db). Results are expressed as means±SEM.

Figure 26:
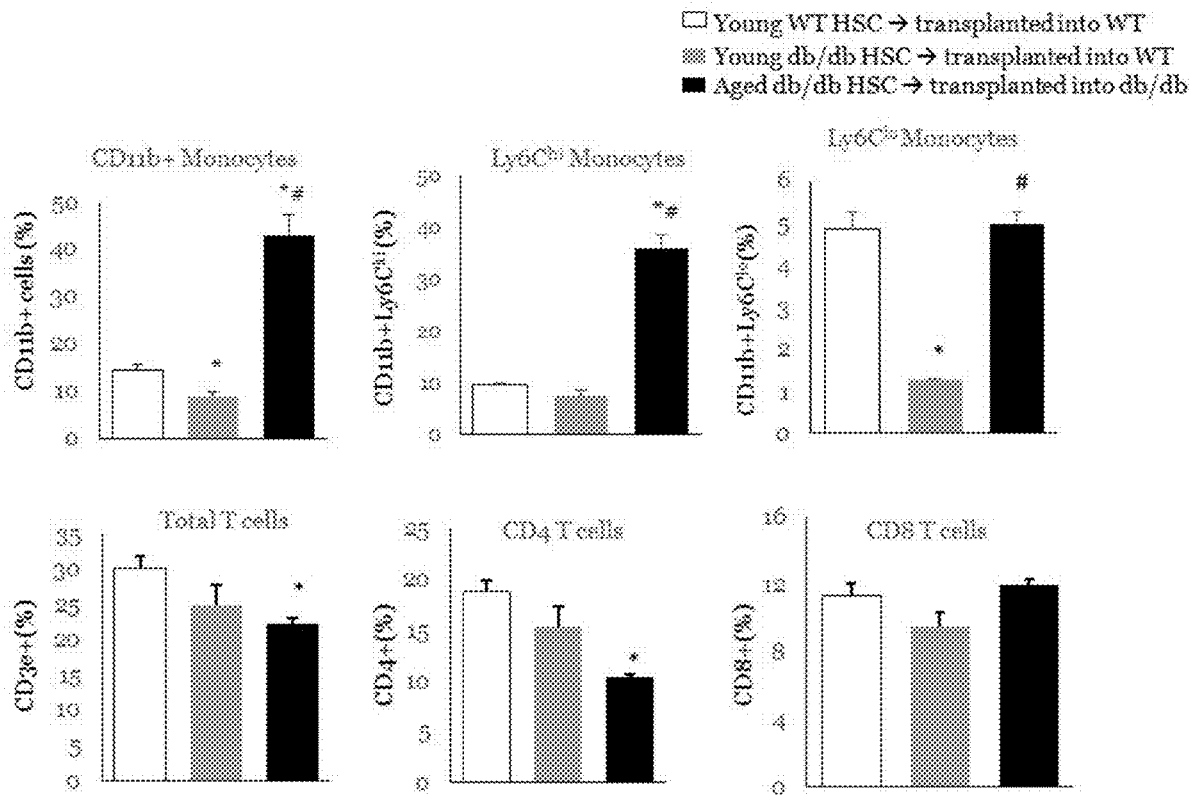

FIG. 26: Quantification of HSC induced differentiation towards monocytes and T-cells in vivo (*, p<0.05 vs young WT HSC into WT; #, p<0.05 vs young db/db HSC into WT). Young WT HSC were transplanted into WT mice, young db/db HSC were transplanted into WT mice, and aged db/db HSC were transplanted into db/db mice. Results are expressed as means±SEM.

Figure 27A:
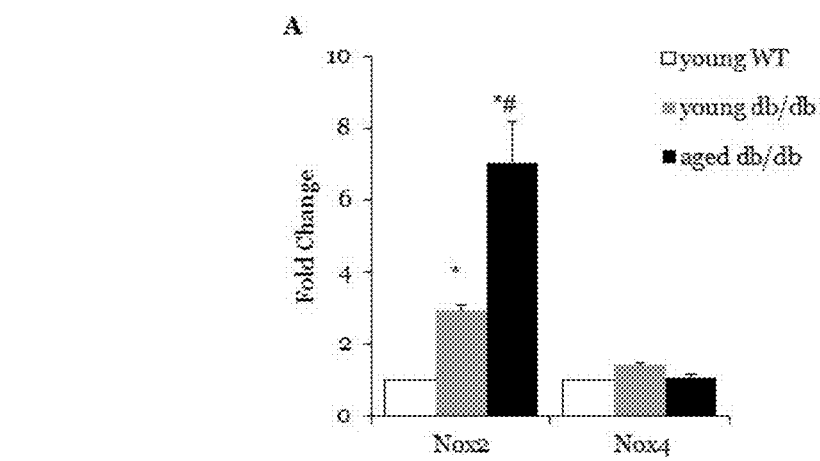

FIG. 27A: Quantification of NAPDH oxidases (NOX1, NOX2 and NOX4) in young WT, HSC, young db/db HSC, and aged db/db HSC (*, p<0.05 vs WT). Results are expressed as means±SEM.

Figure 27B:
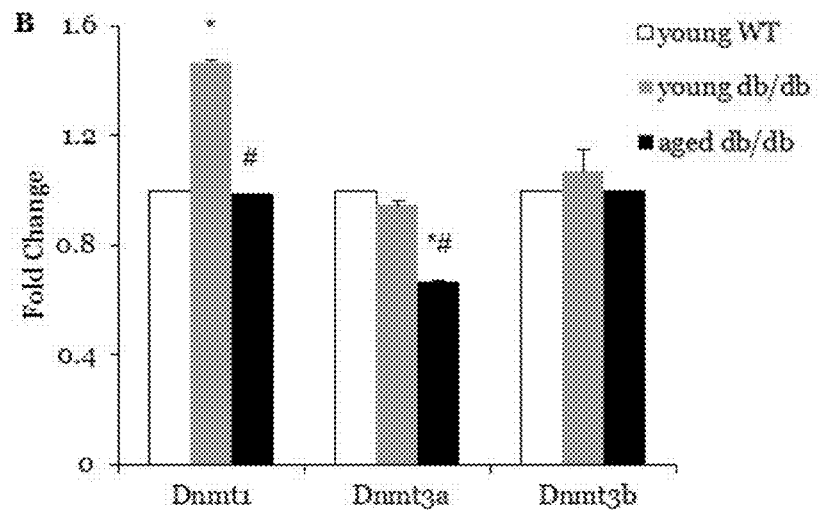

FIG. 27B: Quantification of DNMT1, DNMT3a and DNMT3b in young WT HSC, young db/db HSC, and aged db/db HSC (*, p<0.05 vs WT). Results are expressed as means±SEM.

Figure 27C:
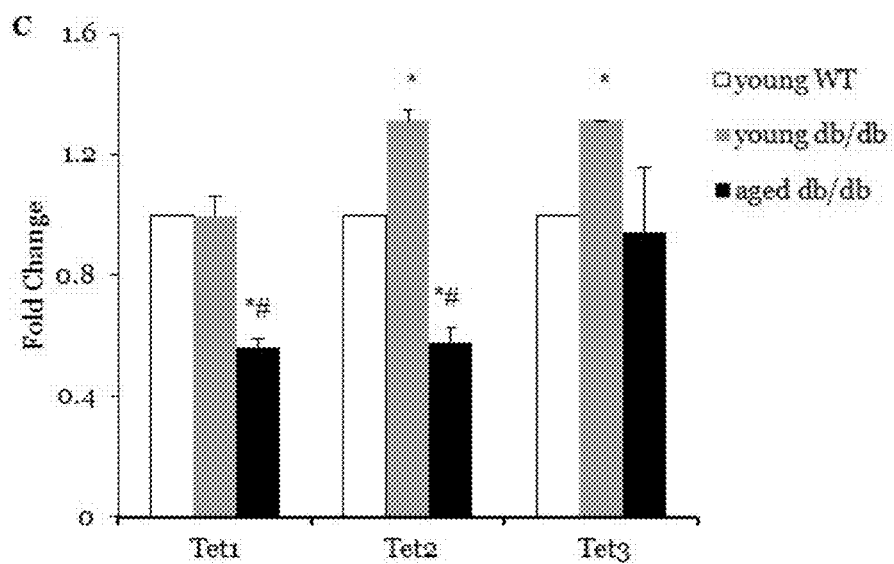

FIG. 27C: Quantification of TET1, TET2 and TET3 in young WT HSC, young db/db HSC, and aged db/db HSC (*, p<0.05 vs WT). Results are expressed as means±SEM.

FIG. 28: Quantification of human HSC differentiation towards monocytes and T-cells in a single human replicate for young adult, aged adult and aged T2DM (*, p<0.05 vs young adult).

FIG. 29: Quantification of NAPDH oxidases (NOX1, NOX2 and NOX4) in a single human replicate for young adult, aged adult and aged T2DM.

FIG. 30A: Quantification of DNMT1, DNMT3a and DNMT3b in a single human replicate for young adult, aged adult and aged T2DM.

Figure 30B:
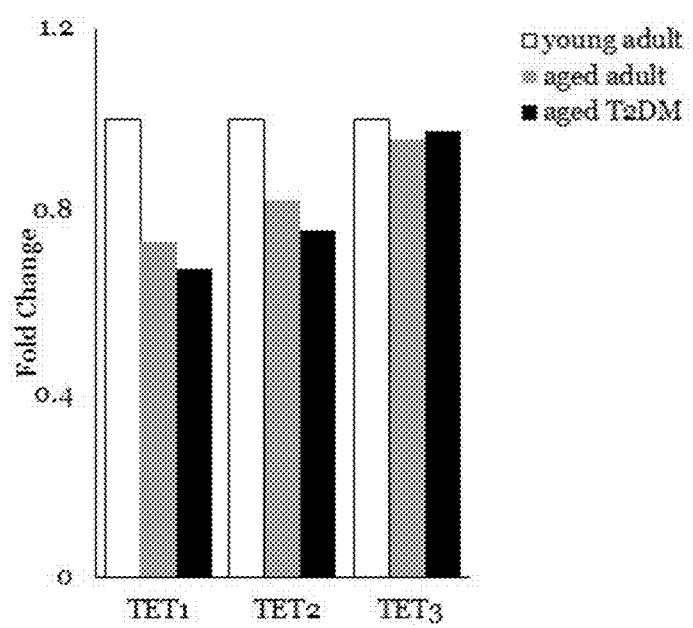

FIG. 30B: Quantification of TET1, TET2 and TET3 in a single human replicate for young adult, aged adult and aged T2DM.

Figure 31A:
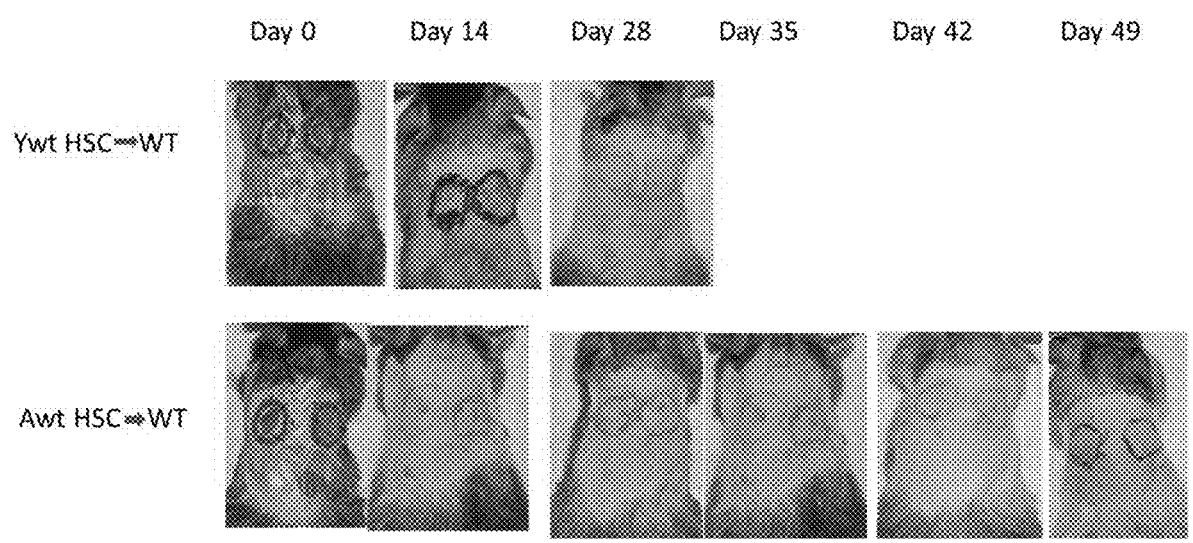

FIG. 31A: Representative wounding images of young WT mice transplanted with WT HSC, young WT mice transplanted with aged WT HSC (awt HSC).

Figure 31B:
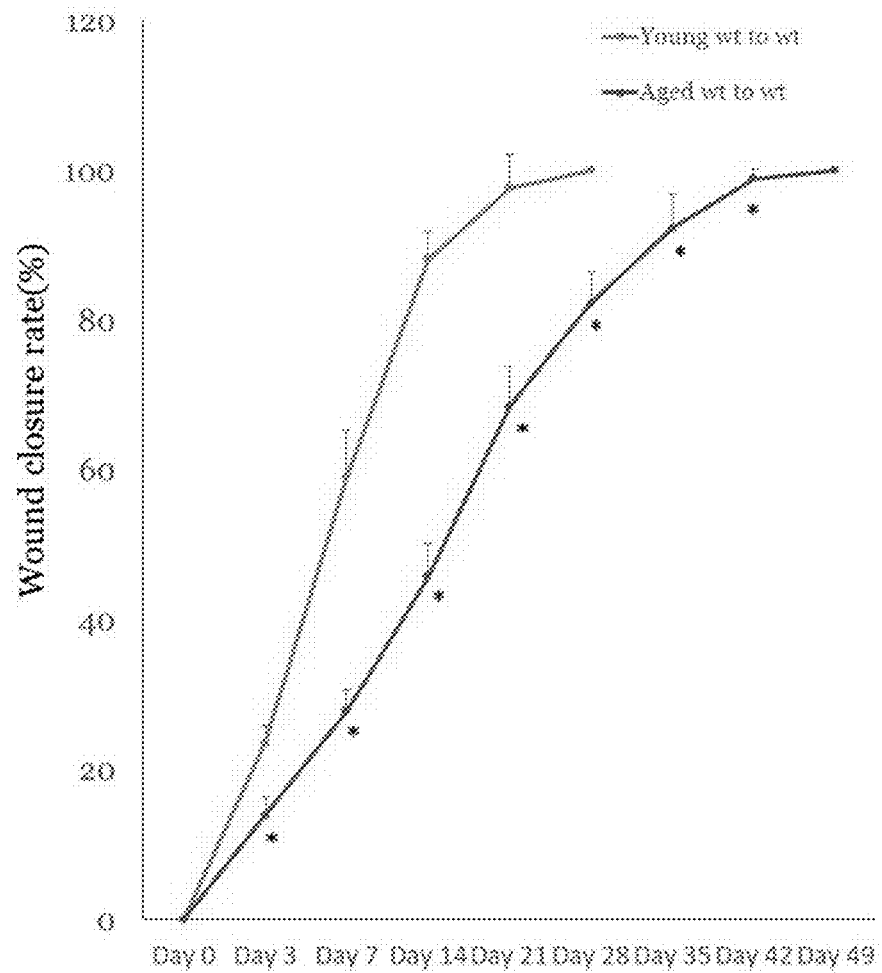

FIG. 31B: Wound closure rate measurements of young WT HSC transplanted into young WT mice and aged WT HSC transplanted into young WT mice (n=3, *, p<0.05 vs young WT HSC young WT). Results are expressed as means±SEM. Two-tailed unpaired student's t-test was used.

Figure 32A:
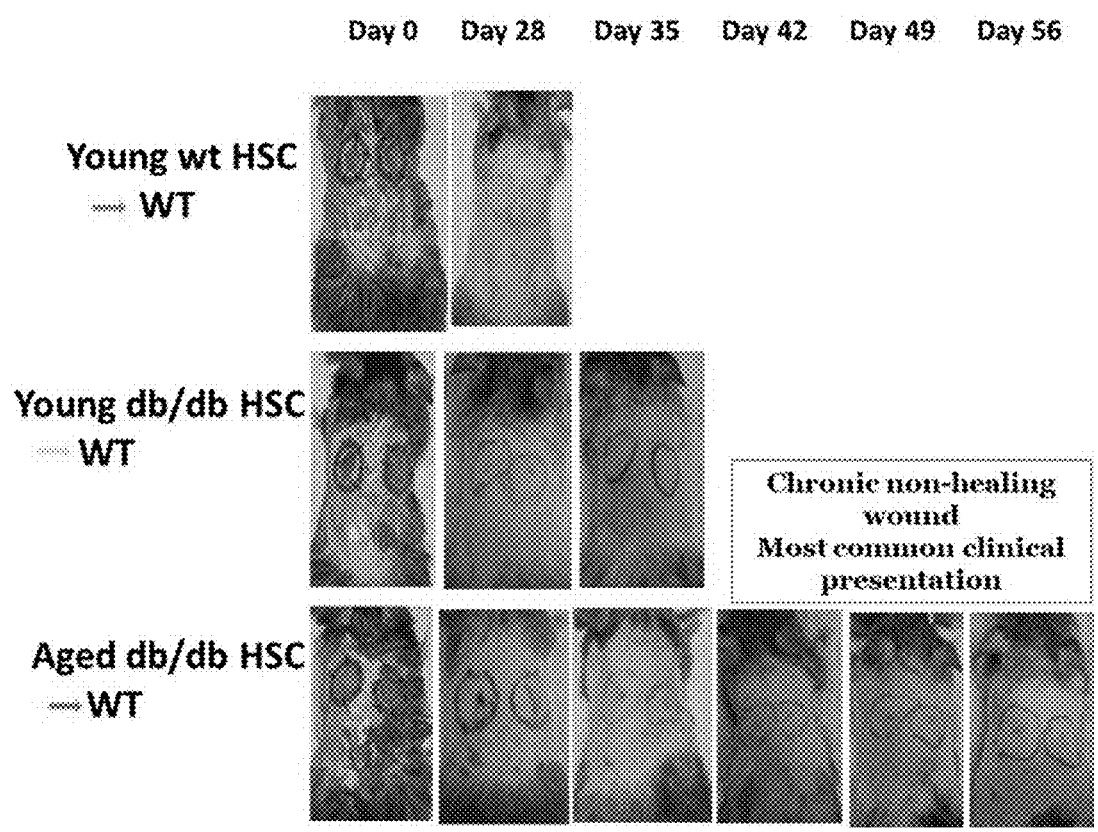

FIG. 32A: Representative wounding images of young WT mice transplanted with WT HSC, young WT mice transplanted with aged WT HSC (awt HSC).

Figure 32B:
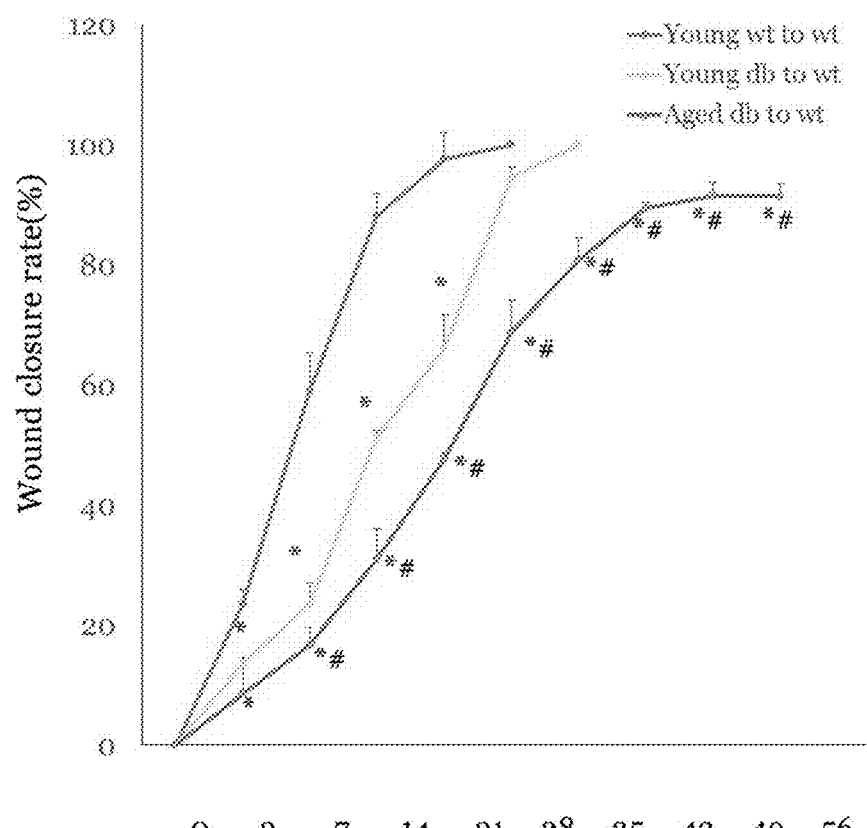

FIG. 32B: Wound closure rate measurements of young WT HSC transplanted into young WT mice, young db/db HSC transplanted into young WT mice, and aged db/db HSC transplanted into young WT mice (n=3, *, p<0.05 vs young WT HSC young WT, #, p<0.5 vs young db/db HSC young WT). Results are expressed as means±SEM. Two-tailed unpaired student's t-test was used.

DETAILED DESCRIPTION

Normal wound healing involves three overlapping phases: (1) acute inflammation, (2) angiogenesis/proliferation and (3) remodeling. Monocytes/macrophages derived from hematopoietic stem cells (HSCs), represent one of the most abundant inflammatory cell types during all stages of wound healing (Willenborg & Eming (2014) J. Dtsch Dermatol. Ges. 12: 214-221). Monocyte-derived macrophages can polarize into either M1 (classically activated) or M2 (alternatively activated) subtypes in the presence of specific cues when recruited into peripheral tissues and wounds (Mantovani et al. (2005) Immunity 23: 344-346; Martinez et al. (2009) Annu Rev. Immunol. 27: 451-483). In general, M1 macrophages are characterized by their pro-inflammatory function. M2 macrophages mainly induce angiogenesis and tissue remodeling in the early phases of wound healing as well as reduce inflammation in the late phase of wound healing. T2DM wounds are characterized by excessive and prolonged inflammation due to the predominant presence of M1 macrophages (Zykova et al. (2000) Diabetes 49: 1451-1458; Khanna et al. (2010) PLoS One 5: e9539; Gallagher et al. (2015) Diabetes 64: 1420-1430; Bannon et al. (2013) Dis. Model Mech. 6: 1434-1447). However, the mechanism remains unknown (Maruyama et al. (2007) Am. J. Pathol. 170: 1178-1191; Wood et al. (2014) PLoS One 9: e91574; Tepper et al. (2010) Diabetes 59: 1974-1983).

Epigenetic modifications, including DNA methylation, histone modification and small non-coding RNAs, are essential in maintaining proper lineage commitment and self-renewal of HSCs (Cullen et al. (2014) Curr Top Dev Biol. 107: 39-75; Luo et al. (2015) Cell Stem Cell 16: 426-438; Haetscher et al. (2015) Nat. Commun. 6: 8928; Trowbridge et al. (2009) Cell Stem Cell 5: 442-449). A recent study suggested that T2DM decreases the repressive histone methylation marker H3K27me3 in the promoter of the IL-12 gene in bone marrow progenitors. This epigenetic signature appears to be passed down to terminally differentiated wound-resident macrophages in T2DM mice. These findings lead to a potentially novel paradigm that T2DM may epigenetically "preprogram" HSCs to reduce their differentiation towards monocytes and increase polarization towards M1 macrophages and thereby negatively impact wound repair. This potentially novel mechanism may be responsible for the conflicting evidence existing between the observations made at different stages of wound healing in T2DM patients and in animal models. However, there are two critical links missing in this hypothesis. First, even under conditions of normal wound healing, the evidence for a mechanism(s) that regulates monocyte tissue infiltration and the dynamics of their M1/M2 polarization is scarce. Second, the mechanisms by which T2DM reduces monocyte/macrophage tissue infiltration and their M1/M2 polarization remain unknown.

Traditionally, wound healing has been described as a process that requires a finely tuned orchestrated recruitment of terminally differentiated cells by different external cues to wound sites. While it is well established that this process is delayed in T2DM, to date, the mechanism(s) responsible for such a delay had not been well defined. Without wishing to be bound by theory, the present results provide evidence that T2DM induces an HSC-autonomous mechanism that causes impaired wound healing. Specifically, T2DM causes a Nox 2-induced oxidant stress in HSCs that decreased microRNA let-7d-3p, which, in turn, directly increased the expression of DNA methyltransferase 1 (DNMT1), a key enzyme mediating DNA methylation and histone modifications. DNMT1-dependent repressive modifications reduced the expression of Notch1, PU.1 and Klf4, genes that are central in the differentiation of HSCs towards monocytes/macrophages. In fact, this T2DM induced-repression of these genes is responsible for the impaired differentiation of HSCs towards monocytes/macrophages as well as for their skewed polarization towards M1 macrophages throughout the phases of wound healing. From a larger perspective, these novel findings reveal a new mechanism that regulates inflammation: T2DM induces changes in gene expression in HSCs that, together, can reduce the number and function of terminally differentiated inflammatory cells. Thus, the changes in terminally differentiated cells are predetermined at the level of HSCs. These insights pave a path towards an effective cellular or molecular therapy to reverse the impaired wound healing phenotype commonly seen in patients with T2DM.

As shown herein, Type 2 Diabetes Mellitus (T2DM) impairs wound healing through an HSC-autonomous mechanism whereby a Nox-2-dependent increase in HSC oxidant stress decreases microRNA Let-7d-3p, which, in turn, directly increases the expression of DNMT1. This increase in DNMT1 expression downregulates the genes responsible for HSC differentiation towards monocytes/macrophages, and consequently causes a reduction in macrophage infiltration into the wound and skewes their polarization towards M1 macrophages. Thus, the concentration of macrophages in wounds of T2D mice is significantly lower than that in WT mice in early inflammatory and new tissue regeneration phases, but remains at significantly greater levels in the tissue remodeling phase. In agreement with previous findings, the present inventors showed that M1 macrophages comprise the absolute majority of macrophages in the wounds of T2D mice (Zykova et al. (2000) Diabetes 49: 1451-1458; Khanna et al. (2010) PLoS One 5: e9539; Gallagher et al. (2015) Diabetes 64: 1420-1430).

As shown herein, DNMT1 was specifically upregulated in HSCs from both db/db and HFD mice. This supports the fact that the impairment of wound healing was not due to other metabolic abnormalities of db/db mice. The inhibition of DNMT1 in HSCs from T2D mice increased the differentiation from HSCs towards monocytes/macrophages and restored the balance of M1/M2 polarization in vivo. These are the first findings to indicate that DNMT1 in HSCs functions as a critical determinant in their differentiation towards monocytes and macrophages as well as in their polarization. In addition, DNMT1 knockdown in HSCs from T2D mice restores their differentiation towards monocytes/macrophages. More importantly, the transplantation with DNMT1-knockdown HSCs from db/db mice restores the rate of wound healing in T2D recipients to levels similar to those seen in WT mice. These novel findings not only demonstrate that HSC dysfunction in T2D mice is the central underlying cause of impaired wound healing, but also creates a new paradigm that might facilitate therapeutically relevant manipulation of HSCs. Notch1, PU.1 and Klf4 have been shown to be among the regulators of the differentiation and polarization of monocytes/macrophages. As shown herein, Notch1, PU.1 and Klf4 were downregulated in HSCs from T2D mice. As is known, Notch1 deficiency leads to decreased macrophage recruitment and TNFα expression in response to wounding (Outtz et al. (2010) J. Immunol. 185: 436304373). Klf4 is a downstream target gene of PU.1 and Notch 1 (Georgantas et al. (2004) Cancer Res. 64: 4434-4441; Feinberg et al. (2007) EMBO J. 26: 4138-4148) and induces an M2 phenotype while inhibiting the M1 phenotype. Klf4 deficiency in myeloid cells results in delayed wound healing and increased pro-inflammatory M1 macrophages (Liao et al. (2011) J. Clin. Invest. 121: 2736-2749). In agreement with these findings, the inhibition of Notch1, PU.1 or Klf4 in HSCs reduced the differentiation and polarization of monocytes/macrophages under in vitro conditions.

The mechanism by which Dnmt1 regulates the expression of Notch1, PU.1 and Klf4 is through the modification of their methylation status. Indeed, the DNA methylation status of Notch1, PU.1 and Klf4 increased in HSCs from db/db mice. Furthermore, Dnmt1 can also participate in the regulation of histone modifications (Gilbert et al. (2007) J. Cell Biol. 177:401-411; and Esteve et al., (2006) Genes Dev.

20:3089-3103). ChIP-PCR showed that the dimethylation (H3K9me2) and trimethylation (H3K9me3) of H3K9 were increased in Klf4, PU.1 and Notch1 genes in HSCs from T2D mice. When Dnmt1 was inhibited, these repressive modifications at H3K9 were reduced, and the expression of these genes was restored in HSCs from T2D mice. These findings indicate that the upregulation of Dnmt1 increased the repressive histone modifications in Notch1, PU.1 and Klf4, thereby inhibiting the expression of these genes in HSCs from T2D mice. Taken together, pathological HSC oxidant stress can reduce the number and function of terminally differentiated inflammatory cells. Oxidant stress induced epigenetic mechanisms lead to changes in HSC gene expression that are carried down through progenitor cells to terminally differentiated cells. This supports the concept that changes in gene expression of terminally differentiated inflammatory cells are actually "preprogrammed" at the HSC level. These insights into the mechanism by which T2DM impairs wound healing opens multiple avenues to new potentially highly effective techniques to restore normal wound healing and thereby reduce the risk of amputation in people with T2DM. Moreover, the identification of a single microRNA that regulates the expression of a single epigenetic enzyme that, in turn, regulates the genes responsible for HSC differentiation towards monocytes as well as their M1/M2 polarization creates an excellent opportunity for the development of biological therapeutics to restore normal wound healing in people with T2DM. Furthermore, we showed that normal human HSCs have the same response to hyperinsulinemia-induced oxidant stress as do murine HSCs only further raising hope for what would be the first treatment for impaired wound healing for people with T2DM. Indeed, hyperinsulinemia increased the expression of NOX2 and Dnmt1 in human HSCs. This led to a reduction of human HSC differentiation towards macrophages and skewed human macrophages towards M1 polarization.

The majority of non-healing cutaneous wounds are seen in people over 65 years of age, 25% of whom have diabetes, and 95% of these individuals have type 2 diabetes mellitus (T2DM) (Gould (2013) R I Med J 2016. 99(2): p. 34-6; American Diabetes, Diabetes Care, 2018. 41(Suppl 1): p. S119-S125). The combination of aging and T2DM makes the treatment of cutaneous wounds more difficult than aging alone. Non-healing wounds in aging patients with T2DM results in substantial morbidity, disability, hospitalization, and even mortality. In fact, non-healing foot ulcers occur in up to 25% of diabetics during their lifetime, and the cost to treat foot ulcers is more than $13 billion annually (Falanga (2005) Lancet, 366(9498): p. 1736-43; Caravaggi et al., (2013) J Cardiovasc Surg (Torino), 54(6): p. 737-54).

Wound healing requires a finely tuned, orchestrated recruitment of terminally differentiated immune and inflammatory cells to wound sites in response to external cues. It is well established that wound healing is impaired in older patients with or without T2DM; however, to date, the mechanisms responsible for impaired wound healing remain largely unknown. Persistent inflammation is a hallmark of impaired wound healing in aging patients and aging patients with T2DM (Yan et al., (2018) Nat Commun, 9(1): p. 33; Gould et al., (2015) J Am Geriatr Soc, 63(3): p. 427-38; Zhao et al., (2016) Int J Mol Sci, 17(12)). Throughout the phases of wound healing, especially the inflammatory and tissue formation phases, the most essential and abundant cell types are macrophages and T lymphocytes. Dysregulated macrophages and T lymphocytes infiltration in wounds has been observed in both healthy aging patients and aging patients with T2DM (Krzyszczyk et al., (2018). Front Physiol, 9: p. 419; MacLeod et al., (2014) J Immunol, 192(12): p. 5695-702; Plowden et al., (2004) Aging Cell, 3(4): p. 161-7; Gerstein et al., (1993) Dermatol Clin, 11(4): p. 749-57). Identification of the underlying mechanisms that cause this dysregulation will accelerate the development of innovative strategies to improve tissue repair and regeneration that will reduce the substantial disability from non-healing wounds.

Hematopoietic stem cells (HSCs) give rise to the terminally differentiated immune and inflammatory cells that mediate wound healing. To the best of the inventor's knowledge, no studies have examined how the combined effects of aging and T2DM affect the process of HSC differentiation towards these immune and inflammatory cells to impair wound healing.

Without wishing to be bound by theory, the results provided herein demonstrate in aged mice that 1) the alterations in circulating monocytes and T lymphocytes observed in aged wild type (WT) and aged T2DM mice are primarily due to intrinsic impairments in HSCs (HSC-autonomous mechanism); 2) significantly increased Nox2 expression and dysregulated expression of epigenetic enzymes were observed in HSCs from aged WT and aged T2DM mice. The restoration of the expression of epigenetic enzymes in HSCs from aged mice can normalize their differentiation towards monocytes/macrophage and T lymphocytes simultaneously, and can reestablish normal dynamic infiltration of macrophages and T lymphocytes in cutaneous wounds and improve wound healing.

Aged mouse models were used to recapitulate the macrophage and lymphocyte changes that are observed in human aging and T2DM. The data provided herein shows that in aged mice, there was a significantly decreased concentrations of total monocytes, anti-inflammatory Ly6clowCD11b+ monocytes, and T lymphocyte populations in the peripheral blood of healthy aged WT mice, which was in agreement with the decrease in monocytes and lymphocytes that has been shown in healthy aged adults (Gould et al., (2015) Wound Repair Regen, 23(1): p. 1-13; Tavares et al., (2014) Rev Bras Hematol Hemoter, 36(3): p. 180-3). Additionally, the data showed that in aged T2DM mice there were significantly increased concentrations of total monocytes and proinflammatory Ly6chiCD11b+ monocytes in peripheral blood, as well as decreased CD3e+ and CD4+ lymphocyte concentrations. These results were comparable to the changes observed in aged T2DM adults, which show increased proinflammatory monocytes and decreased T lymphocytes in the peripheral blood (Prattichizzo et al., (2016) Oxid Med Cell Longev, 2016: p. 1810327; Fadini et al., (2013) Diabetologia, 56(8): p. 1856-66). In summary, 1) both clinical and experimental evidence indicate that the effects of aging alone are not identical to the combined effects of aging and T2DM and therefore must be considered as a unique pathological process that needs to be fully characterized; 2) The aged mouse model closely recapitulates the effects of aging in humans to greatly increase the clinical relevance of our aged WT and aged T2DM mouse models.

Furthermore, HSCs from aged healthy human donors and aged T2DM human donors had identical defects in their differentiation towards monocytes/macrophage and T-lymphocytes. In addition, increased expression of NOX2 and decreased expression of the DNA methyltransferase (DNMT) and Ten-Eleven demethylases (TET) were observed in human HSCs from an aged healthy and a T2DM donor, and aged human HSCs show defects in dysregulated differentiation towards myeloid and lymphoid lineages. The mechanisms for this defect dysregulation as well as the combined effects of T2DM on human HSC function remain largely unknown. The results provided herein indicate that the effects of aging and T2DM on mouse HSCs share many similarities to the effects of aging and T2DM on human HSCs.

Methods of Treatment

The present methods include the use of one or both of a DNMT1 inhibitor (e.g., a DNMT1 inhibitory nucleic acid or a small molecule) or a NOX2 inhibitor (e.g., a NOX2 inhibitory nucleic acid or a small molecule), for treating a wound in a subject who is in need of, or who has been determined to be in need of, such treatment.

The methods of accelerating wound healing in a subject can include administering to the subject a therapeutically effective amount of one or both of a DNMT1 inhibitor and/or a NOX2 inhibitor.

For example, the methods can include administering to a subject a therapeutically effective amount of hematopoietic stem cells (HSCs) expressing one or both of a DNMT1 inhibitory nucleic acid and/or a NOX2 inhibitory nucleic acid.

The methods can also include administering to a subject a therapeutically effective amount of hematopoietic stem cells (HSCs) treated with N-acetylcysteine (NAC).

The term "subject" refers to any mammal. In some embodiments, the subject or "subject suitable for treatment" may be a canine (e.g. a dog), feline (e.g. a cat), equine (e.g. a horse), ovine, bovine, porcine, caprine, primate, e.g., a simian (e.g. a monkey (e.g. marmoset, baboon) or an ape (e.g. a gorilla, chimpanzee, orangutan, or gibbon)) or a human; or rodent (e.g., a mouse, guinea pig, a hamster, or a rat). In some embodiments, the subject or "subject suitable for treatment" may be a non-human mammal, especially mammals that are conventionally used as models for demonstrating therapeutic efficacy in humans (e.g., murine, lapine, porcine, canine, or primate animals) may be employed. In some embodiments, the subject has diabetes.

In some embodiments of any of the methods described herein, the subject is between 1 and 60 years old (e.g., between 1 and 55 years old, between 1 and 50 years old, between 1 and 45 years old, between 1 and 40 years old, between 1 and 35 years old, between 1 and 30 years old, between 1 and 25 years old, between 1 and 20 years old, between 1 and 18 years old, between 1 and 15 years old, between 1 and 10 years old, between 1 and 5 years old, between 5 and 60 years old, between 5 and 55 years old, between 5 and 50 years old, between 5 and 45 years old, between 5 and 40 years old, between 5 and 35 years old, between 5 and 30 years old, between 5 and 25 years old, between 5 and 20 years old, between 5 and 15 years old, between 5 and 10 years old, between 10 and 60 years old, between 10 and 55 years old, between 10 and 50 years old, between 10 and 45 years old, between 10 and 40 years old, between 10 and 35 years old, between 10 and 30 year old, between 10 and 25 years old, between 10 and 20 years old, between 10 and 18 years old, between 10 and 15 years old, between 15 and 60 years old, between 15 and 50 years old, between 15 and 40 years old, between 15 and 30 years old, between 15 and 20 years old, between 15 and 18 years old, between 20 and 60 years old, between 20 and 50 years old, between 20 and 40 years old, between 20 and 30 years old, between 20 and 25 years old, between 30 and 60 years old, between 30 and 50 years old, between 30 and 40 years old, between 30 and 35 years old, between 40 and 60 years old, between 40 and 50 years old, between 40 and 45 years old, between 50 and 60 years old, between 50 and 55 years old).

In some embodiments of any of the methods described herein, the subject is over 60 years old (e.g., over 65 years old, over 70 years old, over 75 years old, over 80 years old, over 85 years old, over 90 years old, over 95 years old, over 100 years old; 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105 or 106).

In some embodiments of any of the methods described herein, the subject has diabetes and is over 60 years old (e.g., over 65 years old, over 70 years old, over 75 years old, over 80 years old, over 85 years old, over 90 years old, over 95 years old, over 100 years old; 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105 or 106).

These methods can be used to treat a subject, e.g., a diabetic subject (i.e., a subject with diabetes, e.g., who has been diagnosed with diabetes), by administering to the subject a composition (e.g., as described herein) comprising one or both of an oligonucleotide that targets DNMT1 or an oligonucleotide that targets NOX2. Examples of oligonucleotides and target sequences are provided herein.

As used herein, treating includes "prophylactic treatment," which means delaying or reducing the incidence of, or delaying or preventing (or reducing risk of), a sign or symptom of a disease in a patient at risk for the disease, and "therapeutic treatment", which means reducing or delaying signs or symptoms of a disease, reducing or delaying progression of a disease, reducing severity of a disease, re-occurrence in a patient diagnosed with the disease.

As used in this context, to "treat" means to accelerate wound healing in a subject (e.g., a diabetic subject or a subject that has hyperinsulinemia). In some embodiments, treatment may include reducing the levels of oxidant stress (e.g., NOX2- and/or NOX4-induced oxidant stress) in hematopoietic stem cells (HSC), downregulating the expression of DNMT1 and/or NOX2 in HSC, reducing DNMT1 and/or NOX2 activity in HSC, increasing the expression and/or activity of let-7d-3p in HSC, upregulating the expression levels of Notch 1, PU.1 and/or Klf4 in HSC, reducing DNA hypermethylation in Notch1, PU.1 and Klf4, and/or removing di-(H3K9me2) and trimethylation (H3K9me3) at the promoters of Notch 1, PU.1, and/or Klf4 and increasing H3K9 acetylation at the promoters of Notch 1, PU.1 and/or Klf4.

In some embodiments, administering comprises restoring the number and M1/M2 macrophage polarization during the three phases of wound healing as compared to a matched healthy subject (e.g., a non-diabetic subject). For example, in some embodiments, administering comprises an increase in the number of M1 and M2 macrophages within the wound during the inflammatory phase of wound healing. In some embodiments, administering comprises restoring the expression of DNMT1 and/or NOX2 to a level that is comparable to the expression of DNMT1 and/or NOX2 in a matched healthy subject (e.g., a subject that does not have a wound, a subject that is not in need thereof, or a non-diabetic subject). In some embodiments, administering comprises an increase in the differentiation of HSC towards monocytes/macrophages.

Restoring the differentiation of HSC towards monocytes/macrophages in a subject may improve the capacity of the subject to accelerate the rate of wound healing (e.g., the wound closure rate), in particular minimize the expansion of a wound already present in the subject and/or decrease the risk of developing a wound in the subject. In some embodiments, the increase in HSC differentiation towards monocytes/macrophages is effective to reduce wound progression and the pathological severity of the wound. The presence of M1 macrophages within a wound causes impaired wound healing (e.g., an increased presence of M1 macrophages during the new tissue formation phase, a reduced presence of M2 macrophages during the new tissue formation phase, an increased presence of M1 macrophages in the remodeling phase, or a skewed polarization towards the M1 phenotype), which results in a pro-inflammatory environment.

In some embodiments, the methods described herein include administering a composition, e.g., a sterile composition, comprising an inhibitor of DNMT1 or NOX2 (e.g., an inhibitory nucleic acid that is complementary to DNMT1 or NOX2, or a small molecule as described herein). In some embodiments, the composition comprises one or both of a DNMT1 inhibitory nucleic acid or a NOX2 inhibitory nucleic acid. In some embodiments, the composition comprises one or both of a small molecule targeting DNMT1 or NOX2. In some embodiments, the composition comprises a let-7d-3p analogue. Inhibitory nucleic acids for use in practicing the methods described herein are described below.

Inhibitory nucleic acids have been employed as therapeutic moieties in the treatment of disease states in animals, including humans. Inhibitory nucleic acids can be useful therapeutic modalities that can be configured to be useful in treatment regimens for the treatment of cells, tissues and animals, especially humans.

For therapeutics, an animal, preferably a human, having diabetes or suspected of having diabetes, or at increased risk of developing diabetes (e.g., by virtue of family history, genetic testing, or presence of other identified risk factor), is treated by administering an inhibitor (e.g., an inhibitory nucleic acid or small molecule) in accordance with this disclosure. For example, in some embodiments, the methods comprise the step of administering to the animal in need of treatment a therapeutically effective amount of one or both of a DNMT1 inhibitory nucleic acid (e.g., a DNMT1 antisense molecule, a DNMT1 small interfering RNA, a DNMT1 small hairpin RNA, a let-7d-3p analogue) or a NOX2 inhibitory nucleic acid (e.g., a NOX2 antisense molecule, a NOX2 small interfering RNA, a NOX2 small hairpin RNA) as described herein.

In some embodiments, the methods described herein include administering a therapeutically effective amount of one or both of a small molecule targeting DNMT and/or a small molecule targeting NOX2.

Diabetes

As used herein, the term "diabetes" refers to multiple conditions generally characterized by loss of insulin regulation (American Diabetes Association, Diabetes Care January 2015, 38(Supplement 1): S8-S16). Type 1 diabetes mellitus (T1DM), also known as juvenile diabetes and autoimmune diabetes, is a chronic disease characterized by the loss or absence of pancreatic β-cells that are responsible for producing insulin (see, e.g., Katsarou et al. (2017) Nat. Rev. Dis. Primers 3: 17016). Genetic and environmental factors are believed to be involved that lead to T-cell mediated destruction of β-cell islets. T2DM, the most common form of diabetes, also known as non-insulin-dependent diabetes or adult-onset diabetes, is characterized by insulin resistance. T2DM can result from mutations in the insulin receptor (Sesti et al. (2001) Diabetes Metab. Res. Rev. 17(5): 363-373; Sesti et al. (2000) Pharmacogenomics 1(1): 49-61) and/or altered insulin receptor signaling (Folli et al. (2011) PLoS One 6(11): e28050). T2DM is most often seen in people who are obese (i.e. people who have a body mass index that is greater than 30). Another form of diabetes is gestational diabetes mellitus, also known as gestational diabetes, which causes a woman to develop diabetes during pregnancy and affects 3-9% of pregnancies (Donovan et al. (2010) Australian Prescriber 33(5): 141-144). In some diabetic subjects, diabetes is also associated with diabetic neuropathy. Diabetic neuropathy is often associated with a loss of touch and feeling in one's extremities (i.e. fingers, hands, toes and feet).

Diabetes is currently diagnosed by blood tests to determine the levels of A1C, plasma glucose (either fasting plasma glucose (FPG) or the plasma glucose determined two hours after a 75 g oral glucose tolerance test (2-h PG)). Criteria for the diagnosis of diabetes include 6.5% or greater (126 mg/dL or 7 mmol/L or greater) of hemoglobin A1c (A1C), 126 mg/dL or greater (or 7.0 mmol/L or greater) of (FPG) and/or 200 mg/dL or greater (or 11.1 mmol/L or greater) of 2-h PG. Additional T1DM can be diagnosed an autoantibody testing (Sosenko et al. (2013) Diabetes Care 36: 2615-2620; Ziegler et al. (2013) JAMA 309: 2473-2479).

One of the most common and serious complications of diabetes is poor wound healing (e.g., slower wound healing, or insufficient wound healing). Foot ulcers are the most wounds seen in diabetic subjects (Reiber et al. (1999) Diabetes Care 22: 157-162; Brem et al. (2006) Plast. Reconstr. Surg. 117: 193S-209S; Boulton et al. (2005) Lancet 366: 1719-1724). Impaired wound healing in diabetic subjects has been attributed to over 100 factors (Brem & Tomic-Canic (2007) J. Clin. Invest. 117(5): 1219-1222). For example, increased levels of glucose in the blood can cause stiffening of arteries and narrowing of blood vessels which can lead to a reduction in blood and oxygen flow to the site of the wound (Falanga (2005) Lancet 366: 1736-1743). Furthermore, diabetes affects the immune system and lowers the ability of the immune system to fight infection, and therefore makes a diabetic subject more prone and susceptible to infection (Maruyama et al. (2007) Am. J. Pathol. 170: 1178-1191). The severity of an untreated wound may also have progressed longer than typically expected as the diabetic subject can also be afflicted with diabetic neuropathy.

DNMT 1

Three families of DNA methyltransferases have been identified in mammals: DNMT1, DNMT2 and DNMT3a/b. DNMT1 has been shown to play a key role in the maintenance of DNA methylation during replication, while DNMT3a/b are known for de novo methylation (Jackson et al. (2004) Mol. Cell. Biol. 24: 8862-8871). Deletion of DNMT1 and DNMT3b respectively cause embryonic lethality in mice underscoring the importance of these enzymes in development (Li et al. (1992) Cell 69: 915-926; Okano et al. (1999) Cell 99: 247-257). Furthermore, loss of DNMT1 in human embryonic stem cells causes global demethylation and cell death (Liao et al. (2015) Nat. Genet. 47(5): 469-478). Mutations in these enzymes have been associated with several diseases including hereditary sensory neuropathy with dementia and hearing loss (Klein et al. (2011) Nat. Genet. 43: 595-600), autosomal dominant cerebellar ataxia (Winkelmann et al. (2012) Hum. Mol. Genet. 21: 2205-2210), acute myeloid leukemia (Shah et al. (2011) Nat. Genet. 43: 289-90), and immunodeficiency-centromeric instability syndrome (Jin et al. (2008) Hum. Mol. Genet. 17: 690-709).

SEQ ID NO: 1 is an exemplary sequence of human DNMT1:
ATGCCGGCGCGTACCGCCCCAGCCCGGGTGCCCACACTGGCCGTCCCGGC
CATCTCGCTGCCCGACGATGTCCGCAGGCGGCTCAAAGATTTGGAAAGAG
ACAGCTTAACAGAAAAGGAATGTGTGAAGGAGAAATTGAATCTCTTGCAC
GAATTTCTGCAAACAGAAATAAAGAATCAGTTATGTGACTTGGAAACCAA
ATTACGTAAAGAAGAATTATCCGAGGAGGGCTACCTGGCTAAAGTCAAAT
CCCTTTTAAATAAAGATTTGTCCTTGGAGAACGGTGCTCATGCTTACAAC
CGGGAAGTGAATGGACGTCTAGAAAACGGGAACCAAGCAAGAAGTGAAGC
CCGTAGAGTGGGAATGGCAGATGCCAACAGCCCCCCAAACCCCTTTCCA
AACCTCGCACGCCCAGGAGGAGCAAGTCCGATGGAGAGGCTAAGCGTTC
AAGAGACCCTCCTGCCTCAGCCTCCCAAGTAACTGGGATTAGAGCTGAAC
CTTCACCTAGCCCCAGGATTACAAGGAAAAGCACCAGGCAAACCACCATC
ACATCTCATTTTGCAAAGGGCCCTGCCAAACGGAAACCTCAGGAAGAGTC
TGAAAGAGCCAAATCGGATGAGTCCATCAAGGAAGAAGACAAAGACCAG
GATGAGAAGAGACGTAGAGTTACATCCAGAGAACGAGTTGCTAGACCGC
TTCCTGCAGAAGAACCTGAAAGAGCAAAATCAGGAACGCGCACTGAAAA
GGAAGAAGAAAGAGATGAAAAAGAAGAAAAGAGACTCCGAAGTCAAAC
CAAAGAACCAACACCCAAACAGAAACTGAAGGAGGAGCCGGACAGAGA
AGCCAGGGCAGGCGTGCAGGCTGACGAGGACGAAGATGGAGACGAGAAA
GATGAGAAGAAGCACAGAAGTCAACCCAAAGATCTAGCTGCCAAACGGA
GGCCCGAAGAAAAGAACCTGAAAAAGTAAATCCACAGATTTCTGATGA
AAAAGACGAGGATGAAAAGGAGGAGAAGAGACGCAAAACGACCCCCAA
AGAACCAACGGAGAAAAAAATGGCTCGCGCCAAAACAGTCATGAACTCC
AAGACCCACCCTCCCAAGTGCATTCAGTGCGGGCAGTACCTGGACGACCC
TGACCTCAAATATGGGCAGCACCCACCAGACGCGGTGGATGAGCCACAG
ATGCTGACAAATGAGAAGCTGTCCATCTTTGATGCCAACGAGTCTGGCTT
TGAGAGTTATGAGGCGCTTCCCCAGCACAAACTGACCTGCTTCAGTGTGT
ACTGTAAGCACGGTCACCTGTGTCCCATCGACACCGGCCTCATCGAGAAG
AATATCGAACTCTTCTTTTCTGGTTCAGCAAAACCAATCTATGATGATGA
CCCATCTCTTGAAGGTGGTGTTAATGGCAAAAATCTTGGCCCCATAAATG
AATGGTGGATCACTGGCTTTGATGGAGGTGAAAAGGCCCTCATCGGCTTC
AGCACCTCATTTGCCGAATACATTCTGATGGATCCCAGTCCCGAGTATGC
GCCCATATTTGGGCTGATGCAGGAGAAGATCTACATCAGCAAGATTGTGG
TGGAGTTCCTGCAGAGCAATTCCGACTCGACCTATGAGGACCTGATCAAC
AAGATCGAGACCACGGTTCCTCCTTCTGGCCTCAACTTGAACCGCTTCAC
AGAGGACTCCCTCCTGCGACACGCGCAGTTTGTGGTGGAGCAGGTGGAGA
GTTATGACGAGGCCGGGACAGTGATGAGCAGCCCATCTTCCTGACACCC
TGCATGCGGGACCTGATCAAGCTGGCTGGGGTCACGCTGGGACAGAGGCG
AGCCCAGGCGAGGCGGCAGACCATCAGGCATTCTACCAGGGAGAAGGACA
GGGGACCCACGAAAGCCACCACCACCAAGCTGGTCTACCAGATCTTCGAT
ACTTTCTTCGCAGAGCAAATTGAAAAGGATGACAGAGAAGACAAGGAGAA
CGCCTTTAAGCGCCGGCGATGTGGCGTCTGTGAGGTGTGTCAGCAGCCTG
AGTGTGGGAAATGTAAAGCCTGCAAGGACATGGTTAAATTTGGTGGCAGT
GGACGGAGCAAGCAGGCTTGCCAAGAGCGGAGGTGTCCCAATATGGCCAT
GAAGGAGGCAGATGACGATGAGGAAGTCGATGATAACATCCCAGAGATG
CCGTCACCCAAAAAAATGCACCAGGGGAAGAAGAAGAAACAGAACAAGA
ATCGCATCTCTTGGGTCGGAGAAGCCGTCAAGACTGATGGGAAGAAGAGT
TACTATAAGAAGGTGTGCATTGATGCGGAAACCCTGGAAGTGGGGGACTG
TGTCTCTGTTATTCCAGATGATTCCTCAAAACCGCTGTATCTAGCAAGGG
TCACGGCGCTGTGGGAGGACAGCAGCAACGGGCAGATGTTTCACGCCCAC
TGGTTCTGCGCTGGGACAGACACAGTCCTCGGGGCCACGTCGGACCCTCT
GGAGCTGTTCTTGGTGGATGAATGTGAGGACATGCAGCTTTCATATATCC
ACAGCAAAGTGAAAGTCATCTACAAAGCCCCCTCCGAAAACTGGGCCATG
GAGGGAGGCATGGATCCCGAGTCCCTGCTGGAGGGGACGACGGGAAGAC
CTACTTCTACCAGCTGTGGTATGATCAAGACTACGAGAGATTCGAGTCCC
CTCCAAAAACCCAGCCAACAGAGGACAACAAGTTCAAATTCTGTGTGAGC
TGTGCCCGTCTGGCTGAGATGAGGCAAAAAGAAATCCCCAGGGTCCTGGA
GCAGCTCGAGGACCTGGATAGCCGGGTCCTCTACTACTCAGCCACCAAGA
ACGGCATCCTGTACCGAGTTGGTGATGGTGTGTACCTGCCCCCTGAGGCC
TTCACGTTCAACATCAAGCTGTCCAGTCCCGTGAAAGCCCACGGAAGGA
GCCCGTGGATGAGGACCTGTACCCAGAGCACTACCGGAAATACTCCGACT
ACATCAAAGGCAGCAACCTGGATGCCCCTGAGCCCTACCGAATTGGCCGG
ATCAAAGAGATCTTCTGTCCCAAGAAGAGCAACGGCAGGCCCAATGAGAC
TGACATCAAAATCCGGGTCAACAAGTTCTACAGGCCTGAGAACACCCACA
GTCCACTCCAGCGAGCTACCACGCAGACATCAACCTGCTCTACTGGAGC
GACGAGGAGGCCGTGGTGGACTTCAAGGCTGTGCAGGGCCGCTGCACCGT
GGAGTATGGGGAGGACCTGCCCGAGTGCGTCCAGGTGTACTCCATGGGCG
GCCCCAACCGCTTCTACTTCCTCGAGGCCTATAATGCAAAGAGCAAAAGC
TTTGAAGATCCTCCCAACCATGCCCGTAGCCCTGGAAACAAAGGGAAGGG
CAAGGGAAAAGGGAAGGGCAAGCCCAAGTCCCAAGCCTGTGAGCCGAGCG
AGCCAGAGATAGAGATCAAGCTGCCCAAGCTGCGGACCCTGGATGTGTTT
TCTGGCTGCGGGGGGTTGTCGGAGGGATTCCACCAAGCAGGCATCTCTGA
CACGCTGTGGGCCATCGAGATGTGGGACCCTGCGGCCCAGGCGTTCCGGC
TGAACAACCCCGGCTCCACAGTGTTCACAGAGGACTGCAACATCCTGCTG
AAGCTGGTCATGGCTGGGGAGACCACCAACTCCCGCGGCCAGCGGCTGCC
CCAGAAGGGAGACGTGGAGATGCTGTGCGGCGGGCCGCCCTGCCAGGGC
TTCAGCGGCATGAACCGCTTCAATTCGCGCACCTACTCCAAGTTCAAAAA
CTCTCTGGTGGTTTCCTTCCTCAGCTACTGCGACTACTACCGGCCCCGGT
TCTTCCTCCTGGAGAATGTCAGGAACTTTGTCTCCTTCAAGCGCTCCATG
GTCCTGAAGCTCACCCTCCGCTGCCTGGTCCGCATGGGCTATCAGTGCAC
CTTCGGCGTGCTGCAGGCCGGTCAGTACGGCGTGGCCCAGACTAGGAGGC -continued
GGGCCATCATCCTGGCCGCGGCCCCTGGAGAGAAGCTCCCTCTGTTCCCG

GAGCCACTGCACGTGTTTGCTCCCCGGGCCTGCCAGCTGAGCGTGGTGGT

GGATGACAAGAAGTTTGTGAGCAACATAACCAGGTTGAGCTCGGGTCCTT

TCCGGACCATCACGGTGCGAGACACGATGTCCGACCTGCCGGAGGTGCGG

AATGGAGCCTCGGCACTGGAGATCTCCTACAACGGGGAGCCTCAGTCCTG

GTTCCAGAGGCAGCTCCGGGGCGCACAGTACCAGCCCATCCTCAGGGACC

ACATCTGTAAGGACATGAGTGCATTGGTGGCTGCCCGCATGCGGCACATC

CCCTTGGCCCCAGGGTCAGACTGGCGCGATCTGCCCAACATCGAGGTGCG

GCTCTCAGACGGCACCATGGCCAGGAAGCTGCGGTATACCCACCATGACA

GGAAGAACGGCCGCAGCAGCTCTGGGGCCCTCCGTGGGGTCTGCTCCTGC

GTGGAAGCCGGCAAAGCCTGCGACCCCGCAGCCAGGCAGTTCAACACCCT

CATCCCCTGGTGCCTGCCCCACACCGGGAACCGGCACAACCACTGGGCTG

GCCTCTATGGAAGGCTCGAGTGGGACGGCTTCTTCAGCACAACCGTCACC

AACCCCGAGCCCATGGGCAAGCAGGGCCGCGTGCTCCACCCAGAGCAGCA

CCGTGTGGTGAGCGTGCGGGAGTGTGCCCGCTCCCAGGGCTTCCCTGACA

CCTACCGGCTCTTCGGCAACATCCTGGACAAGCACCGGCAGGTGGGCAAT

GCCGTGCCACCGCCCCTGGCCAAAGCCATTGGCTTGGAGATCAAGCTTTG

TATGTTGGCCAAAGCCCGAGAGAGTGCCTCAGCTAAAATAAAGGAGGAG

GAAGCTGCTAAGGACTAG (SEQ ID NO: 1; Accession

Number: NM_001130823.2).

Inhibitory nucleic acids useful in the present methods and compositions include those that are designed to inhibit DNMT1. SEQ ID NO: 2 and SEQ ID NO: 3 are exemplary siRNA sequences that target DNMT1: sense, 5'-AAGCAUGAGCACCGUUCUCCdTdT-3' (SEQ ID NO: 2) and anti-sense, 5'-GGA GAACGGUGCUCAUGC-UUdTdT-3' (SEQ ID NO:3) (Kawasaki & Taira (2004) Nature 431: 211-217; and Fan et al. (2007) Eur. J. Gastroenterol. Hepatol. 19(11): 952-961). In some embodiments, the DNMT1 inhibitory nucleic acid comprises SEQ ID NO: 2. In some embodiments, the DNMT1 inhibitory nucleic acid is a nucleic acid comprising a sequence that is complementary to a contiguous sequence of at least 5 (e.g., at least 6, at least 7, at least 8, at least 9, at least 10, at least 11, at least 12, at least, 13, at least 14, at least 15, at least 16, at least 17, at least 18, at least 19, at least 20, at least 21, 5, 6, 7, 8, 9, 10, 11, 12, 13, 14, 15, 16, 17, 18, 19, 20, 21, or 22) nucleotides present in SEQ ID NO: 2. In some embodiments, the DNMT1 inhibitory nucleic acid comprises SEQ ID NO: 3. In some embodiments, the DNMT1 inhibitory nucleic acid is a nucleic acid comprising a sequence that is complementary to a contiguous sequence of at least 5 (e.g., at least 6, at least 7, at least 8, at least 9, at least 10, at least 11, at least 12, at least, 13, at least 14, at least 15, at least 16, at least 17, at least 18, at least 19, at least 20, at least 21, 5, 6, 7, 8, 9, 10, 11, 12, 13, 14, 15, 16, 17, 18, 19, 20, 21, or 22) nucleotides present in SEQ ID NO: 3.

Additional exemplary siRNA sequences that target DNMT1 include: sense, 5'-AGAUGACGGAUGCCUA-GAGUU-3' (SEQ ID NO: 4) and anti-sense 5'-CUCUAGG-CAUCCGUCAUCUUU-3' (SEQ ID NO: 5) (Kurita et al. (2010) Cancer Science 101(6): 1431-1439). In some embodiments, the DNMT1 inhibitory nucleic acid comprises SEQ ID NO: 4. In some embodiments, the DNMT1 inhibitory nucleic acid is a nucleic acid comprising a sequence that is complementary to a contiguous sequence of at least 5 (e.g., at least 6, at least 7, at least 8, at least 9, at least 10, at least 11, at least 12, at least, 13, at least 14, at least 15, at least 16, at least 17, at least 18, at least 19, at least 20, at least 21, 5, 6, 7, 8, 9, 10, 11, 12, 13, 14, 15, 16, 17, 18, 19, 20, 21, or 22) nucleotides present in SEQ ID NO: 4. In some embodiments, the DNMT1 inhibitory nucleic acid comprises SEQ ID NO: 5. In some embodiments, the DNMT1 inhibitory nucleic acid is a nucleic acid comprising a sequence that is complementary to a contiguous sequence of at least 5 (e.g., at least 6, at least 7, at least 8, at least 9, at least 10, at least 11, at least 12, at least, 13, at least 14, at least 15, at least 16, at least 17, at least 18, at least 19, at least 20, at least 21, 5, 6, 7, 8, 9, 10, 11, 12, 13, 14, 15, 16, 17, 18, 19, 20, 21, or 22) nucleotides present in SEQ ID NO: 5.

In some embodiments, the DNMT1 inhibitory nucleic acid is any DNMT1 inhibitory nucleic acid that decreases, reduces or silences the expression and/or activity of DNMT1. In some embodiments, the DNMT1 inhibitory nucleic acid decreases or reduces the expression and/or activity of DNMT1 to a reference level that is similar to the level of expression and/or activity of DNMT1 in a matched healthy subject (e.g., a healthy subject, a subject that does not have a wound, a non-diabetic subject).

As shown herein, DNMT1-dependent repressive modifications reduced the expression of Notch1, PU.1 and Klf4, genes that are central in the differentiation of HSCs towards monocytes/macrophages. In some embodiments, the DNMT1 inhibitory nucleic acid is any DNMT1 inhibitory nucleic acid that increases or upregulates the expression and/or activity of Notch 1, PU.1 and/or Klf4. In some embodiments, the DNMT1 inhibitory nucleic acid increases or upregulates the expression and/or activity of Notch1, P.U.1 and/or Klf4 to a reference level that is similar to the level of expression and/or activity of Notch1, P.U.1 and/or Klf4 in a matched healthy subject (e.g., a healthy subject, a subject that does not have a wound, a non-diabetic subject).

In some embodiments, the DNMT1 inhibitor is a small molecule. In some embodiments, the DNMT1 inhibitor is a nucleoside analog (e.g., 5'-azacitidine (azacitidine), Zebularine (1-(β-D-ribofuranosyl)-1,2-dihydropyrimidin-2-one) and decitabine (5-aza-2'-deoxycytidine), 4'Thio-2'-deoxycytidine (TdCyd); 5-fluoro-2'-deoxycytidine). See, e.g., Foulks et al. (2012) J Biol Screen 17: 2-17. In some embodiments, the DNMT1 inhibitor is a pro-drug (e.g., CP-4200, SGI-110 (guadecitabine). In some embodiments, the DNMT1 inhibitor is a non-nucleoside analog (e.g., procainamide, hydralazine, Curcumin, RG-108, RG-108-1; Procaine). See, e.g., Castellano et al. (2008) J Med Chem 51(7): 2321-2325; Zhu et al. (2014) Bioorganic & Med Chemistry 23(12): 2917-2927. In some embodiments, the DNMT1 inhibitor is laccaic acid A (see, e.g., Fagan et al. (2013) J Biol Chemistry 288: 23858-23867), SGI-1027, epigallocatechin-3-gallate (EGCG), MG98 (an oligonucleotide antisense inhibitor of human DNA methyltransferase 1), hydralazine, RG108 (N-Phthalyl-L-tryptophan), Chlorogenic acid, γ-Oryzanol, nanaomycin A, or SW155246 (see, e.g., Castillo-Aguilera et al. (2017) Biomolecules 7(1): 3).

Let-7d-3p

As described herein, let-7d-3p is a microRNA that recognizes DNA methyltransferase 1 (DNMT1) and binds to its 3'untranslated region (UTR) (FIG. 8C).

Inhibitory nucleic acids useful in the present methods and compositions include those that are designed to mimic let-7d-3p. See, e.g., Choo et al. (2014) J. Biomed. Sci. 21:95; Wong et al. (2016) Circulation Research 119: A54. SEQ ID NO: 6 is an exemplary mature human sequence of let-7d-3p: 5'-CUAUACGACCUGCUGCCUUUCU-3' (SEQ ID NO: 6) (miRBase accession number: MIMAT0004484). In some embodiments, the DNMT1 inhibitory nucleic acid is any let-7d-3p analogue that increases the expression or activity of let-7d-3p (e.g., mature let-7d-3p or precursor let-7d-3p). As used herein, the term "analogue" or "mimic" refers to any nucleic acid chemically modified and/or double-stranded miRNA-like RNA that has a function that is identical to mature endogenous let-7d-3p (e.g., a let-7d-3p analogue can bind to a let-7d-3p target gene (e.g., DNMT1)). In some embodiments, the 5' end of a let-7d-3p analogue is complementary to the 3' untranslated region (UTR) of a let-7d-3p target gene (e.g., DNMT1).

In some embodiments, the DNMT1 inhibitory nucleic acid is a let-7d-3p analogue. In some embodiments, the let-7d-3p analogue is a nucleic acid comprising a sequence that is at least 80% (e.g., at least 85%, at least 90%, at least 95%, 80%, 81%, 82%, 83%, 84%, 85%, 86%, 87%, 88%, 89%, 90%, 91%, 92%, 93%, 94%, 95%, 96%, 97%, 98%, 99% or 100%) identical to SEQ ID NO: 6, e.g., to the full length of SEQ ID NO:6. In some embodiments, the DNMT1 inhibitory nucleic acid is a nucleic acid comprising a sequence that is identical to a contiguous sequence of at least 7 (e.g., at least 8, at least 9, at least 10, at least 11, at least 12, at least, 13, at least 14, at least 15, at least 16, at least 17, at least 18, at least 19, at least 20, at least 21, 7, 8, 9, 10, 11, 12, 13, 14, 15, 16, 17, 18, 19, 20, 21, or 22) nucleotides present in SEQ ID NO: 6.

NOX2

Inhibitory nucleic acids useful in the present methods and compositions include those that are designed to inhibit nicotinamide adenine dinucleotide phosphate to oxidase 2 (NOX2; also known as cytochrome b-245 beta chain (CYBB)). In some embodiments, the NOX2 inhibitory nucleic acid directly targets NOX2 expression and/or activity.

```
SEQ ID NO: 7 is an exemplary sequence of human
NOX2:
ATGGGGAACTGGGCTGTGAATGAGGGGCTCTCCATTTTTGTCATTCTGGT

TTGGCTGGGGTTGAACGTCTTCCTCTTTGTCTGGTATTACCGGGTTTATG

ATATTCCACCTAAGTTCTTTTACACAAGAAAACTTCTTGGGTCAGCACTG

GCACTGGCCAGGGCCCCTGCAGCCTGCCTGAATTTCAACTGCATGCTGAT

TCTCTTGCCAGTCTGTCGAAATCTGCTGTCCTTCCTCAGGGGTTCCAGTG

CGTGCTGCTCAACAAGAGTTCGAAGACAACTGGACAGGAATCTCACCTTT

CATAAAATGGTGGCATGGATGATTGCACTTCACTCTGCGATTCACACCAT

TGCACATCTATTTAATGTGGAATGGTGTGTGAATGCCCGAGTCAATAATT

CTGATCCTTATTCAGTAGCACTCTCTGAACTTGGAGACAGGCAAAATGAA

AGTTATCTCAATTTTGCTCGAAAGAGAATAAAGAACCCTGAAGGAGGCCT

GTACCTGGCTGTGACCCTGTTGGCAGGCATCACTGGAGTTGTCATCACGC

TGTGCCTCATATTAATTATCACTTCCTCCACCAAAACCATCCGGAGGTCT

TACTTTGAAGTCTTTTGGTACACACATCATCTCTTTGTGATCTTCTTCAT

TGGCCTTGCCATCCATGGAGCTGAACGAATTGTACGTGGGCAGACCGCAG

AGAGTTTGGCTGTGCATAATATAACAGTTTGTGAACAAAAAATCTCAGAA

TGGGGAAAAATAAAGGAATGCCCAATCCCTCAGTTTGCTGGAAACCCTCC

TATGACTTGGAAATGGATAGTGGGTCCCATGTTTCTGTATCTCTGTGAGA

GGTTGGTGCGGTTTTGGCGATCTCAACAGAAGGTGGTCATCACCAAGGTG

GTCACTCACCCTTTCAAAACCATCGAGCTACAGATGAAGAAGAAGGGGTT

CAAAATGGAAGTGGGACAATACATTTTTGTCAAGTGCCCAAAGGTGTCCA

AGCTGGAGTGGCACCCTTTTACACTGACATCCGCCCCTGAGGAAGACTTC

TTTAGTATCCATATCCGCATCGTTGGGGACTGGACAGAGGGGCTGTTCAA

TGCTTGTGGCTGTGATAAGCAGGAGTTTCAAGATGCGTGGAAACTACCTA

AGATAGCGGTTGATGGGCCCTTTGGCACTGCCAGTGAAGATGTGTTCAGC

TATGAGGTGGTGATGTTAGTGGGAGCAGGGATTGGGGTCACACCCTTCGC

ATCCATTCTCAAGTCAGTCTGGTACAAATATTGCAATAACGCCACCAATC

TGAAGCTCAAAAAGATCTACTTCTACTGGCTGTGCCGGGACACACATGCC

TTTGAGTGGTTTGCAGATCTGCTGCAACTGCTGGAGAGCCAGATGCAGGA

AAGGAACAATGCCGGCTTCCTCAGCTACAACATCTACCTCACTGGCTGGG

ATGAGTCTCAGGCCAATCACTTTGCTGTGCACCATGATGAGGAGAAAGAT

GTGATCACAGGCCTGAAACAAAAGACTTTGTATGGACGGCCCAACTGGGA

TAATGAATTCAAGACAATTGCAAGTCAACACCCTAATACCAGAATAGGAG

TTTTCCTCTGTGGACCTGAAGCCTTGGCTGAAACCCTGAGTAAACAAAGC

ATCTCCAACTCTGAGTCTGGCCCTCGGGGAGTGCATTTCATTTTCAACAA

GGAAAACTTCTAA (SEQ ID NO: 7; Accession Number:

NM_000397.3)
```

In some embodiments, the NOX2 inhibitory nucleic acid is a short interfering RNA (siRNA). SEQ ID NO: 8 and SEQ ID NO: 9 are exemplary siRNA sequences that target human NOX2: 5'-GGAUACUAACCAAUAGGAUTT-3' (SEQ ID NO: 8) and 5'-AUCCUAUUGGUUAGUAUCCTT-3' (SEQ ID NO: 9) (see, e.g., Buttigieg et al. (2012) Am. J. Physiol. Lung Cell Mol. Physiol. 303(7): L598-L607).

In some embodiments, the NOX2 inhibitory nucleic acid comprises SEQ ID NO: 8. In some embodiments, the NOX2 inhibitory nucleic acid is a nucleic acid comprising a sequence that is complementary to a contiguous sequence of at least 5 (e.g., at least 6, at least 7, at least 8, at least 9, at least 10, at least 11, at least 12, at least, 13, at least 14, at least 15, at least 16, at least 17, at least 18, at least 19, at least 20, at least 21, 5, 6, 7, 8, 9, 10, 11, 12, 13, 14, 15, 16, 17, 18, 19, 20, 21, or 22) nucleotides present in SEQ ID NO: 8. In some embodiments, the NOX2 inhibitory nucleic acid comprises SEQ ID NO: 9. In some embodiments, the NOX2 inhibitory nucleic acid is a nucleic acid comprising a sequence that is complementary to a contiguous sequence of at least 5 (e.g., at least 6, at least 7, at least 8, at least 9, at least 10, at least 11, at least 12, at least, 13, at least 14, at least 15, at least 16, at least 17, at least 18, at least 19, at least 20, at least 21, 5, 6, 7, 8, 9, 10, 11, 12, 13, 14, 15, 16, 17, 18, 19, 20, 21, or 22) nucleotides present in SEQ ID NO: 9. In some embodiments, the NOX2 inhibitory nucleic acid is a short hairpin that targets NOX2. SEQ ID NO: 10-16 are exemplary human shNOX2 sequences.

```
                                                        (SEQ ID NO: 10)
TGCTGTTGACAGTGAGCGACAGTGAAGATGTGTTCAGCTATAGTGAAGCC
ACAGATGTATAGCTGAACACATCTTCACTGGTGCCTACTGCCTCGGA;

(SEQ ID NO: 11)
TGCTGTTGACAGTGAGCGCGCTCAAATAATGCTAATTGATTAGTGAAGCC
ACAGATGTAATCAATTAGCATTATTTGAGCATGCCTACTGCCTCGGA;

(SEQ ID NO: 12)
TGCTGTTGACAGTGAGCGAGCCACCAATCTGAAGCTCAAATAGTGAAGCC
ACAGATGTATTTGAGCTTCAGATTGGTGGCGTGCCTACTGCCTCGGA;

(SEQ ID NO: 13)
TGCTGTTGACAGTGAGCGACACCTAAGTTCTTTTACACAATAGTGAAGCC
ACAGATGTATTGTGTAAAAGAACTTAGGTGGTGCCTACTGCCTCGGA;

(SEQ ID NO: 14)
TGCTGTTGACAGTGAGCGCCCAGTGCGTGCTGCTCAACAATAGTGAAGCC
ACAGATGTATTGTTGAGCAGCACGCACTGGATGCCTACTGCCTCGGA;

(SEQ ID NO: 15)
TGCTGTTGACAGTGAGCGATCAACAAGAGTTCGAAGACAATAGTGAAGCC
ACAGATGTATTGTCTTCGAACTCTTGTTGAGTGCCTACTGCCTCGGA;

(SEQ ID NO: 16)
TGCTGTTGACAGTGAGCGATAAGTTCTTTTACACAAGAAATAGTGAAGCC
ACAGATGTATTTCTTGTGTAAAAGAACTTAGTGCCTACTGCCTCGGA.
```

In some embodiments, the NOX2 inhibitor is a small molecule. In some embodiments, the NOX2 inhibitor is GSK2795039 (see, e.g. Hirano et al. (2015) Antioxid Redox Signal 23(5): 358-374). In some embodiments, the NOX2 inhibitor is antioxidant N-acetyl cysteine, apocynin, diphenylene iodonium (DPI), VAS2870, ML171, ebselen, GKT136901, Phox-I1, gliotoxin, celastrol, or aminoethylbenzenesulfono-fluoride (see, e.g., Diebold et al. (2015) Antioxid Redox Signal 23(5): 375-405).

Inhibitory Nucleic Acids

The methods described herein can include the administration of inhibitory nucleic acids that hybridize specifically to DNMT1 or NOX2 to treat a wound in a subject, e.g., a wound in a diabetic subject. In some embodiments, the methods include contacting cells (e.g., HSC) with the inhibitory nucleic acids, or expressing the inhibitory nucleic acids in the cells.

A nucleic acid that "specifically" binds primarily to the target, i.e., to DNMT1 or NOX2 but not to other non-target RNAs. The specificity of the nucleic acid interaction thus refers to its function (e.g., inhibiting DNMT1 or inhibiting NOX2) rather than its hybridization capacity. Oligonucleotides may exhibit nonspecific binding to other sites in the genome or other mRNAs, without interfering with binding of other regulatory proteins and without causing degradation of the non-specifically-bound RNA. Thus this nonspecific binding does not significantly affect function of other non-target RNAs and results in no significant adverse effects. Inhibitory agents useful in the methods of treatment described herein include inhibitory nucleic acid molecules that decrease the expression or activity of DNMT1 or NOX2.

Inhibitory nucleic acids useful in the present methods and compositions include antisense oligonucleotides, siRNA compounds, single- or double-stranded RNA interference (RNAi) compounds, such as siRNA compounds, and other oligomeric compounds, or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); or a short, hairpin RNA (shRNA); or combinations thereof.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29, or 30 nucleotides in length, or any range there within.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA: DNA or RNA: RNA hybrids. Chimeric inhibitory nucleic acids of the invention may be formed as composite structures of two or more oligonucleotides, modified oligonucleotides, oligonucleosides, and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, $2^1$-O-alkyl-O-alkyl or 2'-fluoro-modified nucleotide. In other preferred embodiments, RNA modifications include 2'-fluoro, 2'-amino, and 2' O-methyl modifications on the ribose of pyrimidines, abasic residues, or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligodeoxynucleotide—the modified oligos survive intact for a longer time than unmodified oligonucleotides. Specific examples of modified oligonucleotides include those comprising modified backbones, for example, phosphorothioates, phosphotriesters, methyl phosphonates, short-chain alkyl or cycloalkyl intersugar linkages, or short-chain heteroatomic or heterocyclic intersugar linkages. Most preferred are oligonucleotides with phosphorothioate backbones and those with heteroatom backbones, particularly $CH_2$—NH—O—$CH_2$, CH~N($CH_3$)~O~$CH_2$ (known as a methylene(methylimino) or MMI backbone], $CH_2$—O—N ($CH_3$)—$CH_2$, $CH_2$—N ($CH_3$)—N ($CH_3$)—$CH_2$ and O—N ($CH_3$)—$CH_2$—$CH_2$ backbones, wherein the native phosphodiester backbone is represented as O—P—O—CH,); amide backbones (see De Mesmaeker et al., Ace. Chem.

Res. 28:366-374, 1995); morpholino backbone structures (see U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 254: 1497, 1991). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050 (each of which is incorporated by reference).

Morpholino-based oligomeric compounds are described in Braasch et al., Biochemistry 41(14):4503-4510, 2002; Genesis, volume 30, issue 3, 2001; Heasman, J., Dev. Biol., 243:209-214, 2002; Nasevicius et al., Nat. Genet. 26: 216-220, 2000; Lacerra et al., Proc. Natl. Acad. Sci. U.S.A. 97:9591-9596, 2000; and U.S. Pat. No. 5,034,506. Cyclohexenyl nucleic acid oligonucleotide mimetics are described in Wang et al., J. Am. Chem. Soc. 122, 8595-8602, 2000.

Modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439 (each of which is herein incorporated by reference).

One or more substituted sugar moieties can also be included, e.g., one of the following at the 2' position: OH, SH, $SCH_3$, F, OCN, $OCH_3$, $OCH_3O(CH_2)n$ $CH_3$, $O(CH_2)n$ $NH_2$ or $O(CH_2)n$ $CH_3$, where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2CH_2OCH_3$, also known as 2'-O-(2-methoxyethyl)] (Martin et al., Helv. Chim. Acta 78:486, 1995). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics, such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC, and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. See Kornberg, A., DNA Replication, W. H. Freeman & Co., San Francisco, 1980, pp 75-77; and Gebeyehu et al., Nucl. Acids Res. 15:4513, 1987. A "universal" base known in the art, e.g., inosine, can also be included. 5-Me-C substitutions have been shown to increase nucleic acid duplex stability by 0.6-1.2<0>C (Sanghvi, Y. S., in Crooke, S. T. and Lebleu, B., Eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science 254:1497-1500, 1991.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C), and uracil (U). Modified nucleobases comprise other synthetic and natural nucleobases, such as 5-methylcytosine (5-me-C), 5-hydroxymethyl cytosine, xanthine, hypoxanthine, 2-aminoadenine, 6-methyl, and other alkyl derivatives of adenine and guanine, 2-propyl and other alkyl derivatives of adenine and guanine, 2-thiouracil, 2-thiothymine, and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine, and 7-deazaadenine, and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., Ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines, and N-2, N-6 and 0-6 substituted purines, comprising 2-aminopropyladenine, 5-propynyluracil, and 5-propynylcytosine. 5-methylcytosine substitutions have been shown to increase nucleic acid duplex stability by 0.6-1.2° C. (Sanghvi, Crooke, and Lebleu, Eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,750,692, and 5,681,941 (each of which is herein incorporated by reference).

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. U.S.A. 86:6553-6556, 1989), cholic acid (Manoharan et al., Bioorg. Med. Chem. Lett. 4:1053-1060, 1994), a thioether, e.g., hexyl-S-tritylthiol (Manoharan et al, Ann. N. Y. Acad. Sci. 660:306-309, 1992; Manoharan et al., Bioorg. Med. Chem. Lett. 3:2765-2770, 1993), a thiocholesterol (Oberhauser et al., Nucl. Acids Res. 20, 533-538, 1992), an aliphatic chain, e.g., dodecandiol or undecyl residues (Kabanov et al., FEBS Lett. 259:327-330, 1990; Svinarchuk et al., Biochimie 75:49-54, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett. 36:3651-3654, 1995; Shea et al., Nucl. Acids Res. 18:3777-3783, 1990), a polyamine or a polyethylene glycol chain (Mancharan et al., Nucleosides & Nucleotides 14:969-973, 1995), or adamantane acetic acid (Manoharan et al., Tetrahedron Left. 36:3651-3654, 1995), a palmityl moiety (Mishra et al., Biochim. Biophys. Acta 1264: 229-237, 1995), or an octadecylamine or hexylamino-carbonyl-t oxycholesterol moiety (Crooke et al., J. Pharmacol. Exp. Ther. 277:923-937, 1996). See also U.S. Pat. Nos. 4,828,979; 4,948,882; 5,218, 105; 5,525,465; 5,541,313; 5,545,730; 5,552, 538; 5,578, 717, 5,580,731; 5,580,731; 5,591,584; 5,109,124; 5,118, 802; 5,138,045; 5,414,077; 5,486, 603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082, 830; 5,112,963; 5,214,136; 5,082, 830; 5,112,963; 5,214,136; 5, 245,022; 5,254,469; 5,258, 506; 5,262,536; 5,272,250; 5,292,873; 5,317,098; 5,371, 241, 5,391, 723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599, 928 and 5,688,941 (each of which is herein incorporated by reference).

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism, or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941 (each of which is incorporated by reference).

The inhibitory nucleic acids useful in the present methods are sufficiently complementary to the target miRNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a miRNA, then the bases are considered to be complementary to each other at that position. In some embodiments, 100% complementarity is not required. In some embodiments, 100% complementarity is required. Routine methods can be used to design an inhibitory nucleic acid that binds to the target sequence with sufficient specificity.

Inhibitory nucleic acids are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of an mRNA molecule, then the inhibitory nucleic acid and the mRNA are considered to be complementary to each other at that position. The inhibitory nucleic acids and the mRNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the inhibitory nucleic acid and the mRNA target. For example, if a base at one position of an inhibitory nucleic acid is capable of hydrogen bonding with a base at the corresponding position of a mRNA, then the bases are considered to be complementary to each other at that position. 100% complementarity is not required.

It is understood in the art that a complementary nucleic acid sequence need not be 100% complementary to that of its target nucleic acid to be specifically hybridizable. A complementary nucleic acid sequence for purposes of the present methods is specifically hybridisable when binding of the sequence to the target mRNA molecule interferes with the normal function of the target mRNA to cause a loss of expression or activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci. U.S.A. 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within a mRNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol. 215:403-410, 1990; Zhang and Madden, Genome Res. 7:649-656, 1997). Antisense and other compounds of the invention that hybridize to a mRNA are identified through routine experimentation. In general, the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2007/0191294 (siRNA analogues); US2008/0249039 (modified siRNA); and WO2010/129746 and WO2010/040112 (inhibitory nucleic acids).

Antisense

Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to DNMT1 or NOX2. Thus, oligonucleotides are chosen that are sufficiently complementary to DNMT1 or NOX2, i.e., that hybridize sufficiently well and with sufficient specificity, to give the desired effect.

siRNA

In some embodiments, the nucleic acid sequence that is complementary to a target mRNA can be an interfering RNA, including but not limited to a short interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, 2002; Lee et al., Nature Biotechnol., 20, 500-505, 2002; Miyagishi and Taira, Nature Biotechnol. 20:497-500, 2002; Paddison et al., Genes & Dev. 16:948-958, 2002; Paul, Nature Biotechnol. 20, 505-508, 2002; Sui, Proc. Natl. Acad. Sci. U.S.A., 99(6):5515-5520, 2002; Yu et al., Proc. Natl. Acad. Sci. U.S.A. 99:6047-6052, 2002.

The target RNA cleavage reaction guided by siRNAs is highly sequence specific. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general, the siRNAs must retain specificity for their target, i.e., must not directly bind to, or directly significantly affect expression levels of, transcripts other than the intended target.

Making and Using Inhibitory Nucleic Acids Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g., in vitro, bacterial, fungal, mammalian, yeast, insect, or plant cell expression systems.

Nucleic acid sequences of the invention (e.g., any of the inhibitory nucleic acids or sense nucleic acids described herein) can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. *Molecular Cloning: A Laboratory Manual.* (1989)), Coffin et al. (Retroviruses. (1997)) and "RNA Viruses: A Practical Approach" (Alan J. Cann, Ed., Oxford University Press, (2000)).

As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, herpes virus, adenovirus, adeno-associated virus, pox virus, or alphavirus. The recombinant vectors (e.g., viral vectors) capable of expressing the nucleic acids of the invention can be delivered as described herein, and persist in target cells (e.g., stable transformants).

The nucleic acids provided herein (e.g., the inhibitory nucleic acids) can be further be complexed with one or more cationic polymers (e.g., poly-L-lysine and poly(ethylenimine), cationic lipids (e.g., 1,2-dioleoyl-3-trimethylammonium propone (DOTAP), N-methyl-4-(dioleyl)methylpyridinium, and 3β-[N—(N',N'-dimethylaminoethane)-carbamoyl] cholesterol), and/or nanoparticles (e.g., cationic polybutyl cyanoacrylate nanoparticles, silica nanoparticles, or polyethylene glycol-based nanoparticles) prior to administration to the subject (e.g., injection or infusion into the cerebrospinal fluid of the subject). Additional examples of cationic polymers, cationic lipids, and nanoparticles for the therapeutic delivery of nucleic acids are known in the art. The therapeutic delivery of nucleic acids has also been shown to be achieved following intrathecal injection of polyethyleneimine/DNA complexes (Wang et al., Mol. Ther. 12:314-320, 2005). The methods for delivery of nucleic acids described herein are non-limiting. Additional methods for the therapeutic delivery of nucleic acids to a subject are known in the art.

In some embodiments, the inhibitory nucleic acids (e.g., one or both inhibitory nucleic acids targeting DNMT1 and/or inhibitory nucleic acids target NOX2) can be administered systemically (e.g., intravenously, intaarterially, intramuscularly, subcutaneously, or intraperitoneally) or intrathecally (e.g., epidural administration). In some embodiments, the inhibitory nucleic acid is administered in a composition (e.g., complexed with) one or more cationic lipids. Non-limiting examples of cationic lipids that can be used to administer one or more inhibitory nucleic acids (e.g., any of the inhibitory nucleic acids described herein) include: Lipofectamine, the cationic lipid molecules described in WO 97/045069, and U.S. Patent Application Publication Nos. 2012/0021044, 2012/0015865, 2011/0305769, 2011/0262527, 2011/0229581, 2010/0305198, 2010/0203112, and 2010/0104629 (each of which is herein incorporated by reference). Nucleic acid sequences used to practice this invention can be synthesized in vitro by well-known chemical synthesis techniques, as described in, e.g., Adams, J. Am. Chem. Soc. 105:661, 1983; Belousov, Nucleic Acids Res. 25:3440-3444, 1997; Frenkel, Free Radic. Biol. Med. 19:373-380, 1995; Blommers, Biochemistry 33:7886-7896, 1994; Narang, Meth. Enzymol. 68:90, 1994; Brown, Meth. Enzymol. 68:109, 1979; Beaucage, Tetra. Lett. 22:1859, 1981; and U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290, 2005; Koshkin et al., J. Am. Chem. Soc., 120(50):13252-13253, 1998). For additional modifications see US 2010/0004320, US 2009/0298916, and US 2009/0143326 (each of which is incorporated by reference).

Techniques for the manipulation of nucleic acids used to practice this invention, such as, e.g., subcloning, labeling probes (e.g., random-primer labeling using Klenow polymerase, nick translation, amplification), sequencing, hybridization, and the like are well described in the scientific and patent literature, see, e.g., Sambrook et al., Molecular Cloning; A Laboratory Manual 3d ed. (2001); Current Protocols in Molecular Biology, Ausubel et al., Eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, Ed. Elsevier, N.Y. (1993).

Pharmaceutical Compositions

The methods described herein can include the administration of pharmaceutical compositions and formulations comprising any one or more (e.g., two, three, four, or five) of the DNMT1 inhibitors or NOX2 inhibitors described herein (e.g., inhibitory nucleic acids targeting DNMT1, inhibitory nucleic acids targeting NOX2, DNMT1 targeting small molecules, or NOX2 targeting small molecules). In some embodiments, the compositions include one or more inhibitory nucleic acids targeting both DNMT1 and NOX2. In some embodiments, the compositions include one or more of inhibitory nucleic acids targeting DNMT1. In some embodiments, the compositions include one or more of inhibitory nucleic acids targeting NOX2. In some embodiments of any of the compositions described herein one or more of the inhibitory nucleic acids targeting DNMT1 is a let-7d-3p analogue. In some embodiments, the compositions include one or more of any DNMT1 inhibitors or NOX2 inhibitors described herein. In some embodiments, the compositions include one or more of any DNMT1 inhibitors described herein. In some embodiments, the compositions include one or more of any NOX2 inhibitors described herein. In some embodiments, the compositions include one or more of any DNMT1 inhibitors and any NOX2 inhibitors described herein. In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The inhibitors (e.g., inhibitory nucleic acids or small molecules) can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives, and antioxidants can also be present in the compositions. In some embodiments, one or more cationic lipids, cationic polymers, or nanoparticles can be included in compositions containing the one or more inhibitors (e.g., compositions containing one or more inhibitory nucleic acids targeting DNMT1 (e.g., one or more let-7d-3p analogues) and/or one or more inhibitory nucleic acids targeting NOX2; compositions containing the one or more small molecules targeting DNMT1 and/or one or more small molecules targeting NOX2).

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect.

Pharmaceutical formulations of this invention can be prepared according to any method known to the art for the manufacture of pharmaceuticals. Such drugs can contain sweetening agents, flavoring agents, coloring agents, and preserving agents. A formulation can be admixtured with nontoxic pharmaceutically acceptable excipients which are suitable for manufacture. Formulations may comprise one or more diluents, emulsifiers, preservatives, buffers, excipients, etc., and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., small molecules, inhibitory nucleic acids or sense nucleic acids described herein) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth, and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long-chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame, or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil, or coconut oil, or in a mineral oil such as liquid paraffin; or a mixture of these. See e.g., U.S. Pat. No. 5,716,928, describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin, or cetyl alcohol. Sweetening agents can be added to provide a palatable oral preparation, such as glycerol, sorbitol, or sucrose. These formulations can be preserved by the addition of an anti-oxidant such as ascorbic acid. As an example of an injectable oil vehicle, see Minto, J. Pharmacol. Exp. Ther. 281:93-102, 1997.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters, or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate, and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi, J. Clin. Pharmacol. 35:1187-1193, 1995; Tjwa, Ann. Allergy Asthma Immunol. 75:107-111, 1995). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao, J. Biomater Sci. Polym. Ed. 7:623-645, 1995; as biodegradable and injectable gel formulations, see, e.g., Gao, Pharm. Res. 12:857-863, 1995; or, as microspheres for oral administration, see, e.g., Eyles, J. Pharm. Pharmacol. 49:669-674, 1997.

In some embodiments, the pharmaceutical compounds can be parenterally administered, such as by intravenous (IV) administration or administration into a body cavity, a lumen of an organ, or into the cranium (e.g., intracranial injection or infusion) or the cerebrospinal fluid of a subject. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose, any bland fixed oil can be employed including synthetic mono- or diglycerides. In addition, fatty acids, such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate, and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitor (e.g., an inhibitory nucleic acid, a sense nucleic acid, or a small molecule) can be made by lyophilizing a solution comprising a pharmaceutical of the invention and a bulking agent, e.g., mannitol, trehalose, raffinose, and sucrose, or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5, but less than 6.5. See, e.g., US2004/0028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989.

The formulations of the invention can be administered for prophylactic and/or therapeutic treatments. In some embodiments, for therapeutic applications, compositions are administered to a subject who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to reduce the number of symptoms or reduce the severity, duration, or frequency of one or more symptoms of a neurodegenerative disorder in a subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age, and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones, J. Steroid Biochem. Mol. Biol. 58:611-617, 1996; Groning, Pharmazie 51:337-341, 1996; Fotherby, Contraception 54:59-69, 1996; Johnson, J. Pharm. Sci. 84:1144-1146, 1995; Rohatagi, Pharmazie 50:610-613, 1995; Brophy, Eur. J. Clin. Pharmacol. 24:103-108, 1983; Remington: The Science and Practice of Pharmacy, 21st ed., 2005). The state of the art allows the clinician to determine the dosage regimen for each individual patient, active agent, and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, and the like. The formulations should provide a sufficient quantity of active agent to effectively treat, prevent or ameliorate conditions, diseases, or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray, or inhalation. Actual methods for preparing parenterally or non-parenterally administrable formulations will be known or apparent to those skilled in the art and are described in more detail in such publications as Remington: The Science and Practice of Pharmacy, 21st ed., 2005.

In some embodiments, the methods described herein can include administering to a subject a therapeutically effective amount of hematopoietic stem cells (HSCs) expressing one or more of a DNMT1 inhibitory nucleic acid or a NOX2 inhibitory nucleic acid. In some embodiments, the HSCs express a let-7d-3p analogue.

Recombinant Expression Vectors, Host Cells and Genetically Engineered Cells

Described herein are methods for generating hematopoietic stem cells (HSCs) that express one or more of a DNMT1 inhibitory nucleic acid or a NOX2 inhibitory nucleic acid. In some embodiments, the HSCs expressing one or more of a DNMT1 inhibitory nucleic acid have downregulated levels of DNMT1. In some embodiments, the HSCs expressing one or more of a NOX2 inhibitory nucleic acid have downregulated levels of NOX2. The present inventors found that DNMT1 inhibition and/or NOX2 inhibition in HSCs dramatically increases the differentiation of HSCs towards monocytes/macrophages, reduces oxidant stress and increases the rate of wound healing in mice. Based on these findings, the present methods can be used to provide human HSCs expressing one or more of a DNMT1 inhibitory nucleic acid or a NOX2 inhibitory nucleic acid for wound healing by restoring DNMT1 and/or NOX2 expression levels to those of healthy subjects (e.g., a non-diabetic subject, a subject that does not have a wound). In some embodiments, the HSCs are obtained from a subject who is in need of, or who has been determined to be in need of, such treatment, i.e., the cells are autologous; alternatively, they can be allogeneic. Methods for obtaining enriched populations of HSC are known in the art and include cell sorting based on expression of one or more cell surface markers; in some embodiments, the HSC used in the present methods are CD34$^+$; in some embodiments, the cells are CD34$^+$, Thy$^{-1+}$; in some embodiments, the cells are CD34$^+$, CD59$^+$, Thy1/CD90+, CD38$^{lo/-}$, C-kit/CD117$^+$, and/or lin$^-$. For example, primary human CD34$^+$-enriched cells can be obtained from peripheral blood, e.g., after treatment of the donor with a mobilizing cytokine such as granulocyte-colony stimulating factor (GCSF). Other sources of HSC include bone marrow and umbilical cord blood. A number of methods are known in the art for preparing enriched populations of HSC, e.g., as described in Rector et al., Methods Mol Biol. 2013; 976:1-15. For example, the cells can be sorted, e.g., using columns (e.g., the MiniMACS LS+ separation columns (Miltenyi Biotec, Auburn, Calif.)), e.g., using commercially available kits, e.g., the CD34-progenitor cell isolation kit (StemCell Technologies, Vancouver, BC, Canada), according to the manufacturer's protocol. A population of cells that is enriched for HSCs is at least 20% HSC, e.g., is at least 30%, 40%, 50%, 60%, 70%, 80%, 90%, or 95% HSCs. In some embodiments, the HSCs used in the present methods are obtained by enriching for cells that are CD34$^+$; in some embodiments, the cells are obtained by enriching for cells that are CD34$^+$, Thy-1$^+$; in some embodiments, the cells are obtained by enriching for cells that are CD34$^+$, CD59$^+$, Thy1/CD90$^+$, CD38$^{lo/-}$, C-kit/CD117$^+$, lin$^-$.

Generally speaking, the HSC are engineered to express one or both of a DNMT1 inhibitory nucleic acid or a NOX2 inhibitory nucleic acid by transduction with a nucleic acid, e.g., expression vectors, containing a nucleic acid encoding a DNMT1 inhibitory polypeptide and/or a NOX2 inhibitory polypeptide described herein. As used herein, the term "vector" refers to a nucleic acid molecule capable of transporting another nucleic acid to which it has been linked and can include, e.g., a plasmid, cosmid or viral vector. The vector can be capable of autonomous replication or it can integrate into a host DNA. Viral vectors include, e.g., replication defective retroviruses, recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or CaPO$_4$ precipitation carried out in vivo.

A preferred approach for introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors can provide effective delivery of genes into cells. Whereas the transgene within a retroviral vector is typically stably integrated into the chromosomal DNA of the host, the transgene of an AAV vector usually exists as extrachromosomal episomes within the cytoplasm of infected cells. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., Current Protocols in Molecular Biology, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al. (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

Typically, an expression vector includes the nucleic acid in a form suitable for expression of the DNMT1 inhibitory nucleic acid and/or the NOX2 inhibitory nucleic acid in a HSC. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the level of expression of protein desired and whether regulated or inducible expression is desired. The expression vectors can be introduced into HSCs. The expression vector is preferably a vector suitable for expression in mammalian cells, and the expression vector's control functions can be provided by viral regulatory elements. For example, commonly used promoters are derived from polyoma, Adenovirus 2, cytomegalovirus and Simian Virus 40. See, e.g., Wang et al., Exp Hematol. 2008 July; 36(7):823-31.

In another aspect the invention provides HSC that include and optionally express a DNMT1 inhibitory nucleic acid or a NOX2 inhibitory nucleic acid described herein, e.g., a DNMT1 inhibitory nucleic acid molecule within a recombinant expression vector, a NOX2 inhibitory nucleic acid molecule within a recombinant expression vector, a DNMT1 and NOX2 inhibitory nucleic acid molecule within a recombinant expression vector, a DNMT1 inhibitory nucleic acid containing sequences which allow it to homologously recombine into a specific site of the HSC's genome, a NOX2 inhibitory nucleic acid containing sequences which allow it to homologously recombine into a specific site of the HSC's genome, or DNMT1 and NOX2 inhibitory nucleic acids containing sequences which allow it to homologously recombine into a specific site of the HSC's genome. The term HSC refers not only to the particular subject cell that is transduced but to the progeny or potential progeny of such a cell that contain the DNMT1 inhibitory nucleic acid and/or the NOX2 inhibitory nucleic acid. Because certain modifications may occur in succeeding generations due to either mutation or environmental influences, such progeny may not, in fact, be identical to the parent cell, but are still included within the scope of the term as used herein.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

In another aspect, the invention features an HSC cell or purified preparation of HSCs that express DNMT1 and/or NOX2 inhibitory nucleic acids or express DNMT1 and/or NOX2 inhibitory nucleic acids in response to a stimulus.

The methods can also include identifying, selecting, and/or purifying those cells that express one or more of a DNMT1 inhibitory nucleic acid or a NOX2 inhibitory nucleic acid, or that express one or more of a DNMT1 inhibitory nucleic acids or a NOX2 inhibitory nucleic acid over a desired level.

The HSCs expressing one or more of a DNMT1 inhibitory nucleic acid or a NOX2 inhibitory nucleic acid (e.g., one or both of a DNMT1 inhibitory nucleic acid and a NOX2 inhibitory nucleic acid) can be used for administration to a subject, can be frozen or otherwise stored for later administration to a subject, or can be maintained under conditions such that the HSC differentiate into monocytes/macrophages (see, e.g., Ko et al. (2011) PNAS 108: 14566-14571).

Monocytes can be identified by methods known in the art, e.g., by the presence of C14 and TLR2 in monocytes or CD49a (see, e.g. Daigneault et al. (2010) PLoS One 5(1): e8668; Mittar et al. (2011) BD Biosciences); macrophages can be identified by methods known in the art, e.g., by the presence of CD11b, CD11c, CD49d, CD305 or β2-μGlob (see, e.g., Mittar et al. (2011) BD Biosciences; Jablonski et al. (2015) PLoS One 10(12): e0145342; Ko et al. (2011) PNAS 108: 14566-14571; Francke et al. (2011) J Histochem Cytochem 59: 813-825; and Breslin et al. (2013) Journal of Immunological Methods, 390(1-2): 1-8). The cells can be maintained in culture until a desired number of cells, e.g., of HSC or monocytes/macrophages, is obtained, and then harvested for use or freezing. The methods can also include purifying the monocytes/macrophages away from the HSC expressing one or more of a DNMT1 inhibitory nucleic acid or a NOX2 inhibitory nucleic acid (e.g., one or both of a DNMT1 inhibitory nucleic acid or a NOX2 inhibitory nucleic acid), to provide purified populations of monocytes/macrophages.

Methods of Administering HSCs to a Subject

The methods of treating a wound or accelerating wound healing in a subject to can include administering to the subject a therapeutically effective amount of one or both of a DNA methyltransferase 1 (DNMT1) inhibitor and/or a nicotinamide adenine dinucleotide phosphate oxidase 2 (NOX2) inhibitor, as described herein.

Alternatively or in addition, the methods of treating a wound or accelerating wound healing in a subject can include providing a population of hematopoietic stem cells (HSCs); contacting the HSCs with one or both of a DNA methyltransferase 1 (DNMT1) inhibitor or a nicotinamide adenine dinucleotide phosphate oxidase 2 (NOX2) inhibitor;

and administering a therapeutically effective amount of the HSCs to the subject. In some embodiments, the HSCs express a DNMT1 inhibitory nucleic acid, e.g., express a let-7d-3p analogue (e.g., any of the let-7d-3p analogues described herein). In some embodiments of any of the methods, the DNMT1 inhibitor or NOX2 inhibitor is an inhibitory nucleic acid. In some embodiments of any of the methods, the DNMT1 inhibitory nucleic acid is a let-7d-3p analogue. In some embodiments of any of the methods, the DNMT1 inhibitor or the NOX2 inhibitor is a small molecule. In some embodiments of any of the methods, the method further includes administering a therapeutically effective amount of N-acetylcysteine (NAC) to the subject.

EXAMPLES

The invention is further described in the following examples, which do not limit the scope of the invention described in the claims.

Example 1. T2DM Reduces the Differentiation of HSCs Towards Monocytes/Macrophages and Skews Their Polarization Towards M1 Macrophages In An Hsc Autonomous Manner Animals 8-12 weeks old male C57BL/6J wild type (WT) and B6.BKS(D)-Leprd (db/db) mice were used in the studies. All mice were purchased from Jackson Laboratories and were maintained in mouse barrier facilities. Care and use of mice was in accordance with NIH guidelines and the Institutional Animal Care and Use Committee of the University of Massachusetts Medical School approved protocols. db/db and WT mice were fed standard chow diet (5.4 g/100 g diet, 0% cholesterol) and HFD mice were generated by feeding C57BL/6J mice a high fat diet (60% fat calories; Research Diet, New Brunswick, N.J.). N-acetylcysteine (NAC) was given for 8 weeks (150 mg/kg/day via drinking water).

Induction of Cutaneous Wounds

Cutaneous wounds were induced as previously described (Luo et al. (2015) Cell Stem Cell 16: 426-438). In brief, mice were anesthetized using isoflurane. The dorsal surface was shaved, washed with povidone-iodine solution and cleaned with an alcohol swab. Two wounds, one on each side of the midline, were patterned on the shaved dorsum of the mice using a sterile 6-mm punch biopsy tool (Miltex, Inc. York, Pa. 17402, U.S.A.). A silicone stent was secured around the perimeter of the wound. To improve adherence of the wound dressing, tincture benzoin was applied to the perimeter of the wound and allowed to dry. Finally, the wound was covered with a transparent, bio-occlusive dressing (Opsite, Smith and Nephew Medical Limited, Hull, England) thereby creating a moist wound chamber environment. Following surgery, the mice were placed in individual cages, and allowed to fully recover from the anesthesia. The animals were housed in the institutional animal facility.

Morphometric Analysis of Wounds

Wound closure rate was calculated by macroscopic quantification and histological analysis. For macroscopic quantification, wound photographs were taken with a Nikon camera at the indicated time points and the wound areas were measured by imageJ software. For histological analysis, 5 µm paraffin section swere stained with hematoxylin-eosin (H&E). Images were taken using a NikonEclipse 90i microscope. The distance between the epithelial tips/the edges of panniculus carnosus and granulation tissue were measured by NIS-Element AR analysis.

Immunohistochemistry of Wounds

Immunohistochemical staining was performed on 5 µm cryosections of day 7 wounds. Briefly, 5 µm cryosections were fixed either in 4% paraformaldehyde (CD144 and SMC vessels) or in acetone (F4/80 macrophages) and blocked with 5% goat serum. For macrophage staining primary antibodies, rat mAbs against F4/80 (1:40, AbD serotec MCA497G, cloneCI: A3-1), rabbit mAbs against iNOS (1:800, Novus biologicals NBP1-33780, clone: K13-A), rat mAbs against TNFα *1:10, AbD serotec MCA 1488, clone: MP6-XT22), rabbit pAbs against CD206 (1:400, Santa Cruz sc-48758), and rabbit pAbs against Arginase (1:400, Novus biologicals NBP1-32731) were used. For secondary antibodies, Alexa Fluor 488 goat anti-rat IgG (1:500, Invitrogen A11006), Alexa Fluor 555 goat anti-rat IgG (1:500, Invitrogen A21434), or Alexa Fluor 555 goat antirabbit IgG (1:500, Invitrogen A21428) were used. For vessel staining, CD144 (1:40, BD pharmingen 550548) and FITC conjugated α-smooth muscle actin (α-SMA, 1:2000, Sigma-Aldrich F3777, clone:1A4) were used. Immunofluorescent images were taken using a Zeiss microscope axiocam at ×200 magnification.

Hematopoietic Stem Cell Sorting and Transplantation

Whole bone marrow cells were flushed out from femurs and tibialis. Bone marrow cells were stained with antibodies for the identification of HSCs (c-Kit$^+$Sca1$^+$lineage$^-$CD90.1$^{lo/-}$). The antibodies used were: c-Kit (1:50, eBioscience 12-1171, clone: 2B8), Sca-1 (1:50, eBioscience 11-5981, clone: D7), CD90.1 (1:50, eBioscience 45-0900, clone:HIS51) and a lineage cocktail antibody (1:50, BD Bioscience 558074). As for the gating strategy for flow cytometry, we first gated on single, viable cells and eliminated any debris, dead cells and clumps or doublets. Next, gates were drawn on the c-Kitpositive/Sca1-positive/lineage-negative/CD90.1$^{low}$-negative population for HSC sorting. Cell sorting was performed on a MoFlow cell Sorter or FACSAria cell sorter.

To reconstitute the hematopoiesis, the recipient mice were lethally irradiated (with a split dose of 1100 Gy) and 3,000 HSCs were transplanted to each recipient by retro-orbital injection. For Lentiviral-shRNA transfected HSCs, around 10,000 cells were transplanted to each recipient.

Lentivirus Conjugated shRNA Transduction

Lentiviral-shRNA constructs were tagged with GFP and purchased from the RNAi core facility at UMASS medical school. Lentiviral particles were generated in 293T cells. Sorted HSCs were incubated with lentiviral supernatant with 8 µg/ml polybrene at 37° C. for 20-30 minutes and then spun down at 25° C., 3000 rpm for 1.5 hours. The supernatant was then replaced with lentiviral supernatant and HSC medium with 4ug/ml polybrene in 6 well plates and incubated overnight. The medium was replaced after 24 hours and the cells were cultured for an additional 1-2 days. Finally, GFP positive cells were purified by FACS sorting.

HSC Induced Differentiation Towards Macrophages

HSCs were cultured in complete RPMI 1640 medium [20% FBS, 100U/ml penicillin, 100U/ml streptomycin, 50 ug/ml beta-mercaptoethanol, 1% Glutamax (GIBCO), 1% nonessential amino acid (GIBCO), and 1% sodium pyruvate (GIBCO)] supplemented with 50 ng/ml SCF, 10 ng/ml TPO and 10 ng/ml Flt3 with either 6 ng/ml IL-3 and 10 ng/ml IL-6 or 10 ng/ml M-CSF or 40 ng/ml M-CSF (Peprotech). After 6 days, cells were induced to differentiate towards M1/M2 macrophage by changing the medium to the M1 induction medium (HSC basic medium, 5% FBS, 50 ng/mlLPS and 5 ng/ml IFNγ) or the M2 induction medium (HSC basic medium, 5% FBS, 10 ng/ml IL-4) overnight. Cells were then collected and stained with macrophage markers (F4/80 (1:50, eBioscience 12-4801, clone:BM8), CD115(1:50, eBioscience 17-1152-82, clone: AFS98), CD11b (1:50, eBioscience 45-0112-82, clone:M1/70)), M1 macrophage markers (TNFα(1:50, eBioscience 17-7321-81, clone:MP6-XT22), iNOS (1:50, BD Bioscience 610331), IL-12(1:50, eBioscience 45-7123-80, clone:C17.8)), or M2 macrophage markers (Arginase 1(1:400, Novus biologicals NBP1-32731), CD206(1:50, Biolegend 141708, clone:C068C2), IL-10(1:50, eBioscience 11-7101-82, clone:JESS-16E3)). Stained cells were run through a BD FACSCalibur flow cytometer and data were analyzed using the FlowJo software. All the cytokines were purchased from Peprotech and all the antibodies were purchased from BD Biosciences.

Macrophage Concentration and M1/M2 Macrophage Identification In Cutaneous Wounds Wound cutaneous samples were collected by 2 mm biopsy punch and minced to 2 mm$^2$ sections on ice followed by digestion with dispase (Roche, overnight at 4° C.), and hyaluronidase (Sigma) and Collagenase (Roche, 2 hours at 37° C.). Single cell suspensions (10$^6$ cells/μl) were incubated with rat anti-mouse CD16/CD32 antibody (1:50, eBioscience 14-0161-82, clone:93) at 4° C. for 15-30 minutes to minimize nonspecific staining of leukocyte Fc receptors. After incubation, cells were washed once and resuspended in FACS buffer for antibody staining. For macrophage identification, we used F4/80, CD115 and CD11b antibodies. For M1 macrophage identification, we used TNFα, iNOS and IL 12 antibodies. For M2 macrophage identification, we used Arginase 1, CD206 and IL10 antibodies. All the antibodies were purchased from BD Biosciences. Stained cells were read by BD FACSCalibur flow cytometer and data were analyzed using FlowJo software.

Quantitative Real-Time PCR

RNA was extracted from cells using RNAqueous Micro Kit as directed by the manufacturer (Ambion). cDNA synthesis was performed using Superscript III reverse transcriptase as directed by the manufacturer (Invitrogen). Quantitative Real Time PCR (qRT-PCR) was performed using SYBR Green Mix (Bio-Rad) on an Eppendorf Master Cycler. Primers are listed in Tables 1 and 2.

TABLE 1

Mouse primers used for quantitative real time PCR

| | Dnmt 1 | SEQ ID NO: |
|---|---|---|
| Forward Primer (5'-3') | CACCTAGACGACCCTAACCTG | 17 |
| Reverse Primer (5'-3') | AGGTGGAGTCGTAGATGGACA | 18 |
| | Dnmt 3a | |
| Forward Primer (5'-3') | AGCGTCACACAGAAGCATATC CAGGAG | 19 |
| Reverse Primer (5'-3') | GGCCAGTACCCTCATAAAGTC CCTTGC | 20 |
| | Dnmt 3b | |
| Forward Primer (5'-3') | ATGGAATTGCAACGGGGTAC TTGGTGC | 21 |
| Reverse Primer (5'-3') | CTGGCCTTCATGCTTAACAGT TCCCAC | 22 |
| | Notch 1 | |
| Forward Primer (5'-3') | ATGCTGCTGTTGTGCTCCT | 23 |
| Reverse Primer (5'-3') | CAGTCTCATAGCTGCCCTCAC | 24 |
| | PU.1 | |
| Forward Primer (5'-3') | CCTCAGTCACCAGGTTTCC TACA | 25 |
| Reverse Primer (5'-3') | CTCTCACCCTCCTCATCTG | 26 |
| | Klf4 | |
| Forward Primer (5'-3') | CGGATCCGATGAGGCAGCCAC CTGGC | 27 |
| Reverse Primer (5'-3') | CGACGCGTGCAAAGTGCCTCT TCATGTGTAAG | 28 |

TABLE 2

Human primers used for quantitative real time PCR

| | Dnmt 1 | SEQ ID NO: |
|---|---|---|
| Forward Primer (5'-3') | TACCTGGACGACCCTGACCTC | 29 |
| Reverse Primer (5'-3') | CGTTGGCATCAAAGATGGACA | 30 |
| | Notch 1 | |
| Forward Primer (5'-3') | CACCCATGACCACTACCCAGTT | 31 |
| Reverse Primer (5'-3') | CCTCGGACCAATCAGAGATGTT | 32 |
| | PU.1 | |
| Forward Primer (5'-3') | GAGAAATAACTTTAGGGGACC ATGT | 33 |
| Reverse Primer (5'-3') | ATTGATTCATTCATTCAGGAAA TGT | 34 |
| | Klf4 | |
| Forward Primer (5'-3') | GGCGGGCTGATGGGCAAGTT | 35 |
| Reverse Primer (5'-3') | TGCCGTCAGGGCTGCCTTTG | 36 |
| | 18S | |
| Forward Primer (5'-3') | GTAACCCGTTGAACCCCATT | 37 |
| Reverse Primer (5'-3') | CCATCCAATCGGTAGTAGCG | 38 |

Western Blot Analysis

Cells were homogenized in lysis buffer (50 mM N-2-hydroxyethylpiperazine-N'-2-ethanesulfonic acid [pH 7.5], 150 mM magnesium chloride, 1 mM ethylenediaminetetraacetic acid, 100 mM sodium chloride, 1% NP40). Protein extracts underwent sodium dodecyl sulfate polyacrylamide gel electrophoresis (SDS-PAGE) and were transferred to a nitrocellulose membrane. The membrane was blocked with 5% milk for 1 hour at RT followed by incubation with one of the following primary antibodies overnight at 4° C.: Dnmt1 (1:1000, Sigma D4567), Dnmt3a (1:1000, ThermoFisher MA1-91490, clone:64B814), Dnmt3b (1:1000, ThermoFisher Scientific PA1-884), and α-tubulin (1:5000, Sigma T6074, clone:B-5-1-2). Following washes, membranes were incubated with a specific horseradish peroxidase-conjugated secondary antibody which include anti-mouse IgG (1:3000, Promega W4021) and anti-rabbit IgG (1:3000, Promega W4011) for 1 h at room temperature and proteins were visualized by incubation with ECL (ThermoFisher Scientific). Quantification was performed using ImageJ software.

Pyrosequencing

Genomic DNA was isolated by traditional phenol-chloroform extraction and isopropanol precipitation. DNA concentration was measured using a Nano Drop spectrophotometer. Around 500 ng genomic DNA were bisulfite converted by EZ DNA methylation-Gold kit following the manufacturer's instructions (Zymo Research). PCR amplification was performed using 2×HiFi Hotstart Uracil+ready mix PCR (Kapa Biosystems). PCR and pyrosequencing primer sets with one biotin-labeled primer were used to amplify the bisulfite converted DNA. Primers were designed using PyroMark Assay Design software version 2.0.1.15 (Qiagen). The size of the amplicons was 200 bp or less. Briefly, 5 μl master mix, 5 μmol of each primer, 20 ng genomic DNA and ultra-pure water to a final volume of 10 μl were mixed for each reaction and run at thermal cycling conditions: 95° C. for 3 min and then 50 cycles: 20 sec at 98° C.; 15 sec at the optimized primer-specific annealing temperature; 15 sec at 72° C. and a final extension for 1 min at 72° C. The amplified DNA was confirmed by electrophoresis on a 2% agarose gel. 2 μl streptavidin beads (GE Healthcare, Buckinghamshire, UK), 40 μl PyroMark binding buffer, 10 μl PCR product and 28 μl water were mixed and incubated for 10 min on a shaking platform at 1300 rpm. Using the Biotage Q96 Vaccum Workstation, amplicons were separated, denatured, washed and added to 25 μl annealing buffer containing 0.33 μM of pyrosequencing primer. Primer annealing was performed by incubating the samples at 80.0 for 2 min and allowed to cool to room temperature prior to pyrosequencing. PyroGold reagents were used for the pyrosequencing reaction and the signal was analyzed using the PSQ 96MA system (Biotage, Uppsala, Sweden). Target CGs were evaluated by instrument software (PSQ96MA 2.1), which converts the pyrograms to numerical values for peak heights and calculates the methylation at each base as a C/T ratio. Primers are listed in Table 3.

TABLE 3

List of primers used for pyrosequencing

| | Notch 1 | SEQ ID NO: |
|---|---|---|
| Forward Primer (5'-3') | GAAGGTAGGGGTTTTGTTT TGATA | 39 |
| Reverse Primer (5'-3') | CCTTCCCCCAAACTTAAAA TACT | 40 |
| Sequencing Primer | AGGGGTTTTGTTTTGATAA | 41 |

Amplicon size: 147 basepairs (bp)

| | PU.1 | |
|---|---|---|
| Forward Primer (5'-3') | TTGGTTTTTTTATAGATTATT ATTGGGATT | 43 |
| Reverse Primer (5'-3') | AACCAACAACACACACCTA ATA | 44 |
| Sequencing Primer | TTTTATAGATTATTATTGGG ATTTT | 45 |

Amplicon size: 222 bp

| | KLF4 | |
|---|---|---|
| Forward Primer (5'-3') | GGGGATTTGTGATTGTATT GG | 46 |
| Reverse Primer (5'-3') | ATCCCTAAAAACCCATTTAA AC | 47 |
| Sequencing Primer | GTAGGAAAGGAGGGTA | 48 |

Amplicon size: 238 bp

ChIP-PCR

1×10⁶ HSCs were sorted and cross-linked with 1% formaldehyde at room temperature for 10 min, and the reaction was stopped by adding Glycine to a final concentration of 0.125M and incubating at room temperature for 5 min. Cross-linked cells were lysed in lysis buffer and sonicated to 200-500 bp fragments (Bioruptor, Diagenode). The sonicated chromatin was centrifuged at 4° C. for 5 min. The cross-linked DNA was immunoprecipitated with H3K9me3, H3K9me2 or H3K9Ac antibodies (Millipore, USA) overnight at 4° C. with rotation, DNA-Antibody complexes were bound to ChIP beads, pulled down, washed and then eluted from the beads. Following reversal of cross-linkage, purified DNA was used for quantitative PCR using ChIP PCR primers purchased from IDT (MA, USA). Immunoprecipitation efficiency was calculated by normalizing sample CT values against control IgG values and calculating ratios of sample CT values relative to input values. Primers are listed in Table 4.

TABLE 4

List of primers used for ChIP-qPCR

| | Notch 1 | SEQ ID NO: |
|---|---|---|
| Forward Primer (5'-3') | GCTGAGTCACTGCAAAAGCC | 49 |
| Reverse Primer (5'-3') | AAGAAAAGGATGCAGGGCCT C | 50 |

| | PU.1 | |
|---|---|---|
| Forward Primer (5'-3') | GATGGGCTGGAGAGATGAGC | 51 |

TABLE 4-continued

List of primers used for ChIP-qPCR

| | |
|---|---|
| Reverse Primer (5'-3') | TCCCCTCCCAGCTAAGTACC 52 |
| KLF4 | |
| Forward Primer (5'-3') | ACTCGAGAGCGCGATTATCC 53 |
| Reverse Primer (5'-3') | GGCCGCTCTCTTTCATAGCA 54 |

MiRNA Microarray Expression Profiling

HSCs were isolated as described. Total RNA was isolated using the mirVana miRNA isolation kit according to the manufacturer's instructions (Applied Biosystems). RNA quality and quantity were analyzed using a NanoDrop ND-1000 spectrophotometer and a PicoRNA kit (Invitrogen). miRNA expression was measured by Affymetrix miRNA 3.0 array (Affymetrix, Santa Clara, Calif., USA). The sample labeling, microarray hybridization and washing were performed based on manufacturer's standard protocols. Briefly, total RNA were tailed with Poly A and then labeled with Biotin. Afterwards, the labeled RNAs were hybridized onto the microarray. The slides were washed and stained and the arrays were scanned by the Affymetrix Scanner 3000 (Affymetrix). The scanned images were analyzed using Expression Console software (version 1.3.1 Affymetrix). The CEL files generated from the assays were analyzed with the Affymetrix Expression Console Software. The data discussed in this study have been deposited in NCBI's Gene Expression Omnibus which is accessible through the GEO series accession number GSE89842. Based on our microarray results and a review of the literature, candidate miRNAs were chosen for further validation with qRT-PCR. All experiments were conducted in the Genomic Core Facility of the University of Massachusetts Medical School.

qRT-PCR Analysis of MicroRNA Expression

Total RNA was isolated using the mirVana miRNA isolation kit (Applied Biosystems). cDNA was synthesized using the QuantiMir RT Kit small RNA quantification system (SBI). qRT-PCR was performed as described previously. Mouse U6 was used as an endogenous control. The let-7d-3p mimic and inhibitor were purchased from Life Technologies (catalog numbers 4464066 and 4464084, respectively).

miRNA Target Prediction

The predicted target genes of differentially expressed miRNAs were obtained using the following tools: TargetScan v6.2, miRDB and Affymetrix Expression Console Software. The search was performed on the 3'-UTR regions of target mRNAs with a p value of 0.05 defining the probability distribution of random matches set in the software with a minimum miRNA seed length of 7.

mRNA 3'-UTR Cloning and Luciferase Reporter Assay

HEK293T cells grown in 96-well plates were transfected with pmirGLO containing the Dnmt1 3' UTR region that includes the let-7d-3p binding sites. The cells were co-transfected with let-7d-3p using Lipofectamine (Invitrogen). The Firefly and Renilla luciferase activities in the cell lysates were assayed with a Dual-Luciferase Reporter Assay System (Promega) at 48 h post-transfection. To generate the mutant variants, point mutations in the binding sites of let-7d-3p in the 3'-UTR region of Dnmt1 were introduced by PCR according to the site-directed mutagenesis protocol from Agilent. The two mutants that were generated are labeled "Dnmt1 M1" and "Dnmt1 M2". The binding sequence of let-7d-3p in mouse Dnmt1 3'UTR is:

(SEQ ID NO: 55)
TGCTCTCACCCAGAGCCCCACGTGCACTGATGTTTTTAACCCTTTGAGCC

CCATCATTTGAAGTCTTGTGCTCAGTGTCTGTGGCCATGGCTGACACTAA

GCTGTTTGTATGAGGTTTGTTTTGTGACCAAGCTGTGTAGTACTTTGTGC

ATTCTGAATTTTAAGGTTTTTTTTTTGTTTGGTTTGGTTTGGTTTGGTT

TTTTTCTTATCCTGTATTCTATCAGATCTGCCACTGTGCAGGTGGCAAGT

GAGACTTGATGTAGTTTTATATGTTGTAATATTTCTTCAAAATAAAGCGC

TTCTGTCAAGCACCC.

Analysis of Intracellular ROS by DCF-DA Staining

Cells were resuspended in phosphate-buffered saline (PBS) and incubated with 5 μM DCF-DA (Sigma) for 30 min at 37 degrees in the dark. Cells were then washed twice with PBS and analyzed on a BD FACSCalibur analyzer (excitation wavelength 492-495 nm; emission wavelength 517-527 nm). The resulting data was analyzed using FlowJo software.

Dot Blotting

Dot blotting was performed following the method described in Hainer et al. (Elife 5, e21964 (2016)). Briefly, serial dilutions of genomic DNA starting at 300 ng were denatured at 95° C. for 10 min, then put on ice immediately for 10 min. Denatured DNA samples were spotted onto Amersham Hybond N+nylon membrane (GE Healthcare, Uppsala, Sweden) and the membranes were UV crosslinked. The membrane was incubated in 0.1% SDS overnight, blocked with 5% nonfat milk and 3% BSA for 2 h, incubated with anti-5mC (1:1000, Eurogentec BI-MECY, RRID: AB 2616058) for 1 h, washed three times with PBS-T, incubated with HRP conjugated anti-mouse secondary (1:10,000, Bio-Rad, Hercules, Calif., USA, 170-6516, RRID: AB 11125547) for 1 h, washed three times with PBS-T, and detected with enhanced chemiluminescence. For loading, gDNA samples were diluted simultaneously, spotted directly onto Amersham Hybond N+nylon membrane (GE Healthcare) and the membranes were UV crosslinked. Membranes were incubated with 0.2% methylene blue for 5 min and washed five times with water.

Human HSCs

Fresh whole human bone marrow was purchased from ALL Cells (1301 Harbor Bay Pkwy #200, Alameda, Calif. 94502). Mononuclear cells were isolated with Ficoll-Paque PLUS (1.077 density) and CD34+ cells were sorted and cultured in RPMI 1640 supplemented with cytokines (50 ng/ml SCF, 50 ng/ml Flt3, 20 ng/ml TPO, 20 ng/ml IL-3, 20 ng/ml IL-6) with or without 174 nM (equal to 1.0 ug/ml) insulin. For induced differentiation towards macrophages, $1.0 \times 10^5$ HSCs were seeded in 6-well plates with 1.5 ml medium containing 25 ng/ml M-CSF for 3 days. Fresh medium was added every other day. For M1/M2 differentiation, on day 3, cells were washed with PBS and RPMI1640 containing 5% FBS, 1% PS, 100 ng/ml IFNγ (for M1) or 10 ng/ml IL-4 and IL-13(for M2) was added for 24 hours. The human macrophage markers used are: CD68(1:50, eBioscience 12-0689-41, clone:eBioY1/82 A), CD14(1:50, eBioscience 11-0149-42, clone:61D3), CD206(1:50, eBioscience 12-2069-41, clone:19.2), CD163 (1:50, eBioscience 17-1639-41, clone:eBioGHI/61).

Statistical Analysis

All data are shown as means±SEM. Statistical analyses were carried out with GraphPad Prism (GraphPad Software) software. Statistical significance was evaluated by using a one-way analysis of variance (ANOVA) or an unpaired t-test. Significance was established for p values of at least <0.05.

Figure 1A:
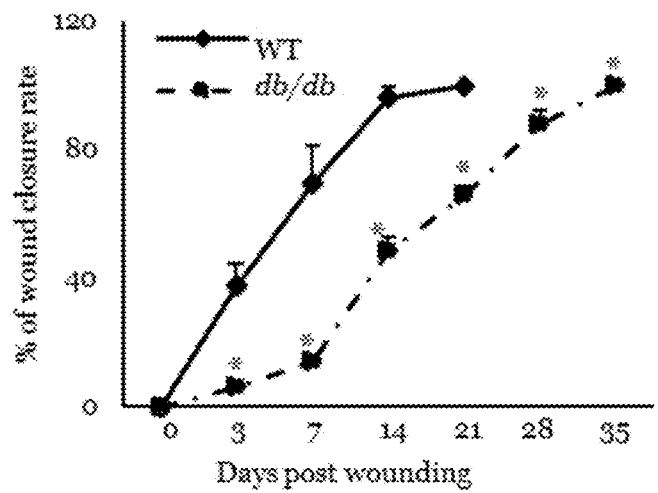
FIG. 1A: Wound closure rate measurement (n=8; *, p<0.05 vs wild type (WT)). Results are expressed as means±SEM. Two-tailed unpaired student's t-test was used.
Figure 1B:
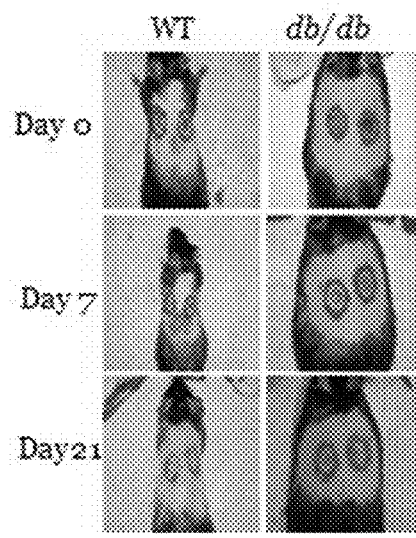
FIG. 1B: Representative wounding images of wild-type and B6.BKS(D)-Lepr$^{db}$/J (db/db) mice.
Figure 1C:
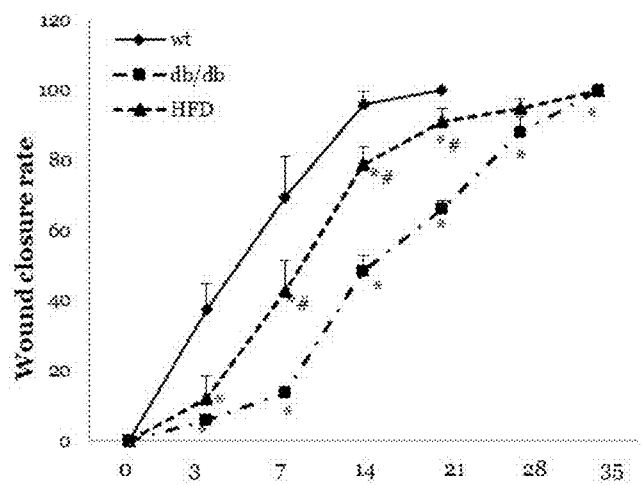
FIG. 1C: Wound closure rate measurement (n=8.*, p<0.05 vs WT; #, p<0.05 vs. db/db). Results are expressed as means±SEM. One way ANOVA was used.
Figure 1D:
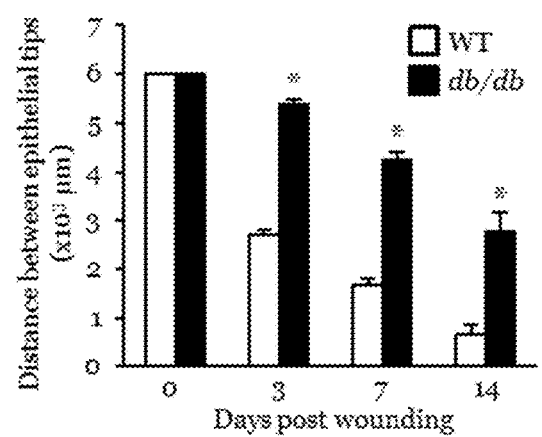
FIG. 1D: Histological quantification of distance between epithelial tips (n=4, *, p<0.05 vs WT). Results are expressed as means±SEM. Two-tailed unpaired student's t-test was used.

Diabetes impairs wound healing making patients with T2DM susceptible to chronic non-healing wounds that often culminate in limb amputations (Guo & Dipietro (2010) *J Dent. Res.* 89: 219-29). As shown herein, wound closure rates in T2D mice (db/db mice or in WT mice fed high fat diet (HFD)) were significantly slower than those in WT mice (FIGS. 1A-C). Histological analysis revealed a longer distance between epithelial tips and a longer distance between the edges of the panniculus carnosus in T2D wound tissues at days 3, 7 and 14 after wound induction (FIGS. 1D-F), suggesting that the re-epithelialization and wound contraction were significantly impaired in T2D mice. Furthermore, the wound tissues from T2D mice showed much less granulation tissue, resulting in a thinner and more fragile epithelium (FIGS. 1F-G). Revascularization was also reduced in the wounds of T2D mice, as measured by artery and total vessel density (FIGS. 1H-J). These results indicate that wound healing kinetics are significantly impaired in T2D mice.

Figure 2E:
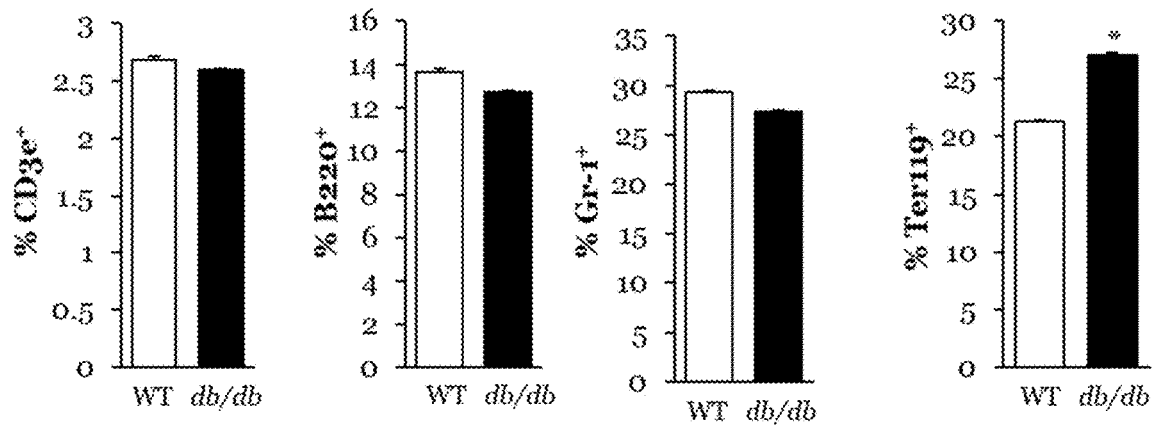
FIG. 2E: Quantification of cell lineages (CD3e$^+$ cells, B220$^+$ cells, Gr-1$^+$ cells, Ter119$^+$ cells) in the bone marrow of WT and db/db Type 2 diabetic mice by flow cytometry (n=6; *, p=0.05 vs. WT). Results are expressed as means±SEM. Two-tailed unpaired student's t-test was used.
Figure 2F:
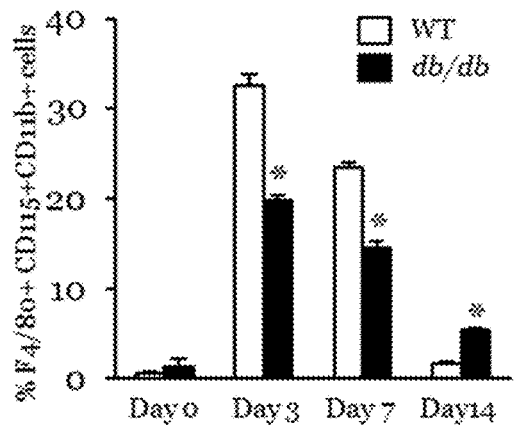
FIG. 2F: Quantification of F4/80$^+$CD115$^+$CD11b$^+$ macrophage concentration in the cutaneous wounds on day 0, day 3, day 7 and day 14 by flow cytometry (n=6, *, p<0.05 vs WT). Results are expressed as means±SEM. Two-tailed unpaired student's t-test was used.
Figure 2G:
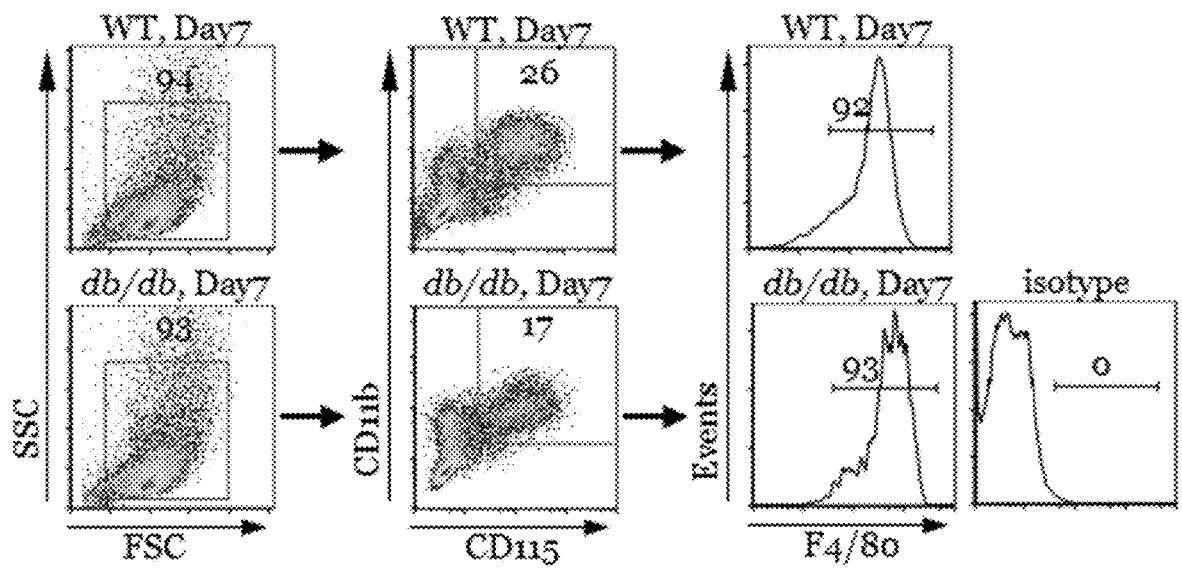
FIG. 2G: Schematic of flow cytometry gating for F4/80$^+$CD115$^+$CD11b$^+$ macrophages in WT and db/db mice.
Figure 2H:
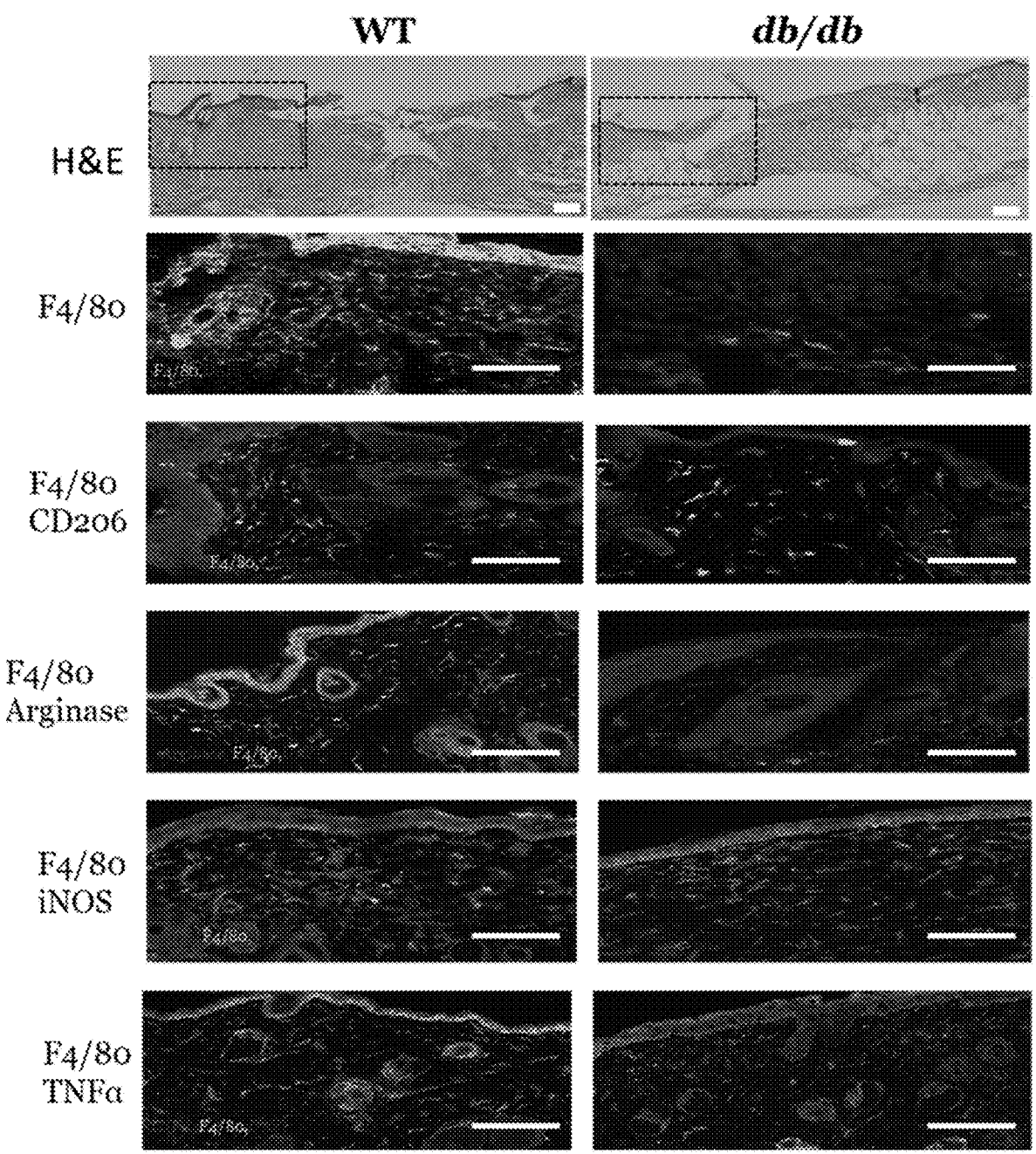
FIG. 2H: Histological and immunohistochemical staining of day 7 wound from WT and db/db mice. Marked area in H&E images are the locations for macrophage staining images. Magnification ×40 in H&E staining and Magnification ×200 in macrophage staining. Scale bar 100 μm.

Monocytes and macrophages are the major cellular components that promote wound healing. Both the proportion and absolute number of $CD115^+CD11b^+$ monocytes was significantly reduced in the bone marrow of db/db and HFD mice (FIGS. 2A-D). Other terminally differentiated blood cells derived from hematopoietic cells were measured. With the exception of an increase in red blood cells, T cells, B cells, and granulocytes numbers were not significantly different in db/db mice (FIG. 2E). After induction of cutaneous wounds, total macrophage infiltration in db/db mice was significantly lower on day 3 (inflammatory phase) and day 7 (new tissue formation phase), but significantly greater on day 14 (tissue remodeling phase) than in WT mice (FIGS. 2F-H).

Figure 3B:
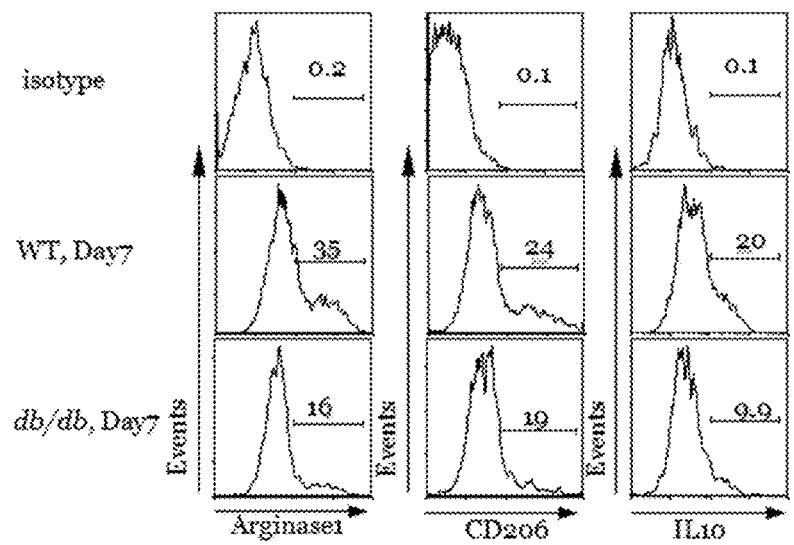
FIG. 3B: Schematic of flow cytometry gating of M2 macrophages (Arginase 1, CD206, IL10).
Figure 3C:
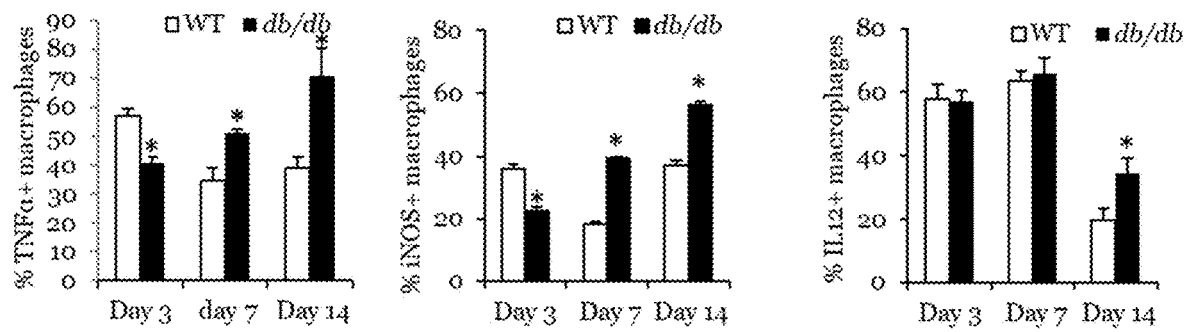
FIG. 3C: Quantification of M1 macrophage concentrations in wounds on days 3, 7, and 14 (n=6, *, P<0.05 vs WT). Results are expressed as means±SEM. Two-tailed unpaired student's t-test was used.
Figure 3D:
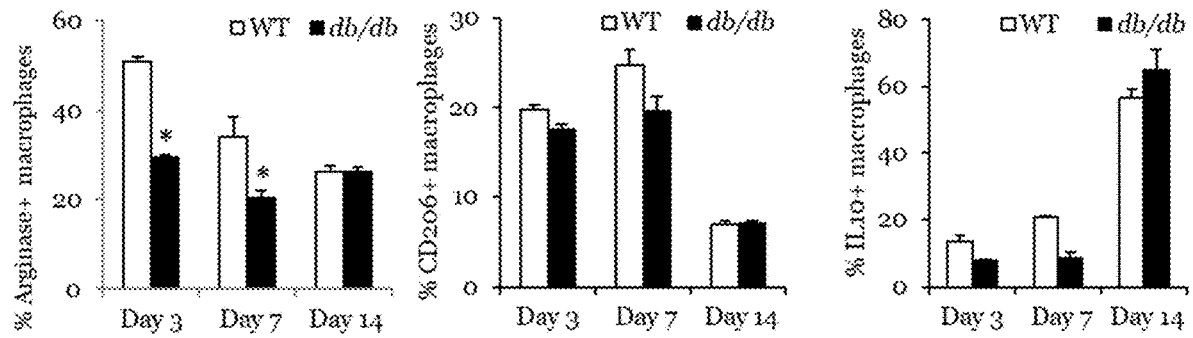
FIG. 3D: Quantification of M2 macrophage concentrations in wounds on days 3, 7 and 14 14 (n=6, *, P<0.05 vs WT). Results are expressed as means±SEM. Two-tailed unpaired student's t-test was used.
Figure 3E:
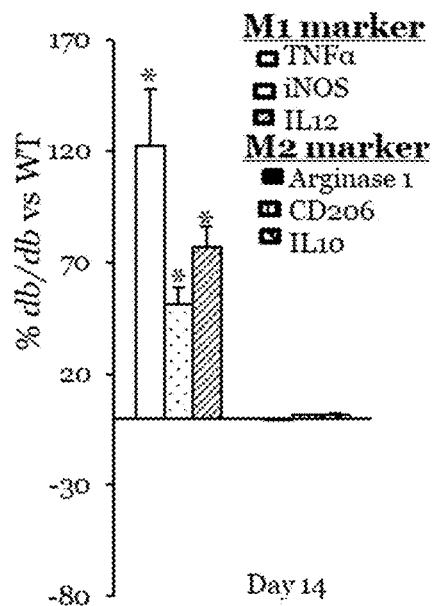
FIG. 3E: Quantification of M1/M2 polarization in the cutaneous wounds on day 14 by flow cytometry (n=6, *, p<0.05 vs WT). Results are expressed as means±SEM. Two-tailed unpaired student's t-test was used.
Figure 4A:
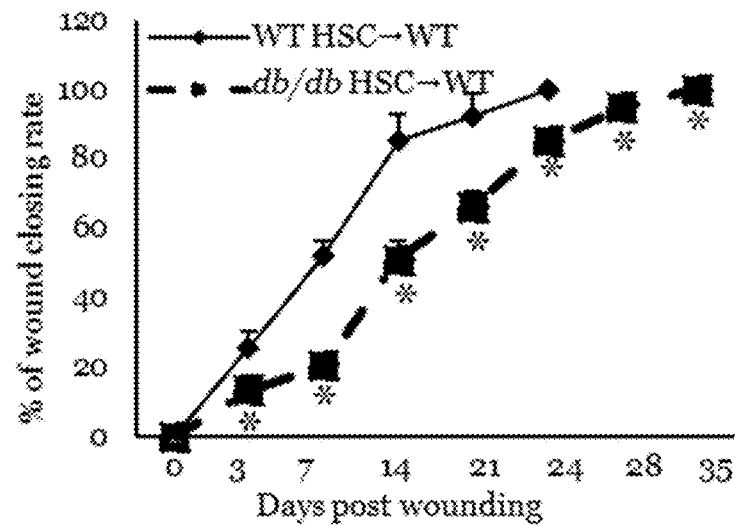
FIG. 4A: Wound closure rate measurement of WT HSC transplanted into WT mice and db/db HSC transplanted into WT mice (n=8, *, p<0.05 vs WT HSC→WT). Results are expressed as means±SEM. Two-tailed unpaired student's t-test was used.
Figure 4B:
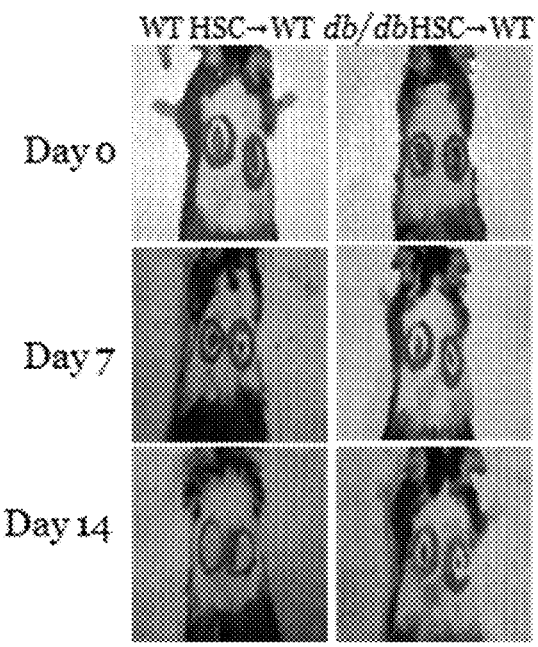
FIG. 4B: Representative images of wound closure in WT mice transplanted with WT HSC or db/db HSC on days 0, 7 and 14.
Figure 4C:
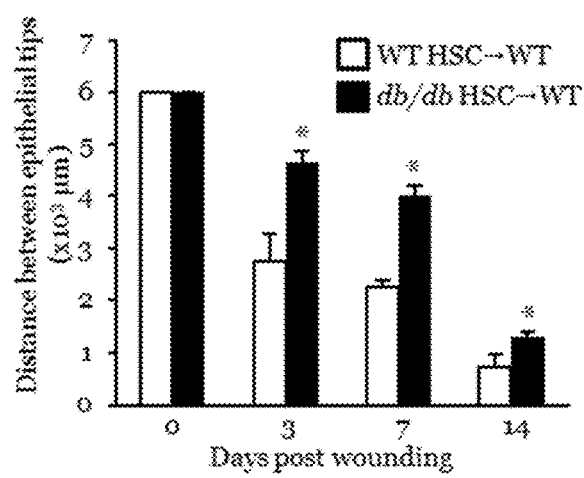
FIG. 4C: Histological quantification of distance between epithelial tips in WT HSC transplanted into WT mice and db/db HSC transplanted into WT mice on days 0, 3, 7 and 14 post-wounding (n=4, *, p<0.05 vs WT HSC→WT). Results are expressed as means±SEM. Two-tailed unpaired student's t-test was used.
Figure 4D:
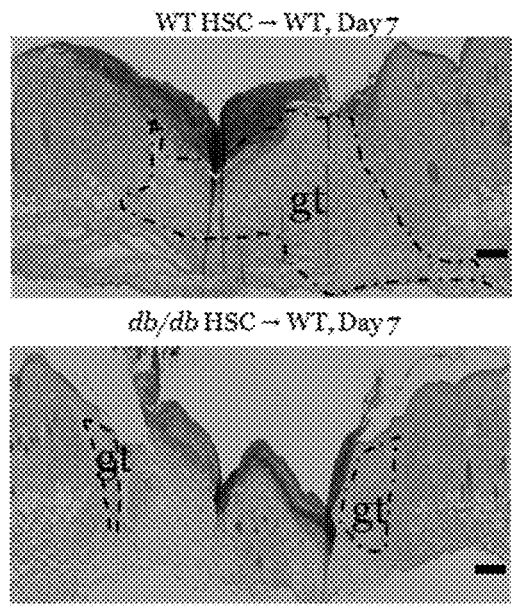
FIG. 4D: Representative H&E staining wound images on day 7, magnification ×40. Scale bar, 100 μm. gt, granulation tissue. Results are expressed as means±SEM. Two-tailed unpaired student's t-test was used.
Figure 4E:
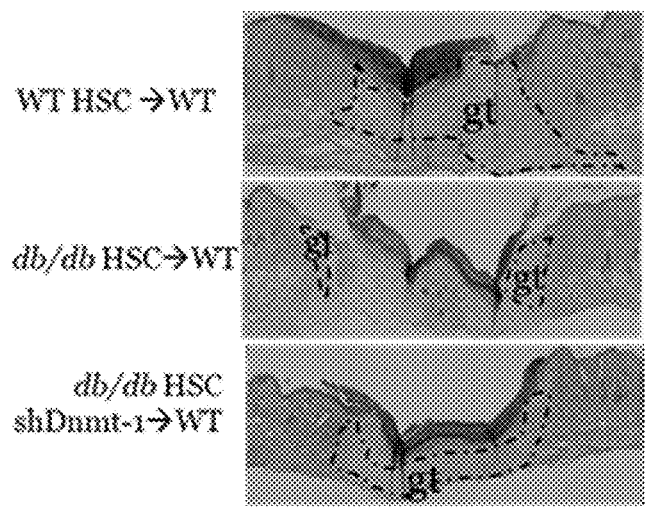
FIG. 4E: Representative H&E staining images on day 7 post-wounding in WT mice transplanted with WT HSC, WT mice transplanted with db/db HSC and WT mice transplanted with db/db HSC expressing shDnmt1 (scale bar, 100 μm). gt: granulation tissue.
Figure 4F:
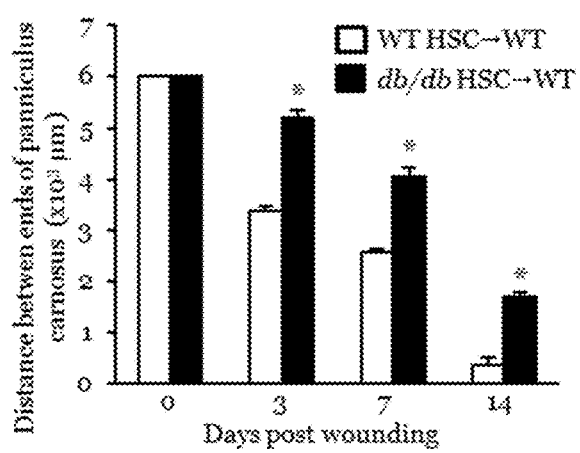
FIG. 4F: Histological quantification of distance between ends of panniculus carnosus in WT HSC transplanted into WT mice and db/db HSC transplanted into WT mice on days 0, 3, 7 and 14 post-wounding (n=4, *, p<0.05 vs WT HSC→WT).
Figure 4G:
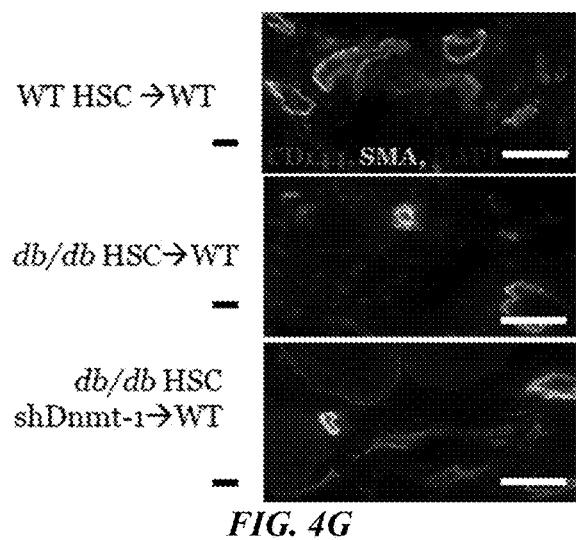
FIG. 4G: Representative images of CD44 and SMA staining in WT mice transplanted with WT HSC, WT mice transplanted with db/db HSC and WT mice transplanted with db/db HSC expressing shDnmt1. Magnification ×200; scale bar, 100 μm (n=4).
Figures 4H, 4I:
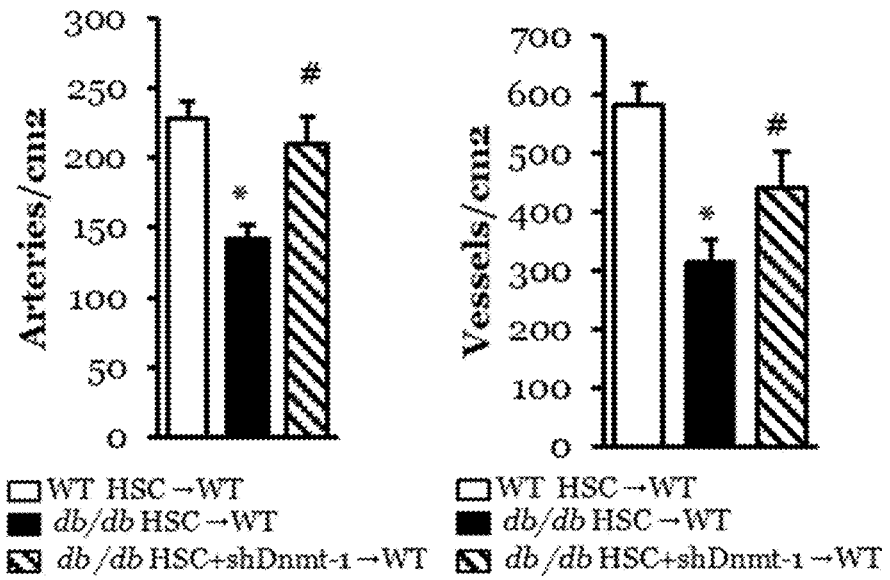
FIG. 4H: Quantification of arteries by CD144 and SMC double positive staining (n=4, *, p<0.05 vs WT HSC→WT, #, p<0.05 vs db/db HSC→WT).
FIG. 4I: Quantification of vessels by CD144 (n=4, *, p<0.05 vs WT HSC→WT, #, p<0.05 vs db/db HSC→WT).
Figures 4J, 5A:
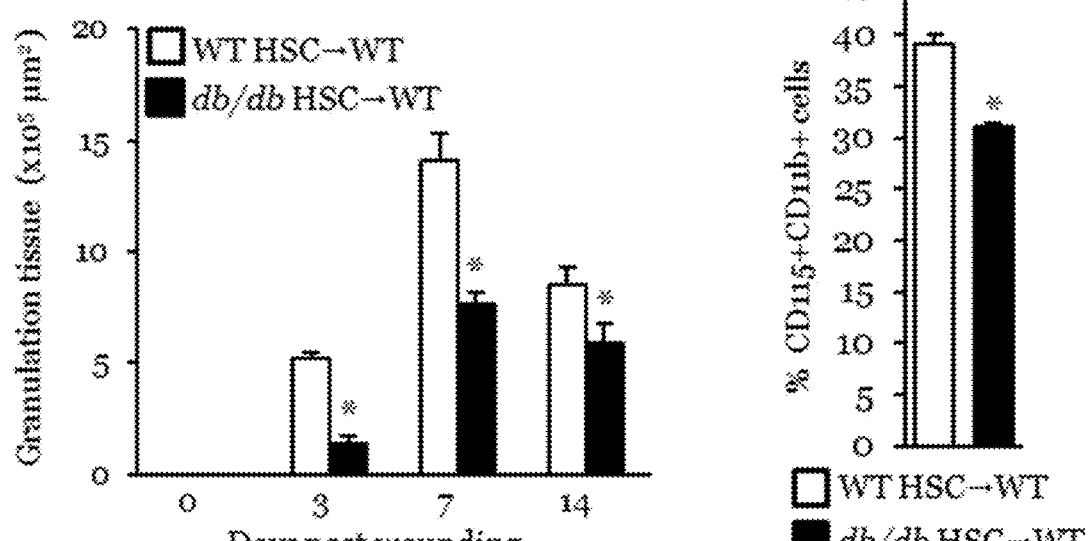
FIG. 4J: Histological quantification of distance between granulation tissue on day 0, 3, 7 and 14 post-wounding (n=4, *, p<0.05 vs WT HSC→WT).
FIG. 5A: Quantification of CD115$^+$CD11b$^+$ monocytes concentration in bone marrow by flow cytometry (n=6, *, p<0.05 vs WT HSC→WT). Results are expressed as means±SEM. Two-tailed unpaired student's t-test was used.
Figure 5B:
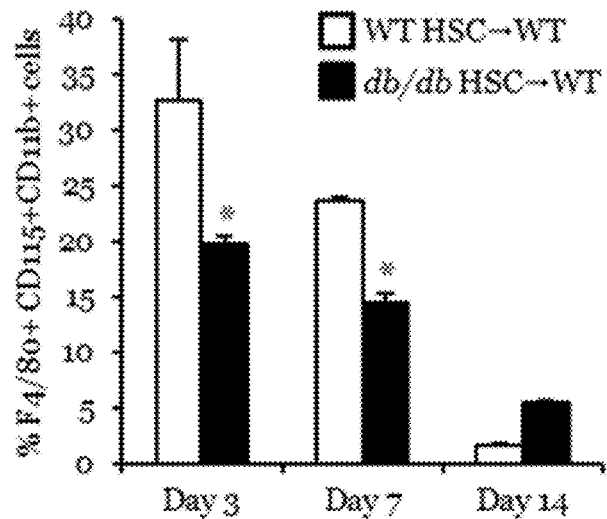
FIG. 5B: Quantification of F4/80$^+$CD115$^+$CD11b$^+$ macrophage concentration in the cutaneous wounds on days 3, 7 and 14 by flow cytometry (n=6, *, p<0.05 vs WT HSC→WT). Results are expressed as means±SEM. Two-tailed unpaired student's t-test was used.
Figure 5C:
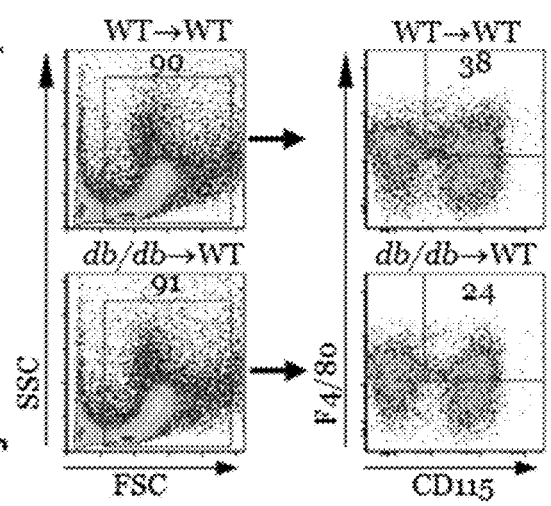
FIG. 5C: Flow cytometry gating of the monocyte population (F4/80 and CD115) in the bone marrow in WT recipient mice.
Figure 5D:
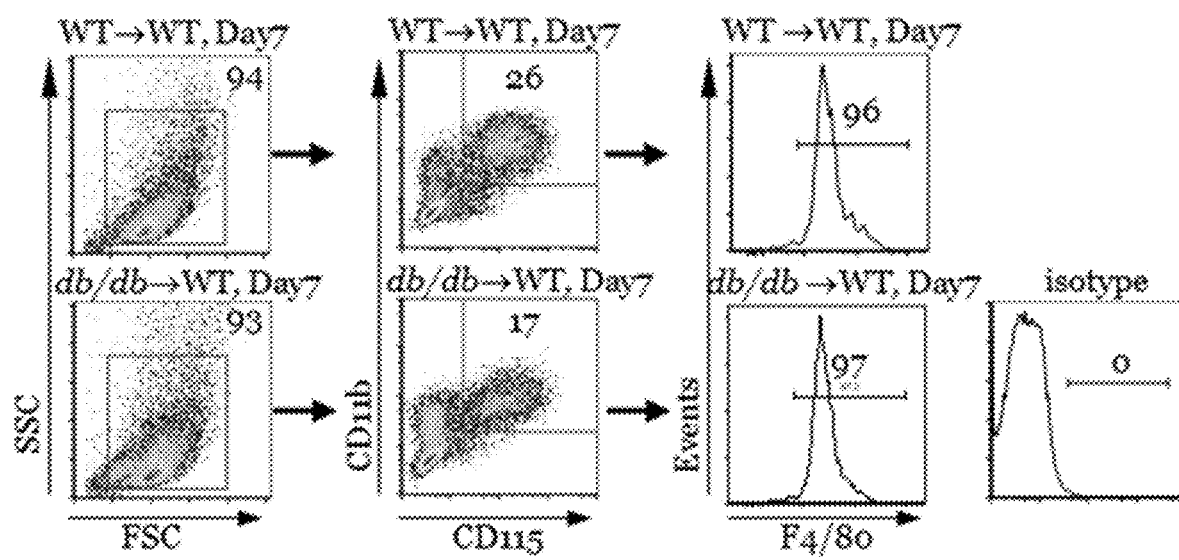
FIG. 5D: Flow cytometry gating of the macrophage population (CD11b, CD115, F4/80) in wounds.
Figure 5J:
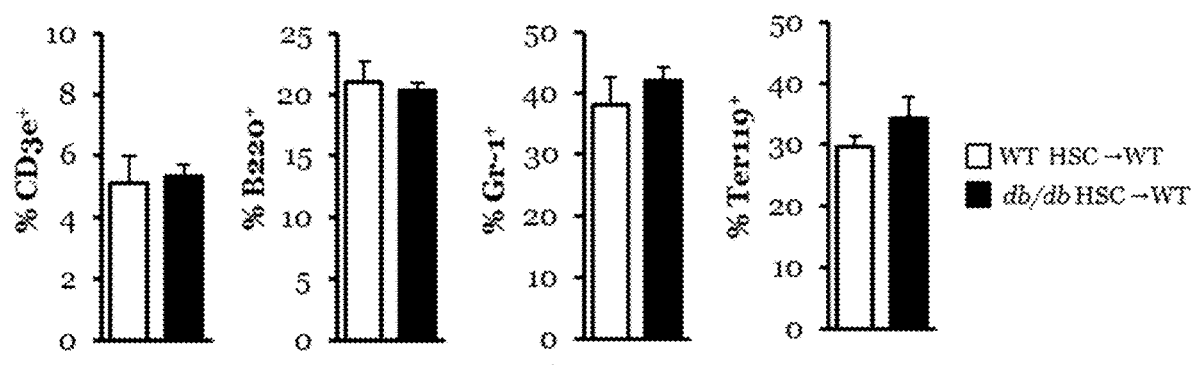
FIG. 5J: Quantification of cell lineages (CD3e$^+$ cells, B220$^+$ cells, Gr-1$^+$ cells, Ter119$^+$ cells) in WT recipient mice by flow cytometry.

In addition, we compared the dynamic changes in M1/M2 polarization during the three phases of wound healing in WT and db/db mice. Both M1 and M2 macrophages were significantly reduced during the inflammatory phase in db/db mice (FIG. 2I). During the new tissue formation phase, M1 macrophages in the wounds of db/db mice were increased to a level much greater than those in the wounds of WT mice, while M2 macrophages remained at very low levels (FIG. 2J, FIGS. 3A-D). In the remodeling phase, M1 macrophages were still at a significantly greater concentration in the wounds of db/db mice, while M2 macrophages were at a level equivalent to the wounds of WT mice (FIG. 3E). In order to test the hypothesis that T2DM causes an HSC autonomous defect that impairs wound closure kinetics by dysregulation of HSC lineage specification towards monocytes and macrophage polarization, wound closure kinetics in a chimeric model were investigated whereby hematopoiesis was reconstituted in lethally irradiated WT recipient mice with HSCs from either db/db or WT mice. The wound closure rates in WT mice were significantly delayed in the recipients reconstituted with db/db HSCs (FIGS. 4A-B). A significant decrease in the rates of re-epithelialization was observed (FIGS. 4C-E), wound contraction (FIGS. 4D-F) and revascularization (FIGS. 4G-I) as well as a significant decrease in granulation tissue (FIG. 4D, FIG. 4E, FIG. 4J). The recipients reconstituted with db/db HSCs also recapitulated the defects in monocyte and macrophage frequency (FIGS. 5A-D) as well as the skewed M1 polarization of macrophages in wounds (FIGS. 5E-I). No change was found in T cells, B cells, granulocytes and red blood cells (FIG. 5J). These results indicate that T2DM reduces the differentiation of HSCs towards monocytes/macrophages, and skews their polarization towards the M1 phenotype, which results in a pro-inflammatory environment that impairs wound healing.

Figure 6A:
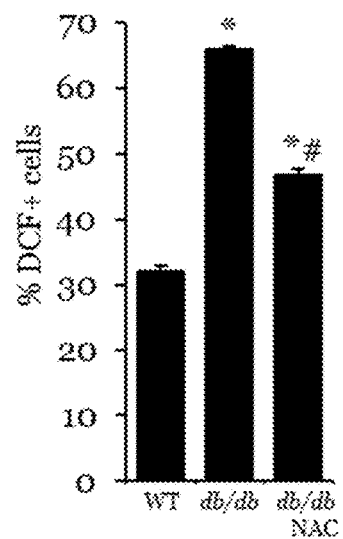
FIG. 6A: Quantification by flow cytometry of CM-H$_2$DCFDA (DCF) positive cells in WT mice, db/db mice and db/db mice treated with N-acetylcysteine (NAC) (n=6, *, p<0.05 vs WT; #, p<0.05 vs db/db). Results are expressed as means±SEM. One way ANOVA was used.
Figure 6A:
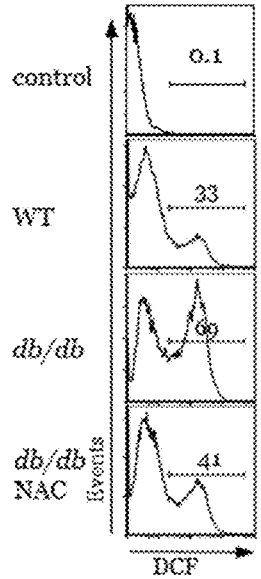
Figure 6B:
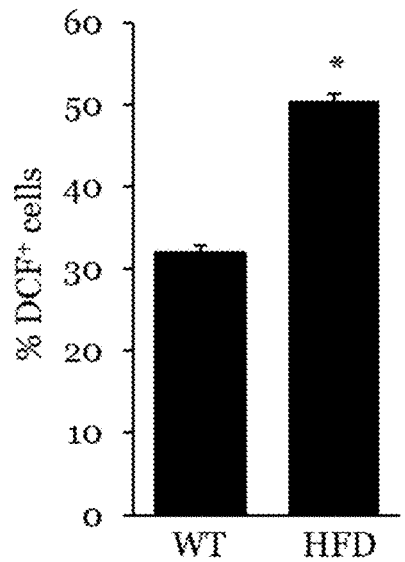
FIG. 6B: Quantification of DCF positive cells in WT and HFD mice by flow cytometry (n=6, *, p<0.05 vs WT). Results are expressed as means±SEM. Two-tailed unpaired student's t-test was used.
Figure 6C:
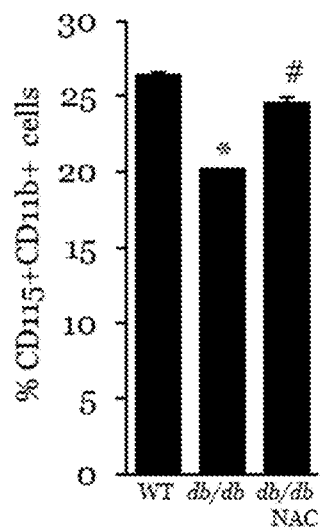
FIG. 6C: Quantification of CD115$^+$CD11b$^+$ monocytes concentration in bone marrow of WT mice, db/db mice and db/db mice treated with NAC (n=6, *, p<0.05 vs WT; #, p<0.05 vs db/db). Results are expressed as means±SEM. One way ANOVA was used.

Example 2. Type 2 Diabetes Upregulates the Expression of DNMT1 In HSCs Through An Oxidant Stress Dependent Pathway HSCs from T2D mice had significantly greater oxidant stress than HSCs from WT mice (FIGS. 6A-B). N-acetylcysteine (NAC) supplementation reversed the oxidant stress and restored monocyte concentration in bone marrow of db/db mice (FIG. 6A and 6C).

Figure 6D:
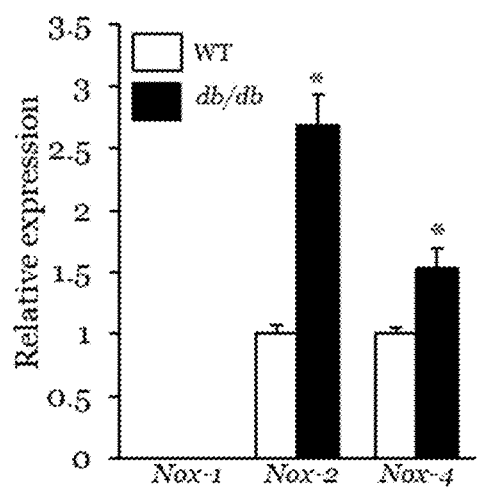
FIG. 6D: Quantification of nicotinamide adenine dinucleotide phosphate (NADPH) oxidase gene expression: Nox-1, Nox-2 and Nox-4 in WT and db/db mice (n=6, *, p<0.05 vs WT). Results are expressed as means±SEM. Two-tailed unpaired student's t-test was used.
Figure 6E:
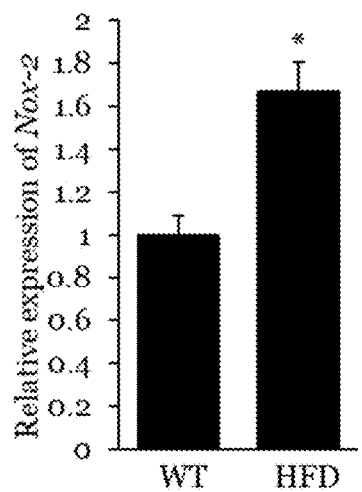
FIG. 6E: Quantification of Nox-2 gene expression in WT and HFD mice (n=6, *, p<0.05 vs WT). Results are expressed as means±SEM. Two-tailed unpaired student's t-test was used.
Figure 6F:
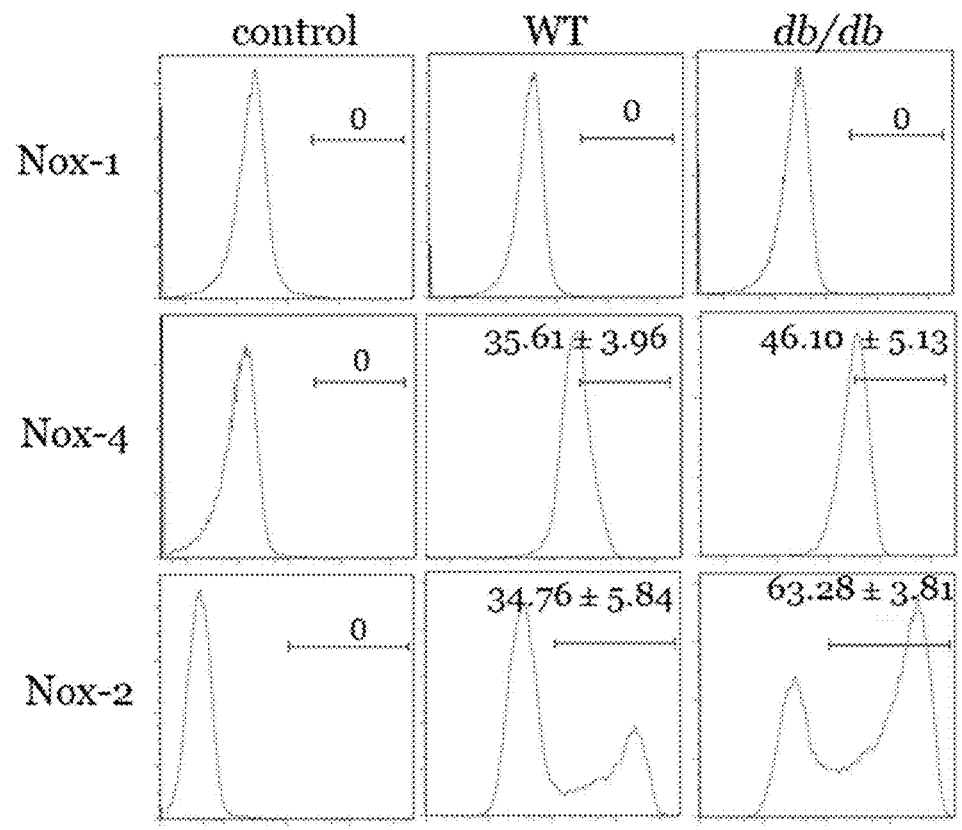
FIG. 6F: Quantification of Nox family genes (Nox-1, Nox-4 and Nox-2) by flow cytometry in WT and db/db mice. Results are expressed as means±SEM. Two-tailed unpaired student's t-test was used.
Figure 6G:
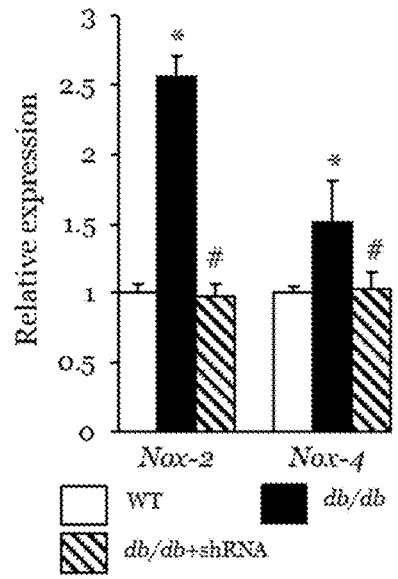
FIG. 6G: Quantification of Nox-2 and Nox-4 gene expression after knockdown of Nox-2 or Nox-4 in db/db mice (n=6, *, p<0.05 vs WT; #, p<0.05 vs db/db). Results are expressed as means±SEM. One way ANOVA was used.
Figure 6H:
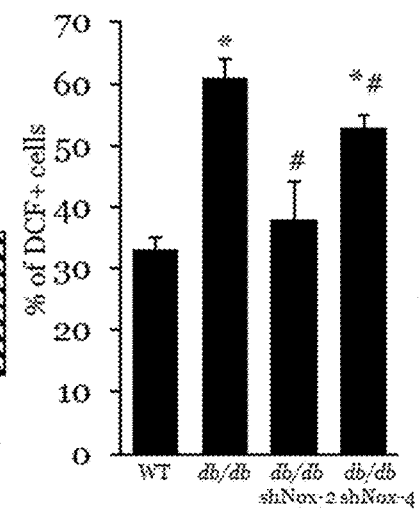
FIG. 6H: Quantification of DCF positive cells after knockdown of Nox-2 or Nox-4 in db/db mice (n=6, *, p<0.05 vs WT; #, p<0.05 vs db/db). Results are expressed as means±SEM. One way ANOVA was used.

The NOX family of NADPH oxidases is an important source of reactive oxygen species (Bedard & Krause (2007) *Physiol. Rev.* 87: 245-313). Among them, Nox-1, Nox-2 and Nox-4 have been reported to be expressed in HSCs (Piccoli et al. (2007) *Biochem. Biophys. Res. Commun.* 353: 965-972; Wang et al. (2010) *Free Radic. Biol. Med.* 48: 348-356). A significant increase in NOX2 and NOX4 expression was observed in HSCs from db/db mice (FIGS. 6D-F). The inhibition of NOX2 and NOX 4 reduced the oxidant stress in HSCs from db/db mice (FIGS. 6G-H). Since NOX2 induced a much higher level of oxidant stress in HSCs from db/db and HFD mice (FIG. 6E, FIG. 6G and FIG. 6H), we focused on identifying the role of NOX2 in HSC differentiation towards monocytes/macrophages in db/db mice.

Figure 6I:
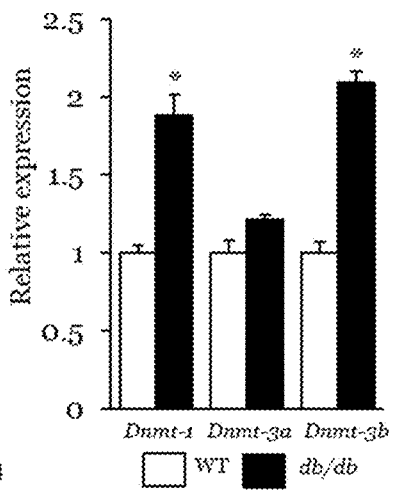
FIG. 6I: Quantification of Dnmt gene expression (Dnmt-1, Dnmt-3a, Dnmt-3b) in WT and db/db mice (n=6, *, p<0.05 vs WT). Results are expressed as means±SEM. Two-tailed unpaired student's t-test was used.
Figure 7A:
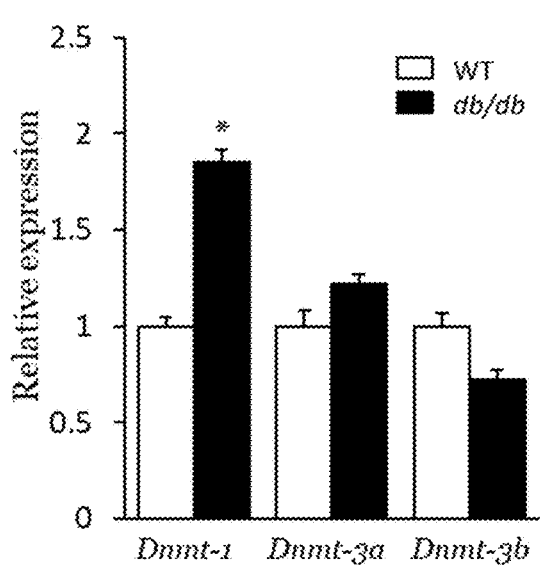
FIG. 7A: Quantification of Dnmt family expression in HSCs from WT and db/db mice. Results are expressed as means±SEM. Two-tailed unpaired student's t-test was used.
Figure 7B:
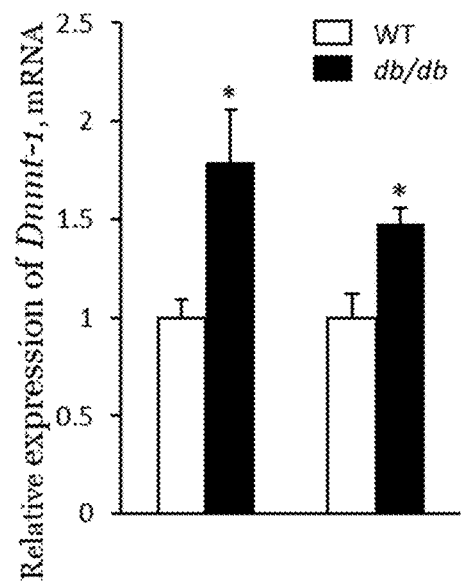
FIG. 7B: Quantification of Dnmt-1 expression in bone marrow monocytes and wound macrophages by qRT-PCR (n=6, *, p<0.05 vs wt, #, p<0.05 vs db/db). Results are expressed as means±SEM. Two-tailed unpaired student's t-test was used.
Figure 7E:
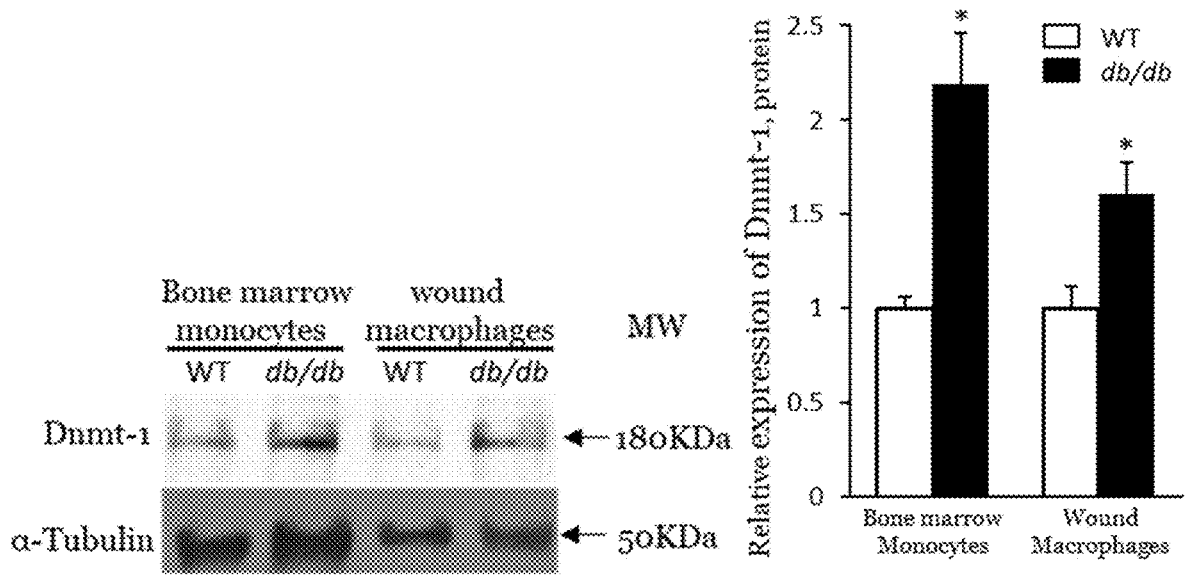
FIG. 7E: Quantification of Dnmts expression (Dnmt-1, Dnmt3a, Dnmt-3b) after knockdown of Nox-2 or NAC antioxidant treatment (n=6, *, p<0.05 vs WT; #, p<0.05 vs db/db). Results are expressed as means±SEM. One way ANOVA was used.
Figure 7E:
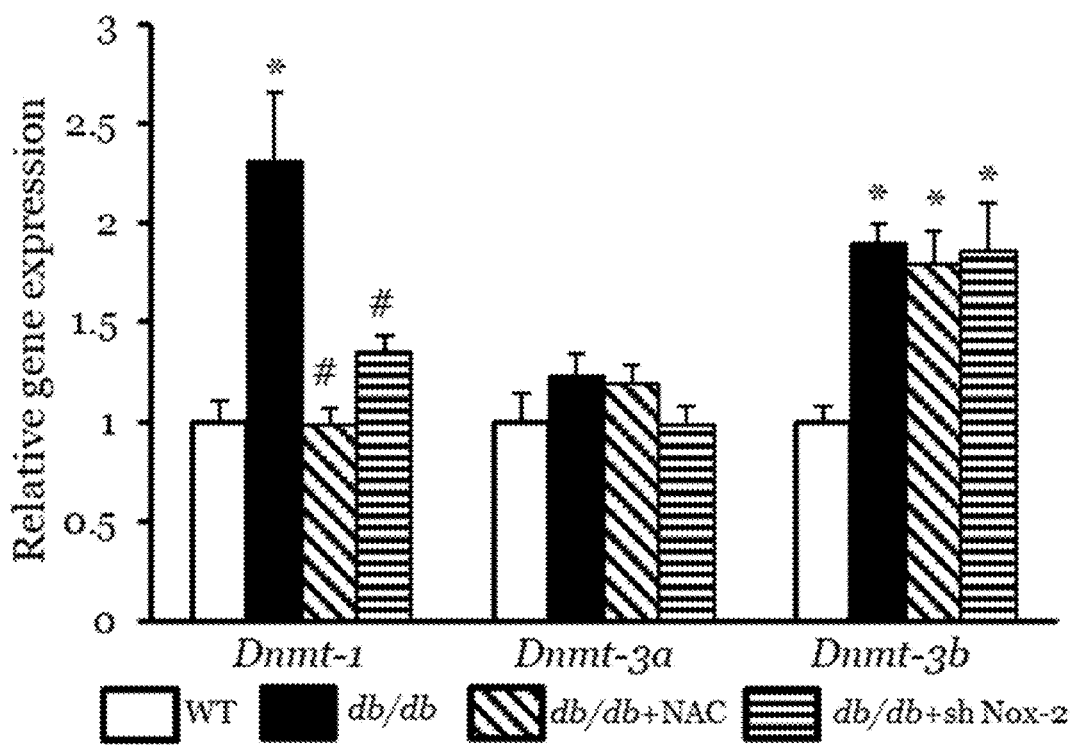
Figure 7F:
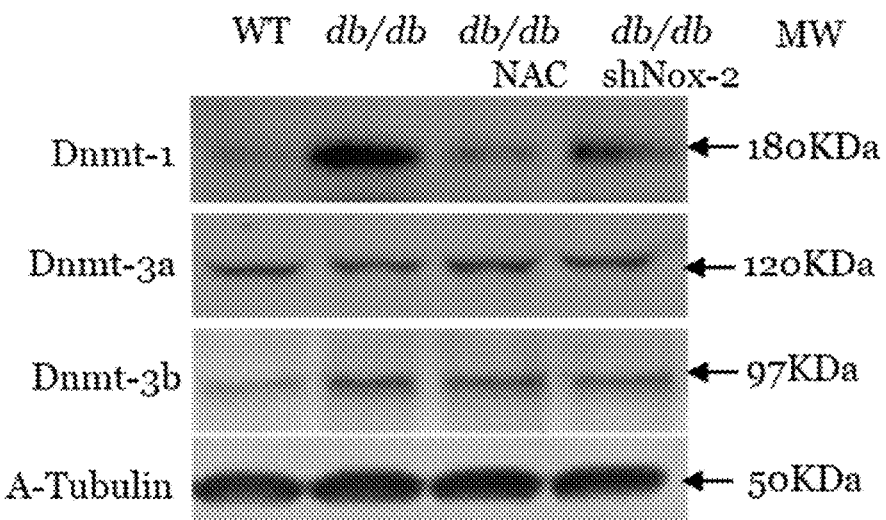
FIG. 7F: Western blot analysis of Dnmts protein levels after knockdown of Nox-2 or NAC antioxidant treatment (n=3).
Figure 7G:
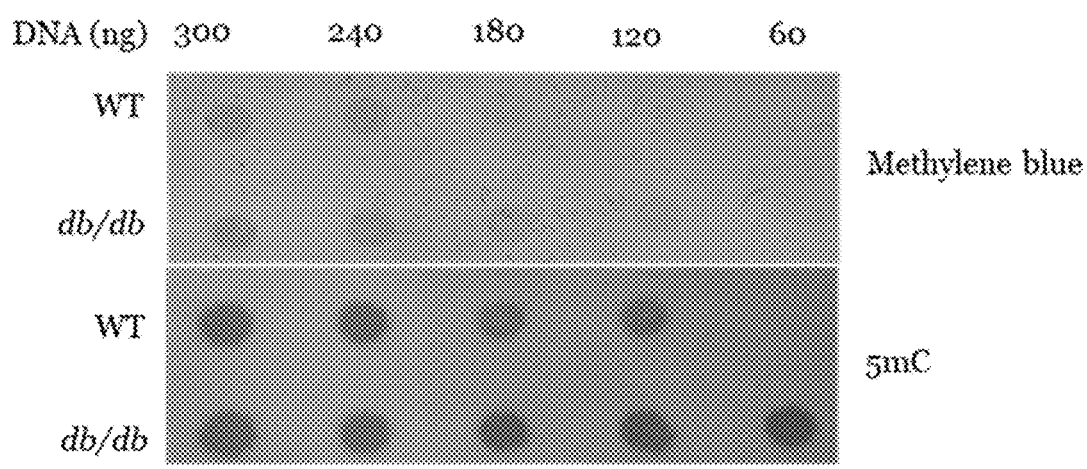
FIG. 7G: Global DNA methylation analysis by dot blot. 5mC-5'methylcytosine.

DNA methylation plays an important role in HSC commitment to lymphoid and myeloid lineages. DNA methylation of CpG nucleotides, a key epigenetic modification, is established and maintained by a family of DNA methyltransferases (Dnmts), named Dnmt1, Dnmt3a and Dnmt3b (Okano et al. (1998) *Nat. Genet.* 19: 219-220). As shown herein, DNMT1 was consistently upregulated in HSCs from both db/db and HFD mice, while DNMT3b was only increased in HSCs from db/db mice (FIG. 6I and FIG. 7A). Dnmt1 mRNA and protein levels were also increased in bone marrow monocytes and wound macrophages (FIGS. 7B-D). The inhibition of NOX2 or the treatment with NAC both restored the expression of DNMT1 in db/db HSCs to a level comparable to that in WT HSCs, but did not change the mRNA or the protein levels of Dnmt3a and DNMT3b (FIGS. 7E-F). Consistent with the upregulation of Dnmt1, the total DNA methylation status in db/db HSCs was higher than in WT HSCs (FIG. 7G). These results indicate that T2DM upregulates the expression of DNMT1 and DNMT3b. However, only Dnmt1 was upregulated by Nox-2-dependent oxidant stress.

Figure 8A:
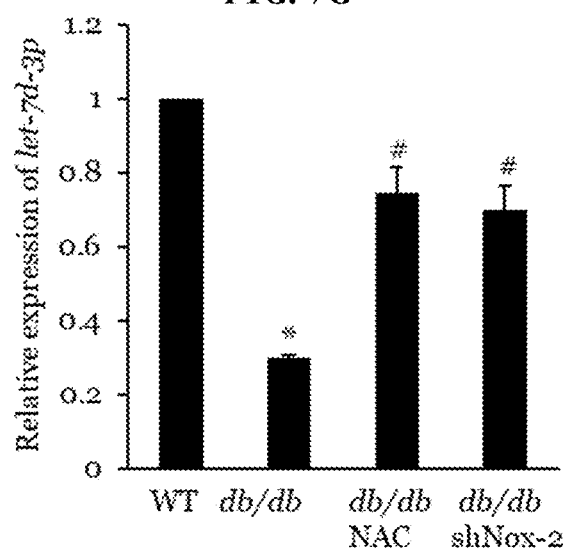
FIG. 8A: Relative expression of let-7d-3p in WT HSCs, db/db HSCs, db/db HSCs treated with NAC or shNox-2 (n=6, *, p<0.05 vs WT; #, p<0.05 vs db/db). Results are expressed as means±SEM. One way ANOVA was used.
Figure 8B:
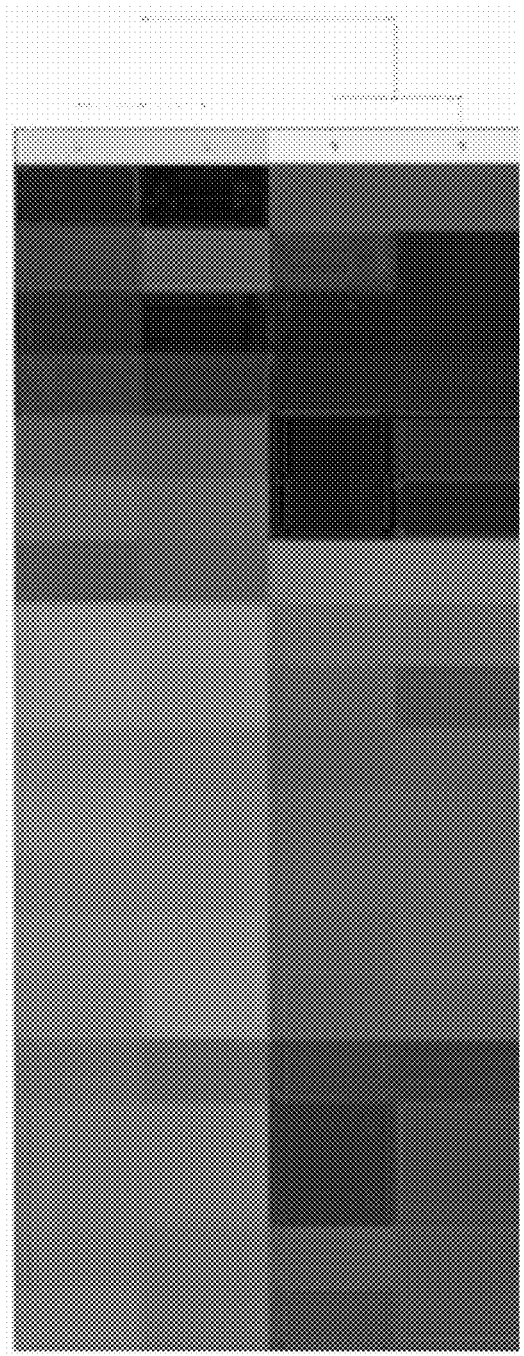
FIG. 8B: Heatmap of microRNA microarray expression data from WT HSCs and db/db HSCs.

Example 3. Let-7d-3p Mediates the Upregulation of Dnmt1 in HSCs Isolated from T2D Mice In order to identify the mechanism regulating Dnmt1 expression in T2D HSCs, we next investigated the role of microRNAs, which are non-coding RNAs that regulate gene expression by binding to the 3' untranslated region (UTR) of protein coding genes (Gangaraju & Lin (2009) *Nat. Rev. Mol. Cell. Biol.* 10: 116-125). To identify microRNAs that are regulated by T2DM, a microRNA microarray was performed in HSCs from WT and db/db mice. Among the differentially expressed microRNAs, let-7d-3p, which is predicted to directly target Dnmt1, showed a significant oxidant stress dependent downregulation in HSCs from db/db mice (FIGS. 8A-B). To determine if let-7d-3p binds directly to Dnmt1, the mouse Dnmt1 3' UTR region (labeled as Dnmt1 in FIG. 8C) was cloned and a luciferase activity was performed in HEK293T cells transfected with let-7d-3p mimics/analogues. Let-7d-3p significantly repressed the luciferase activity when an intact 3' UTR construct was used, but didn't affect the luciferase activity when the binding sites of let-7d-3p in Dnmt1 3' UTR region were mutated (labeled as Dnmt1 M1 and Dnmt1 M2; FIG. 8C). In addition, a let-7d-3p inhibitor increased Dnmt1 expression in WT HSCs, while let-7d-3p mimics/analogues decreased Dnmt1 expression in db/db HSCs (FIGS. 8D-G). These results provide compelling evidence that let-7d-3p mediates the impact of oxidant stress on Dnmt1 expression in HSCs.

Figure 9B:
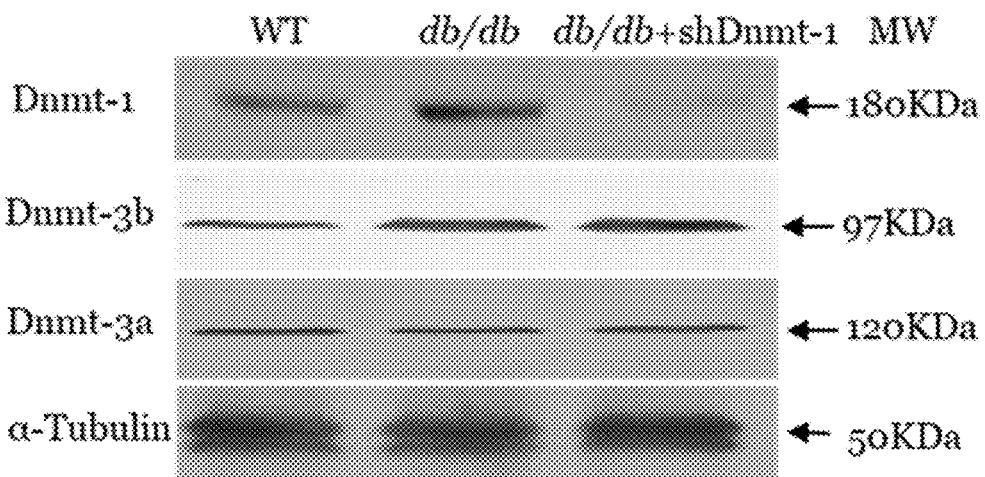
FIG. 9B: Western blot analysis of Dnmt-1, Dnmt-3a and Dnmt-3b protein levels in WT HSC, db/db HSC and db/db HSC expressing shDnmt1.
Figure 9C:
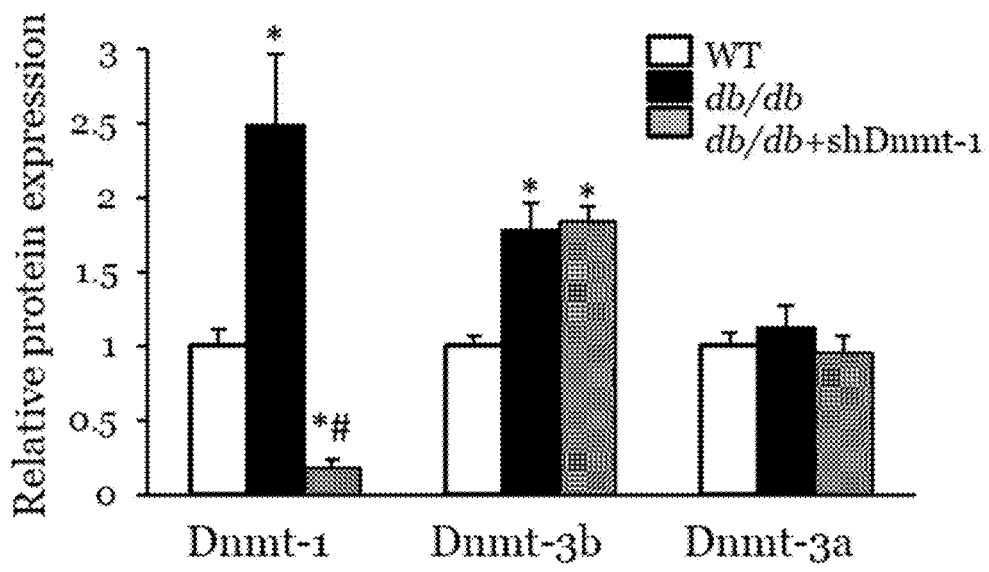
FIG. 9C: Quantification of Dnmts protein expression by western blot (n=6, *, p<0.05 vs wt, #, p<0.05 vs db/db). Results are expressed as means±SEM. One way ANOVA was used.
Figure 9D:
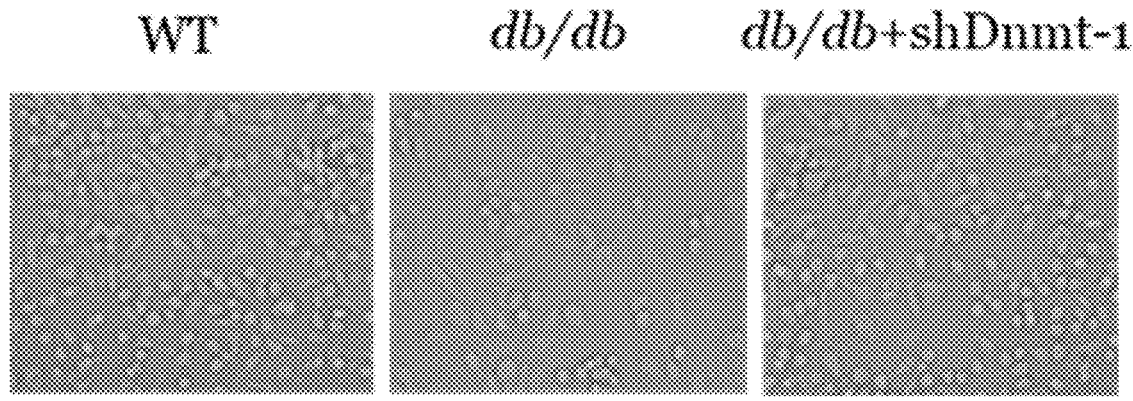
FIG. 9D: Representative images of WT, db/db and db/db+ shDnmt-1 differentiation towards macrophages.
Figure 9E:
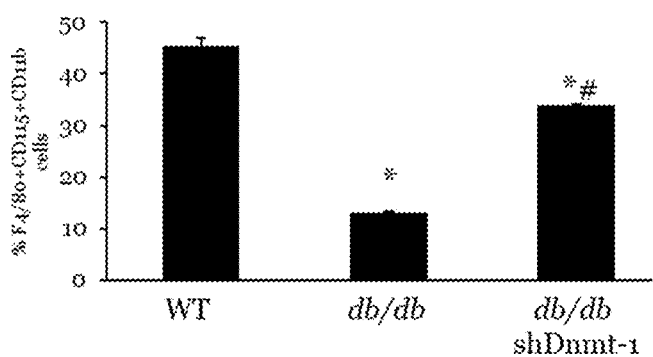
FIG. 9E: Quantification of F4/80$^+$CD115$^+$CD11b$^+$ cells following knockdown of Dnmt-1 (n=6, *, p<0.05 vs WT; #, p<0.05 vs db/db). Results are expressed as means±SEM. One way ANOVA was used.
Figure 9F:
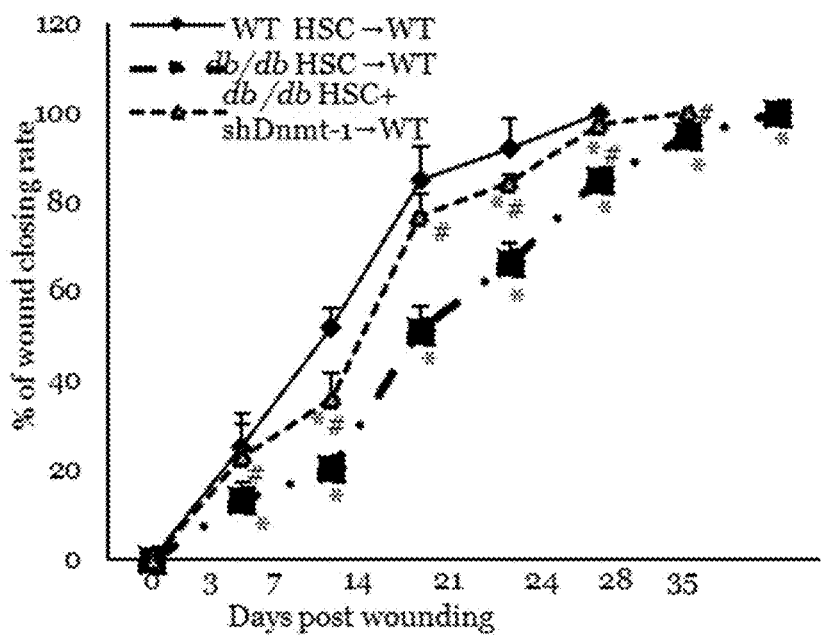
FIG. 9F: Wound closure rate measurement in WT mice transplanted with WT HSC, WT mice transplanted with db/db HSC, and WT mice transplanted with db/db HSC+ shDnmt1 (n=8, *p<0.05 vs WT HSC→WT, #, p<0.05 vs db/db HSC→WT). Results are expressed as means±SEM. One way ANOVA was used.
Figure 9G:
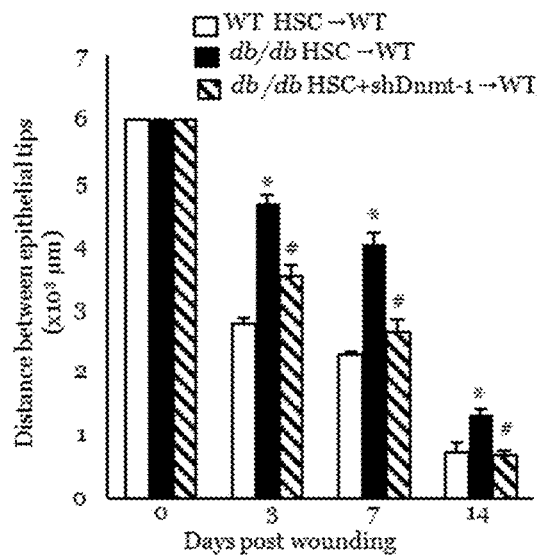
FIG. 9G: Histological quantification of distance between epithelial tips (n=4, *, p<0.05 vs WT HSC→WT, #, p<0.05 vs db/db HSC→WT). Results are expressed as means±SEM. One way ANOVA was used.
Figures 9H, 9I, 9J:
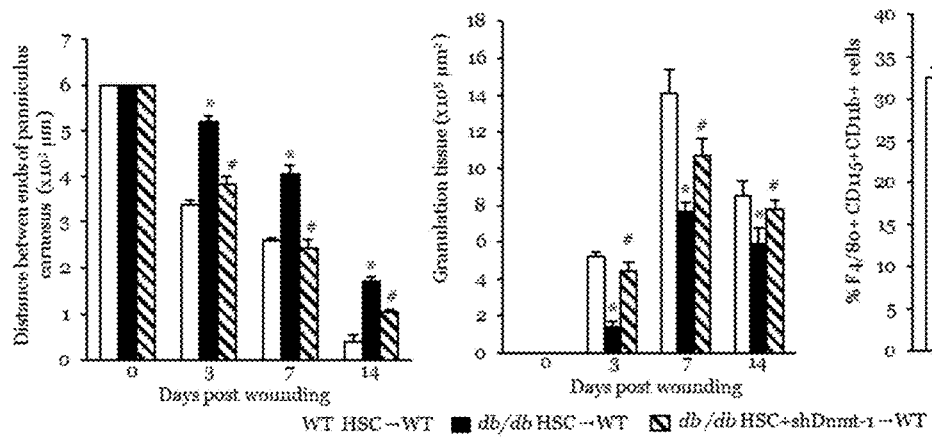
FIG. 9H: Histological quantification of distance between ends of panniculus carnosus (n=4, *, p<0.05 vs WT HSC→WT, #, p<0.05 vs db/db HSC→WT). Results are expressed as means±SEM. One way ANOVA was used.
FIG. 9I: Histological quantification of distance between granulation tissue (n=4, *, p<0.05 vs WT HSC→WT, #, p<0.05 vs db/db HSC→WT). Results are expressed as means±SEM. One way ANOVA was used.
FIG. 9J: Quantification of F4/80$^+$CD115$^+$CD11b$^+$ macrophage concentration in the cutaneous wounds on days 3, 7 and 14 by flow cytometry (n=6, *p<0.05 vs WT HSC→WT, #, p<0.05 vs db/db HSC→WT). Results are expressed as means±SEM. One way ANOVA was used.
Figures 9K, 9L, 9M:
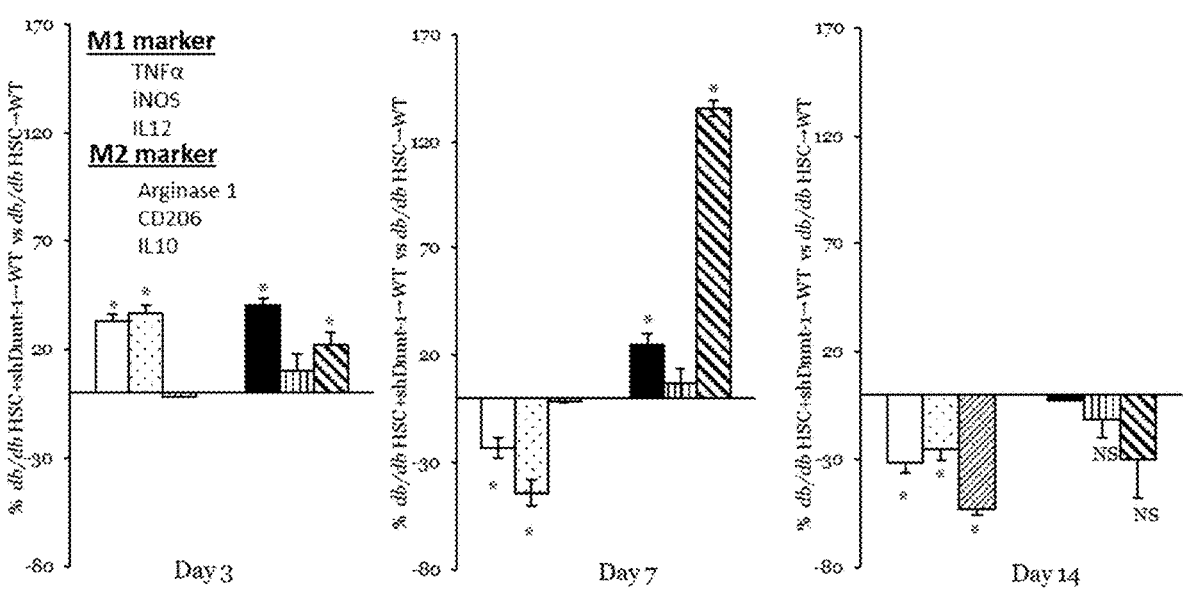
FIG. 9K: Quantification of M1/M2 polarization in cutaneous wounds on day 3 by flow cytometry (n=6, #, p<0.05 vs db/db HSC→WT). Results are expressed as means±SEM. Two-tailed unpaired student's t-test was used.
FIG. 9L: Quantification of M1/M2 polarization in cutaneous wounds in day 7 by flow cytometry (n=6, #, p<0.05 vs db/db HSC→WT). Results are expressed as means±SEM. Two-tailed unpaired student's t-test was used.
FIG. 9M: Quantification of M1/M2 polarization in cutaneous wounds in day 14 by flow cytometry (n=6, #, p<0.05 vs db/db HSC→WT). Results are expressed as means±SEM. Two-tailed unpaired student's t-test was used.

Example 4. T2DM-Induced Upregulation of DNMT1 in HSCs Reduces Their Differentiation Towards Monocytes/macrophages and Thereby Impairs Wound Healing The expression of Dnmt1 in db/db HSCs was downregulated following the to addition of an shRNA against Dnmt1 (FIGS. 9A-C). Under in vitro conditions, the knockdown of Dnmt1 in db/db HSCs consistently increased their differentiation towards monocytes/macrophages (FIGS. 9D-E). WT recipients reconstituted with Dnmt1-knockdown db/db HSCs showed a significantly higher rate of wound healing than WT recipients reconstituted with db/db HSCs (FIGS. 9F-I). In WT mice reconstituted with Dnmt1-knockdown db/db HSCs, the infiltration of monocytes/macrophages as well as their M1/M2 polarization throughout the three phases of wound healing were restored to levels comparable to those in WT mice reconstituted with WT HSCs (FIGS. 9J-M). These findings indicate that sustained upregulation of Dnmt1 expression in HSCs mediates the deleterious effects of T2DM on wound healing by inhibiting their differentiation towards monocytes/macrophages and skewing toward the M1 polarization of macrophages.

Example 5. Dnmt1 Knockdown In HSCs Increases Wound Healing In T2D Mice

Figure 10A:
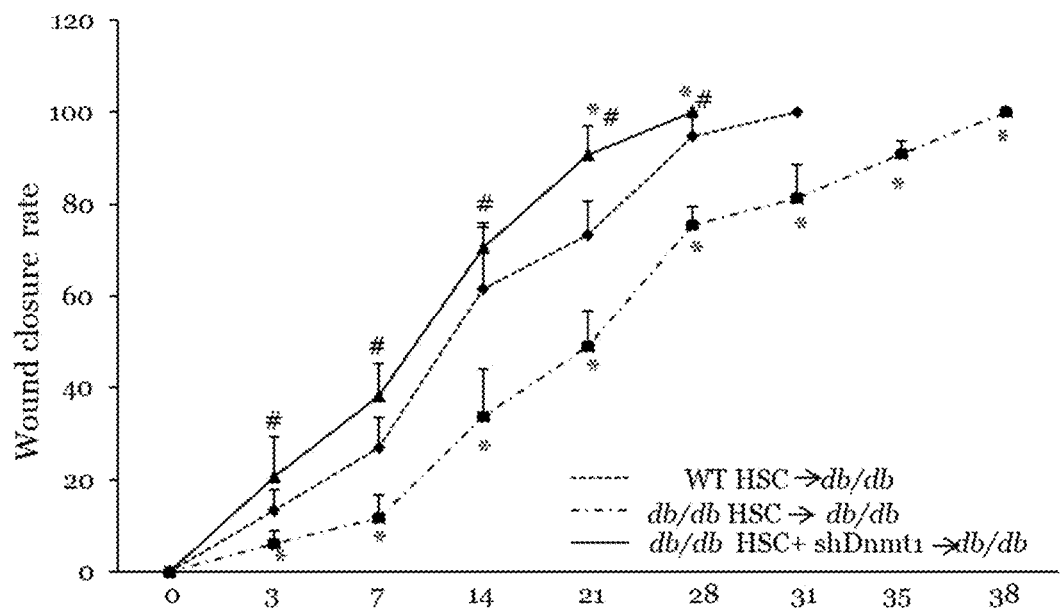
FIG. 10A: Wound closure rate measurement (n=8, *p<0.05 vs WT HSC→db/db #, p<0.05 vs db/db HSC→db/db). Results are expressed as means±SEM. One way ANOVA was used.
Figure 10B:
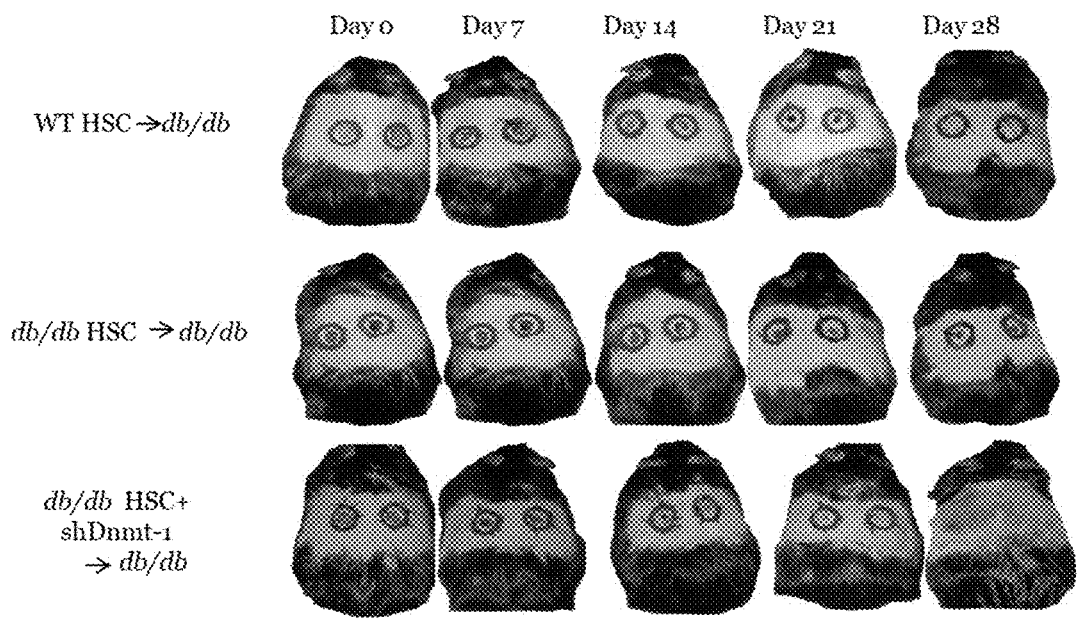
FIG. 10B: Representative wounding images of db/db mice transplanted with WT HSC, db/db mice transplanted with db/db HSC and db/db mice transplanted with db/db HSC+shDnmt-1.
Figure 11E:
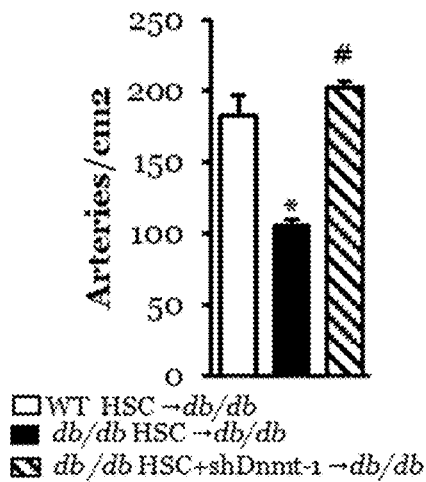
FIG. 11E: Quantification of arteries in day 7 wound in db/db recipient mice by CD144 and αSMA staining. (n=4, *, p<0.05 vs WT HSC db/db, #, p<0.05 vs db/db HSC db/db). Results are expressed as means±SEM. One way ANOVA was used.
Figure 11F:
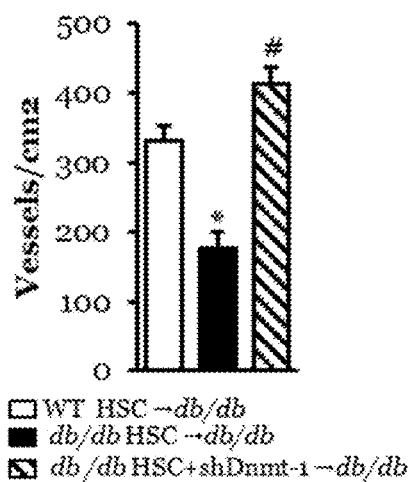
FIG. 11F: Quantification of vessels in day 7 wound in db/db recipient mice by CD144 and αSMA staining. (n=4, *, p<0.05 vs WT HSC db/db, #, p<0.05 vs db/db HSC db/db). Results are expressed as means±SEM. One way ANOVA was used.
Figure 11G:
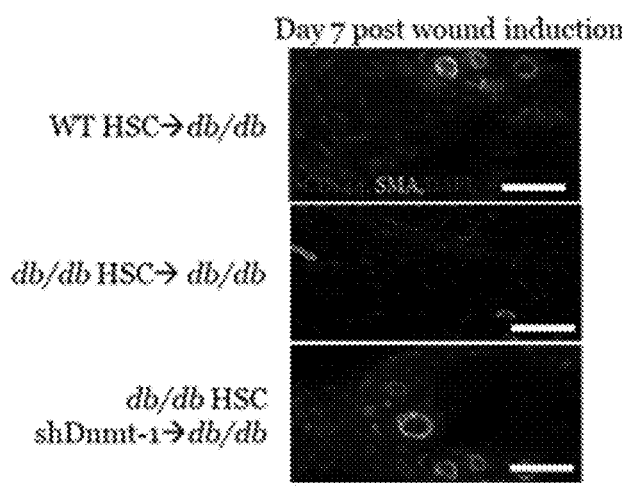
FIG. 11G: Representative IHC staining images of vascularization in db/db recipient mice by CD144 and αSMA staining. Magnification ×200; scale bar, 100 μm.

In order to determine in vivo if Dnmt1-knockdown HSCs from T2D mice rescue normal wound healing, Dnmt1-knockdown db/db HSCs were transplanted into lethally irradiated T2D recipients, and then induced wounds 2 months after HSC transplantation. As shown herein, the wound closure rate was significantly increased in T2D recipients transplanted with either WT HSCs or Dnmt1-knockdown db/db HSCs. Meanwhile, the most impaired wound closure rate was observed in db/db recipients transplanted with db/db HSCs (FIGS. 10A-B). Histological analysis also showed that the transplantation of Dnmt1-knockdown db/db HSCs significantly improved reepithelialization (FIG. 11A, and 11D), wound contraction (FIGS. 11B and 11D) and revascularization (FIGS. 11E-G), as well as significantly increased granulation tissue (FIGS. 11C-D). These findings indicate that the transplantation of autologous Dnmt1-knockdown HSCs from T2D mice may provide a potential therapeutic option in T2DM patients.

Figure 12A:
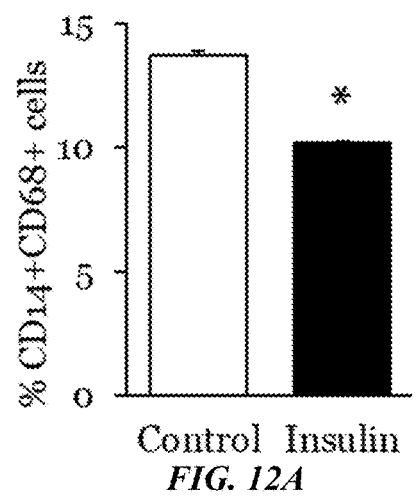
FIG. 12A: Quantification of CD14$^+$CD68$^+$ human macrophage numbers by flow cytometry (n=3, *p<0.05 vs control). Results are expressed as means±SEM. Two-tailed unpaired student's t-test was used.
Figure 12B:
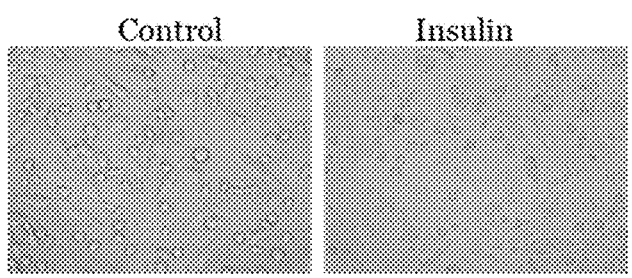
FIG. 12B: Representative images of human HSC differentiation towards macrophages in the presence or absence of hyperinsulinemia.
Figure 12C:
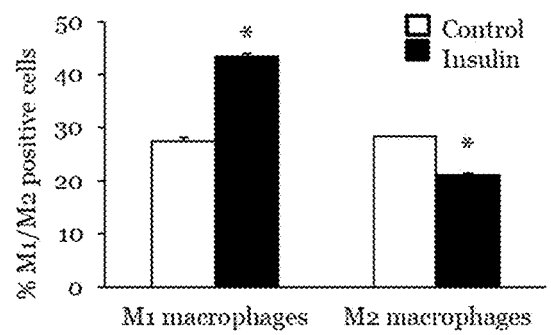
FIG. 12C: Quantification of M1 and M2 human macrophages by flow cytometry (n=3, *p<0.05 vs control). Results are expressed as means±SEM. Two-tailed unpaired student's t-test was used.
Figure 12D:
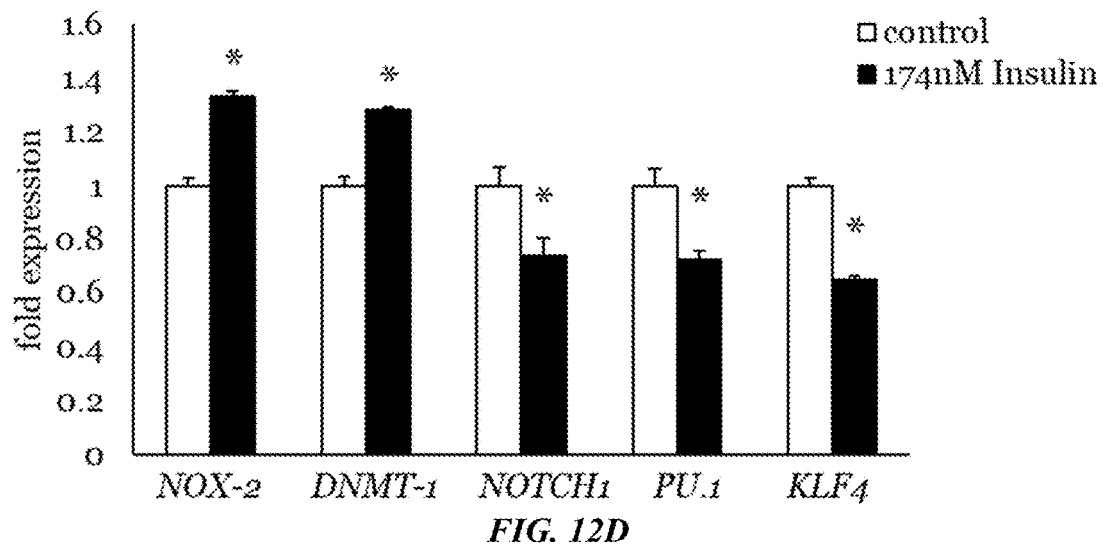
FIG. 12D: Relative gene expression of Nox-2, Dnmt-1, Notch1, PU.1 and Klf4 (n=3, *, p<0.05 vs control). Results are expressed as means±SEM. Two-tailed unpaired student's t-test was used.

Example 6. Hyperinsulinemia Reduced Differentiation of Human HSCs Towards Monocytes/Macrophages and Skewed them Towards M1 Macrophages Insulin resistance and the consequent hyperinsulinemia is a key feature of T2DM. Hyperinsulinemia induced oxidant stress impairs the function of stem and progenitor cells (Yan et al. (2012) J. Am. Heart Assoc. 1: e002238; Cubbon et al. (2009) Clin. Sci. 117: 173-190). As shown herein, hyperinsulinemia reduced in vitro human HSC differentiation towards macrophages (FIGS. 12A-B). In addition, hyperinsulinemia skewed human macrophages towards M1 polarization (FIG. 12C). Hyperinsulinemia also increased the expression of NOX2 and DNMT 1 in human HSCs (FIG. 12D). These findings suggest that hyperinsulinemia impairs the differentiation of human HSCs towards monocytes/macrophages by oxidant stress dependent upregulation of DNMT1.

Example 7. Upregulated Dnmt1 In HSCs from T2D Mice Represses Klf4, PU.1 and Notch1

Figure 13A:
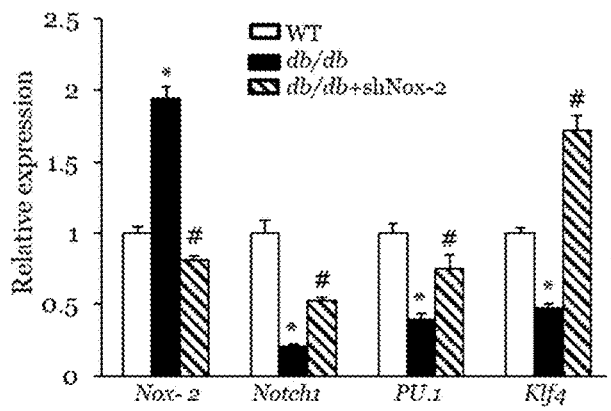
FIG. 13A: Relative gene expression of Nox-2, Notch1, PU.1, Klf4 following Nox-2 knockdown in db/db mice (n=6. *, p<0.05 vs WT; #, p<0.05 vs db/db). Results are expressed as means±SEM. One way ANOVA was used.
Figure 13B:
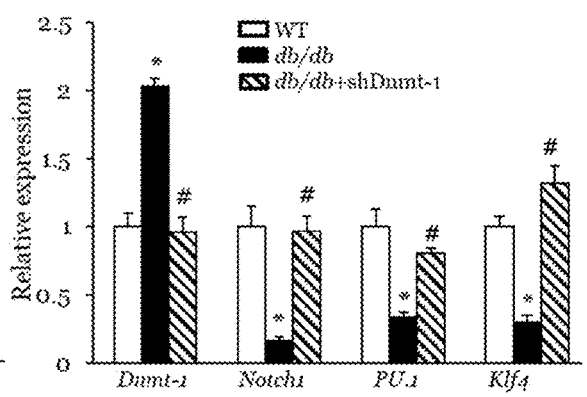
FIG. 13B: Relative gene expression analysis following Dnmt1 knockdown in db/db mice (n=6. *, p<0.05 vs WT; #, p<0.05 vs db/db). Results are expressed as means±SEM. One way ANOVA was used.

Transcription factors play a major role in the regulation of HSC lineage commitment. Among them, PU.1 and Klf4 were reported to guide monocyte and macrophage subtype-specific programs (Geissmann et al. (2010) Science 327: 656-661; Huber et al. (2014) Cell Mol Life SCi. 71: 63-92; Kastner & Chan (2008) Int. J. Biochem. Cell. Biol. 40: 22-27; Dakic et al. (2005) J. Exp. Med. 201: 1487-1502; McKercher et al. (1996) EMBO J. 15: 5647-5658; Laslo et al. (2006) Cell 126: 755-766), while Notch1 was shown to be an important extrinsic regulator of myeloid commitment that targets transcription factor PU.1 (Schroeder et al. (2003) J. Immunol. 170: 5538-5548; Kim et al. (2014) EMBO J. 33: 2363-2373; Outtz et al. (2010) J. Immunol. 185: 4363-4373). As shown herein, the expression of Notch1, PU.1 and Klf4 in HSCs from T2D mice was significantly decreased in an oxidant stress dependent manner (FIG. 13A). Furthermore, knocking down Dnmt1 increased the expression of Notch1, PU.1 and Klf4 in db/db HSCs (FIG. 13B). These results suggest that oxidant stress dependent upregulation of Dnmt1 in HSCs from T2D mice induced repressive modification of Klf4, PU.1 and Notch1.

Figure 13C:
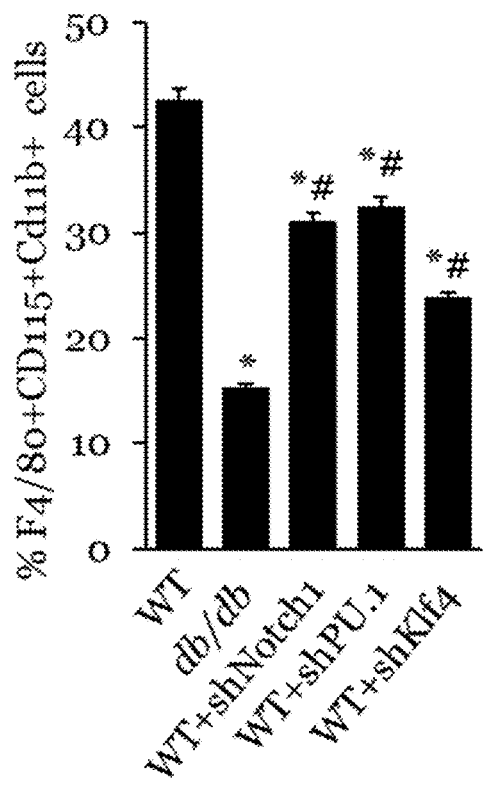
FIG. 13C: Quantification of HSC induced differentiation towards F4/80$^+$CD115$^+$CD11b$^+$ macrophages under in vitro conditions (n=6, *, p<0.05 vs WT; #, p<0.05 vs db/db). Results are expressed as means±SEM. One way ANOVA was used.
Figure 13D:
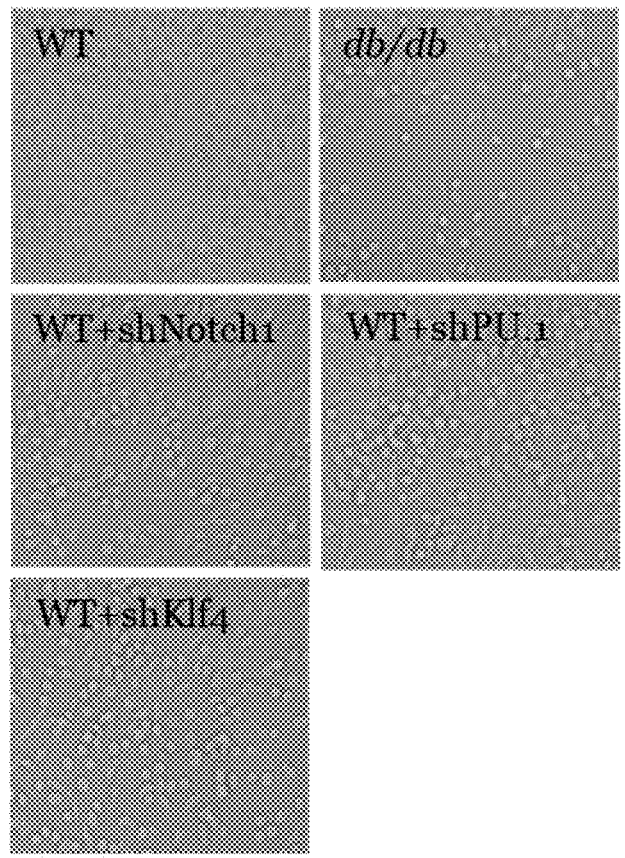
FIG. 13D: Representative images of cells of FIG. 13C.

To ascertain the pathological significance caused by the decrease in Notch1, PU.1 and Klf4 on the differentiation and polarization of monocytes and macrophages, the expression of all three genes was knocked down in WT HSCs. Knockdown of Notch1, PU.1 and Klf4 reduced WT HSC differentiation towards monocytes/macrophages (FIGS. 13C-D). These results indicate that Dnmt1-dependent downregulation of Notch1, PU.1 and Klf4 in HSCs is likely responsible for the attenuation of monocyte/macrophage differentiation in T2D mice, at least under in vitro conditions.

Figure 13E:
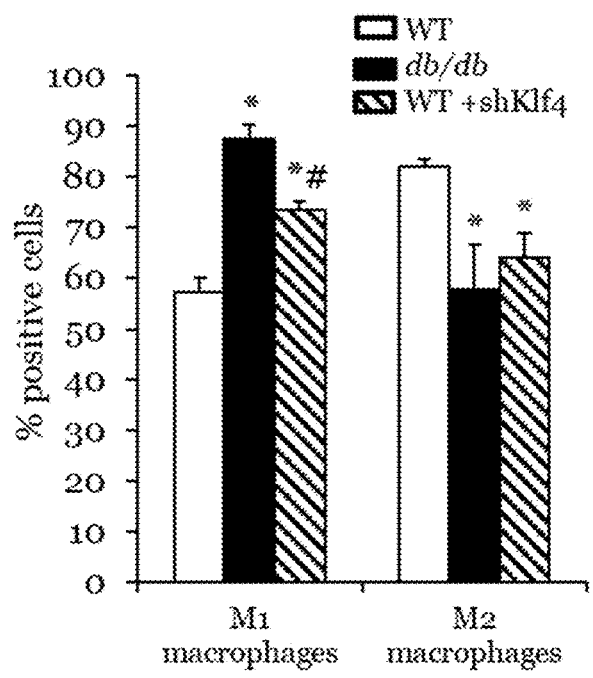
FIG. 13E: Quantification of M1/M2 macrophages cells (n=6. *, p<0.05 vs WT; #, p<0.05 vs db/db). Results are expressed as means±SEM. One way ANOVA was used.

Knockdown of Klf4 in WT HSCs skewed monocyte polarization toward the M1 phenotype (FIG. 13E). This finding is consistent with a previous study that showed myeloid Klf4 deficiency increased pro-inflammatory M1 macrophages and facilitated the inflammatory response during wound healing (Alder et al. (2008) J. Immunol. 180: 5645-5652; Liao et al. (2011) J. Clin. Invest. 121: 2736-2749). These results support our findings that downregulation of Klf4 in T2DM HSCs is most likely responsible for the polarization towards M1 macrophages. In addition, this supports the novel concept that changes in gene expression of progenitor and terminally differentiated inflammatory cells can be "preprogramed" at the level of HSCs.

Example 8. DNMT1 Induces DNA Methylation of Notch1, PU.1 and Klf4 Genes

Figure 14A:
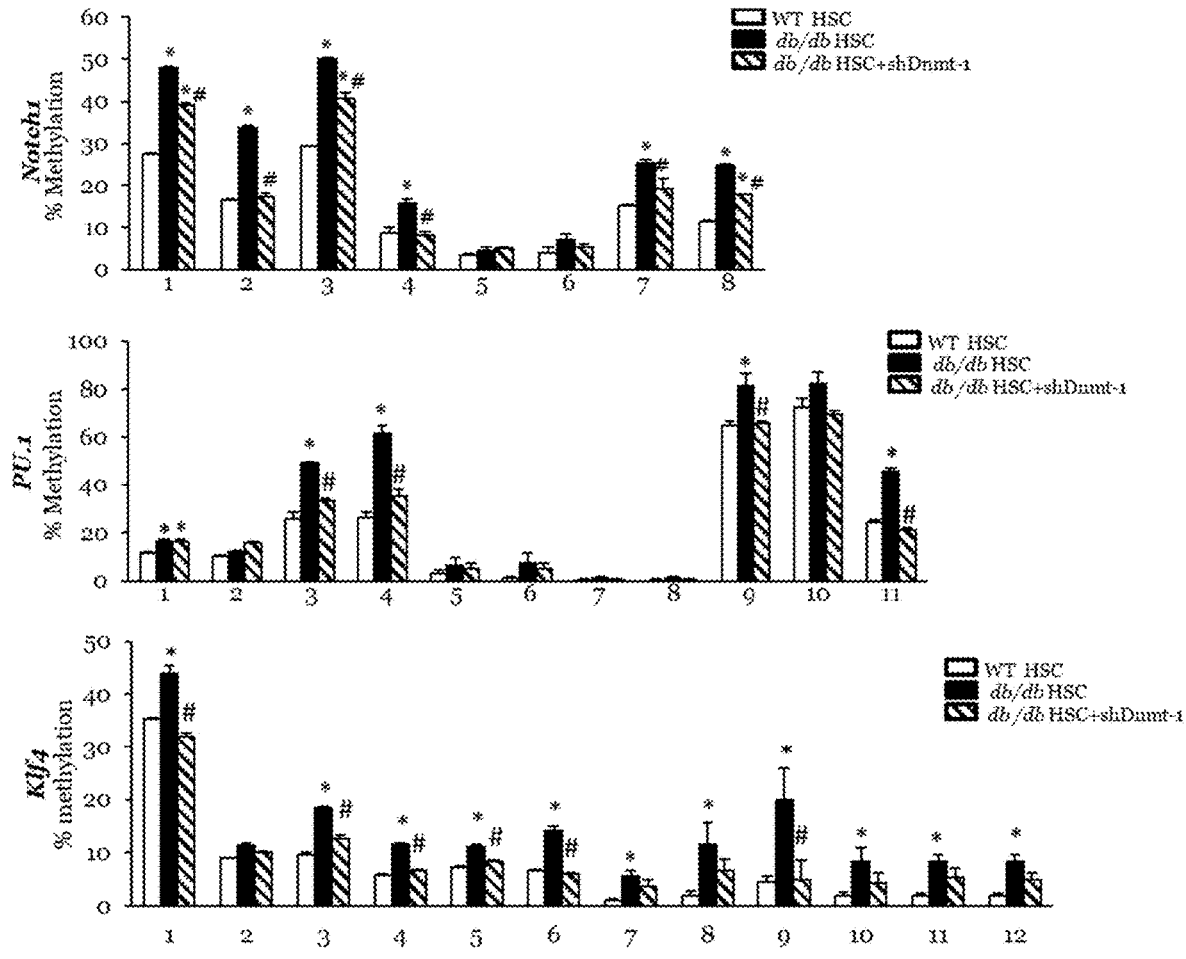
FIG. 14A: Quantification of DNA methylation of Notch1, PU.1 and Klf4 by pyrosequencing (n=6, *, p<0.05 vs WT; #, p<0.05 vs db/db). Results are expressed as means±SEM. One way ANOVA was used.
Figure 15:
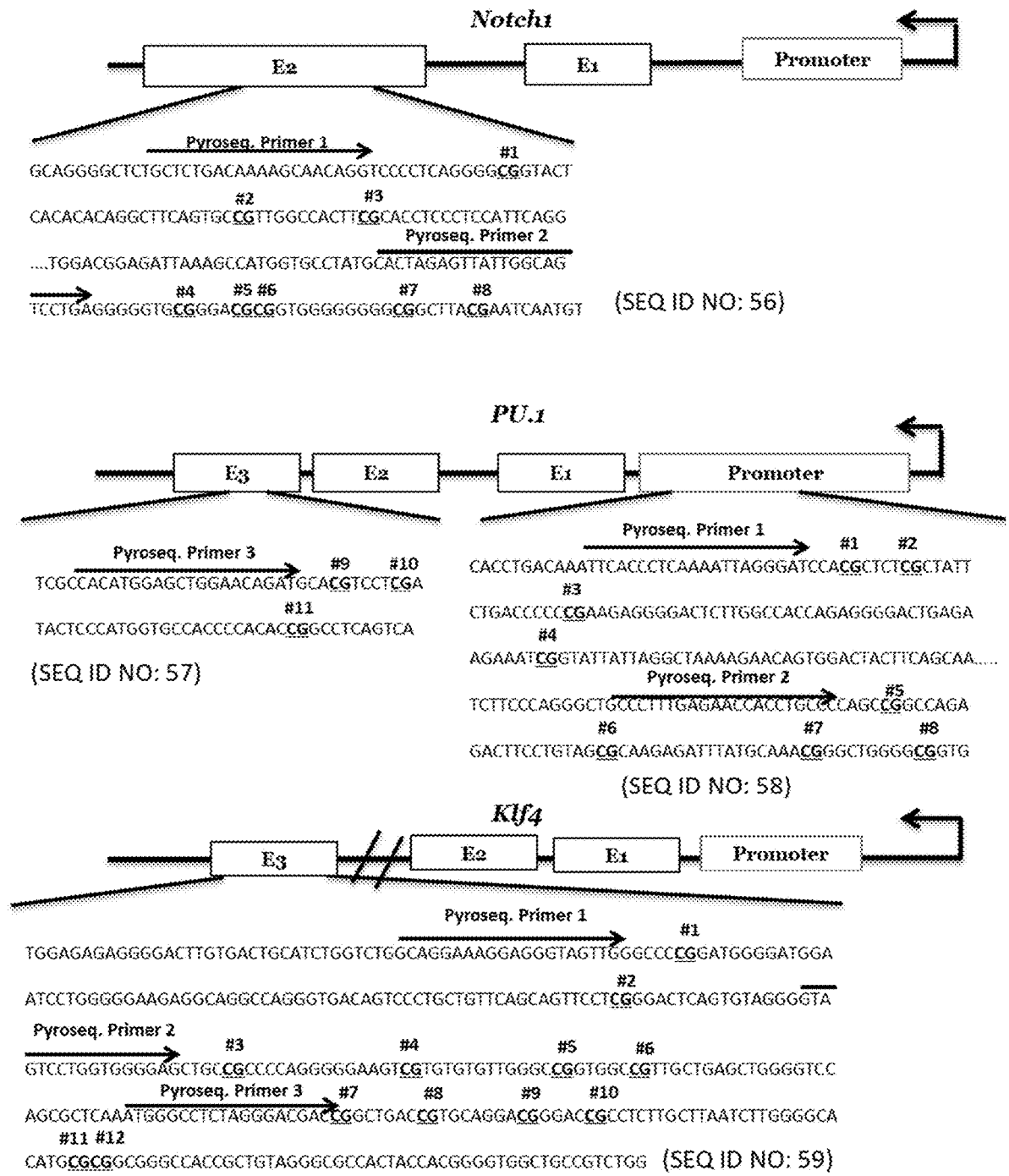
FIG. 15: Schematic of the Notch1, PU.1 and Klf4 genes showing the sequence and location of the primers and the CpG islands tested by pyrosequencing (SEQ ID Nos: 56-59).
Figure 16:
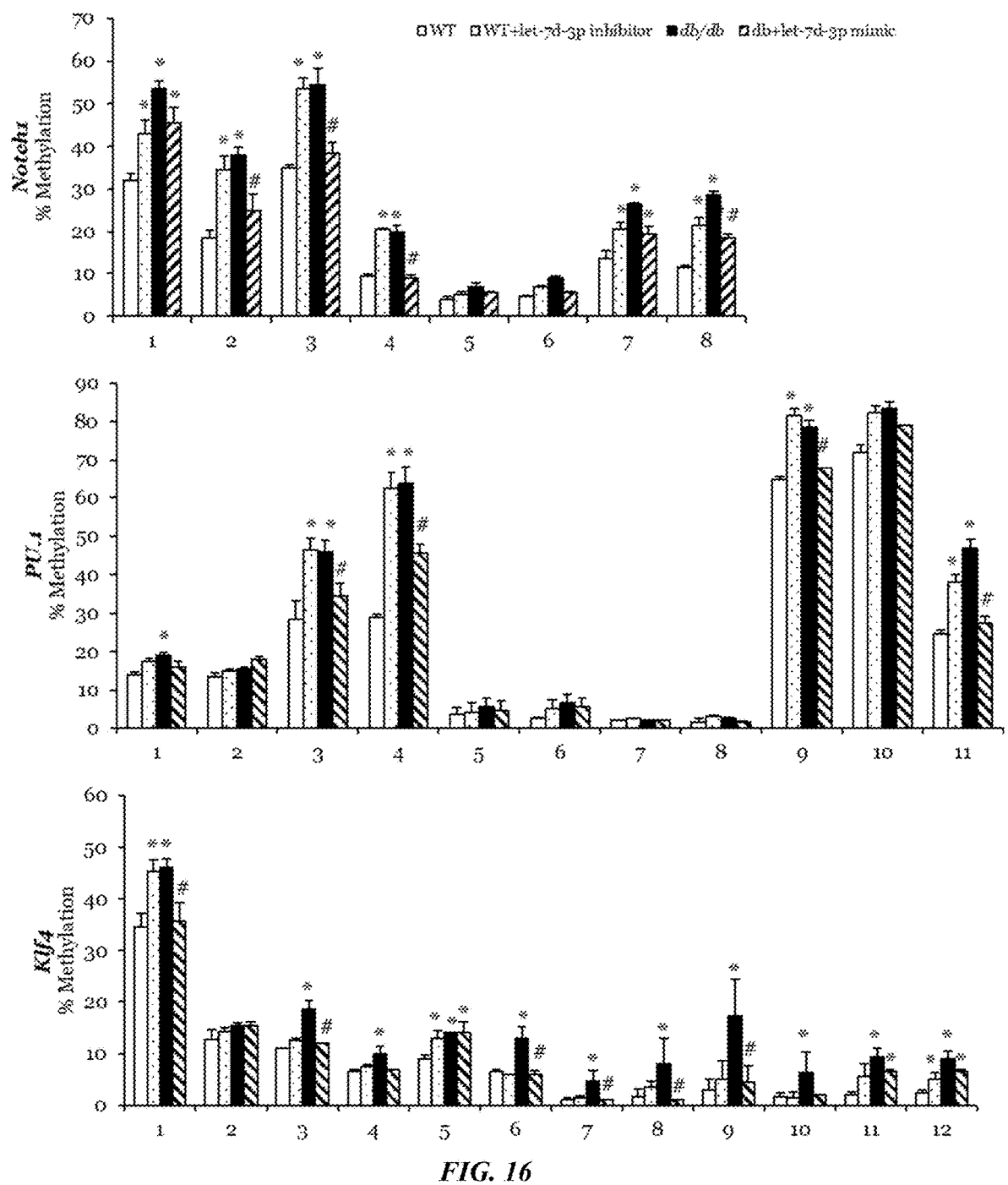
FIG. 16: Quantification of ChIP-PCR analysis of H3K9me3 histone modification of Notch1, PU.1 and Klf4 in WT HSC, WT HSC+let-7d-3p inhibitor, db/db HSC and db/db HSC+let-7d-3p inhibitor (n=6, *, P<0.05 vs WT; #, P<0.05 vs db/db). Results are expressed as means±SEM. One way ANOVA was used for analysis.

To test if the upregulation of Dnmt1 increases the repressive modification of the genes critical in the differentiation towards monocytes/macrophages, the DNA methylation status of Notch1, PU.1 and Klf4 genes was measured in HSCs from WT and db/db mice. Pyrosequencing analysis showed a significant increase in DNA hypermethylation in Notch1, PU.1 and Klf4. On the other hand, increased expression of let-7d-3p and knockdown of Dnmt1 in db/db HSCs decreased the methylation of Notch1, PU.1, Klf4 (FIG. 14A, FIG. 15, and FIG. 16). The results suggest that Dnmt1-induced DNA hypermethylation inhibits the expression of Notch1, PU.1 and Klf4 in HSCs from db/db mice.

Figure 14B:
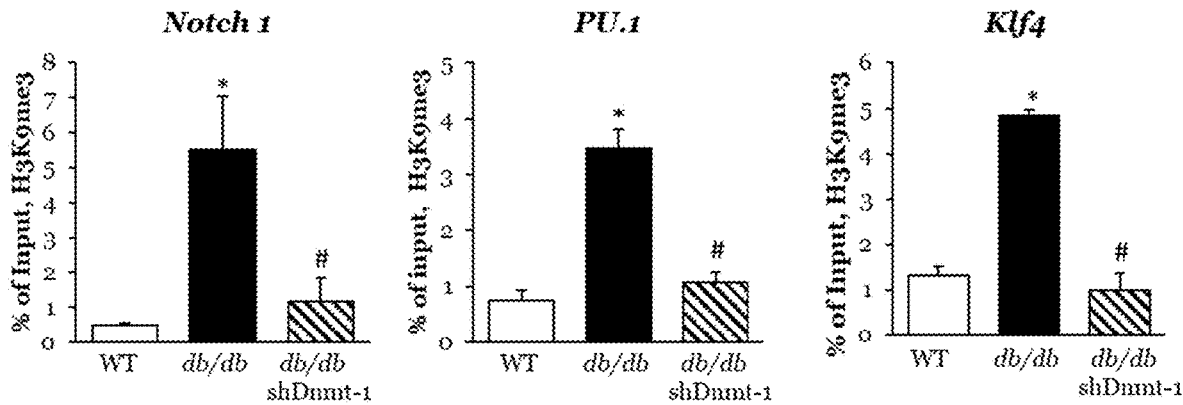
FIG. 14B: Quantification of ChIP-PCR analysis of H3K9me3 histone modification of Notch1, PU.1 and Klf4 in WT HSC, db/db HSC and db/db HSC+shDnmt-1 (n=6. *, p<0.05 vs WT; #, p<0.05 vs db/db). Results are expressed as means±SEM. One way ANOVA was used.
Figure 17A:
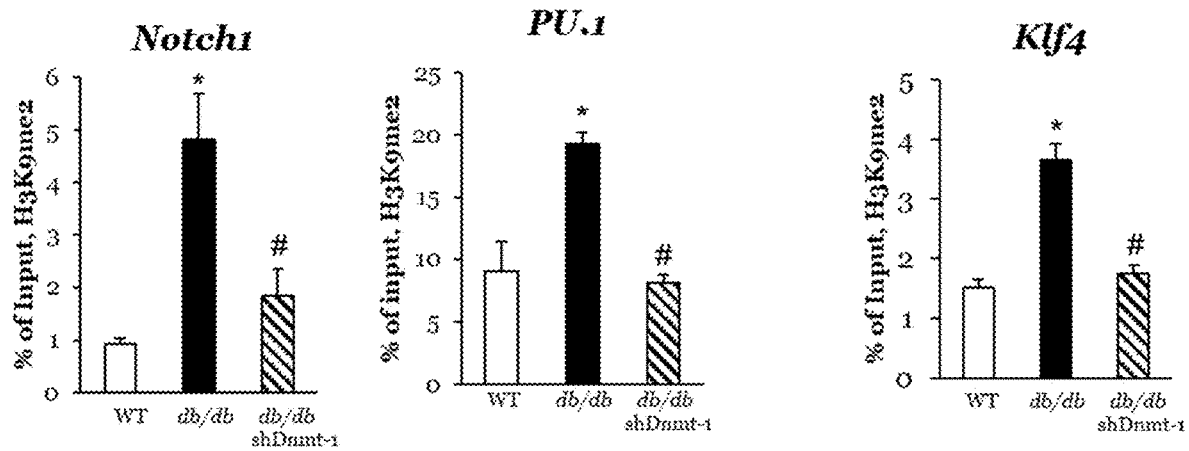
FIG. 17A: Quantification of ChIP-PCR analysis of H3K9me2 histone modification of Notch1, PU.1 and Klf4 normalized to H3 (n=6. *, p<0.05 vs WT; #, p<0.05 vs db/db). Results are expressed as means±SEM. One way ANOVA was used.
Figure 17B:
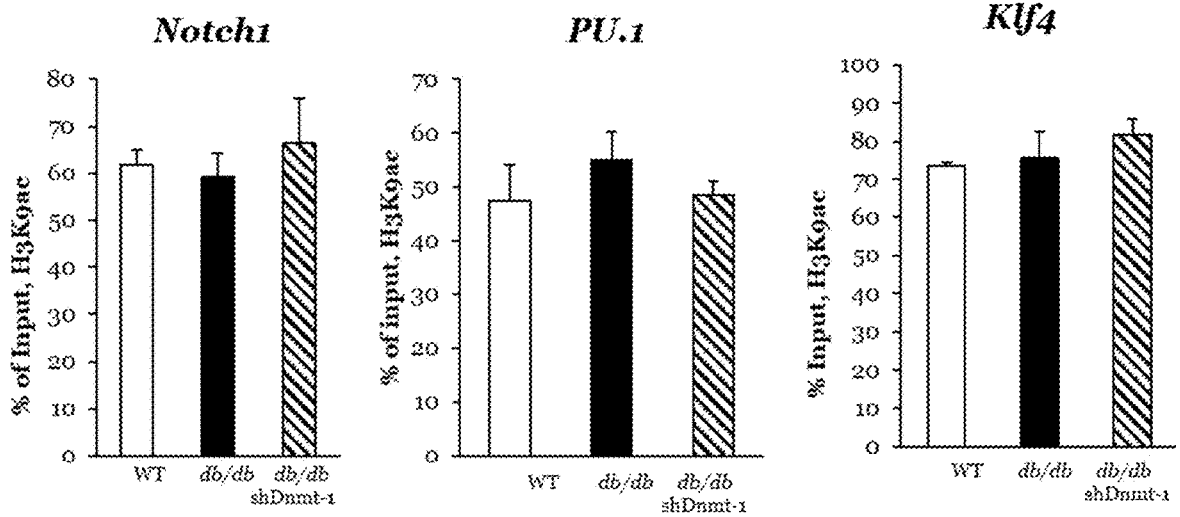
FIG. 17B: Quantification of ChIP-PCR analysis of H3K9ac histone modification of Notch1, PU.1 and Klf4 normalized to H3 (n=6. *, p<0.05 vs WT; #, p<0.05 vs db/db). Results are expressed as means±SEM. One way ANOVA was used.
Figure 18:
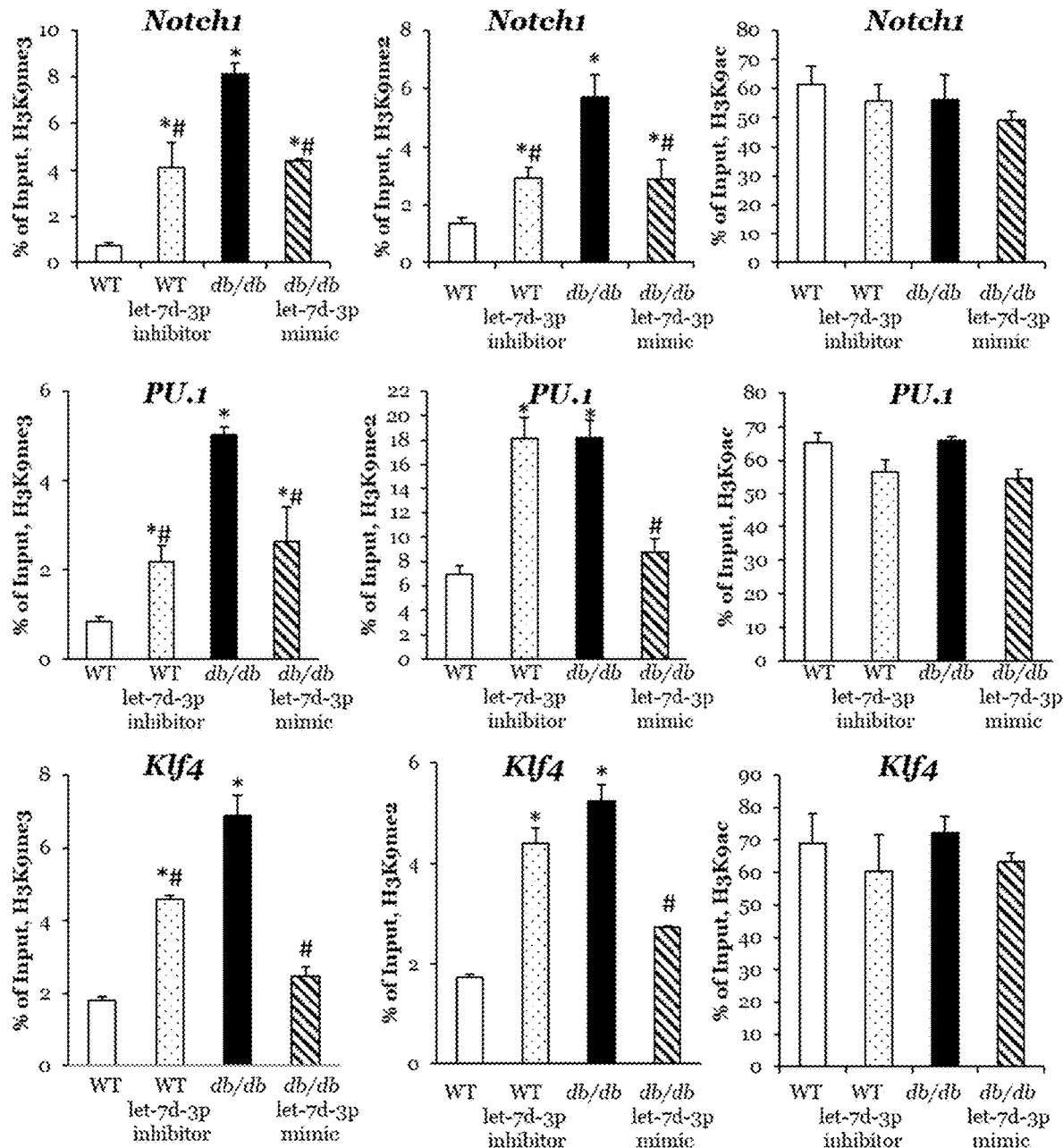
FIG. 18: Quantification of ChIP-PCR analysis of histone modifications (H3K9me3, H3K9me2 and H3K9ac) of Notch1, PU.1 and Klf4 normalized to H3 in WT, WT+let-7d-3p inhibitor, db/db, and db/db+let-7d-3p inhibitor (n=6. *, p<0.05 vs WT; #, p<0.05 vs db/db). Results are expressed as means±SEM. One way ANOVA was used for analysis.

DNMT1 has been shown to regulate histone modifications. Indeed, ablation of DNMT1 resulted in a deletion of dimethylation (H3K9me2) and trimethylation (H3K9me3) at H3K9 and a concomitant increase in H3K9 acetylation (H3K9ac) (Gilbert et al. (2007) J. Cell. Biol. 177: 401-411; Esteve et al. (2006) Genes Dev. 20: 3089-3103). Therefore, ChIP-PCR was performed to test if H3K9 silenced the expression of Klf4, PU.1 and Notch1. Both the dimethylated (H3K9me2) and trimethylated (H3K9me3) histone proteins were increased in the promoters of Klf4, PU.1 and Notch1 genes in HSCs from T2D mice (FIG. 14B and FIG. 17A). However, no difference in H3K9Ac was recorded in the three genes' promoters in WT or T2DM HSCs (FIG. 17B). Both knockdown of Dnmt1 and increased expression of let-7d-3p in db/db HSCs decreased the histone methylation levels (FIG. 17B and FIG. 18). These findings indicate that the oxidant stress-induced inhibition of let-7d-3p leads to an upregulation of Dnmt1 which in turn increases the repressive H3K9 methylation and decreases the expression of Notch1, PU.1 and Klf4 in HSCs from T2D mice.

Example 9. The Effect of Aging on Wound Healing In Mice

To determine the mechanisms by which aging-induced human HSC dysfunction causes chronic wounds in older adults, a novel humanized mouse model is used in which hematopoiesis is reconstituted with human HSCs and in which both the human innate and adaptive immune systems are operant. The effects of aging and type 2 diabetes on human HSC differentiation towards monocytes/macrophages and T-lymphocytes, and wound healing are studied in a humanized mouse model. It is hypothesized that aging epigenetically "reprograms" HSCs to dysregulate their differentiation towards monocytes/macrophages and T-lymphocytes and thereby impairs wound healing.

Impaired wound healing is a major clinical and economic problem, especially as an increasing proportion of the population advances in age. Therefore, it is important to understand the cellular and molecular mechanisms underlying the effect of aging on wound healing. Oxidative stress, through the production of reactive oxygen species (ROS), plays an important role in the development and progression of aging and T2DM (Bonomini et al., (2015) Aging Dis, 6(2): p. 109-20; Liguori et al., (2018) Clin Interv Aging, 13: p. 757-772; Robson et al., (2018) Diabetes Metab Syndr, 12(3): p. 455-462). Oxidative stress also contributes to perturbed HSC function and lineage specification in the context of aging (Oh et al., (2014) Nat Med, 20(8): p. 870-80; Yu et al., (2013) Cell Stem Cell, 12(1): p. 62-74; Pervaiz et al., (2009) Antioxid Redox Signal, 11(11): p. 2777-89; Geiger et al., (2014) Curr Opin Immunol, 29: p. 86-92), but the underlying mechanism has not been completely characterized.

Based on life phase equivalences between humans and mice, The Jackson Laboratory's recommendation is to use 24-month-old C57BL/6J mice for the study of aged wild type (WT) mice and 2-month-old C57BL/6J mice for the study of young WT mice (*American College of Laboratory Animal Medicine*. Second ed, ed. Fox et al., Vol. 2-4. 2007, Boston, Mass.: Elsevier, A P; Fox, J. G., The mouse in biomedical research. 2nd ed. American College of Laboratory Animal Medicine series. 2007, Amsterdam; Boston: Elsevier, AP. v. <2-4>). Both male and female mice are use in the first set of experiments, and if the outcomes are similar, male mice are used for the rest of the study.

Monocytes/macrophages and T-lymphocytes are essential for normal wound healing. The delay in wound healing documented in older adults correlates with the impaired recruitment of monocytes/macrophages and T-lymphocytes to wounds (Gosain et al., (2004) World J Surg, 28(3): p. 321-6; Sgonc et al., (2013) Gerontology, 59(2): p. 159-64; Guo et al., (2010) J Dent Res, 89(3): p. 219-29).

Figure 19A:
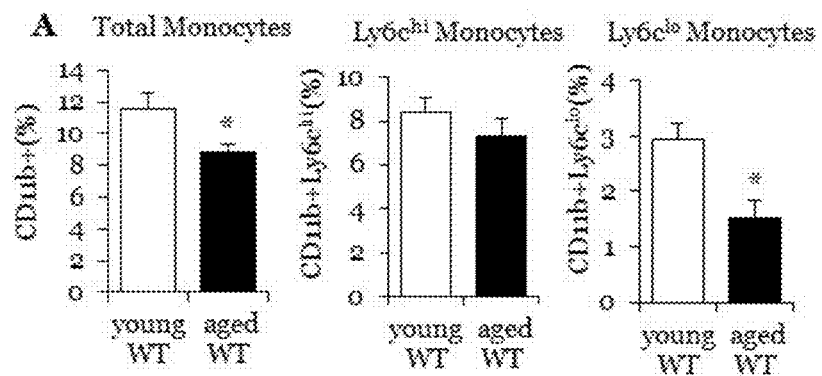
FIG. 19A: Quantification of peripheral blood monocytes in young WT mice and aged WT mice (*, p<0.05 vs young WT). Results are expressed as means±SEM.
Figure 19B:
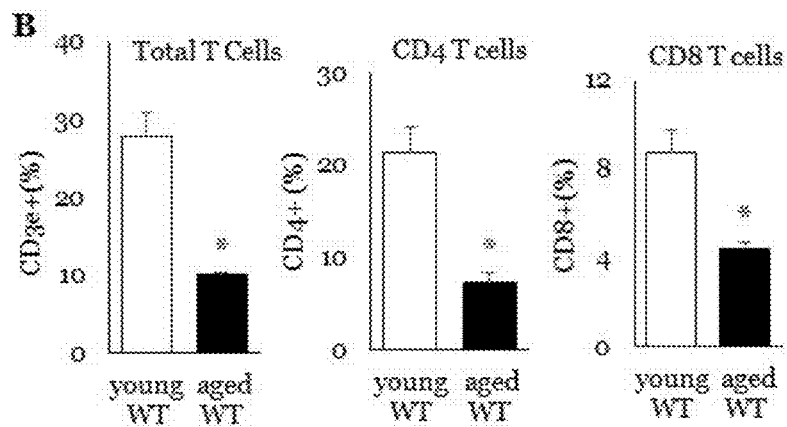
FIG. 19B: Quantification of T-lymphocytes (total T cells, CD4 T cells, and CD8 T cells) in young WT mice and aged WT mice (*, p<0.05 vs young WT). Results are expressed as means±SEM.
Figure 19C:
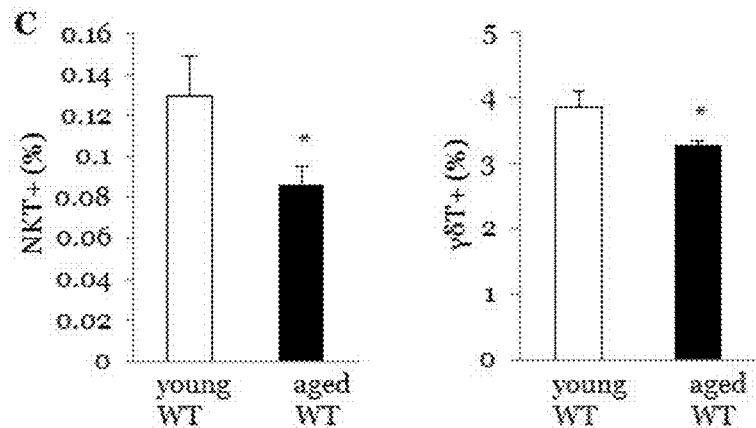
FIG. 19C: Quantification of NKT cells and γδT cells in young WT mice and aged WT mice (*, p<0.05 vs young WT). Results are expressed as means±SEM.

To test the hypothesis that impaired wound healing in older adults is due to age-dependent HSC autonomous mechanism, monocyte and T-lymphocyte populations were analyzed in the peripheral blood of aged mice. As shown in FIG. 19A, percentages of $CD11b^+$ monocytes and $Ly6c^{low}CD11b^+$ anti-inflammatory/angiogenic monocytes were significantly lower in the peripheral circulation of aged WT mice than in young WT mice. The percentages of $CD3e^+$, $CD4^+$, $CD8^+$ T-lymphocytes, NKT cells and γδT cells were also significantly lower in aged WT mice than in young WT mice (FIG. 19B and FIG. 19C).

Figure 20A:
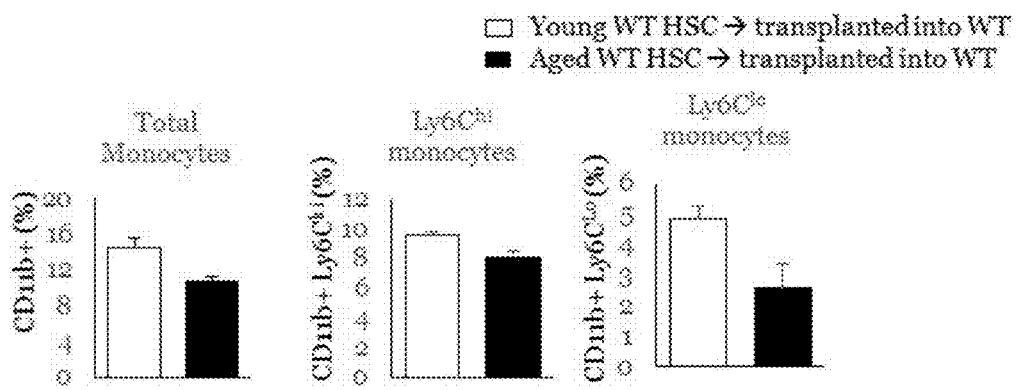
FIG. 20A: Quantification of HSC induced differentiation towards monocytes/macrophages in vivo (*, p<0.05 vs WT). Young WT HSC were transplanted into WT mice, and aged WT HSC were transplanted into WT mice. Results are expressed as means±SEM.
Figure 20B:
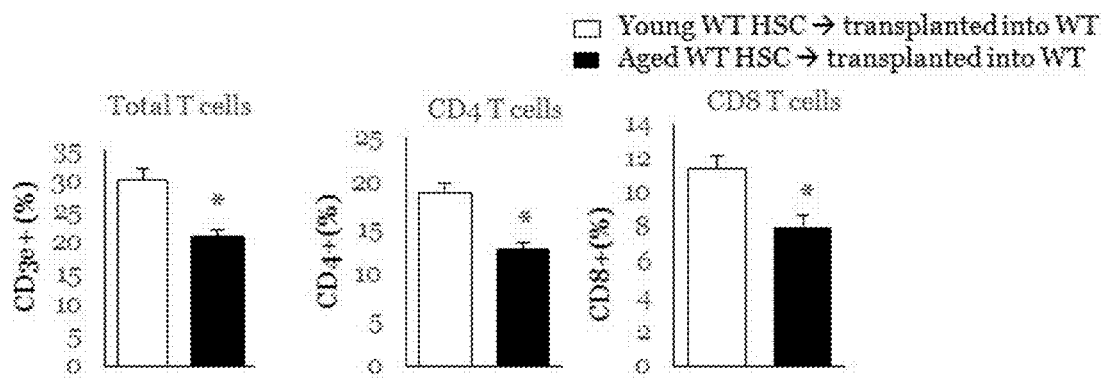
FIG. 20B: Quantification of HSC induced differentiation towards T-lymphocytes in vivo (*, p<0.05 vs WT). Young WT HSC were transplanted into WT mice, and aged WT HSC were transplanted into WT mice. Results are expressed as means±SEM.

To test the hypothesis that impaired wound healing in older adults is due to an age-dependent HSC autonomous mechanism, the concentrations of peripheral blood monocytes and T-lymphocytes in chimeric mice whereby hematopoiesis was reconstituted in lethally irradiated young WT recipient mice with HSCs from either young or aged WT donors was tested. WT mice that received HSCs from aged mice showed lower concentrations of monocytes and T lymphocytes in the peripheral blood similar to that shown in aged mice (FIG. 20A). Under in vitro conditions, HSCs from aged mice showed decreased differentiation capacity towards monocytes/macrophages and T lymphocytes (FIG. 20B). These results indicate that the effects of natural aging on the concentration of monocytes and T lymphocytes in peripheral blood are due to an HSC-autonomous mechanism.

Figure 21A:
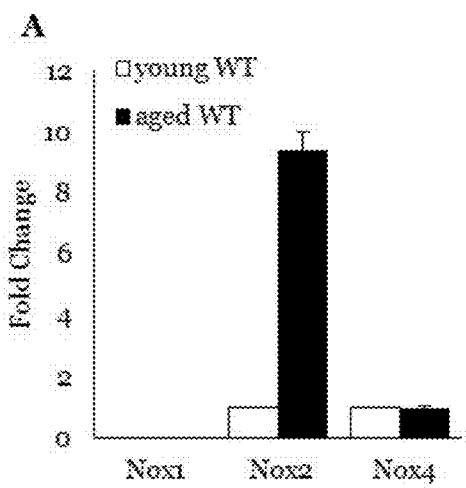
FIG. 21A: Quantification of NAPDH oxidases (NOX1, NOX2 and NOX4) in young WT HSC and aged WT HSC (*, p<0.05 vs WT). Results are expressed as means±SEM.
Figure 21B:
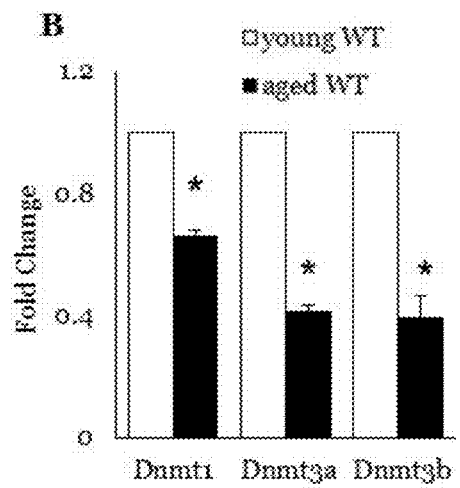
FIG. 21B: Quantification of DNMT1, DNMT3a and DNMT3b in young WT HSC and aged WT HSC (*, p<0.05 vs WT). Results are expressed as means±SEM.
Figure 21C:
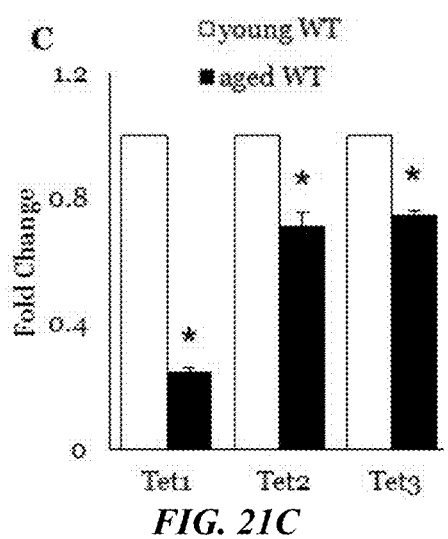
FIG. 21C: Quantification of TET1, TET2 and TET3 in young WT HSC and aged WT HSC (*, p<0.05 vs WT). Results are expressed as means±SEM.

To test the hypothesis that oxidative stress-dependent epigenetic reprogramming of HSCs dysregulates their differentiation towards monocytes/macrophages and T lymphocytes, the expression of NADPH oxidases as well as Dnmt and Tet DNA modifying enzymes were determined in HSCs isolated from aged WT mice. The expression of Nox2 was dramatically higher in HSCs from aged WT mice (FIG. 21A). In addition, the expression levels of all Dnmt (Dnmt1, Dnmt3a, Dnmt3b) and Tet (Tet1, Tet2, Tet3) enzymes were downregulated in HSCs from aged mice (FIG. 21B & FIG. 21C). These results indicate that Nox2 is likely the primary cause of oxidative stress in HSCs from aged mice, and that its effects on HSC function may be mediated through a dysregulation of epigenetic enzymes, namely Dnmt and Tet enzymes.

Example 10. Aging Impairs Wound Healing Through an HSC-Autonomous

To test the hypothesis that aging causes an HSC-autonomous defect in wound healing, wound closure kinetics were evaluated in a chimeric model whereby hematopoiesis was reconstituted in lethally irradiated 2-month-old WT recipient mice with HSCs from either young or aged WT donor mice. After allowing two months for the reconstitution of hematopoiesis, wounds were created in recipient mice. The wound closure rates were quantified by both macroscopic and histological analysis. To confirm that the recipients reconstituted with HSCs recapitulated the same defects as in aged mice, wounds were also created and measured in young and aged WT mice without HSC transplantation. As shown in FIGS. 31A-B, the wound closure rate was significantly decreased in mice transplanted with aged WT HSCs: wounds in young mice transplanted with young WT HSCs were healed by day 28 day, whereas wounds in young mice transplanted with aged WT HSCs were not healed by day 49. These findings indicate that the chronic non-healing wounds in aged WT mice are due to a HSC-autonomous mechanism.

To determine the effects of aging on HSC differentiation towards macrophages and T-lymphocytes in cutaneous wounds in vivo, chimeric mouse models are generated using HSCs isolated from young and aged C57BL/6-Tg(UBC-GFP)30scha/J (EGFP) mice, and wounds are created as described above.

To identify the dynamic changes of macrophage infiltration, M1/M2 polarization, and T-lymphocyte infiltration, cutaneous wounds are collected on post-wounding day 3 (inflammatory phase), day 7 (new tissue formation phase) and day 14 (tissue remodeling phase). Co-localization studies of GFP$^+$F4/80$^+$ macrophages or GFP$^+$ T-lymphocytes, are carried out to determine if macrophages and T-lymphocytes in cutaneous wounds are derived from transplanted HSCs. Images are obtained using a Solamere Technology Group CSU10B Spinning Disk Confocal Microscope. Quantification of M1/M2 polarization in cutaneous wounds is conducted by both flow cytometry and immunohistochemical analysis. The selected M1 macrophage markers are Ly6C$^{hi}$CD11b$^+$, TNFα, iNOS, and IL12; and the selected M2 macrophage markers are Ly6C$^{lo}$CD11b$^+$, Arginase, CD206, and IL10 (Yan et al., (2018) Nat Commun, 9(1): p. 33; Chen et al., (2014) Exp Dermatol, 23(3): p. 189-94).

The role of T-lymphocytes in wound healing is much less defined than that of monocytes/macrophages. HSC-derived infiltrating T cells and their specific subsets which include CD4, CD8, NKT, and ar3 T cells are characterized. These cells have been shown to be key players in impaired wound healing caused by aging in both human and mouse skin (Yu et al., (2013) Cell Stem Cell, 12(1): p. 62-74; Pervaiz et al., (2009) Antioxid Redox Signal, 11(11): p. 2777-89; Geiger et al., (2014) Curr Opin Immunol, 29: p. 86-92; Gore et al., (2016) Exp Hematol, 44(9): p. 783-90; Chambers et al., (2007) PLoS Biol, 5(8): p. e201).

To further characterize the role of HSC in wound resolution versus inflammation, the expression of the key cytokines and growth factors is measured in cutaneous wounds, including TNFα, IL-2, IL-10, IL-12, IGF-1, TGFβ1, PDGF, EGF, IL-8, IL-1β, VEGF, and bFGF (Makrantonaki et al., (2017) J Dtsch Dermatol Ges, 15(3): p. 255-275).

Figure 22:
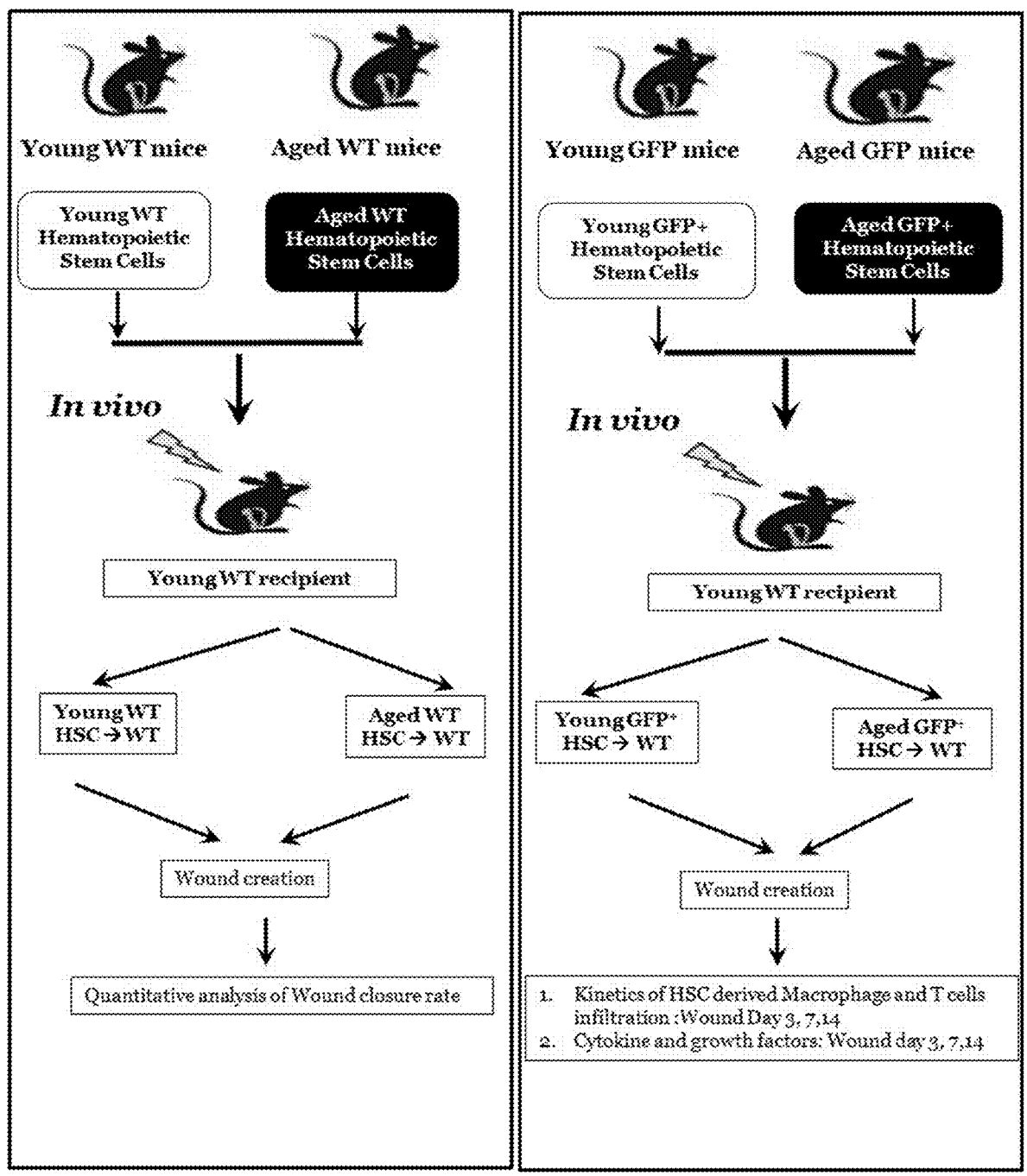
FIG. 22: Schematic illustration of experimental design in Example 10.

To distinguish the role of HSC-derived wound infiltrating macrophages and T cells from that of tissue resident macrophages and T cells in the wound healing process, the dynamic changes of the tissue resident macrophages (GFP$^-$F4/80$^+$) and T-lymphocytes (GFP$^-$γδT$^+$, GFP$^-$αβ$^+$) are measured in the cutaneous wounds of GFP$^+$HSC transplanted chimeric mice. Details on the described experimental groups are illustrated in FIG. 22.

Example 11. Identifying the Oxidative Stress-Dependent Epigenetic Mechanisms that are Involved in Dysregulating HSC Differentiation Towards Monocytes/Macrophages and T-Lymphocytes in Aged Wild Type Mice To understand the proposed Nox2-dependent Dnmt/Tet pathways underlying the reprogramming of aged HSCs in in vitro experiments, the expression of Nox2 is knocked down in aged HSCs and the expression of the individual Dnmt and Tet enzymes is determined by qRT-PCR and Western blot. Next, each of the Dnmt and Tet enzymes is overexpressed in aged HSCs and HSC differentiation is induced towards monocytes/macrophages and T-lymphocyte subsets to identify key Dnmt and Tet enzymes that cause aging-induced reprogramming of HSC differentiation.

Figure 23A:
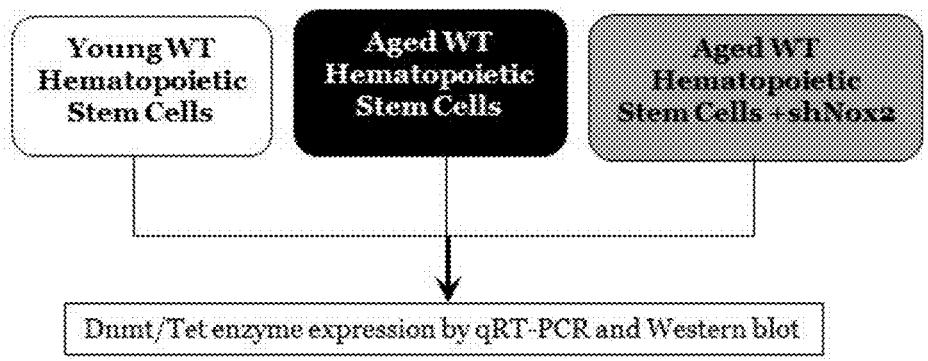
FIG. 23A: Schematic illustration of experimental design in Example 11.
Figure 23B:
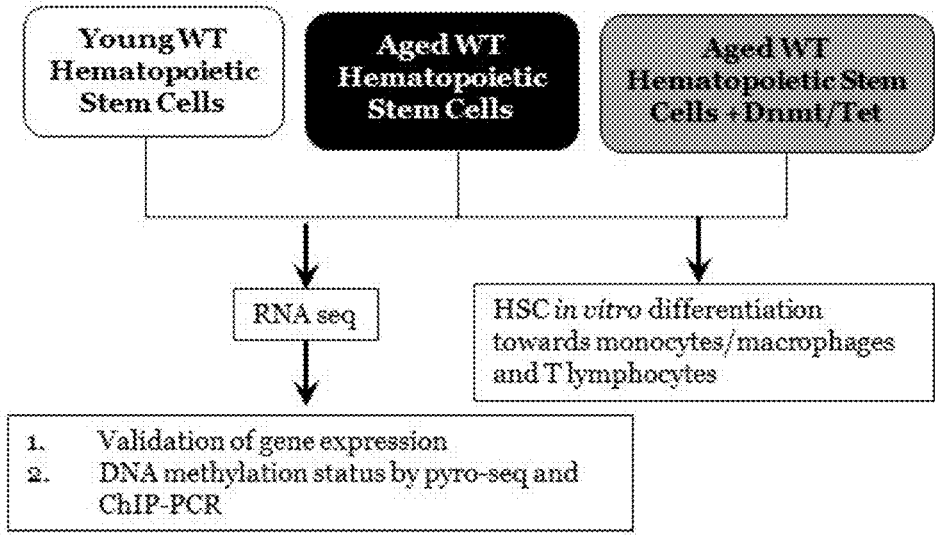
FIG. 23B: Schematic illustration of experimental design in Example 11.

To identify the most important genes and signaling pathways responsible for the lineage priming of HSCs that regulate by aged-induced changes in DNA methylation patterns, total RNA is isolated from HSCs from young and aged mice, as well as from HSCs that overexpress Dnmt or Tet enzymes. All dysregulated genes are identified using RNA sequencing (RNA-seq). Specifically, all genes responsible for monocyte/macrophage and T cell differentiation are screened. These results are confirmed by qRT-PCR, and isolate genomic DNA to quantify the DNA methylation status in the identified dysregulated genes by pyrosequencing. Finally, the histone methylation status of the dysregulated genes is quantified by ChIP-PCR. Details on the experimental groups are illustrated in FIG. 23A & FIG. 23B.

Example 12. Restoration of Epigenetic Enzyme Expression in Aged HSCs can Accelerate the Rate of Wound Healing by Restoring HSC Differentiation Towards Monocytes/Macrophages and T-Lymphocytes In this experiment, it is determined in vivo if the restoration of normal expression of the epigenetic enzyme(s) identified in Example 11 in aged HSCs can reestablish the normal pattern of differentiation towards monocytes/macrophages and T-lymphocytes and thereby reverse the impaired rate of wound healing in aged mice. HSCs from young WT mice, aged WT mice, and aged WT HSCs that overexpress the Dnmt and/or Tet enzyme identified in Example 11, are transplanted into lethally irradiated young WT recipients. Wounds are created 2 months after HSC reconstitution. Wound closure rate, monocyte/macrophage infiltration, M1/M2 polarization, T-lymphocyte infiltration, and changes in cytokine and growth factor levels are analyzed as described in Example 10.

Figure 24:
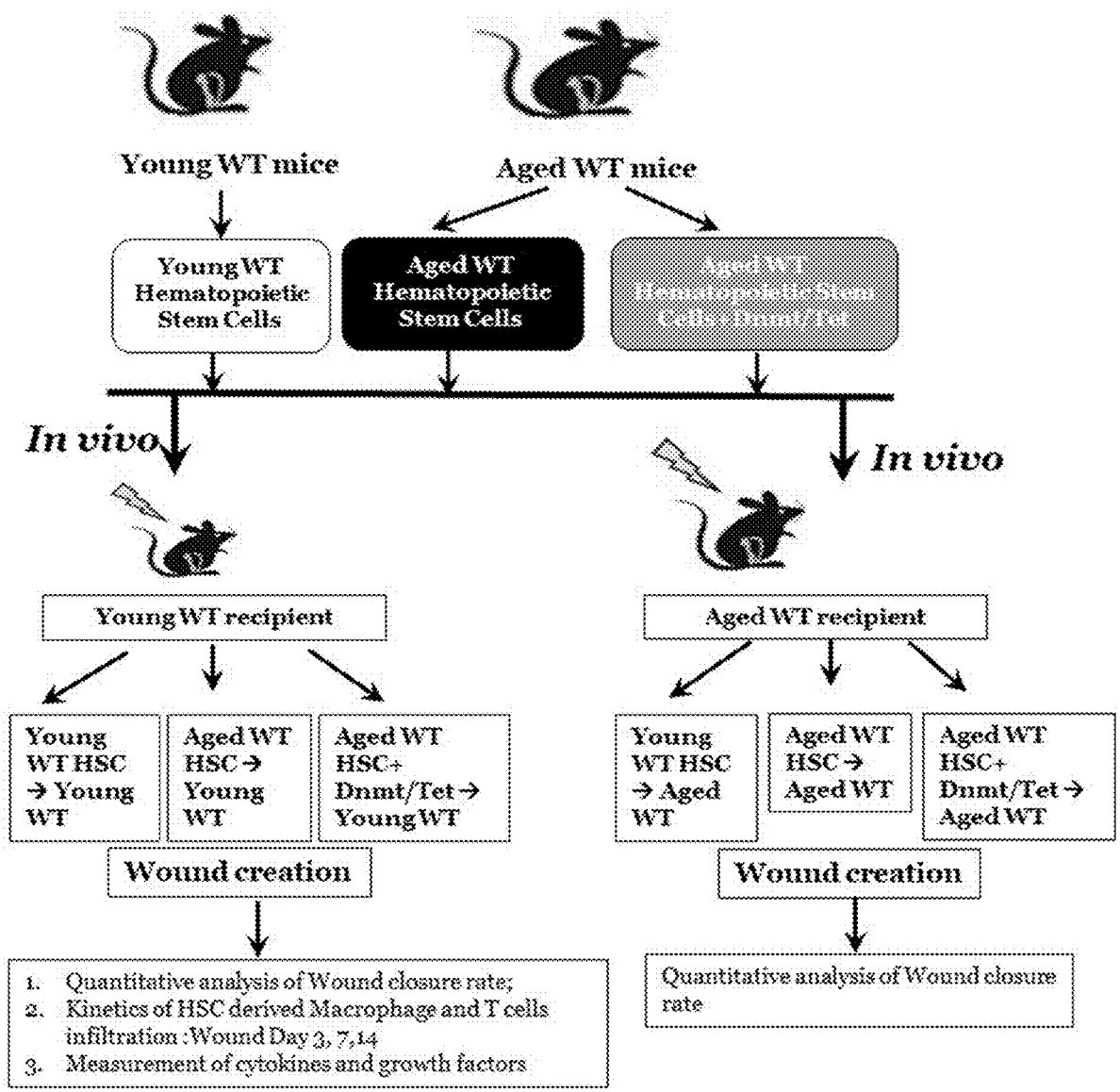
FIG. 24: Schematic illustration of experimental design in Example 12.

To determine in vivo if we can reverse the aged phenotype by restoring the expression of the identified epigenetic enzyme in aged HSCs can therapeutically promote normal wound healing in aged mice, HSCs from young WT donor, aged WT donor and aged WT HSCs that overexpress Dnmt and/or Tet enzyme are transferred into lethally irradiated aged mice. Wounds are created 2 months after HSC reconstitution and wound closure rate is analyzed as described above (FIG. 24).

Example 13. Determining the Combined Effects of Type 2 Diabetes and Aging on Wound Healing In mouse models, the combination of aging and T2DM significantly impairs wound healing relative to young mice (Brem et al., (2007) Exp Gerontol, 42(6): p. 523-31; Liu et al., (2008) J Cell Physiol, 2008. 217(2): p. 319-27). However, the underlying mechanism is not clear. To the best of the inventor's knowledge, no one has studied the combined effects of advanced age and T2DM on HSC function, a potential mechanism for impaired wound healing in aged patients with T2DM. This gap in knowledge severely hampers the development of effective clinical therapies to treat chronic non-healing wounds (Gould et al., (2015) Wound Repair Regen, 23(1): p. 1-13). Substantial research is needed to identify the molecular and cellular mechanisms underlying chronic wound pathology in aging patients with T2DM.

To model human aging, 18-month-old T2DM mice (Brem et al., (2007) Exp Gerontol, 42(6): p. 523-31; Huang et al., (2014) JAMA Intern Med, 174(2): p. 251-8; Omar et al., (2013) Diabetologia, 2013. 56(8): p. 1752-60), are used, which approximately equates to a 60 year-old human. Two different aged T2DM mouse models are used. The first model is an aged db/db leptin receptor mutant type 2 diabetic mouse (db/db T2DM). To exclude the possibility that the results observed in db/db mice are due, in part, to the effects of the leptin receptor deficiency, key results are confirmed in diet-induced type 2 diabetic mice (DIDM) by feeding WT C57BL/6J or C57BL/6-Tg(UBC-GFP)30scha/J mice a high fat diet (60% kcal % fat). These mice are fed the high fat diet from 8 to 18 months of age (Omar et al., (2013) Diabetologia, 2013. 56(8): p. 1752-60). The use of C57BL/6-Tg (UBC-GFP) 30scha/J transgenic mice in transplantation experiments allows tracking of the HSC-derived infiltrating macrophagesmacrophage and T-lymphocytes. The young recipient mice for all experiments are 2-month-old C57BL/ 6J mice on a normal chow diet. Both db/db and DIDM aged T2DM mouse models exhibit a diabetic phenotype, with body weights around 50 grams, as well as fasting blood glucose levels and plasma insulin levels significantly greater than those of aged wildtype mice. Body weight, blood glucose and blood insulin levels of all the mice are measured at regular intervals throughout the study. To avoid bias due to the choices of T2DM mouse models, key experiments are conducted in both mouse models. Both male and female mice are used in the first set of experiments; and if the outcomes are similar, male mice are used for the rest of the study.

Significantly increased concentrations of CD11 monocytes and proinflammatory Ly6c$^{hi}$CD11b$^+$ monocytes were seen in aged T2DM mice, while no changes in Ly6c$^{lo}$CD11b$^+$ monocytes were observed in peripheral blood of aged T2DM mice (FIG. 25A). However, the combination of aging and T2DM significantly decreased CD3e$^+$ and CD4$^+$ lymphocytes but had no effect on CD8$^+$ lymphocytes (FIG. 25B). Interestingly, studies in older T2DM patients also demonstrate a monocytosis, especially proinflammatory monocytes in their peripheral blood (Satoh et al., (2010) Diabetes Care, 2010. 33(1): p. e7; Walsh, N. Annu Rev Pathol, 2017. 12: p. 187-215). All of these results in humans are in agreement with the observations in mice, which indicate that the effects of aging or T2DM alone are not identical to the combined effects of aging and T2DM and need to be further characterized. Taken together, these findings indicate that the pathology observed in aged T2DM mice and older T2DM patients are due to the combined effects of aging and T2DM.

To test the hypothesis that the combination of aging- and T2DM-induced changes in the concentration of monocytes and T lymphocytes monocytes and T-lymphocytes in peripheral blood are due to an HSC-autonomous mechanism, the concentrations of peripheral blood monocytes and T-lymphocytes were measured in chimeric mice, whereby hematopoiesis was reconstituted in lethally irradiated young WT recipient mice with HSCs from aged T2DM donors. Similar changes were observed in the chimeric mice reconstituted with HSCs from aged T2DM donors and aged T2DM mice (FIG. 26). Under in vitro conditions, HSCs from aged T2DM mice showed defects in their differentiation towards monocytes/macrophages and T-lymphocytes (FIG. 26). These results indicate that the combined effects of aging and T2DM on the concentration of monocytes and T-lymphocytes in peripheral blood are HSC-autonomous.

To test the hypothesis that oxidative stress-dependent epigenetic reprogramming in HSCs dysregulates their differentiation towards monocytes/macrophages and T-lymphocytes, we analyzed the gene expression of NADPH oxidases (Nox1, Nox2, and Nox4) as well as Dnmt and Tet DNA modifying enzymes in HSCs isolated from aged db/db and aged DIDM T2DM mice. Consistent with the findings from young T2DM mice, the expression of Nox2 is dramatically higher in HSCs from aged T2DM mice, which indicates that Nox2 is also the primary cause of oxidative stress in HSCs from aged T2DM mice (FIG. 27A). The expression levels of Dnmt3a, Tet1, and Tet2 are decreased in HSCs isolated from aged T2DM mice (FIG. 27B & FIG. 27C).

Example 14. Determining that the Combined Effects of Type 2 Diabetes and Aging on Wound Healing are Due to an HSC-Autonomous Mechanism To test the hypothesis that the combined effects of aging and T2DM on wound healing were due to an HSC-autonomous defect, wound closure kinetics were to determined in a chimeric model whereby hematopoiesis was reconstituted in lethally irradiated young WT recipient mice with HSCs from 3 different groups of mice which include: young WT mice, young T2DM mice, and aged db/db. The wound closure rates were quantified by both macroscopic and histological analysis. FIGS. 32A-B show that the wound closure rate was significantly increased in mice transplanted with young db/db HSC as compared to in mice transplanted with young WT HSC. The most impaired wound closure rate was observed in mice transplanted with aged db/db HSCs: wounds in young mice transplanted with aged db/db HSC were not healed by day 56 (FIGS. 32A-B). These findings indicate that chronic non-healing wounds in aged T2DM mice are due to a HSC-autonomous mechanism.

To determine the dynamic changes of HSC derived infiltrating macrophages and T cells in cutaneous wounds, GFP mice are fed a high fat diet to generate aged GFP/DIDM mice. Two groups of chimeric mice are generated by transplantation of HSCs from young GFP mice or aged GFP/DIDM mice, into lethally irradiated young WT recipient mice. Cutaneous wounds are collected on post wound days 3, 7 and 14. Colocalization of GFP$^+$ macrophages, GFP$^+$ T cells and the levels of cytokines and growth factors are analyzed as in Example 10.

Example 15. Identifying the Oxidative Stress-Dependent Epigenetic Mechanisms that are Involved in Dysregulating HSC Differentiation Towards Monocytes/Macrophages and T-Lymphocytes in Aged T2DM Mice To identify the Nox2-induced Dnmt/Tet-dependent mechanisms that underlie the combined effects of aging and T2DM on HSC dysfunction, the expression of Nox2 is knockdown in aged T2DM HSCs and the expression of Dnmt and Tet enzymes is analyzed by qRT-PCR and western blot. Next, Dnmt and/or Tet enzymes are overexpressed in aged HSCs and HSC differentiation towards monocytes/ macrophage and T-lymphocytes is induced to identify the specific Dnmt and/or Tet enzymes that dysregulates HSC differentiation towards monocytes/macrophages and T-lymphocytes in aging. Last, the Dnmt- and/or Tet-dependent mechanisms are determined in aged T2DM HSCs by RNA-seq, pyrosequencing and ChIP-PCR.

Using the Dnmt and/or Tet enzymes previously identified, it is determined whether the restoration of the Dnmt and/or Tet enzymes expression in HSCs from aged T2DM mice can restore normal wound healing in aged T2DM mice. Aged T2DM HSCs transduced with lentiviral vectors overexpressing Dnmt and/or Tet are transplanted into lethally irradiated young WT recipient mice and wound closure rate, monocytes/macrophages and lymphocytes infiltration are analyzed.

To determine in vivo that the restoration of normal epigenetic enzyme expression in aged HSCs can therapeutically reestablish normal wound healing in aged mice, HSCs from young WT donor, aged T2DM donor, and aged T2DM HSCs that overexpress the Dnmt and/or Tet enzyme are transplanted into lethally irradiated aged T2DM mice. Wounds are created 2 months after HSC reconstitution and wound closure rate are analyzed as described above.

Example 16. Determining the Effects of Aging and Type 2 Diabetes on Human HSC Differentiation Towards Monocytes/Macrophages and T-Lymphocytes, and Thereby on Wound Healing, in a Humanized Mouse Model While animal models of aging and T2DM provide an accessible system for investigation, they do not necessarily successfully recapitulate the processes that take place in humans, resulting in significant time and resource expenditure without definite clinical benefit. Therefore, it is essential to develop methods to investigate pathological mechanisms and treatment options for older adults with or without T2DM using human cells and tissue in order to be able to develop effective biological therapies.

The humanized mouse model, which is engrafted with functional human cells and tissues, has become an increasingly important preclinical animal model for the study of human diseases and their treatments. NOD-scid IL2r$\gamma^{null}$ (NSG) mice are immunodeficient (Shultz et al., (2005) J Immunol, 174(10): p. 6477-89) and can be engrafted with human CD34+HSCs that generate a functional human immune system.

Human bone marrow mononuclear cells from young healthy donor, aged healthy donor (55+) and aged T2DM patients were purchased from AllCells (location) and Axol Bioscience, Ltd. CD34$^+$CD38$^-$Lin$^-$ human HSCs were sorted by flow cytometry and induced to differentiate towards monocytes/macrophages and T-lymphocytes in vitro (Yan et al., (2018) Nat Commun, 9(1): p. 33; Gould et al., (2015) J Am Geriatr Soc, 63(3): p. 427-38). As shown in FIG. 28, aging alone or the combination of aging and T2DM dysregulates human HSC differentiation towards to monocytes/macrophages and T-lymphocytes.

Consistent with the observations in aged WT and aged T2DM mice, the expression of NOX2 is more than 2.5 fold higher in human HSCs from an older person who has T2DM than in an older healthy person, which indicates that NOX2 is also the primary cause of oxidative stress in human HSCs and is induced by aging and T2DM (FIG. 29). In addition, similar to HSCs from aged mice, the expression levels of DNMT1/3a/3b and TET1/2 are more than 20% decreased in human HSCs from an older healthy person. However, in human HSCs from an older T2DM person, only the expression level of DNMT3a and TET1/2 are more than 20% decreased, the expression level of DNMT1 and DNMT3b are unchanged (FIG. 30A & FIG. 30B).

Example 17. Using HSCs Derived from Older Healthy Donors and Older T2DM Donors, Determine if the Effects of Aging and Type 2 Diabetes on Wound Healing are Due to an HSC-Autonomous Mechanism in Humanized NSG Mice Wounds are created in humanized NSG mice that are reconstituted HSCs from four groups of human HSCs: young healthy donors, young T2DM donors, older healthy donors, and older T2DM donors. Wound closure rate and the dynamic changes in infiltrating macrophages and T lymphocytes are analyzed in the cutaneous wounds of human HSC-reconstituted NSG mice using the techniques discussed in Example 10.

To precisely evaluate the clinical relevance of these findings, the human bone marrow donors' main parameters including age, gender, race, body weight, HbA1C levels, and diabetes duration are taken into account. Due to the limited availability of T2DM donors, T2DM donors are recruited irrespective of the diabetes duration, but their HbA1c levels are measured and must be ≥7.

Expression of NOX2, as well as DNMT and TET enzymes is confirmed by Western blotting in human HSCs. The key oxidative stress-dependent DNMT/TET enzymes are identified by knocking-down the identified unregulated NOX2 in HSCs and analyzing the expression levels of these two families of epigenetic regulators. These finding provide insight for investigating the homologous human genes that are responsible for the dysregulated HSC differentiation towards monocytes/macrophages and T-lymphocytes in older adults with or without T2DM. Once the specific dysregulated epigenetic mechanism(s) is identified, in vitro experiments are undertaken with human HSCs in which the expression of DNMT and/or TET enzymes is restored by lentiviral vector-mediated transduction. HSC differentiation towards monocytes/macrophages and T-lymphocytes is analyzed. In the event that the genes responsible for the dysregulated HSC differentiation towards monocytes/macrophages and T-lymphocytes identified in mice are not conserved in human HSCs, RNA-seq analysis is performed to identify the key genes responsible for the dysregulated differentiation of human HSCs into monocytes/macrophages and T-lymphocytes.

To determine in vivo if the restoration of DNMT and/or TET expression in HSCs from older healthy donor and older T2DM donor can rescue normal wound healing, lentiviral vector-transduced DNMT and/or TET human HSCs are transplanted into NSG mice and then wounds are induced following 16-20 weeks of HSC reconstitution (Shultz et al., (2005) J Immunol, 174(10): p. 6477-89). The wound closure rate and dynamic infiltration of macrophages and T-lymphocytes are evaluated.

Taken together, these rather complex but critical experiments can determine how the findings in mouse models translate to human HSCs. These unique and high impact experiments can confirm the manner in which oxidative stress-dependent epigenetic reprogramming in human HSCs from older adults with or without T2DM are the primary determinant of impaired wound healing.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a wound or accelerating wound healing in a subject, the method comprising:
   providing a population of hematopoietic stem cells (HSCs);
   contacting the HSCs with a nicotinamide adenine dinucleotide phosphate oxidase 2 (NOX2) inhibitor, wherein the NOX2 inhibitor is an inhibitory nucleic acid that directly inhibits NOX2; and
   administering a therapeutically effective amount of the HSCs to the subject.

2. The method of claim 1, wherein the NOX2 inhibitory nucleic acid is an antisense molecule, a small interfering RNA, or a small hairpin RNA that is specific for a nucleic acid encoding SEQ ID NO: 7.

3. The method of claim 1, wherein the NOX2 inhibitory nucleic acid is a nucleic acid comprising a sequence that is complementary to a contiguous sequence of at least 10 nucleotides present in NOX2.

4. The method of claim 1, wherein the subject is human.

5. The method of claim 1, wherein the subject has diabetes.

6. The method of claim 1, wherein the subject is between 1 and 60 years old.

7. The method of claim 1, wherein the subject is over 60 years old.

8. The method of claim 1, wherein the HSCs are autologous HSCs.

9. The method of claim 1, further comprising administering a therapeutically effective amount of N-acetylcysteine (NAC) to the subject.

10. The method of claim 9, further comprising contacting the HSCs with NAC.

11. The method of claim 10, wherein the HSCs are autologous HSCs.

12. A method of treating a wound or accelerating wound healing in a subject, the method comprising:
    providing a population of hematopoietic stem cells (HSCs);
    contacting the HSCs with a nicotinamide adenine dinucleotide phosphate oxidase 2 (NOX2) inhibitor, wherein the NOX2 inhibitor is GSK2795039, N-acetyl cysteine (NAC), apocynin, diphenylene iodonium (DPI), VAS2870, ML171, ebselen, GKT136901, Phox-I1, gliotoxin, celastrol, or aminoethyl-benzenesulfono-fluoride; and
    administering a therapeutically effective amount of the HSCs to the subject.

13. The method of claim 12, wherein the small molecule is NAC.

14. The method of claim 12, wherein the subject is human.

15. The method of claim 12, wherein the subject has diabetes.

16. The method of claim 12, wherein the subject is between 1 and 60 years old.

17. The method of claim 12, wherein the subject is over 60 years old.

18. The method of claim 12, wherein the HSCs are autologous HSCs.

* * * * *